US006423689B1

(12) United States Patent
Booth et al.

(10) Patent No.: US 6,423,689 B1
(45) **Date of Patent: *Jul. 23, 2002**

(54) PEPTIDYL CALCIUM CHANNEL BLOCKERS

(75) Inventors: Richard John Booth, Ann Arbor, MI (US); Louis Brogley, Santa Cruz, CA (US); Wayne Livingston Cody, Saline, MI (US); David Thomas Connor, Ann Arbor, MI (US); Harriet Wall Hamilton, Chelsea, MI (US); John Xiaoqiang He, Indianapolis, IN (US); Lain-Yen Hu; Leonard Joseph Lescosky, both of Ann Arbor, MI (US); Thomas Charles Malone, Canton, MI (US); Laszlo Nadasdi, Oakland, CA (US); Michael Francis Rafferty, Ann Arbor; Bruce David Roth, Plymouth, both of MI (US); Diego F. Silva, Burlingame, CA (US); Yuntao Song, Ann Arbor, MI (US); Balazs G. Szoke, Palo Alto; Laszlo Urge, Menlo Park, both of CA (US)

(73) Assignees: Warner-Lambert Company, Morris Plains, NJ (US); Neurex Corporation, Menlo Park, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/212,785

(22) Filed: Dec. 16, 1998

Related U.S. Application Data

(60) Provisional application No. 60/068,485, filed on Dec. 22, 1997.

(51) Int. Cl.[7] .......................... A61K 38/05; C07K 5/06

(52) U.S. Cl. ......................... 514/19; 540/483; 540/607; 544/159; 544/168; 544/391; 546/221; 546/224; 546/233; 548/338.1; 548/538; 548/557; 548/568; 548/953; 548/966; 564/153; 564/155; 564/157

(58) Field of Search .............................. 514/19; 560/13, 560/37, 38, 39, 40, 41, 42; 564/74, 79, 84, 92, 99, 153, 155, 157; 540/483, 607, 610; 544/159, 168, 391; 546/221, 224, 222, 233; 548/338.1, 538, 557, 568, 953, 966

(56) References Cited

U.S. PATENT DOCUMENTS

| | | | |
|---|---|---|---|
| 5,116,835 A | 5/1992 | Rüger et al. ................ | 514/218 |
| 5,496,928 A | 3/1996 | Ishikawa et al. ............ | 530/331 |

FOREIGN PATENT DOCUMENTS

| | | |
|---|---|---|
| EP | 0482539 A2 | 4/1992 |
| WO | 93/06127 | 4/1993 |
| WO | 95/12612 | 5/1995 |
| WO | 96/20725 | 7/1996 |
| WO | 96/22966 | 8/1996 |

*Primary Examiner*—Jeffrey E. Russel
(74) *Attorney, Agent, or Firm*—Todd M. Crissey; Michael J. Atkins; David R. Kurlandsky

(57) ABSTRACT

The present invention provides compounds that block calcium channels having the Formula I shown below.

I

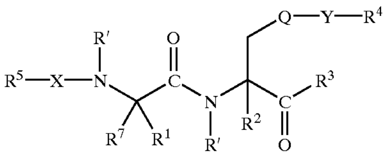

The present invention also provides methods of using the compounds of Formula I to treat stroke, cerebral ischemia, head trauma, or epilepsy and to pharmaceutical compositions that contain the compounds of Formula I.

146 Claims, 3 Drawing Sheets

*VEHICLE: 10%DMSO
60% PEG
30% ETHANOL

** TEST ARTICLE: -28mg/kg (49 μmol/kg)
ONE ANIMAL EXHIBITED A SLIGHT TREMOR WHEN INJECTED (5-8 MIN.)
ONE ANIMAL HAD A ROLLING SEIZURE, THAT LASTED FOR 10 MIN.

PEPTIDYL CALCIUM CHANNEL BLOCKERS

This application is a regular patent application claiming priority of U.S. Provisional Patent Application No. 60/068,485, filed Dec. 22, 1997.

FIELD OF THE INVENTION

The present invention relates to compounds that act to block calcium channels; methods of using the compounds to treat stroke, cerebral ischemia, pain, head trauma or epilepsy; and to pharmaceutical compositions that contain the compounds of the present invention.

BACKGROUND OF THE INVENTION

The entry of excessive amounts of calcium ions into neurons following an ischemic episode or other neuronal trauma has been well documented. Uncontrolled high concentrations of calcium in neurons initiates a cascade of biochemical events that disrupts normal cellular processes. Among these events are the activation of proteases and lipases, breakdown of neuronal membranes and the formation of free radicals, which may ultimately lead to cell death. Several types of calcium channels have been discovered and called the L, N, P, Q, R and T types. Each type possesses distinct structural features, functional properties and cellular/subcellular distributions. Type selective calcium channel blockers have been identified. For example, SNX-111 has been shown to be a selective N-type calcium channel blocker and has demonstrated activity in a number of models of ischemia and pain (Bowersox S. S., et al., *Drug News and Perspective,* 1994:7:261–268 and references cited therein). The compounds of the present invention are calcium channel blockers that can block N-type calcium channels and can be used to treat stroke, pain, cerebral ischemia, head trauma, and epilepsy.

SUMMARY OF THE INVENTION

The present invention provides compounds having the Formula I

I

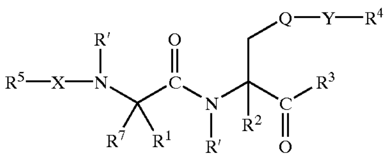

wherein each R' is independently hydrogen, $C_1$–$C_6$ alkyl, or R' together with N to which R' is attached and $R^1$ can form a mono or bicyclic structure;

$R^1$ is $C_1$–$C_6$ alkyl, —$CH_2$-phenyl, hydrogen, —$CH_2$-indolyl, —$(CH_2)_n$—S—$C_1$–$C_6$ alkyl, —$(CH_2)_n$-substituted phenyl, —$(CH_2)_n$ cycloalkyl, —$(CH_2)_n$-heteroaryl, or

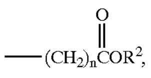

;$R^2$ is hydrogen or $C_1$–$C_6$ alkyl;

$R^3$ is —O($C_1$–$C_6$alkyl), —$O(CH_2)_n$phenyl,

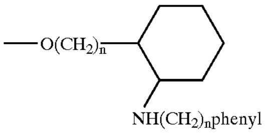 , —$NH_2$,

—NH($C_1$–$C_6$alkyl), —N($C_1$–$C_6$alkyl)$_2$, —$NH(CH_2)_n$ cycloalkyl, —$NH(CH_2)_n$ NH cycloalkyl,

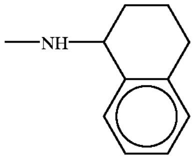 , —NH—substituted phenyl,

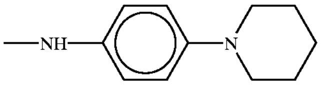 , —NH—$(CH_2)_n$—phenyl,

—NH—$(CH_2)_n$-substituted phenyl, —NH—$(CH_2)_n$-phenyl—$CH_2NH_2$, —NH—$(CH_2)_n$ pyridyl, —NH—$(CH_2)_n$ imidazolyl, —NH—$(CH_2)_n$ furyl,

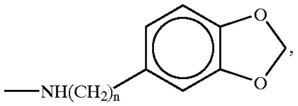

—NH—$(CH_2)_n$-indolyl, —NH—$(CH_2)_n$OH, —NH—$(CH_2)_n$—CN,

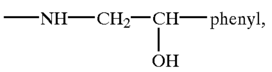 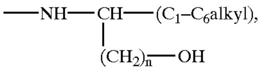

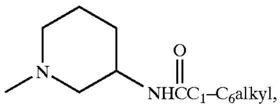 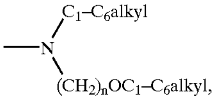

—$NH(CR'R')_nNH(CR'R')_nOH$, 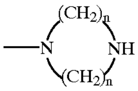 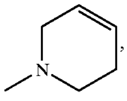

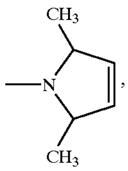 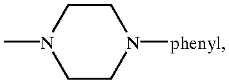

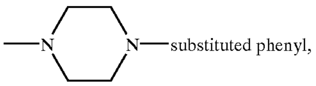

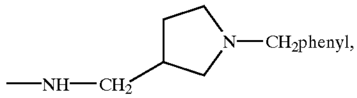

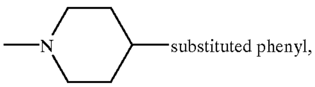 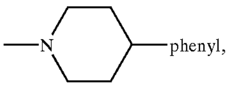

-continued
$—NH(CH_2)_n—NHCH_2phenyl$, 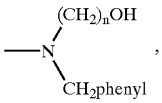 ,
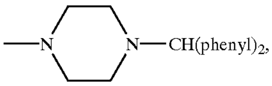
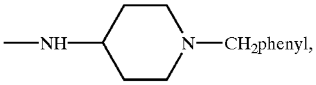 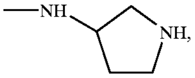
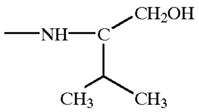 , 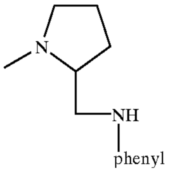 ,
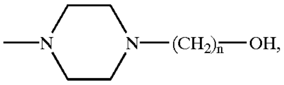 $—NH(CR'R')_nN(CR'R')_nNH_2$,
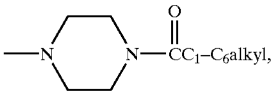 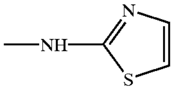 ,
$—NH(CR'R')_nNH(C_1–C_6alkyl)$, $—NH(CH_2)_n$-piperidiny, $—NH(CH_2)_n$-substituted piperidinyl,
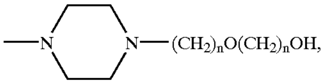
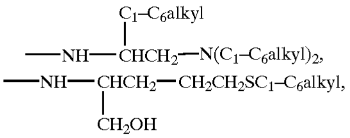
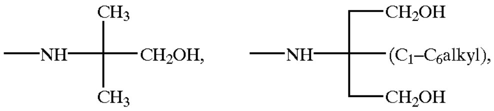
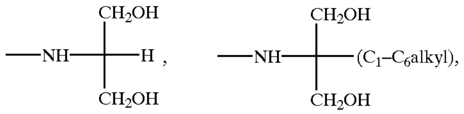
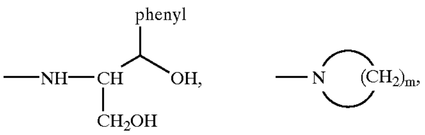
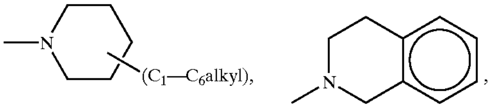
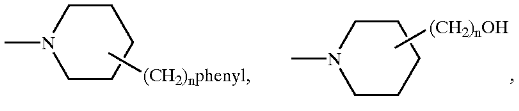
-continued
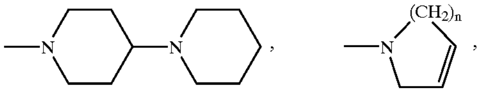
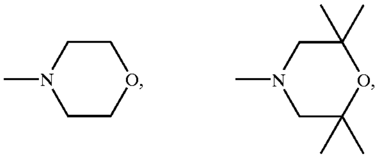
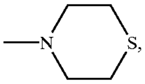 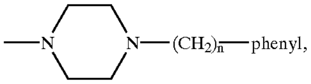
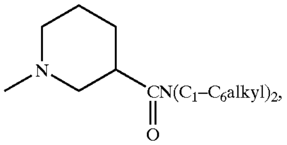 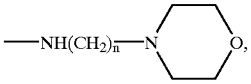
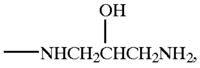 $—NH(CH_2)_nNH(CH_2)_mOH$,
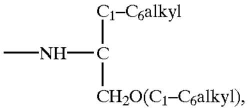 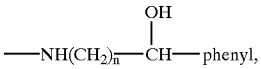
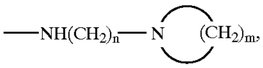 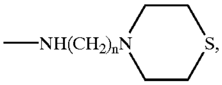
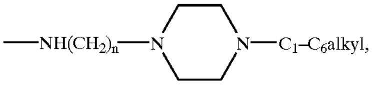
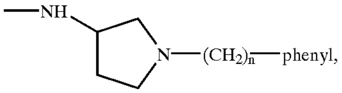
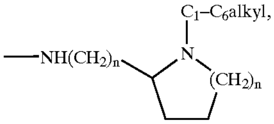
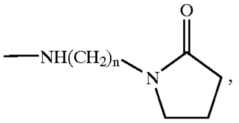 , 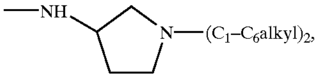
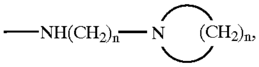 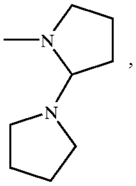 ,
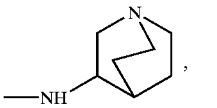 , 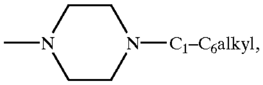
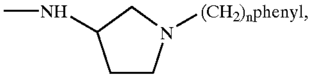
$—NH(CH_2)_nNH(C_1–C_6alkyl)$, or
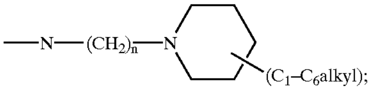

each $R^4$ is independently $-(CH_2)_n$-phenyl, $-(CH_2)_n$-substituted phenyl, $-(CH_2)_n-NH_2$, $-(CH_2)_nN(C_1-C_6alkyl)_2$, $-(CH_2)_nNH(C_1-C_6alkyl)$, $-(CH_2)_n$-pyridyl, $C_1-C_6$ alkyl,

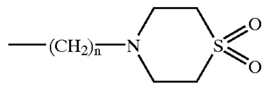

$-(CH_2)_n-C_3-C_8$ cycloalkyl, or $-(CH_2)_n$ substituted $C_3-C_8$ cycloalkyl;

$R^5$ is 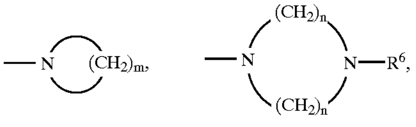

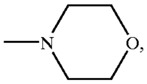

$C_1-C_6$perfluoroalkyl, $C_1-C_6$alkyl,

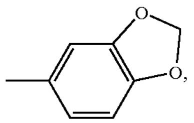

$-NH-C_3-C_8$cycloalkyl, $-NH(CH_2)_nC_2-C_6$ alkenyl, $-NH-(CH_2)_n$-phenyl, $-NH-(CH_2)_n$-substituted phenyl, $-NH(C_1-C_6alkyl)$, $-NH(C_1-C_6alkyl)_2$, $-(CH_2)_nNH_2$, $-(CH_2)_nNH(C_1-C_6alkyl)$, $-(CH_2)_nN(C_1-C_6alkyl)_2$, —NH-naphthyl, —NH-phenyl-phenyl,

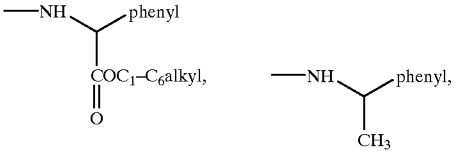

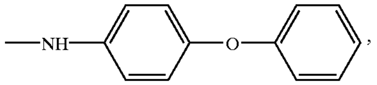

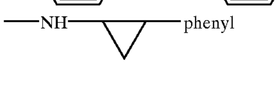

$-NHC_2-C_8$alkenyl, $-NH-(CH_2)_n$-pyridyl, —NH-adamantyl, $-NH(CH_2)_n$-heteroaryl, -substituted phenyl, phenyl, $-(CH_2)_n$ phenyl, $-(CH_2)_n$-substituted phenyl, $-(CH_2)_n$-indolyl, $-(CH_2)_n$-furyl, $-(CH_2)_n$-thienyl,

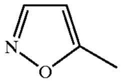 , $-(CH_2)_n$pyridyl, 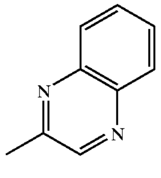 , heteroaryl, heterocycle, aryl, substituted aryl, substituted heteroaryl, substituted heterocycle, $C_1-C_6$ perfluoroalkyl,

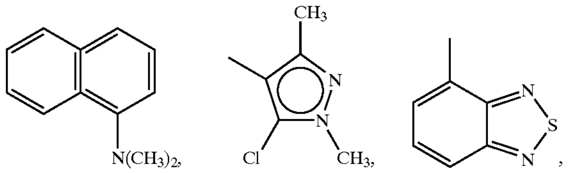

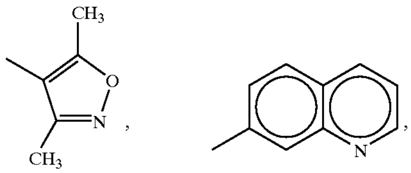

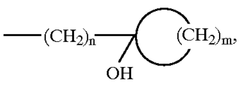

$-NH-(CH_2)_nNH(C_1-C_6alkyl)$, $-NH-(CH_2)_nN(C_1-C_6alkyl)_2$,

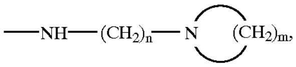

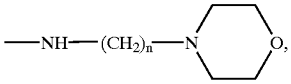 or

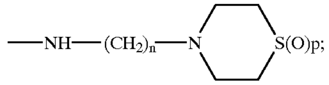

$R^6$ is $C_1-C_6$alkyl, phenyl, substituted phenyl, $-(CH_2)_n$-phenyl, or $-(CH_2)_n$-substituted phenyl;

$R^7$ is hydrogen or $C_1-C_6$ alkyl;

X is 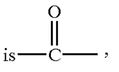 , 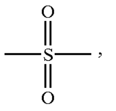 , or 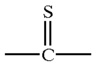 ; Y is —O— or 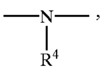 , 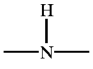 absent, —CH═CH—, or —C≡C—; Q is 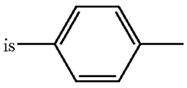 ;

each n is independently 0 to 5; and each m is independently 2 to 7;

each p is 0, 1, or 2, and the pharmaceutically acceptable salts, esters, amides, and prodrugs thereof.

In a preferred embodiment of the compounds of Formula I, $R^5$ is 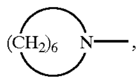 , X is 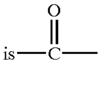 , and each R' is hydrogen.

In another preferred embodiment of the compounds of Formula I, $R^3$ is $-OC_1-C_6$ alkyl, each R' is hydrogen, and X is

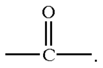

In another preferred embodiment of the compounds of Formula I, $R^3$ is —NH($C_1$–$C_6$alkyl), each R' is hydrogen, and X is

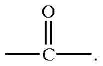

In another preferred embodiment of the compounds of Formula I,

Q is 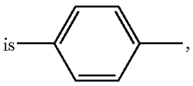,

, Y is —O—, and $R^4$ is —$CH_2$-phenyl or —$CH_2$-substituted phenyl.

In another preferred embodiment of the compounds of Formula I, $R^5$ is 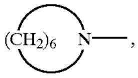, X is 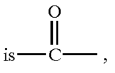, , $R^4$ is —$CH_2$-phenyl, and $R^1$ is isobutyl.

In another preferred embodiment of the compounds of Formula I,

Q is 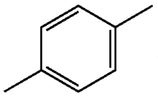,

, Y is —≡—, and $R^4$ is —$(CH_2)_n$ phenyl or —$(CH_2)_n$ substituted phenyl.

In another preferred embodiment of the compounds of Formula I,

Q is 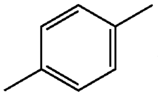,

, Y is absent, and $R^4$ is —$(CH_2)_n$ phenyl or —$(CH_2)_n$ substituted phenyl.

In another preferred embodiment of the compounds of Formula I, $R^3$ is —O-tert-butyl.

In another preferred embodiment of the compounds of Formula I, $R^1$ is —$CH_2$-phenyl.

In another preferred embodiment of the compounds of Formula I,

Q is 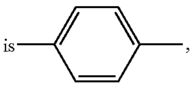,

, Y is O, and $R^4$ is —$(CH_2)_n$ pyridyl.

In another preferred embodiment of the compounds of Formula I,

Q is 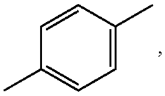,

, Y is —≡—, and $R^4$ is —$(CH_2)_n$ pyridyl.

In another preferred embodiment of the compounds of Formula I,

Q is 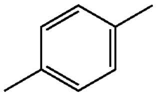,

Y is absent, and $R^4$ is —$(CH_2)_n$ pyridyl.

In another preferred embodiment of the compounds of Formula I, $R^5$ is —NH-phenyl, —NH-substituted phenyl, phenyl, or substituted phenyl.

In another preferred embodiment of the compounds of Formula I, $R^5$ is —NH-phenyl, —NH-substituted phenyl, phenyl, or substituted phenyl; $R^1$ is $C_1$–$C_6$ alkyl; each R' is hydrogen;

X is 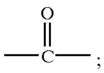;

$R^3$ is —O$C_1$–$C_6$ alkyl;

Q is 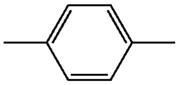;

Y is O; and $R^4$ is —$CH_2$-phenyl.

In another preferred embodiment of the compounds of Formula I,

Q is 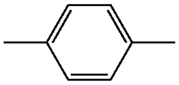;

Y is O; $R^4$ is —$CH_2$-phenyl; each R' is hydrogen;

$R^1$ is isopropyl; and $R^3$ is —O-tert-butyl.

In another preferred embodiment of the compounds of Formula I, $R^5$ is —NH-substituted phenyl.

In another preferred embodiment of the compounds of Formula I,

X is 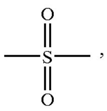, and $R^5$ is phenyl or substituted phenyl.

In another preferred embodiment of the compounds of Formula I,

X is 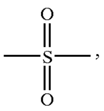, and $R^5$ is —NH substituted phenyl,

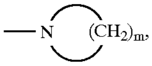 , 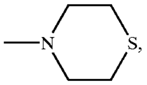 or 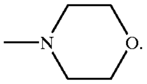

In another preferred embodiment of the compounds of Formula I,

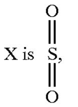

, each R' is hydrogen, and $R^5$ is —NH-substituted phenyl.

Also provided are compounds having the Formula II

II

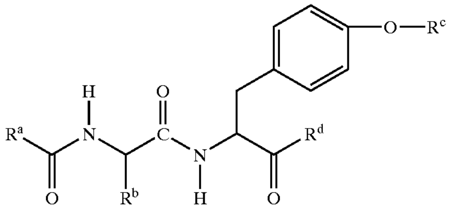

wherein $R^a$ is 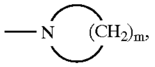

—NH-phenyl, or —NH-substituted phenyl;

$R^b$ is $C_1$–$C_6$ alkyl, —$(CH_2)_n$-aryl, or —$(CH_2)_n$-heteroaryl;

$R^c$ is —$CH_2$-phenyl, $C_1$–$C_6$ alkyl, —$CH_2$-substituted phenyl, or —$CH_2$-heteroaryl;

$R^d$ is —$OC_1$–$C_6$ alkyl, —$N(C_1$–$C_6alkyl)_2$, —NH—$C_1$–$C_6$ alkyl,

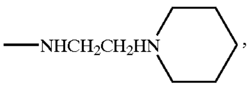, 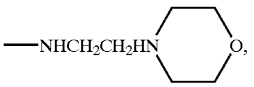

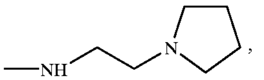

—$NHCH_2CH_2NCH_2$ phenyl,

—$NHCH_2CH_2NCH_2$ pyridyl, 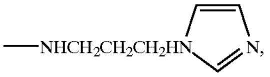

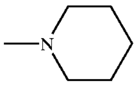, 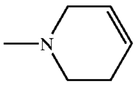, 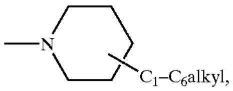

-continued

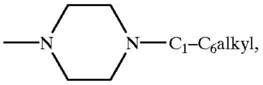

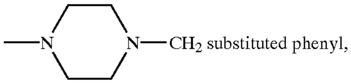

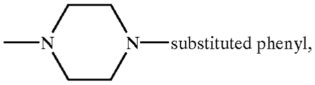

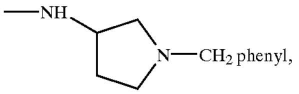

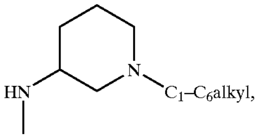 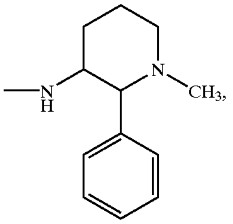

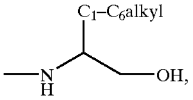 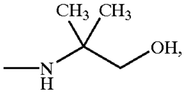

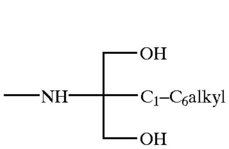 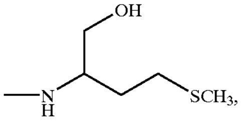

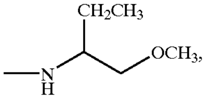 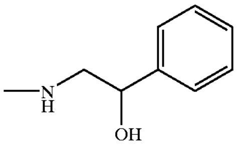

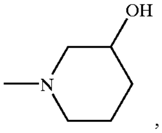, 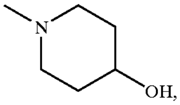 or

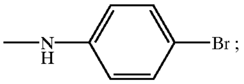

each n is independently 0 to 5; and each m is independently 2 to 7, and the pharmaceutically acceptable salts, esters, amides, and prodrugs thereof.

In a preferred embodiment of Formula II, $R^a$ is 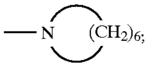

$R^b$ is —$CH_2CH(CH_3)_2$;

$R^c$ is —$CH_2$-phenyl or —$CH_2$ pyridyl; and $R^d$ is O-tert-butyl or —NH-tert-butyl.

In a preferred embodiment, $R^c$ is —$CH_2$pyridyl.

Also provided are compounds having the Formula III

III

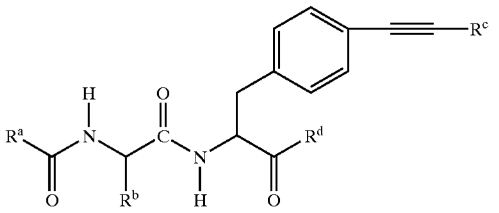

wherein

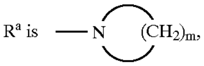

—NH-phenyl, or —NH-substituted phenyl;

$R^b$ is $C_1$–$C_6$ alkyl, —$(CH_2)_n$-aryl, or —$(CH_2)_n$-heteroaryl;

$R^c$ is phenyl, $C_1$–$C_6$ alkyl, substituted phenyl, or heteroaryl;

$R^d$ is —$OC_1$–$C_6$ alkyl, —$N(C_1$–$C_6alkyl)_2$, —NH—$C_1$–$C_6$ alkyl,

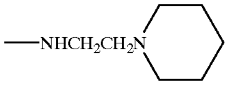,

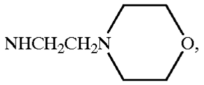

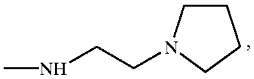,

—$NHCH_2CH_2NCH_2$ phenyl,

—$NHCH_2CH_2NCH_2$ pyridyl,

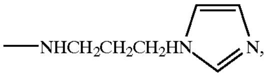

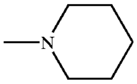,

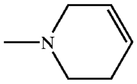,

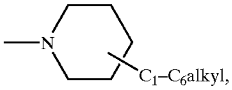

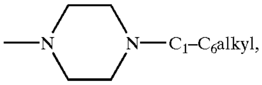

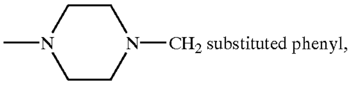

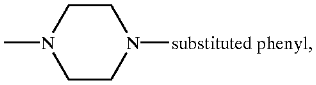

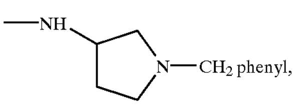

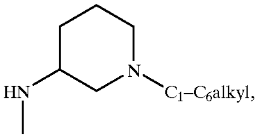

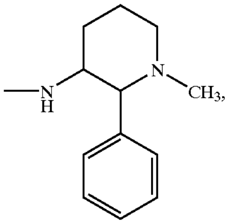

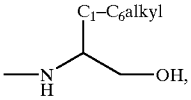

-continued

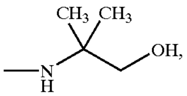

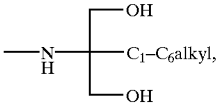

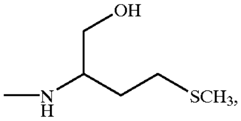

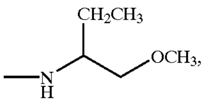

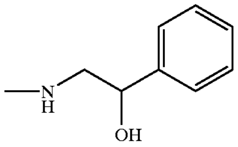

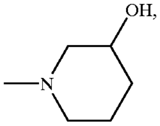

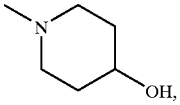 or 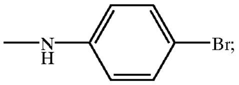

each n is independently 0 to 5; and each m is independently 2 to 7, and the pharmaceutically acceptable salts, esters, amides, and prodrugs thereof.

Also provided are compounds having the Formula IV

IV

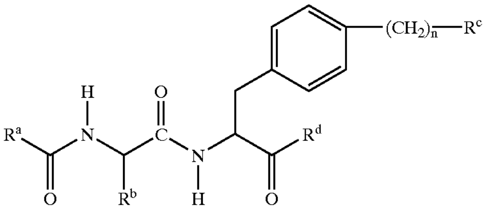

wherein

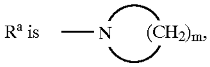

—NH-phenyl, —NH-substituted phenyl, $C_1$–$C_6$ alkyl, aryl, heteroaryl, or substituted aryl;

$R^b$ is $C_1$–$C_6$ alkyl, —$(CH_2)_n$-aryl, or —$(CH_2)_n$-heteroaryl;

$R^c$ is —$CH_2$-phenyl, $C_1$–$C_6$ alkyl, —$CH_2$-substituted phenyl, or —$CH_2$-heteroaryl;

$R^d$ is —$OC_1$–$C_6$ alkyl, —$N(C_1$–$C_6alkyl)_2$, —NH—$C_1$–$C_6$ alkyl,

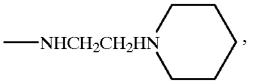,

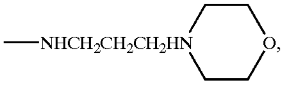

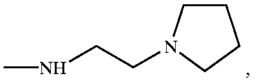,

—$NHCH_2CH_2NCH_2$ phenyl,

—$NHCH_2CH_2NCH_2$ pyridyl,

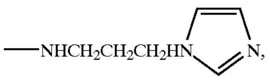

-continued

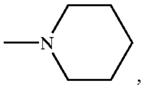, 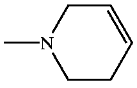, 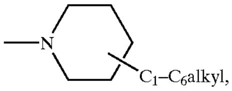

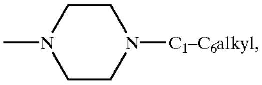

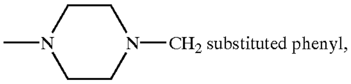

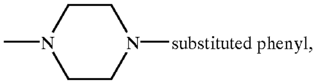

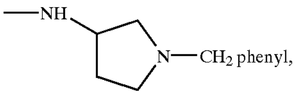

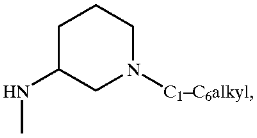 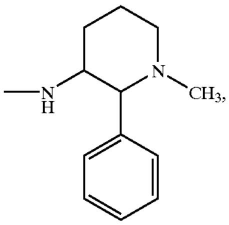

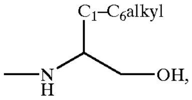 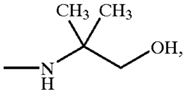

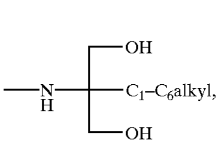 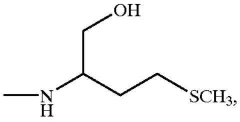

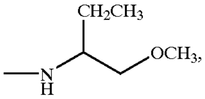 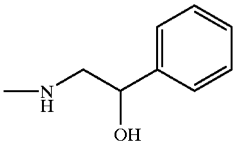,

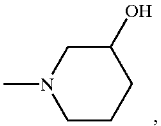, 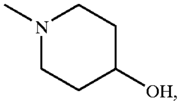 or

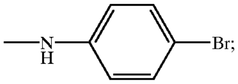

each n is independently 0 to 5; and each m is independently 2 to 7, and the pharmaceutically acceptable salts, esters, amides, and prodrugs thereof.

Also provided are compounds having the Formula V

V

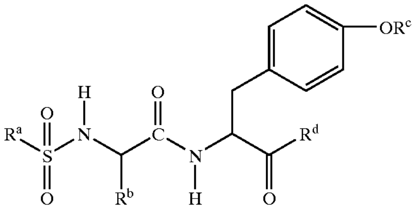

wherein $R^a$ is 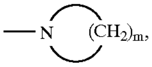

—NH-phenyl, —NH-substituted phenyl, $C_1$–$C_6$ alkyl, aryl heteroaryl, or substituted aryl;

$R^b$ is $C_1$–$C_6$ alkyl, —$(CH_2)_n$-aryl, or —$(CH_2)_n$-heteroaryl;

$R^c$ is —$CH_2$-phenyl, $C_1$–$C_6$ alkyl, —$CH_2$-substituted phenyl, or —$CH_2$-heteroaryl;

$R^d$ is —$OC_1$–$C_6$ alkyl, —$N(C_1$–$C_6alkyl)_2$, —NH—$C_1$–$C_6$ alkyl,

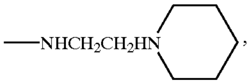, 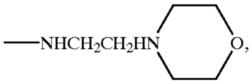

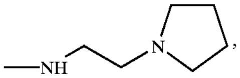, —$NHCH_2CH_2NCH_2$phenyl,

—$NHCH_2CH_2NCH_2$pyridyl, 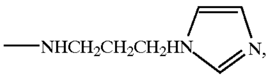

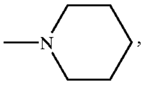, 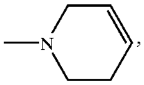, 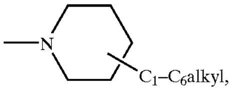

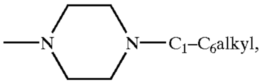

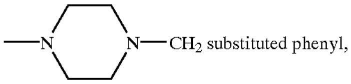

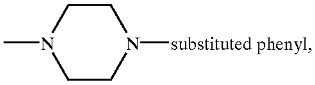

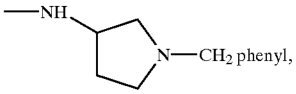

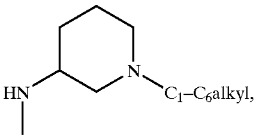 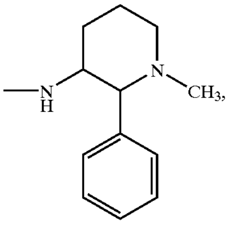

-continued

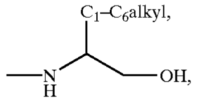 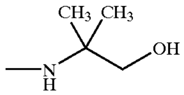

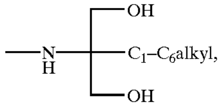 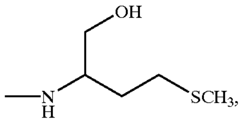

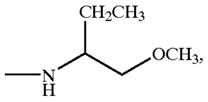 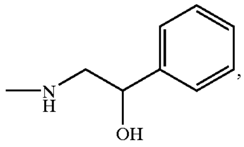

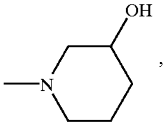, 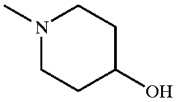, or

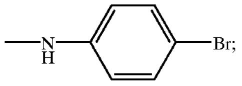

each n is independently 0 to 5; and each m is independently 2 to 7, and the pharmaceutically acceptable salts, esters, amides, and prodrugs thereof. Also provided are compounds having the Formula VI

VI

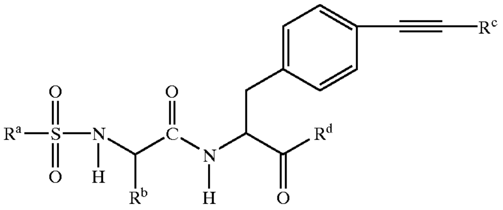

wherein $R^a$ is 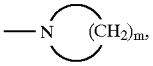

—NH-phenyl, —NH-substituted phenyl, $C_1$–$C_6$ alkyl, aryl heteroaryl, or substituted aryl;

$R^b$ is $C_1$–$C_6$ alkyl, —$(CH_2)_n$-aryl, or —$(CH_2)_n$-heteroaryl;

$R^c$ is phenyl, $C_1$–$C_6$ alkyl, substituted phenyl, or heteroaryl;

$R^d$ is —$OC_1$–$C_6$ alkyl, —$N(C_1$–$C_6alkyl)_2$, —NH—$C_1$–$C_6$ alkyl,

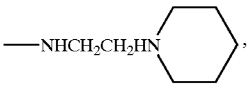, 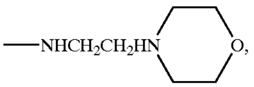

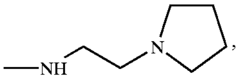, —$NHCH_2CH_2CH_2NCH_2$phenyl,

—$NHCH_2CH_2NCH_2$pyridyl, 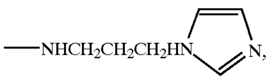

-continued

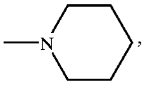, 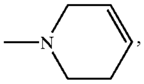, 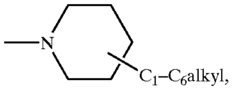

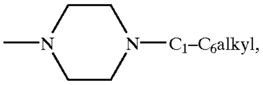

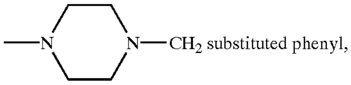

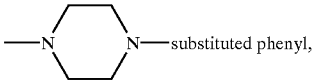

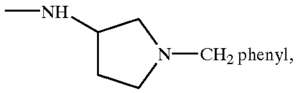

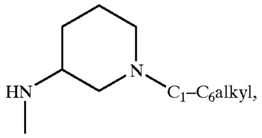 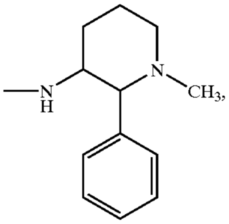

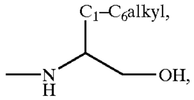 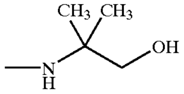

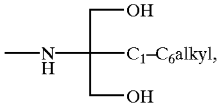 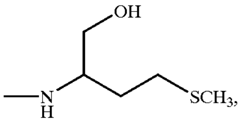

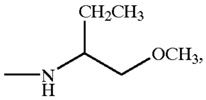 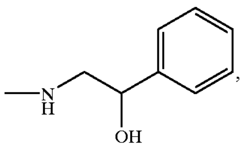

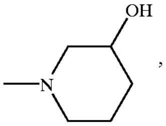, 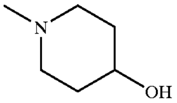, or

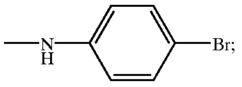

each n is independently 0 to 5; and each m is independently 2 to 7, and the pharmaceutically acceptable salts, esters, amides, and prodrugs thereof. Also provided are compounds having the Formula VII

VII

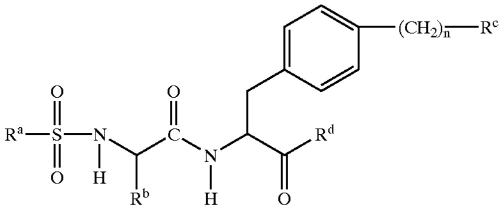

wherein $R^a$ is 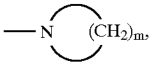

—NH-phenyl, —NH-substituted phenyl, $C_1$–$C_6$ alkyl, aryl, heteroaryl, or substituted aryl;

$R^b$ is $C_1$–$C_6$ alkyl, —$(CH_2)_n$-aryl, or —$(CH_2)_n$-heteroaryl;

$R^c$ is —$CH_2$-phenyl, $C_1$–$C_6$ alkyl, —$CH_2$-substituted phenyl, or —$CH_2$-heteroaryl;

$R^d$ is —$OC_1$–$C_6$ alkyl, —$N(C_1$–$C_6alkyl)_2$, —NH—$C_1$–$C_6$ alkyl,

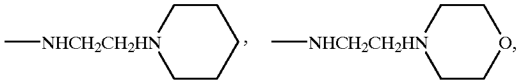

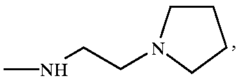 —$NHCH_2CH_2NCH_2$phenyl,

—$NHCH_2CH_2NCH_2$pyridyl, 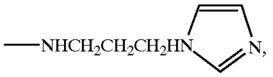

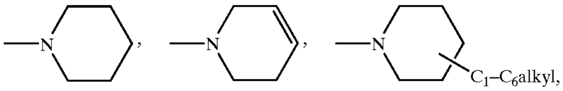

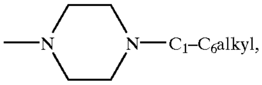

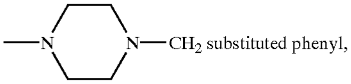

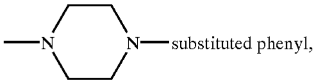

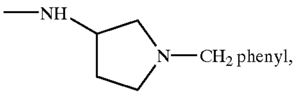

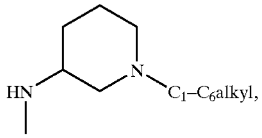 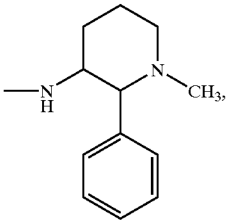

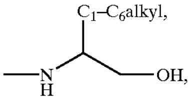 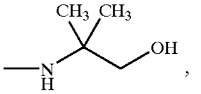

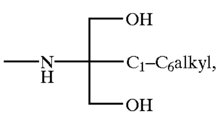 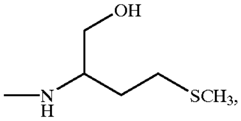

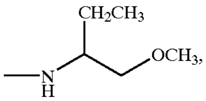 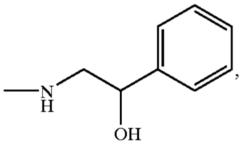

-continued

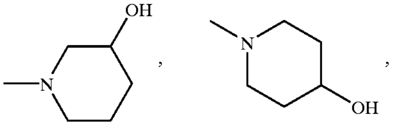 or

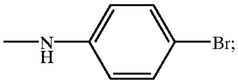

each n is independently 0 to 5; and each m is independently 2 to 7, and the pharmaceutically acceptable salts, esters, amides, and prodrugs thereof.

Also provided are compounds having the Formula VIII

VIII

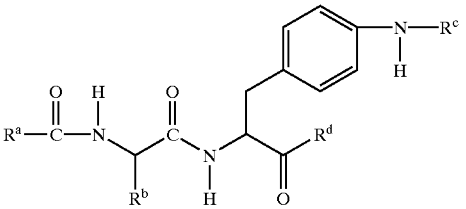

wherein $R^a$ is 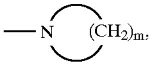

—NH-phenyl, or —NH-substituted phenyl;

$R^b$ is $C_1$–$C_6$ alkyl, —$(CH_2)_n$-aryl, or —$(CH_2)_n$-heteroaryl;

$R^c$ is —$CH_2$-phenyl, $C_1$–$C_6$ alkyl, —$CH_2$-substituted phenyl, or —$CH_2$-heteroaryl;

$R^d$ is —$OC_1$–$C_6$ alkyl, —$N(C_1$–$C_6alkyl)_2$, —NH—$C_1$–$C_6$ alkyl,

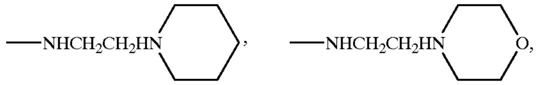

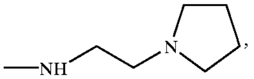 —$NHCH_2CH_2NCH_2$ phenyl,

—$NHCH_2CH_2NCH_2$ pyridyl, 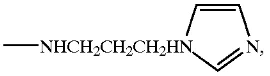

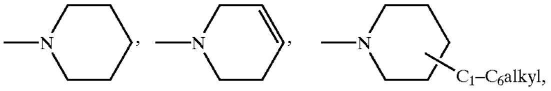

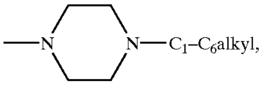

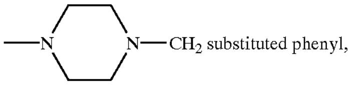

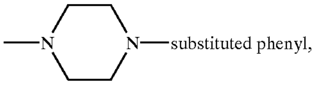

-continued

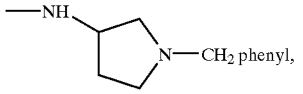

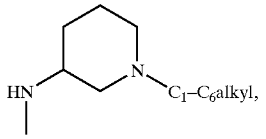

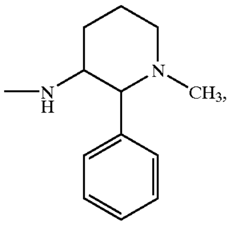

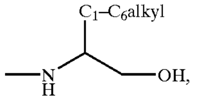

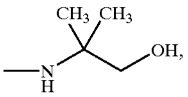

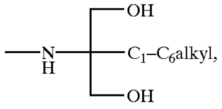

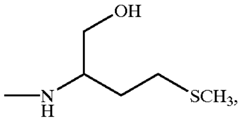

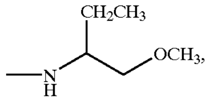

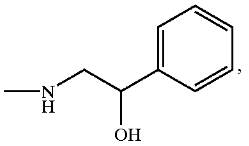

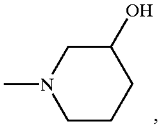

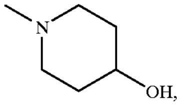

or

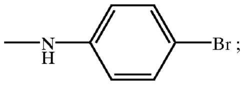

each n is independently 0 to 5; and each m is independently 2 to 7, and the pharmaceutically acceptable salts, esters, amides, and prodrugs thereof.

Also provided are compounds having the Formula IX

IX

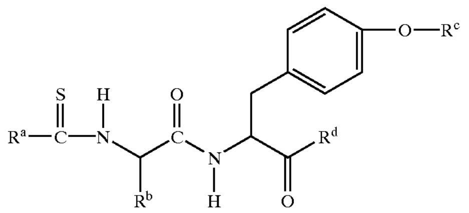

wherein $R^a$ is 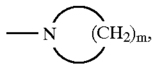

—NH-phenyl, or —NH-substituted phenyl;

$R^b$ is $C_1$–$C_6$ alkyl, —$(CH_2)_n$-aryl, or —$(CH_2)_n$-heteroaryl;

$R^c$ is —$CH_2$-phenyl, —$CH_2$-substituted phenyl, or —$CH_2$-heteroaryl;

$R^d$ is —$OC_1$–$C_6$ alkyl, —$N(C_1$–$C_6alkyl)_2$, —NH—$C_1$–$C_6$ alkyl,

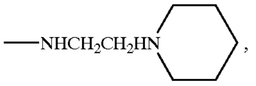

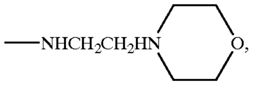

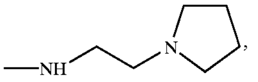

—$NHCH_2CH_2NCH_2$ phenyl,

—$NHCH_2CH_2NCH_2$ pyridyl,

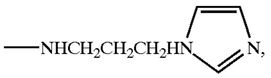

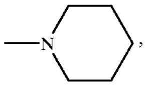

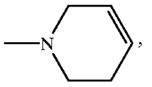

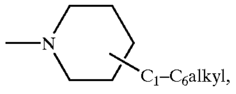

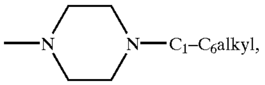

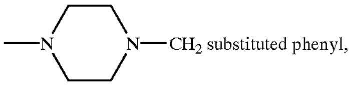

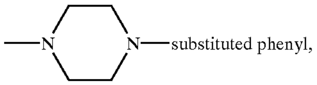

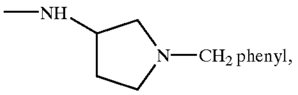

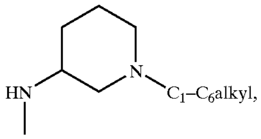

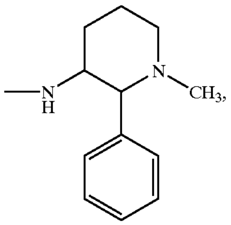

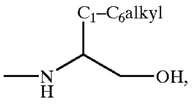

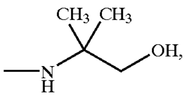

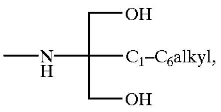

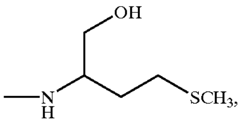

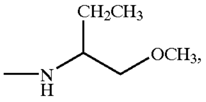

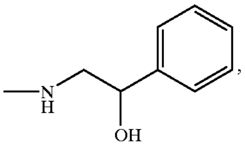

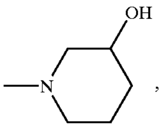

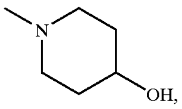

or

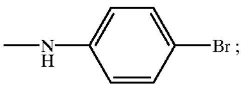

each n is independently 0 to 5; and each m is independently 2 to 7, and the pharmaceutically acceptable salts, esters, amides, and prodrugs thereof.

Also provided are compounds having the Formula X

X

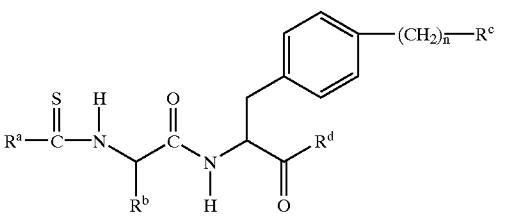

wherein $R^a$ is 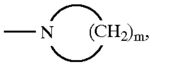

—NH-phenyl, or —NH-substituted phenyl;

$R^b$ is $C_1$–$C_6$ alkyl, —$(CH_2)_n$-aryl, or —$(CH_2)_n$-heteroaryl;

$R^c$ is —$CH_2$-phenyl, $C_1$–$C_6$ alkyl, —$CH_2$-substituted phenyl, or —$CH_2$-heteroaryl;

$R^d$ is —$OC_1$–$C_6$ alkyl, —$N(C_1$–$C_6alkyl)_2$, —NH—$C_1$–$C_6$ alkyl,

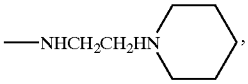,

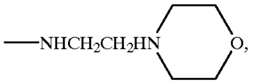

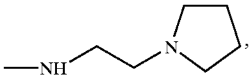,

—$NHCH_2CH_2NCH_2$ phenyl,

—$NHCH_2CH_2NCH_2$ pyridyl,

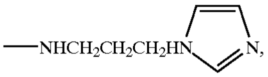

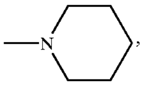, 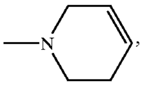, 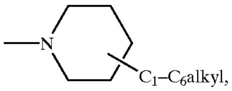

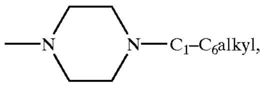

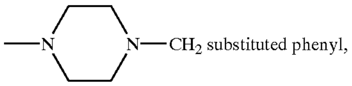

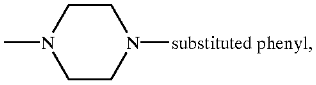

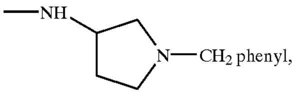

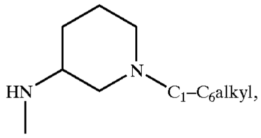

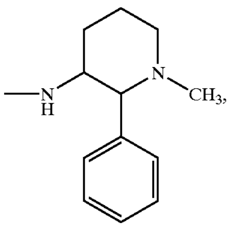

-continued

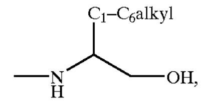

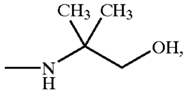

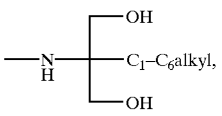

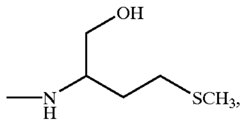

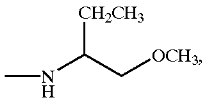

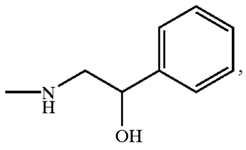

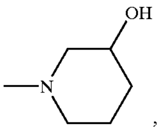,

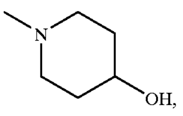

or

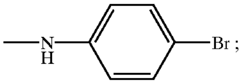

each n is independently 0 to 5; and each m is independently 2 to 7, and the pharmaceutically acceptable salts, esters, amides, and prodrugs thereof.

Also provided is a pharmaceutical composition comprising a compound of Formula I.

Also provided is a pharmaceutical composition comprising a compound of Formula II.

Also provided is a pharmaceutical composition comprising a compound of Formula III.

Also provided is a pharmaceutical composition comprising a compound of Formula IV.

Also provided is a pharmaceutical composition comprising a compound of Formula V.

Also provided is a pharmaceutical composition comprising a compound of Formula VI.

Also provided is a pharmaceutical composition comprising a compound of Formula VII.

Also provided is a pharmaceutical composition comprising a compound of Formula VIII.

Also provided is a pharmaceutical composition comprising a compound of Formula IX.

Also provided is a pharmaceutical composition comprising a compound of Formula X.

Also provided is a method of blocking calcium channels, the method comprising administering to a patient in need of calcium channel blocking a therapeutically effective amount of a compound of Formulas I–X to block calcium channels.

In a preferred embodiment of the methods, the calcium channels are N-type calcium channels.

Also provided is a method of blocking N-type calcium channels, the method comprising administering to a patient in need of N-type calcium channel blocking a therapeutically effective amount of a compound of Formulas I–X to block N-type calcium channels.

Also provided is a method of treating stroke, the method comprising administering to a patient having a stroke a therapeutically effective amount of a compound of Formulas I–X.

Also provided is a method of preventing a stroke, the method comprising administering to a patient at risk of having a stroke a therapeutically effective amount of a compound of Formulas I–X.

Also provided is a method of treating cerebral ischemia, the method comprising administering to a patient having cerebral ischemia a therapeutically effective amount of a compound of Formulas I–X.

Also provided is a method of treating head trauma, the method comprising administering to a patient having head trauma a therapeutically effective amount of a compound of Formulas I–X.

Also provided is a method of treating epilepsy, the method comprising administering to a patient having epilepsy a therapeutically effective amount of a compound of Formulas I–X.

Also provided is a method of treating pain, the method comprising administering to a patient having pain a therapeutically effective amount of a compound of Formulas I–X.

Also provided are the compounds:

[S-(R*,R*)]-2-{2-[(Azepane-1-carbonyl-carbonyl)-amino] 4-methyl-pentanoylamino}-3-(4-benzyloxy-phenyl)-propionic acid tert-butyl ester;

2(R)-{2(S)-[(Azepane-1-carbonyl)-amino]-4-methyl-pentanoylamino}-3-(4-benzyloxy-phenyl)-propionic acid tert-butyl ester (L,D);

2(S)-{2(R)-[(Azepane-1-carbonyl)-amino]-4-methyl-pentanoylamino}-3-(4-benzyloxy-phenyl)-propionic acid tert-butyl ester (D,L);

[S-(R*,R*)]-2-{2-(Azepane-1-carbonyl)-amino]-4-methyl-pentanoylamino}-3-(4-benzyloxy-phenyl)-propionic acid tert-butyl ester;

[S-(R*,R*)]-2-{2-[(Azepane-1-carbonyl)-amino]-3-methyl-pentanoylamino}-3-(4-benzyloxy-phenyl)-propionic acid tert-butyl ester;

[S-(R*,R*)]-2-{2-[(Azepane-1-carbonyl)-amino]-3-methyl-butyrylamino}-3-(4-benzyloxy-phenyl)-propionic acid tert-butyl ester;

[S-(R*,R*)]-2-(S)-{2-[(Azepane-1-carbonyl)-amino]-propionylamino}-3-(4-benzyloxy-phenyl)-propionic acid tert-butyl ester;

[S-(R*,R*)]-2-{2-[(Azepane-1-carbonyl)-amino]-acetylamino}-3-(4-benzyloxy-phenyl)-propionic acid tert-butyl ester;

[S-(R*,R*)]-3-(4-Benzyloxy-phenyl)-2-{4-methyl-2-[(4-methyl-piperazine-1-carbonyl)-amino]-pentanoylamino}-propionic acid tert-butyl ester;

[S-(R*,R*)]-3-(4-Benzyloxy-phenyl)-2-{4-methyl-2-[(4-phenyl-piperazine-1-carbonyl)-amino]-pentanoylamino}-propionic acid tert-butyl ester;

[S-(R*,R*)]-2-{2-[(Azepane-1-carbonyl)-amino]-4-methyl-pentanoylamino}-3-(4-benzyloxy-phenyl)-2-methyl-propionic acid tert-butyl ester;

2(R)-{2(S)-[(Azepane-1-carbonyl)-amino]-4-methyl-pentanoylamino}-3-(4-benzyloxy-phenyl)-2-methyl-propionic acid tert-butyl ester;

[S-(R*,R*)]-2-{2-[(Azepane-1-carbonyl)-amino]-4-methyl-pentanoylamino}-3-(4-tert-butoxy-phenyl)-propionic acid tert-butyl ester;

[S-(R*,R*)]-2-{2-[(Azepane-1-carbonyl)-amino]-4-methyl-pentanoylamino}-3-(4-methoxy-phenyl)-propionic acid tert-butyl ester;

[S-(R*,R*)]-2-{2-[(Azepane-1-carbonyl)-amino]-4-methyl-pentanoylamino}-3-(4-benzyloxy-phenyl)-propionic acid benzyl ester;

[S-(R*,R*)]-2(S)-{2(S)-[(Azepane-1-carbonyl)-amino]-4-methyl-pentanoylamino}-3-(4-benzyloxy-phenyl)-propionic acid methyl ester;

[S-(R*,R*)]-2-{2-[(Azepane-1-carbonyl-carbonyl)-amino]-3-phenyl-propionylamino}-3-(4-benzyloxy-phenyl)-propionic acid tert-butyl ester;

[S-(R*,R*)]-2-[2-[(Azepane-1-carbonyl)-amino]-3-(1H-indol-3-yl)-propionylamino]-3-(4-benzyloxy-phenyl)-propionic acid tert-butyl ester;

[S-(R*,R* )]-2-{2-[(Azepane-1-carbonyl)-amino]-3-phenyl-propionylamino}-3-(4-benzyloxy-phenyl)-propionic acid tert-butyl ester;

[S-(R*,R*)]-2-{2-[(Azepane-1-carbonyl)-amino]-3-phenyl-propionylamino}-3-[4-(4-methyl-benzyloxy)-phenyl]-propionic acid tert-butyl ester;

=[S-(R*,R*)]-2-[2-[(Azepane-1-carbonyl)-amino]-3-(1H-indol-3-yl)-propionylamino]-3-(4-benzyloxy-phenyl)-propionic acid tert-butyl ester;

[S-(R*,R*)]-Azepane-1-carboxylic acid {1-[2-(4-benzyloxy-phenyl)-1-carbamoyl-ethylcarbamoyl]-3-methyl-butyl}-amide;

[S-(R*,R*)]-2-{2-[(Azepane-1-carbonyl)-amino]-4-methyl-pentanoylamino}-3-(4-tert-butoxy-phenyl)-propionic acid methyl ester;

[S-(R*,R*)]-Azepane-1-carboxylic acid {1-[2-(4-benzyloxy-phenyl)-1-tert-butylcarbamoyl-ethylcarbamoyl]-3-methyl-butyl}-amide;

[S-(R*,R*)]-2-{2-[(Azepane-1-carbonyl)-amino]-4-methyl-pentanoylamino}-3-[4-(pyridin-2-ylmethoxy)-phenyl]-propionic acid tert-butyl ester;

[S-(R*,R*)]-2-{2-[(Azepane-1-carbonyl)-amino]-4-methyl-pentanoylamino}-3-[4-(pyridin-4-ylmethoxy)-phenyl]-propionic acid tert-butyl ester;

[S-(R*,R*)]-2-{2-[(Azepane-1-carbonyl)-amino]-4-methyl-pentanoylamino}-3-[4-(4-cyano-benzyloxy)-phenyl]-propionic acid tert-butyl ester;

[S-(R*,R*)]-2-{2-[(Azepane-1-carbonyl)-amino]4-methyl-pentanoylamino}-3-[4-(3-tert-butoxycarbonylamino-benzyloxy)-phenyl]-propionic acid tert-butyl ester;

[S-(R*,R*)]-3-[4-(3-Amino-benzyloxy)-phenyl]-2-{2-[(azepane-1-carbonyl)-amino]-4-methyl-pentanoylamino}-propionic acid tert-butyl ester;

[S-(R*,R*)]-2-{2-[(Azepane-1-carbonyl)-amino]-4-methyl-pentanoylamino}-3-(4-cyclohexylmethoxy-phenyl)-propionic acid tert-butyl ester;

[S-(R*,R*)]-2-{2-[(Azepane-1-carbonyl)-amino]-4-methyl-pentanoylamino}-3-[4-(pyridin-3-ylmethoxy)-phenyl]-propionic acid tert-butyl ester;

[S-(R*,R*)]-2-{2-[(Azepane-1-carbonyl)-amino]-4-methyl-pentanoylamino}-3-[4-(4-methoxy-benzyloxy)-phenyl]-propionic acid tert-butyl ester;

[S-(R*,R*)]-3-(4-Benzyloxy-phenyl)-2-{4-methyl-2-[(piperidine-1-carbonyl)-amino]-pentanoylamino}-propionic acid tert-butyl ester;

[S-(R*,R*)]-3-(4-Benzyloxy-phenyl)-2(S)-{4-methyl-2(S)-[(morpholine-4-carbonyl)-amino]-pentanoylamino}-propionic acid tert-butyl ester;

[S-(R*,R*)]-3-(4-Benzyloxy-phenyl)-2-(2-methanesulfonylamino-4-methyl-pentanoylamino)-propionic acid tert-butyl ester;

[S-(R*,R* )]-3-(4-Benzyloxy-phenyl)-2(S)-[2(S)-(4-tert-butyl-benzenesulfonylamino)-4-methyl-pentanoylamino]-propionic acid tert-butyl ester;

[S-(R*,R*)]-3-(4-Benzyloxy-phenyl)-2(S)-[2(S)-(4-isopropyl-benzenesulfonylamino)-4-methyl-pentanoylamino]-propionic acid tert-butyl ester;

[S-(R*,R*)]-2-{2-[(4-Bromobenzene-1-sulfonyl-carbonyl)-amino]-4-methyl-pentanoylamino-3-(4-benzyloxyphenyl)-propionic acid, tert-butyl ester;

[S-(R*,R*)]-3-(4-Benzyloxy-phenyl)-2-[4-methyl-2-(4-nitro-benzenesulfonylamino)-pentanoylamino]-propionic acid tert-butyl ester;

[S-(R*,R* )]-2-[2-(Azepane-1-sulfonylamino)-4-methyl-pentanoylamino]-3-(4-benzyloxy-phenyl)-propionic acid tert-butyl ester;

[S-(R*,R*)]-3-(4-Benzyloxy-phenyl)-2-[4-methyl-2-(piperidine-1-sulfonylamino)-pentanoylamino]-propionic acid tert-butyl ester;

[S-(R*,R*)]-3-(4-Benzyloxy-phenyl)-2-[4-methyl-2-(morpholine-4-sulfonylamino)-pentanoylamino]-propionic acid tert-butyl ester;

[S-(R*,R*)]-3-(4-Benzyloxy-phenyl)-2-{2-[3-(4-isopropyl-phenyl)-thioureido]-4-methyl-pentanoylamino}-propionic acid, tert-butyl ester;

[S-(R*,R*)]-3-(4-Benzyloxy-phenyl)-2-{2-[3-(4-tert-butyl-phenyl)-thioureido]-4-methyl-pentanoylamino}-propionic acid, tert-butyl ester;

[S-(R*,R* )]-3-(4-Benzyloxy-phenyl)-2-{2-[3-(4-bromophenyl)-thioureido]-4-methyl-pentanoylamino}-propionic acid, tert-butyl ester;

[S-(R*,R*)]-3-(4-Benzyloxy-phenyl)-2-{2-[3-(1-adamantyl)-thioureido]-4-methyl pentanoylamino}-propionic acid, tert-butyl ester;

[S-(R*,R*)]-3-(4-benzyloxy-phenyl)-2-[2-(3-cyclohexyl-thioureido)-4-methyl-pentanoylamino}-propionic acid, tert-butyl ester;

[S-(R*,R*)]-3-(4-Benzyloxy-phenyl)-2-{2-[3-(2-chloro-phenyl)-thioureido]-4-methyl-pentanoylamino}-propionic acid tert-butyl ester;

[S-(R*,R*)]-3-(4-Benzyloxy-phenyl)-2-[2-(3-butyl-thioureido)4-methyl-pentanoylamino]-propionic acid tert-butyl ester;

[S-(R*,R*)]-3-(4-Benzyloxy-phenyl)-2-[4-methyl-2-(3-p-tolyl-thioureido)-pentanoylamino]-propionic acid tert-butyl ester;

[S-(R*,R* )]-3-(4-Benzyloxy-phenyl)-2-[4-methyl-2-(3-methyl-thioureido)-pentanoylamino]-propionic acid tert-butyl ester;

[S-(R*,R*)]-Azepane-1-carboxylic acid (1-{1-tert-butylcarbamoyl-2-[4-(2,6-dichloro-benzyloxy)-phenyl]-ethylcarbamoyl}-3-methyl-butyl)-amide;

[S-(R*,R*)]-Azepane 1-carboxylic acid {1-[2-(4-benzyl-phenyl)-1-tert-butylcarbamoyl-ethylcarbamoyl]-3-methyl-butyl}-amide;

[S-(R*,R*)]-3-(4-Benzyloxy-phenyl)-2-[4-methyl-2-(3-phenyl-ureido)-pentanoylamino]propionic acid tert-butyl ester;

[S-(R*,R* )]-3-(4-Benzyloxy-phenyl)-2-{4-methyl-2-[3-(4-nitro-phenyl)-ureido]pentanoylamino}-propionic acid tert-butyl ester;

[S-(R*,R*)]-3-(4-Benzyloxy-phenyl)-2-[2-(3-cyclohexyl-ureido)-4-methyl-pentanoylamino]propionic acid tert-butyl ester;

[S-(R*,R*)]-3-(4-Benzyloxy-phenyl)-2-{2-[3-(3-methoxy-phenyl)-ureido]-4-methyl-pentanoylamino}-propionic acid tert-butyl ester;

[S-(R*,R*)]-3-(4-Benzyloxy-phenyl)-2-[4-methyl-2-(3-p-tolyl-ureido)-pentanoylamino]propionic acid tert-butyl ester;

[S-(R*,R*)]-3-(4-Benzyloxy-phenyl)-2-[2-(3-butyl-ureido) 4-methyl-pentanoylamino]-propionic acid tert-butyl ester;

[S-(R*,R*)]-3-(4-Benzyloxy-phenyl)-2-[2-(3-benzyl-ureido)4-methyl-pentanoylamino]-propionic acid tert-butyl ester;

[S-(R*,R*)]-3-(4-Benzyloxy-phenyl)-2-[4-methyl-2-(3-o-tolyl-ureido)-pentanoylamino]-propionic acid tert-butyl ester;

[S-(R*,R*)]-3-(4-Benzyloxy-phenyl)-2-{2-[3-(2,6-dimethyl-phenyl)-3ureido]-4-methyl-pentanoylamino}-propionic acid tert-butyl ester;

[S-(R*,R*)]-3-(4-Benzyloxy-phenyl)-2-{4-methyl-2-[3-(1-phenyl-ethyl)-ureido]-pentanoylamino}-propionic acid tert-butyl ester;

[S-(R*,R*){-3-(4-Benzyloxy-phenyl)-2-{4-methyl-2-[3-(4-methylsulfanyl-phenyl)-ureido]-pentanoylamino}-propionic acid tert-butyl ester;

[S-(R*,R*)]-3-(4-Benzyloxy-phenyl)-2-{4-methyl-2-[3-(4-phenoxy-phenyl)-ureido]pentanoylamino}-propionic acid tert-butyl ester;

[S-(R*,R*)]-3-(4-Benzyloxy-phenyl)-2-{2-[3-(1-methoxycarbonyl-2-phenyl-ethyl)-ureido]-4-methyl-pentanoylamino}-propionic acid tert-butyl ester;

[S-(R*,R*)]-3-(4-Benzyloxy-phenyl)-2-{4-methyl-2-[3-(3,4,5-trimethoxy-phenyl)-ureido]-pentanoylamino}-propionic acid tert-butyl ester;

[S-(R*,R*)-3-(4-Benzyloxy-phenyl)-2-{2-[3-(4-methoxy-phenyl)-ureido]-4-methyl-pentanoylamino}-propionic acid tert-butyl ester;

[S-(R*,R*)]-3-(4-Benzyloxy-phenyl)-2-{2-[3-(2,4-difluoro-phenyl)-ureido]-4-methyl-pentanoylamino}-propionic acid tert-butyl ester;

[S-(R*,R*)]-3-(4-Benzyloxy-phenyl)-2-{4-methyl-2-[3-(4-trifluoromethyl-phenyl)-ureido]-pentanoylamino}-propionic acid tert-butyl ester;

[S-(R*,R*)]-3-(4-Benzyloxy-phenyl)-2-{2-[3-(2-methoxy-phenyl)-ureido]-4-methyl-pentanoylamino}-propionic acid tert-butyl ester;

[S-(R*,R* )]-3-(4-Benzyloxy-phenyl)-2-{2-[3-(3,5-dimethyl-phenyl)-ureido]-4-methyl-pentanoylamino}-propionic acid tert-butyl ester;

[S-(R*,R*)]-3-(4-Benzyloxy-phenyl)-2-{2-[3-(2-chloro-phenyl)-ureido]-4-methyl pentanoylamino}-propionic acid tert-butyl ester;

[S-(R*,R*)]-3-(4-Benzyloxy-phenyl)-2-{2-[3-(3-chloro-phenyl)-ureido]-4-methyl-pentanoylamino}-propionic acid tert-butyl ester;

[S-(R*,R*)-3-(4-Benzyloxy-phenyl)-2-{4-methyl-2-[3-(2-phenyl-cyclopropyl)-ureido]-pentanoylamino}-propionic acid tert-butyl ester;

[S-(R*,R*)]-3-(4-Benzyloxy-phenyl)-2-{4-methyl-2-3-3-trifluoromethyl-phenyl)-ureido]-pentanoylamino}-propionic acid tert-butyl ester;

[S-(R*,R*)]-4-(3-{1-[2-(4-Benzyloxy-phenyl)-1-tert-butoxycarbonyl-ethylcarbamoyl]-3-methyl butyl}-ureido)-benzoic acid ethyl ester;

[S-(R*,R*)]-3-(4-Benzyloxy-phenyl)-2-{2-[3-(4-chloro-3-trifluoromethyl-phenyl)-ureido]-4-methyl-pentanoylamino}-propionic acid tert-butyl ester;

[S-(R*,R*)]-3-(4-Benzyloxy-phenyl)-2-[4-methyl-2-(3-naphthalen-1-yl-ureido)-pentanoylamino]-propionic acid tert-butyl ester;

[S-(R*,R*)]-3-(4-Benzyloxy-phenyl)-2-{2-[3-(4-chloro-phenyl)-ureido]-4-methyl-pentanoylamino}-propionic acid tert-butyl ester;

[S-(R*,R*)]-3-(4-Benzyloxy-phenyl)-2-{2-[3-(2,3-dichloro-phenyl)-ureido]-4-methyl-pentanoylamino}-propionic acid tert-butyl ester;

S-(R*,R*)]-3-(4-Benzyloxy-phenyl)-2-{2-[3-(2,4-dichloro-phenyl)-ureido]-4-methyl-pentanoylamino}-propionic acid tert-butyl ester;

[S(R*,R*)]-3-(4-Benzyloxy-phenyl)-2-{2-[3-(3,5-bis-trifluoromethyl-phenyl)-ureido]-4-methyl-pentanoylamino}-propionic acid tert-butyl ester;

[S-(R*,R*)]-3-(4-Benzyloxy-phenyl)-2-{2-[3-(4-bromo-phenyl)-ureido]-4-methyl-pentanoylamino}-propionic acid tert-butyl ester;

[S-(R*,R*)]-3-(4-Benzyloxy-phenyl)-2-{2-[3-(3,4-dichloro-phenyl)-ureido]-4-methyl-pentanoylamino}-propionic acid tert-butyl ester;

[S-(R*,R*)]-3-(4-Benzyloxy-phenyl)-2-{2-[3-(3,5-dichloro-phenyl)-ureido]4-methyl-pentanoylamino}-propionic acid tert-butyl ester;

[S-(R*,R*)]-3-(4-Benzyloxy-phenyl)-2-[2-(3-isopropyl-ureido)4-methyl-pentanoylamino]-propionic acid tert-butyl ester;

[S-(R*,R*)]-3-(4-Benzyloxy-phenyl)-2-[4-methyl-2-(3-methyl-ureido)-pentanoylamino]-propionic acid tert-butyl ester;

[S-(R*,R*)]-3-(4-Benzyloxy-phenyl)-2-[2-(3-ethyl-ureido)-4-methyl-pentanoylamino]-propionic acid tert-butyl ester;

[S-(R*,R*)]-2-(4-Benzyloxy-benzyl)-5-[(furan-2-carbonyl)-amino]-7-methyl-4-oxo-octanoic acid tert-butyl ester;

[S-(R*,R*)]-3-(4-Benzyloxy-phenyl)-2-[2-(4-ethoxy-benzoylamino)-4-methyl-pentanoylamino]-propionic acid tert-butyl ester;

[S-(R*,R*)]-3-(4-Benzyloxy-phenyl)-2-[4-methyl-2-(3,4,5-trimethoxy-benzoylamino)-pentanoylamino]-propionic acid tert-butyl ester;

[S-(R*,R*)]-3-(4-Benzyloxy-phenyl)-2-[2-(4-tertbutyl-benzoylamino)-4-methyl-pentanoylamino]-propionic acid tert-butyl ester;

[S-(R*,R*)]-3-(4-Benzyloxy-phenyl)-2-[2-(4-fluoro-benzoylamino)-4-methyl-pentanoylamino]-propionic acid tert-butyl ester;

[S-(R*,R*)]-3-(4-Benzyloxy-phenyl)-2-[2-(4-methoxy-benzoylamino)-4-methyl-pentanoylamino]-propionic acid tert-butyl ester;

[S-(R*,R*)]-3-(4-Benzyloxy-phenyl)-2-[2-(3-methoxy-benzoylamino)-4-methyl-pentanoylamino]-propionic acid tert-butyl ester;

[S-(R*,R*)]-2-{2-[(Benzo[1,3]dioxole-5-carbonyl)-amino] 4-methyl-pentanoylamino}-3-(4-benzyloxy-phenyl)-propionic acid tert-butyl ester;

[S-(R*,R*)]-3-(4-Benzyloxy-phenyl)-2-[2-(2-methoxy-benzoylamino)-4-methyl-pentanoylamino]-propionic acid tert-butyl ester;

[S-(R*,R*)]-3-(4-Benzyloxy-phenyl)-2-{4-methyl-2-[(naphthalene-2-carbonyl)-amino]pentanoylamino}-propionic acid tert-butyl ester;

[S-(R*,R*)]-3-(4-Benzyloxy-phenyl)-2-[2-(3,4-dimethoxy-benzoylamino)-4-methyl-pentanoylamino]-propionic acid tert-butyl ester;

[S-(R*,R*)]-3-(4-Benzyloxy-phenyl)-2-{2-[(biphenyl-4-carbonyl)-amino]-4-methyl-pentanoylamino}-propionic acid tert-butyl ester;

[S-(R*,R*)]-5-(Benzo[1,2,5]thiadiazole-4-sulfonylamino)-2-(4-benzyloxybenzyl)-7-methyl-4-oxo-octanoic acid tert-butyl ester;

[S-(R*,R* )]-3-(4-Benzyloxy-phenyl)-2-[2-(4-methoxy-benzenesulfonylamino)4-methyl-pentanoylamino]-propionic acid tert-butyl ester;

[S-(R*,R*)]-3-(4-Benzyloxy-phenyl)-2-[2-(4-fluoro-benzenesulfonylamino)-4-methyl-pentanoylamino]-propionic acid tert-butyl ester;

[S-(R*,R*)]-3-(4-Benzyloxy-phenyl)-2-[4-methyl-2-(toluene-2-sulfonylamino)-pentanoylamino]-propionic acid tert-butyl ester;

[S-(R*,R* )]-3-(4-Benzyloxy-phenyl)-2-[2-(3,5-dichloro-benzenesulfonylamino)-4-methyl-pentanoylamino]-propionic acid tert-butyl ester;

[S-(R*,R*)]-3-(4-Benzyloxy-phenyl)-2-[4-methyl-2-(thiophene-2-sulfonylamino)-pentanoylamino]-propionic acid tert-butyl ester;

[S-(R*,R* )]-3-(4-Benzyloxy-phenyl)-2-[2-(5-dimethylamino-naphthalene-1-sulfonylamino)4-methyl-pentanoylamino]-propionic acid tert-butyl ester;

[S-(R*,R* )]-3-(4-Benzyloxy-phenyl)-2-[4-methyl-2-(quinoline-7-sulfonylamino)-pentanoylamino]-propionic acid tert-butyl ester;

[S-(R*,R*)]-3-(4-Benzyloxy-phenyl)-2-[2-(5-chloro-1,3-dimethyl-1H-pyrazole4-sulfonylamino)-4-methyl-pentanoylamino]-propionic acid tert-butyl ester;

[S-(R*,R*)]-3-(4-Benzyloxy-phenyl)-2-[2-(3,5-dimethyl-isoxazole-4-sulfonylamino)-4-methyl-pentanoylamino]-propionic acid tert-butyl ester;

[S-(R*,R*)]-3-(4-Benzyloxy-phenyl)-2-[2-(3-diethylamino-propionylamino)-4-methyl-pentanoylamino]-propionic acid tert-butyl ester;

[S-(R*,R*)]-2-(4-Benzyloxy-benzyl)-5-(2-1H-indol-3-yl-acetylamino)-7-methyl4-oxo-octanoic acid tert-butyl ester;

[S-(R*,R*)]-3-(4-Benzyloxy-phenyl)-2-(2-heptanoylamino-4-methyl-pentanoylamino)-propionic acid tert-butyl ester;

[S-(R*,R*)]-3-(4-Benzyloxy-phenyl)-2-(2-isobutyrylamino-4-methyl-pentanoylamino)-propionic acid tert-butyl ester;

[S-(R*,R* )]-2-(2-Acetylamino-4-methyl-pentanoylamino)-3-(4-benzyloxy-phenyl)-propionic acid tert-butyl ester;

[S-(R*,R* )]-3-(4-Benzyloxy-phenyl)-2-(4-methyl-2-propionylamino-pentanoylamino)-propionic acid tert-butyl ester;

[S-(R*,R*)]-3-(4-Benzyloxy-phenyl)-2-(2-butyrylamino-4-methyl-pentanoylamino)-propionic acid tert-butyl ester;

[S-(R*,R*)]-3-(4-Benzyloxy-phenyl)-2-[4-methyl-2-(2-pyridin-3-yl-acetylamino)pentanoylamino]-propionic acid tert-butyl ester;

[S-(R*,R*)]-3-(4-Benzyloxy-phenyl)-2-[2-(3-1H-indol-3-yl-propionylamino)-4-methyl-pentanoylamino]-propionic acid tert-butyl ester;

[S-(R*,R*)]-3-(4-Benzyloxy-phenyl)-2-{4-methyl-2-[(5-methyl-2-phenyl-2H-[1,2,3]triazole-4-carbonyl)-amino]-pentanoylamino}-propionic acid tert-butyl ester;

[S-(R*,R*)]-3-(4-Benzyloxy-phenyl)-2-[4-methyl-2-(2-thiophen-2-yl-acetylamino)pentanoylamino]-propionic acid tert-butyl ester;

[S-(R*,R*)]-3-(4-Benzyloxy-phenyl)-2-{2-[(isoxazole-5-carbonyl)-amino]-4-methyl-pentanoylamino}-propionic acid tert-butyl ester;

[S-(R*,R* )]-3-(4-Benzyloxy-phenyl)-2-{4-methyl-2-[(pyridine-3-carbonyl)-amino]pentanoylamino}-propionic acid tert-butyl ester;

[S-(R*,R*)]-3-(4-Benzyloxy-phenyl)-2-{4-methyl-2-[(quinoxaline-2-carbonyl)-amino]pentanoylamino}-propionic acid tert-butyl ester;

[S-(R*,R*)]-2-(4-Benzyloxy-benzyl)-7-methyl-4-oxo-5-(2,2,3,3,3-pentafluoro-propionylamino)-octanoic acid tert-butyl ester;

[S-(R*,R*)]-3-(4-Benzyloxy-phenyl)-2-[4-methyl-2-(2,2,2-trifluoro-acetylamino)pentanoylamino]-propionic acid tert-butyl ester;

[S-(R*,R*)]-3-(4-Benzyloxy-phenyl)-2-[2-(2,2-dimethyl-propionylamino)-4-methyl-pentanoylamino]-propionic acid tert-butyl ester;

[S-(R*,R*)]-2-(2-Benzoylamino-4-methyl-pentanoylamino)-3-(4-benzyloxy-phenyl)-propionic acid tert-butyl ester;

[S-(R*,R*)]-3-(4-Benzyloxy-phenyl)-2-{4-methyl-2-[(5-methyl-3-phenyl-isoxazole-4-carbonyl) amino]-pentanoylamino}-propionic acid tert-butyl ester;

[S-(R*,R*)]-Azepane-1-carboxylic acid {1-[2-(4-benzylamino-phenyl)-1-tert-butylcarbamoyl-ethylcarbamoyl]-3-methyl-butyl}-amide;

[S-(R*,R*)]-Azepane-1-carboxylic acid {1-[2-(4-dibenzylamino-phenyl)-1-tert-butylcarbamoyl-ethylcarbamoyl]-3-methyl-butyl)-amide;

[S-(R*,R*)]-Azepane-1-carboxylic acid {1-[1-tert-butylcarbamoyl-2-(4-phenylethynyl-phenyl)-ethylcarbamoyl]-3-methyl-butyl}-amide;

[S-(R*,R*)]-Azepane-1-carboxylic acid (1-{1-tert-butylcarbamoyl-2-[4-(3,3-dimethyl-but-1-ynyl)-phenyl]-ethylcarbamoyl}-3-methyl-butyl)-amide;

[S-(R*,R*)]-Azepane-1-carboxylic acid {1-[1-tert-butylcarbamoyl-2-($^4$-cyclohexylethynyl-phenyl)-ethylcarbamoyl]-3-methyl-butyl}-amide;

[S-(R*,R*)]-Azepane-1-carboxylic acid {1-[1-tert-butylcarbamoyl-2-(4-pyridin-2-ylethynyl-phenyl)-ethylcarbamoyl]-3-methyl-butyl}-amide;

[S-(R*,R*)]-Azepane-1-carboxylic acid (1-{1-tert-butylcarbamoyl-2-[4-(1-hydroxy-cyclohexylethynyl)-phenyl]-ethylcarbamoyl}-3-methyl-butyl)-amide;

Azepane-1-carboxylic acid (1-{1-tert-butylcarbamoyl-2-[4-(3-dimethylamino-prop-1-ynyl)-phenyl]-ethylcarbamoyl}-3-methyl-butyl)-amide;

Azepane-1-carboxylic acid [1-(1-tert-butylcarbamoyl-2-{4-[3-(1,1-dioxo-11,6-thiomorpholin-4-yl)-prop-1-ynyl]-phenyl}-ethylcarbamoyl)-3-methyl-butyl]-amide;

[S-(R*,R*)]-Azepane-1-carboxylic acid {1-[1-tert-butylcarbamoyl-2-(4-styryl-phenyl)-ethylcarbamoyl]-3-methyl-butyl}-amide;

[S-(R*,R*),Z]-Azepane-1-carboxylic acid (1-{1-tert-butylcarbamoyl-2-[4-(2-cyclohexyl-vinyl)-phenyl]-ethylcarbamoyl}-3-methyl-butyl)-amide;

Azepane-1-carboxylic acid [1-(1-tert-butylcarbamoyl-2-{4-[2-(1-hydroxy-cyclohexyl)-vinyl]-phenyl}-ethylcarbamoyl)-3-methyl-butyl]-amide;

[S-(R*,R*)]-Azepane-1-carboxylic acid {1-[1-tert-butylcarbamoyl-2-(4-phenethyl-phenyl)-ethylcarbamoyl]-3-methyl-butyl}-amide;

[S-(R*,R*)]-Azepane-1-carboxylic acid (1-{1-tert-butylcarbamoyl-2-[4-(3,3-dimethyl-butyl)-phenyl]-ethylcarbamoyl}-3-methyl-butyl)-amide;

[S-(R*,R*)]-Azepane-1-carboxylic acid (1-{1-tert-butylcarbamoyl-2-[4-(2-cyclohexyl-ethyl)-phenyl]-ethylcarbamoyl}-3-methyl-butyl)-amide;

[S-(R*,R*)]-Azepane-1-carboxylic acid (1-{1-tert-butylcarbamoyl-2-[4-(2-pyridin-2-yl-ethyl)-phenyl]-ethylcarbamoyl}-3-methyl-butyl)-amide;

[S-(R*,R*)]-Azepane-1-carboxylic acid [1-(1-tert-butylcarbamoyl-2-{4-[2-(1-hydroxy-cyclohexyl)-ethyl]-phenyl}-ethylcarbamoyl)-3-methyl-butyl]-amide;

[S-(R*,R*)]-Azepane-1-carboxylic acid (1-(1-tert-butylcarbamoyl-2-[4-(3-dimethylamino-propyl)-phenyl]-ethylcarbamoyl}-3-methyl-butyl)-amide;

[S-(R*,R*)]-Azepane-1-carboxylic acid [1-(1-tert-butylcarbamoyl-2-{4-[3-(1,1-dioxo-11,6-thiomorpholin-4-yl)-propyl]-phenyl}-ethylcarbamoyl)-3-methyl-butyl]-amide;

[S-(R*,R*)]-Morpholine-4-carboxylic acid {-[1-(4-benzyloxy-benzyl)-2-oxo-2-piperidin-1-ylethylcarbamoyl]-3-methyl-butyl}-amide;

[S-(R*,R*)]-1-(Azepane-1-carbonyl)-pyrrolidine-2-carboxylic acid [2-(4-benzyloxy-phenyl)-1-(2-piperidin-1-yl-ethylcarbamoyl)-ethyl]-amide;

[S-(R*,R*)]-1-(Azepane-1-carbonyl)-pyrrolidine-2-carboxylic acid [2-(4-benzyloxy-phenyl)-1-tert-butylcarbamoyl-ethyl]-amide;

[S-(R*,R*)]-Azepane-1-carboxylic acid {1-[2-(4-benzyloxy-phenyl)-1-(2-piperidin-1-ylethylcarbamoyl)-ethylcarbamoyl]-3-methylsulfanyl-propyl}-amide;

[S-(R*,R* )]-Azepane-1-carboxylic acid {1-[2-(4-benzyloxy-phenyl)-1-tert-butylcarbamoyl-ethylcarbamoyl]-3-methylsulfanyl-propyl}-amide;

[S-(R*,R*)]-Azepane-1-carboxylic acid [1-[2-(4-benzyloxy-phenyl)-1-(2-piperidin-1-ylethylcarbamoyl)-ethylcarbamoyl]-2-(4-hydroxy-phenyl)-ethyl]-amide;

[S-(R*,R*)]-Azepane-1-carboxylic acid [1-[2-(4-benzyloxy-phenyl)-1-(2-piperidin-1-ylethylcarbamoyl)-ethylcarbamoyl]-2-(4-bromo-phenyl)-ethyl]-amide;

[S-(R*,R*)]-Azepane-1-carboxylic acid [1-[1-(4-benzyloxy-benzyl)-4,4-dimethyl-2-oxo-pentylcarbamoyl]-2-(4-benzyloxy-phenyl)-ethyl]-amide;

[S-(R*,R*)]-Azepane-1-carboxylic acid {1-[2-(4-benzyloxy-phenyl)-1-(2-piperidin-1-ylethylcarbamoyl)-ethylcarbamoyl]-3,3-dimethyl-butyl}-amide;

[S-(R*,R*)]-Azepane-1-carboxylic acid [1-[2-(4-benzyloxy-phenyl)-1-tert-butylcarbamoylethylcarbamoyl]-2-(4-hydroxy-phenyl)-ethyl]-amide;

[S-(R*,R*)]-1-(Azepane-1-carbonyl)-octahydro-indole-2-carboxylic acid [2-(4-benzyloxy-phenyl)-1-tert-butylcarbamoyl-ethyl]-amide;

[S-(R*,R*)]-Azepane-1-carboxylic acid {1-[2-(4-benzyloxy-phenyl)-1-(2-piperidin-1-ylethylcarbamoyl)-ethylcarbamoyl]-2-cyclohexyl-ethyl}-amide;

[S-(R*,R*)]-Azepane-1-carboxylic acid [1-[2-(4-benzyloxy-phenyl)-1-tert-butylcarbamoylethylcarbamoyl]-2-(4-tert-butoxy-phenyl)-ethyl]-amide;

[S-(R*,R*)]-6-[(Azepane-1-carbonyl)-amino]-6-[2-(4-benzyloxy-phenyl)-1-tert-butylcarbamoylethylcarbamoyl]-hexanoic acid tert-butyl ester;

[S-(R*,R*)]-Azepane-1-carboxylic acid {1-[2-(4-benzyloxy-phenyl)-1-(2-hydroxy-ethylcarbamoyl)-ethylcarbamoyl]-3-methyl-butyl}-amide;

[S-(R*,R*)]-Azepane-1-carboxylic acid {1-[1-(4-benzyloxy-benzyl)-2-morpholin4-yl-2-oxo-ethylcarbamoyl]-3-methyl-butyl}-amide;

[S-(R*,R*)]-Azepane-1-carboxylic acid {1-[1-(4-benzyloxy-benzyl)-2-oxo-2-piperidin-1-ylethylcarbamoyl]-3-methyl-butyl}-amide;

[S-(R*,R*)]-Azepane-1-carboxylic acid {1-[2-(4-benzyloxy-phenyl)-1-hexylcarbamoyl-ethylcarbamoyl]-3-methyl-butyl}-amide;

[S-(R*,R*)]-Azepane-1-carboxylic acid {1-[2-(4-benzyloxy-phenyl)-1-propylcarbamoyl-ethylcarbamoyl]-3-methyl-butyl}-amide;

[S-(R*,R*)]-Azepane-1-carboxylic acid (1-{2-(4-benzyloxy-phenyl)-1-[2-(2-oxo-pyrrolidin-1yl)-ethylcarbamoyl]-ethylcarbamoyl}-3-methyl-butyl)-amide;

[S-(R*,R*)]-Azepane-1-carboxylic acid {1-[2-(4-benzyloxy-phenyl)-1-(2-piperidin-1-yl-ethylcarbamoyl)-ethylcarbamoyl]-3-methyl-butyl}-amide;

[S-(R*,R*)]-Azepane-1-carboxylic acid (1-{2-(4-benzyloxy-phenyl)-1-[2-(1H-imidazol-4-yl) ethylcarbamoyl]-ethylcarbamoyl}-3-methyl-butyl)-amide;

[S-(R*,R*)]-Azepane-1-carboxylic acid {1-[2-(4-benzyloxy-phenyl)-1-(4-bromophenylcarbamoyl)-ethylcarbamoyl]-3-methyl-butyl}-amide;

[S-(R*,R*)]-Azepane-1-carboxylic acid {1-[2-(4-benzyloxy-phenyl)-1-(2-furan-2-ylethylcarbamoyl)-ethylcarbamoyl]-3-methyl-butyl}-amide;

[S-(R*,R*)]-Azepane-1-carboxylic acid {1-[2-(4-benzyloxy-phenyl)-1-(2-dimethylamino-ethylcarbamoyl)-ethylcarbamoyl]-3-methyl-butyl}-amide;

[S-(R*,R*)]-Azepane-1-carboxylic acid {1-[1-(4-benzyloxy-benzyl)-2-(4-methyl-piperazin-1-yl)-2-oxo-ethylcarbamoyl]-3-methyl-butyl}-amide;

[S-(R*,R*)]-Morpholine-4-carboxylic acid {1-[2-(4-benzyloxy-phenyl)-1-(2-piperidin-1-ylethylcarbamoyl)-ethylcarbamoyl]-3-methyl-butyl}-amide;

[S-(R*,R*)]-Azepane-1-carboxylic acid (1-{2-(4-benzyloxy-phenyl)-1-[(pyridin-4-ylmethyl)carbamoyl]-ethylcarbamoyl}-3-methyl-butyl)-amide;

[S-(R*,R*)]-Azepane-1-carboxylic acid {1-[1-(4-benzyloxy-benzyl)-2-oxo-2-(2-pyrrolidin-1-ylmethyl-pyrrolidin-1-yl)-ethylcarbamoyl]-3-methyl-butyl}-amide;

[S-(R*,R*)]-Azepane-1-carboxylic acid {1-[1-(4-benzyloxy-benzyl)-2-(4-benzyl-piperazin-1-yl)-2-oxo-ethylcarbamoyl]-3-methyl-butyl}-amide;

[S-(R*,R*)]-Azepane-1-carboxylic acid {1-[2-(4-benzyloxy-phenyl)-1-(2-pyrrolidin-1-ylethylcarbamoyl)-ethylcarbamoyl]-3-methyl-butyl}-amide;

[S-(R*,R*)]-Azepane-1-carboxylic acid {1-[1-(1-aza-bicyclo[2.2.2]oct-3-ylcarbamoyl)-2-(4-benzyloxy-phenyl)-ethylcarbamoyl]-3-methyl-butyl}-amide;

[S-(R*,R*)]-Azepane-1-carboxylic acid {1-[2-(4-benzyloxy-phenyl)-1-(1-benzyl-pyrrolidin-3-ylcarbamoyl)-ethylcarbamoyl-3-methyl-butyl}-amide;

[S-(R*,R*)]-Azepane-1-carboxylic acid {1-[2-(4-benzyloxy-phenyl)-1-(3-cyclohexylamino-propylcarbamoyl)-ethylcarbamoyl]-3-methyl-butyl}-amide;

[S-(R*,R*)]-Azepane-1-carboxylic acid {1-[1-(4-benzyloxy-benzyl)-2-[1,4']bipiperidinyl-1'-yl-2-oxo-ethylcarbamoyl]-3-methyl-butyl}-amide;

[S-(R*,R*)]-Azepane-1-carboxylic acid {1-[2-(4-benzyloxy-phenyl)-1-(2-morpholin-4-ylethylcarbamoyl)-ethylcarbamoyl]-3-methyl-butyl}-amide;

[S-(R*,R*)]-Azepane-1-carboxylic acid (1-{2-(4-benzyloxy-phenyl)-1-[3-(4-methyl-piperazin-1-yl)-propylcarbamoyl]-ethylcarbamoyl}-3-methyl-butyl)-amide;

[S-(R*,R*)]-Azepane-1-carboxylic acid {1-[1-(4-benzyloxy-benzyl)-2-(3-diethylcarbamoyl-piperidin-1-yl)-2-oxo-ethylcarbamoyl]-3-methyl-butyl}-amide;

[S-(R*,R*)]-Azepane-1-carboxylic acid {1-[1-(4-benzyloxy-benzyl)-2-(3-diethylcarbamoyl-piperidin-1-yl)-2-oxo-ethylcarbamoyl]-3-methyl-butyl}-amide;

[S-(R*,R*)]-Azepane-1-carboxylic acid {1-[2-(4-benzyloxy-phenyl)-1-(2-hydroxy-2-phenyl-ethylcarbamoyl)-ethylcarbamoyl]-3-methyl-butyl}-amide;

Azepane-1-carboxylic acid {1-[2-(4-benzyloxy-phenyl)-1-(1,2-dimethyl propylcarbamoyl)-ethylcarbamoyl]-3-methyl-butyl}-amide;

Azepane-1-carboxylic acid {1-[2-(4-benzyloxy-phenyl)-1-(1,2-dimethyl propylcarbamoyl)-ethylcarbamoyl]-3-methyl-butyl}-amide;

[S-(R*,R*)]-Azepane-1-carboxylic acid (1-{2-(4-benzyloxy-phenyl)-1-[2-(1-methyl-pyrrolidin-2-yl)-ethylcarbamoyl]-ethylcarbamoyl}-3-methyl-butyl)-amide;

[S-(R*,R*)]-Azepane-1-carboxylic acid {1-[2-(4-benzyloxy-phenyl)-1-(1-benzyl-pyrrolidin-3-ylcarbamoyl)-ethylcarbamoyl]-3-methyl-butyl}-amide;

[S-(R*,R*)]-Azepane-1-carboxylic acid {1-[2-(4-benzyloxy-phenyl)-1-(1-propyl-piperidin-3-ylcarbamoyl)-ethylcarbamoyl]-3-methyl-butyl}-amide;

[S-(R*,R*)]-Azepane-1-carboxylic acid (1-{2-(4-benzyloxy-phenyl)-1-[3-(2-methyl-piperidin-1-yl)-propylcarbamoyl]-ethylcarbamoyl}-3-methyl-butyl)-amide;

[S-(R*,R*)]-Azepane-1-carboxylic acid {1-[2-(4-benzyloxy-phenyl)-1-(1-methyl-2-phenyl-piperidin-3-ylcarbamoyl)-ethylcarbamoyl]-3-methyl-butyl}-amide;

[S-(R*,R*)]-Azepane-1-carboxylic acid {1-[2-(4-benzyloxy-phenyl)-1-(1-isobutyl-piperidin-3-ylcarbamoyl)-ethylcarbamoyl]-3-methyl-butyl}-amide;

[S-(R*,R*)]-Azepane-1-carboxylic acid {1-[1-(4-benzyloxy-benzyl)-2-(2,6-dimethyl-morpholin-4-yl)-2-oxo-ethylcarbamoyl]-3-methyl-butyl}-amide;

[S-(R*,R*)]-Azepane-1-carboxylic acid {1-[1-(4-benzyloxy-benzyl)-2-(3-methyl-piperidin-1-yl)-2-oxo-ethylcarbamoyl]-3-methyl-butyl}-amide;

[S-(R*,R*)]-Azepane-1-carboxylic acid {1-[1-(4-benzyloxy-benzyl)-2-(3,4-dihydro-1H-isoquinolin-2-yl)-2-oxo-ethylcarbamoyl]-3-methyl-butyl}-amide;

[S-(R*,R*)]-Azepane-1-carboxylic acid (1-{1-(4-benzyloxy-benzyl)-2-[4-(2-hydroxy-ethyl)-piperazin-1-yl]-2-oxo-ethylcarbamoyl}-3-methyl-butyl)-amide;

[S-(R*,R*)]-Azepane-1-carboxylic acid {1-[2-(4-benzyloxy-phenyl)-1-(2,2,6,6-tetramethyl-piperidin4-ylcarbamoyl)-ethylcarbamoyl]-3-methyl-butyl}-amide;

[S-(R*,R*)]-Azepane-1-carboxylic acid {1-[2-(4-acetyl-piperazin-1-yl)-1-(4-benzyloxy-benzyl)-2-oxo-ethylcarbamoyl]-3-methyl-butyl}-amide;

[S-(R*,R*)]-Azepane-1-carboxylic acid {1-[2-(4-benzyloxy-phenyl)-1-(cyclohexylmethyl-carbamoyl)-ethylcarbamoyl]-3-methyl-butyl}-amide;

[S-(R*,R*)]-Azepane-1-carboxylic acid {1-[2-(4-benzyloxy-phenyl)-1-(cyclopropylmethyl-carbamoyl)-ethylcarbamoyl]-3-methyl-butyl}-amide;

[S-(R*,R*)]-Azepane-1-carboxylic acid {1-[2-(4-benzyloxy-phenyl)-1-(thiazol-2-ylcarbamoyl)-ethylcarbamoyl]-3-methyl-butyl}-amide;

[S-(R*,R*)]-Azepane-1-carboxylic acid {1-[2-(4-benzyloxy-phenyl)-1-cycloheptylcarbamoyl-ethylcarbamoyl]-3-methyl-butyl}-amide;

[S-(R*,R*)]-Azepane-1-carboxylic acid {1-[2-(4-benzyloxy-phenyl)-1-cyclopropylcarbamoyl-ethylcarbamoyl]-3-methyl-butyl}-amide;

[S-(R*,R*)]-Azepane-1-carboxylic acid {1-[2-(4-benzyloxy-phenyl)-1-(4-methoxy-phenylcarbamoyl)-ethylcarbamoyl]-3-methyl-butyl)-amide;

[S-(R*,R*)]-Azepane-1-carboxylic acid (1-{2-(4-benzyloxy-phenyl)-1-[4-(2-hydroxy-ethyl)-phenylcarbamoyl]-ethylcarbamoyl}-3-methyl-butyl)-amide;

[S-(R*,R*)]-Azepane-1-carboxylic acid {1-[-(4-acetyl-phenylcarbamoyl)-2-(4-benzyloxy-phenyl)-ethylcarbamoyl]-3-methyl-butyl}-amide;

[S-(R*,R*)]-Azepane-1-carboxylic acid {1-[2-(4-benzyloxy-phenyl)-1-(4-phenoxy-phenylcarbamoyl)-ethylcarbamoyl]-3-methyl-butyl}-amide;

[S-(R*,R*)]-Azepane-1-carboxylic acid {1-[2-(4-benzyloxy-phenyl)-1-(3-trifluoromethyl-phenylcarbamoyl)-ethylcarbamoyl]-3-methyl-butyl}-amide;

[S-(R*,R*)]-Azepane-1-carboxylic acid (1-[2-(4-benzyloxy-phenyl)-1-(4-dimethylamino-phenylcarbamoyl)-ethylcarbamoyl]-3-methyl-butyl}-amide;

[S-(R*,R*)]-Azepane-1-carboxylic acid {1-[1-(4-acetylamino-phenylcarbamoyl)-2-(4-benzyloxy-phenyl)-ethylcarbamoyl]-3-methyl-butyl}-amide;

[S-(R*,R*)]-Azepane-1-carboxylic acid {1-[1-(4-aminomethyl-benzylcarbamoyl)-2-(4-benzyloxy-phenyl)-ethylcarbamoyl]-3-methyl-butyl}-amide;

[S-(R*,R*)]-Azepane-1-carboxylic acid {1-[1-(4-benzyloxy-benzyl)-2-oxo-2-(2-phenylaminomethyl-pyrrolidin-1-yl)-ethylcarbamoyl]-3-methyl-butyl}-amide;

[S-(R*,R*)]-Azepane-1-carboxylic acid {1-[1-(3-amino-2-hydroxy-propylcarbamoyl)-2-(4-benzyloxy-phenyl)-ethylcarbamoyl]-3-methyl-butyl}-amide;

[S-(R*,R*)]-Azepane-1-carboxylic acid (1-{2-(4-benzyloxy-phenyl)-1-[(furan-2-ylmethyl)-carbamoyl]-ethylcarbamoyl}-3-methyl-butyl)-amide;

[S-(R*,R*)]-Azepane-1-carboxylic acid {1-[1-(4-benzyloxy-benzyl)-2-thiomorpholin4-yl-2-oxo-ethylcarbamoyl]-3-methyl-butyl}-amide;

[S-(R*,R*)]-Azepane-1-carboxylic acid {1-[1-[(benzo[1,3]dioxol-5-ylmethyl)-carbamoyl]-2-(4-benzyloxy-phenyl)-ethylcarbamoyl]-3-methyl-butyl}-amide;

[S-(R*,R*)]-Azepane-1-carboxylic acid {1-[2-(4-benzyloxy-phenyl)-1-(3,4,5-trimethoxy-phenylcarbamoyl)-ethylcarbamoyl]-3-methyl-butyl}-amide;

[S-(R*,R*)]-Azepane-1-carboxylic acid (1-{2-(4-benzyloxy-phenyl)-1-[2-(1H-indol-3-yl)-ethylcarbamoyl]-ethylcarbamoyl}-3-methyl-butyl)-amide;

[S-(R*,R*)]-Azepane-1-carboxylic acid (1-{2-(4-benzyloxy-phenyl)-1-[2-(4-hydroxy-phenyl)-ethylcarbamoyl]-ethylcarbamoyl}-3-methyl-butyl)-amide;

[S-(R*,R*)]-Azepane-1-carboxylic acid {1-[2-(4-benzyloxy-phenyl)-1-(1-hydroxymethyl-propylcarbamoyl)-ethylcarbamoyl]-3-methyl-butyl}-amide;

[S-(R*,R*)]-Azepane-1-carboxylic acid {1-[2-(4-benzyloxy-phenyl)-1-(2-hydroxy-1-hydroxymethyl-2-phenyl-ethylcarbamoyl)-ethylcarbamoyl]-3-methyl-butyl}-amide;

[S-(R*,R*)]-Azepane-1-carboxylic acid [1-(1-(4-benzyloxy-benzyl)-2-{4-[2-(2-hydroxy-ethoxy)-ethyl]-piperazin-1-yl}-2-oxo-ethylcarbamoyl)-3-methyl-butyl]-amide;

[S-(R*,R*)]-Azepane-1-carboxylic acid {1-[2-(4-benzyloxy-phenyl)-1-(1,1-bis-hydroxymethyl-propylcarbamoyl)-ethylcarbamoyl]-3-methyl-butyl}-amide;

[S-(R*,R*)]-Azepane-1-carboxylic acid {1-[2-(4-benzyloxy-phenyl)-1-(2-dimethylamino-1-methyl-ethyl carbamoyl)-ethylcarbamoyl]-3-methyl-butyl}-amide;

[S-(R*,R*)]-Azepane-1-carboxylic acid {1-[2-(4-benzyloxy-phenyl)-1-(2-pyridin-1-yl-ethylcarbamoyl)-ethylcarbamoyl]-3-methyl-butyl}-amide;

[S-(R*,R*)]-Azepane-1-carboxylic acid {1-[2-(4-benzyloxy-phenyl)-1-(1,2,3,4-tetrahydro-naphthalen-1-ylcarbamoyl)-ethylcarbamoyl]-3-methyl-butyl}-amide;

[S-(R*,R*)]-Azepane-1-carboxylic acid (1-{2-(4-benzyloxy-phenyl)-1-[2-(2-hydroxy-ethylamino)-ethy carbamoyl]-ethylcarbamoyl}-3-methyl-butyl)-amide;

[S-(R*,R*)]-Azepane-1-carboxylic acid {1-[1-(4-benzyloxy-benzyl)-2-(3-hydroxy-piperidin-1-yl)-2-oxo-ethylcarbamoyl]-3-methyl-butyl}-amide;

[S-(R*,R*)]-Azepane-1-carboxylic acid {1-[1-(4-benzyloxy-benzyl)-2-(4-hydroxy-piperidin-1-yl)-2-oxo-ethylcarbamoyl]-3-methyl-butyl}-amide;

[S-(R*,R*)]-Azepane-1-carboxylic acid {1-[2-(4-benzyloxy-phenyl)-1-(2-cyano-ethylcarbamoyl)-ethylcarbamoyl]-3-methyl-butyl}-amide;

[S-(R*,R*)]-Azepane-1-carboxylic acid {1-[2-(4-benzyloxy phenyl)-1-(3-imidazol-1-yl-propylcarbamoyl)-ethylcarbamoyl]-3-methyl-butyl}-amide;

[S-(R*,R*)]-Azepane-1-carboxylic acid {1-[2-(4-benzyloxy-phenyl)-1-(1-hydroxymethyl-3-methylsulfanyl-propylcarbamoyl)-ethylcarbamoyl]-3-methyl-butyl}-amide;

[S-(R*,R*)]-Azepane-1-carboxylic acid {1-[1-[2-(2-amino-propylamino)-1-methyl-ethylcarbamoyl]-2-(4-benzyloxy-phenyl)-ethylcarbamoyl]-3-methyl-butyl}-amide;

[S-(R*,R*)]-Azepane-1-carboxylic acid (1-{1-(4-benzyloxy-benzyl)-2-[4-(4-fluoro-phenyl)-piperazin-1-yl]-2-oxo-ethylcarbamoyl}-3-methyl-butyl)-amide;

[S-(R*,R*)]-Azepane-1-carboxylic acid {1-[2-(4-benzyloxy-phenyl)-1-(3-iodo-benzylcarbamoyl)-ethylcarbamoyl]-3-methyl-butyl}-amide;

[S-(R*,R*)]-Azepane-1-carboxylic acid {1-[2-(4-benzyloxy-phenyl)-1-(2-isopropylamino-propylcarbamoyl)-ethylcarbamoyl]-3-methyl-butyl-amide;

[S-(R*,R*)]-Azepane-1-carboxylic acid {1-[2-(4-benzyloxy-phenyl)-1-sec-butylcarbamoyl-ethylcarbamoyl]-3-methyl-butyl}-amide;

[S-(R*,R*)]-Azepane-1-carboxylic acid {1-[2-(3-acetylamino-pyrrolidin-1-yl)-1-(4-benzyloxy-benzyl)-2-oxo-ethylcarbamoyl]-3-methyl-butyl}-amide;

[S-(R*,R*)]-Azepane-1-carboxylic acid {1-[2-(4-benzyloxy-phenyl)-1-(1-methoxymethyl-propylcarbamoyl)-ethylcarbamoyl]-3-methyl-butyl}-amide;

[S-(R*,R*)]-Azepane-1-carboxylic acid (1-{2-(4-benzyloxy-phenyl)-1-[3-(2-hydroxy-ethylamino)-1,1-dimethyl-propylcarbamoyl]-ethylcarbamoyl}-3-methyl-butyl)-amide;

[S-(R*,R*)]-Azepane-1-carboxylic acid {1-[1-(4-benzyloxy-benzyl)-2-(3,6-dihydro-2H-pyridin-1-yl)-2-oxo-ethylcarbamoyl]-3-methyl-butyl}-amide;

[S-(R*,R*)]-Azepane-1-carboxylic acid {1-[1-(4-benzyloxy-benzyl)-2-(4-ethyl-piperazin-1-yl)-2-oxo-ethylcarbamoyl]-3-methyl-butyl}-amide;

[S-(R*,R*)]-Azepane-1-carboxylic acid {1-[1-(4-benzyloxy-benzyl)-2-(2,5-dimethyl-2,5-dihydro-pyrrol-1-yl)-2-oxo-ethylcarbamoyl]-3-methyl-butyl}-amide;

[S-(R*,R*)]-Azepane-1-carboxylic acid (1-{2-(4-benzyloxy-phenyl)-1-[(1-benzyl-pyrrolidin-3-ylmethyl)-carbamoyl]-ethyl carbamoyl}-3-methyl-butyl)-amide;

[S-(R*,R*)]-Azepane-1-carboxylic acid {1-[1-[benzyl-(2-hydroxy-ethyl)-carbamoyl]-2-(4-benzyloxy-phenyl)-ethylcarbamoyl]-3-methyl-butyl}-amide;

[S-(R*,R*)]-Azepane-1-carboxylic acid {1-[1-(2-benzylamino-ethylcarbamoyl)-2-(4-benzyloxy-phenyl)-ethylcarbamoyl]-3-methyl-butyl}-amide;

[S-(R*,R*)]-Azepane-1-carboxylic acid {1-[2-(4-benzyloxy-phenyl)-1-(1-hydroxymethyl-2-methyl-propylcarbamoyl)-ethylcarbamoyl]-3-methyl-butyl}-amide;

[S-(R*,R*)]-Azepane-1-carboxylic acid {1-[2-(4-benzyloxy-phenyl)-1-(pyridin-3-ylcarbamoyl)-ethylcarbamoyl]-3-methyl-butyl}-amide;

[S-(R*,R*)]-Azepane-1-carboxylic acid {1-[2-(4-benzyloxy-phenyl)-1-(3-hydroxy-propylcarbamoyl)-ethylcarbamoyl]-3-methyl-butyl}-amide;

[S-(R*,R*)]-Azepane-1-carboxylic acid {1-[1-(4-benzyloxy-benzyl)-2-(3-hydroxymethyl-piperidin-1-yl)-2-oxo-ethylcarbamoyl]-3-methyl-butyl}-amide;

[S-(R*,R*)]-Azepane-1-carboxylic acid {1-[2-(4-benzyloxy-phenyl)-1-(2-hydroxy-1-hydroxymethyl-ethylcarbamoyl)-ethylcarbamoyl]-3-methyl-butyl}-amide;

[S-(R*,R*)]-Azepane-1-carboxylic acid {1-[2-(4-benzyloxy-phenyl)-1-(pyrrolidin-3-ylcarbamoyl)-ethylcarbamoyl]-3-methyl-butyl}-amide;

[S-(R*,R*)]-Azepane-1-carboxylic acid {1-[2-(4-benzyloxy-phenyl)-1-([1,4]diazepane-1-carbonyl)-ethylcarbamoyl]-3-methyl-butyl}-amide;

[S-(R*,R*)]-Azepane-1-carboxylic acid {1-[2-(4-benzyloxy-phenyl)-1-(4-piperidin-1-yl-phenylcarbamoyl)-ethylcarbamoyl]-3-methyl-butyl}-amide;

[S-(R*,R*)]-Azepane-1-carboxylic acid {1-[2-(4-benzyloxy-phenyl)-1-(pyrazole-3-carbonyl)-ethylcarbamoyl]-3-methyl-butyl}-amide;

[S-(R*,R*)]-Azepane-1-carboxylic acid (1-{2-(4-benzyloxy-phenyl)-1-[(piperidin-4-ylmethyl)-carbamoyl]-ethylcarbamoyl}-3-methyl-butyl)-amide;

[S-(R*,R*)]-Azepane-1-carboxylic acid {1-[1-benzylcarbamoyl-2-(4-benzyloxy-phenyl)-ethylcarbamoyl]-3-methyl-butyl}-amide;

[S-(R*,R*)]-Azepane-1-carboxylic acid (1-{1-(4-benzyloxy-benzyl)-2-[4-(4-methoxy-phenyl)-piperazin-1-yl]-2-oxo-ethylcarbamoyl}-3-methyl-butyl)-amide;

[S-(R*,R*)]-Azepane-1-carboxylic acid (1-[1-(4-benzyloxy-benzyl)-2-(4-benzyl-piperidin-1-yl)-2-oxo-ethylcarbamoyl]-3-methyl-butyl}-amide;

[S-(R*,R*)]-Azepane-1-carboxylic acid {1-[2-(4-benzyloxy-phenyl)-1-(2-hydroxy-1,1-dimethyl-ethylcarbamoyl)-ethylcarbamoyl]-3-methyl-butyl}-amide;

[S-(R*,R*)]-Azepane-1-carboxylic acid {1-[2-(4-benzyloxy-phenyl)-1-(4-hydroxy-2,5-dimethyl-phenylcarbamoyl)-ethylcarbamoyl]-3-methyl-butyl}-amide;

[S-(R*,R*)]-Azepane-1-carboxylic acid {1-[2-(4-benzyloxy-phenyl)-1-(3-pyrrolidin-1-yl-propylcarbamoyl)-ethylcarbamoyl]-3-methyl-butyl}-amide;

[S-(R*,R*)]-Azepane-1-carboxylic acid {1-[2-(4-benzyloxy-phenyl)-1-(3-hydroxy-phenylcarbamoyl)-ethylcarbamoyl]-3-methyl-butyl}-amide;

[S-(R*,R*)]-Azepane-1-carboxylic acid {1-[2-(4-benzhydryl-piperazin-1-yl)-1-(4-benzyloxy-benzyl)-2-oxo-ethylcarbamoyl]-3-methyl-butyl}-amide; and

[S-(R*,R*)]-Azepane-1-carboxylic acid {1-[2-(4-benzyloxy-phenyl)-1-(1-benzyl-piperidin4-ylcarbamoyl)-ethylcarbamoyl]-3-methyl-butyl}-amide.

DETAILED DESCRIPTION OF THE INVENTION

Figure 1:
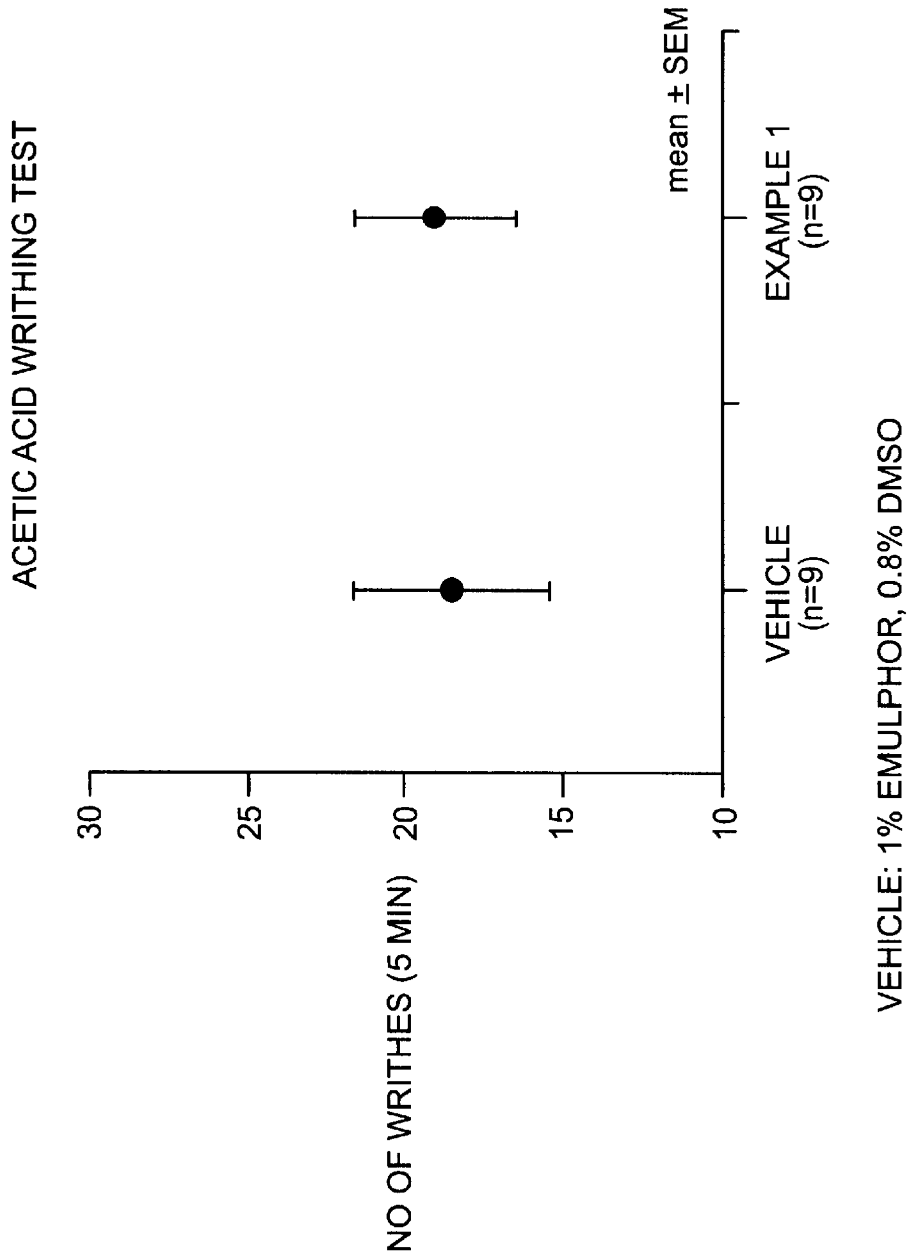
FIG. 1 shows the results of the acetic acid writhing test for Example 1.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "alkoxy" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The term "alkenyl" means a branched or straight chain hydrocarbon having one or more carbon-carbon double bond.

The term "alkynyl" means a branched or straight chain hydrocarbon having one or more carbon-carbon triple bond.

The term "aryl" means an aromatic hydrocarbon. Representative examples of aryl groups include phenyl and naphthyl.

The term "heteroatom" includes oxygen, nitrogen, and sulfur.

The term "heteroaryl" means an aryl group wherein one or more carbon atom of the aromatic hydrocarbon has been replaced with a heteroatom. Examples of heteroaryl radicals include, but are not limited to, pyridyl, imidazolyl, pyrrolyl, thienyl, furyl, pyranyl, pyrimidinyl, pyridazinyl, indolyl, quinolyl, naphthyridinyl, and isoxazolyl.

The term "cycloalkyl" means a cyclic hydrocarbon. Examples of cycloalkyl groups include cyclopropyl, cyclobutyl, cyclopentyl, and cyclohexyl.

The symbol "—" means a bond.

The term "patient" means all animals including humans. Examples of patients include humans, cows, dogs, cats, goats, sheep, and pigs.

The term "substituted" means that the base organic radical has one or more substituents. For example, substituted cyclohexyl means a cyclohexyl radical that has one or more substituents. Substituents include, but are not limited to, halogen, $—CF_3$, $C_1–C_8$ alkyl, —CN, $CF_3$, $—NO_2$,

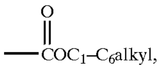 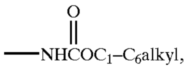

$—NH_2$, —O-phenyl, $—NHC_1–C_8$ alkyl, $—N(C_1–C_8$ $alkyl)_2$, $—SC_1–C_6$ alkyl, $—OC_1–C_8$ alkyl, and —OH. Particularly preferred substituents include, but are not limited to tert-butyl, methyl, —OH, $—NH_2$, $—SCH_3$, —CN, $—OCH_3$,

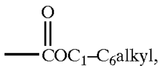 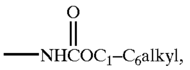

bromine, fluorine, and chlorine.

The term "cycloalkenyl" means a cycloalkyl group having at least one carbon-carbon double bond. Examples of cycloalkenyl groups include cyclopentane, cyclobutene, and cyclohexene.

The term "heterocycle" means a cycloalkyl group wherein one or more carbon atom is replaced with a heteroatom. Examples of heterocycles include, but are not limited to, pyrrolidinyl, piperidinyl, and piperazinyl.

Those skilled in the art are easily able to identify patients having a stroke or at risk of having a stroke; cerebral ischemia; head trauma; or epilepsy. For example, patients who are at risk of having a stroke include, but is not limited to patients having hypertension or undergoing major surgery.

A therapeutically effective amount is an amount of a compound of Formulas I–X, that when administered to a patient, ameliorates a symptom of the disease.

The compounds of the present invention can be administered to a patient either alone or a part of a pharmaceutical composition. The compositions can be administered to patients either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the.active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laureate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, S. M. Berge, et al., "Pharmaceutical Salts," *J. Pharm. Sci.,* 1977;66:1–19 which is incorporated herein by reference.)

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines, and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol 14 of the A.C.S. Symposium Series, and in *Bioreversible Carriers in Drug Design,* ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisomeric forms by virtue of the presence of asymmetric centers in the compounds. It is contemplated that all stereoisomeric forms of the compounds, as well as mixtures thereof including racemic mixtures, form part of this invention.

The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well known to those skilled in the art.

In addition, it is intended that the present invention cover compounds made either using standard organic synthetic techniques, including combinatorial chemistry or by biological methods, such as through metabolism.

The examples presented below are intended to illustrate particular embodiments of the invention and are not intended to limit the scope of the specification, including the claims, in any way.

EXAMPLES

The compounds of the present invention can be synthesized generally as follows.

Scheme 1

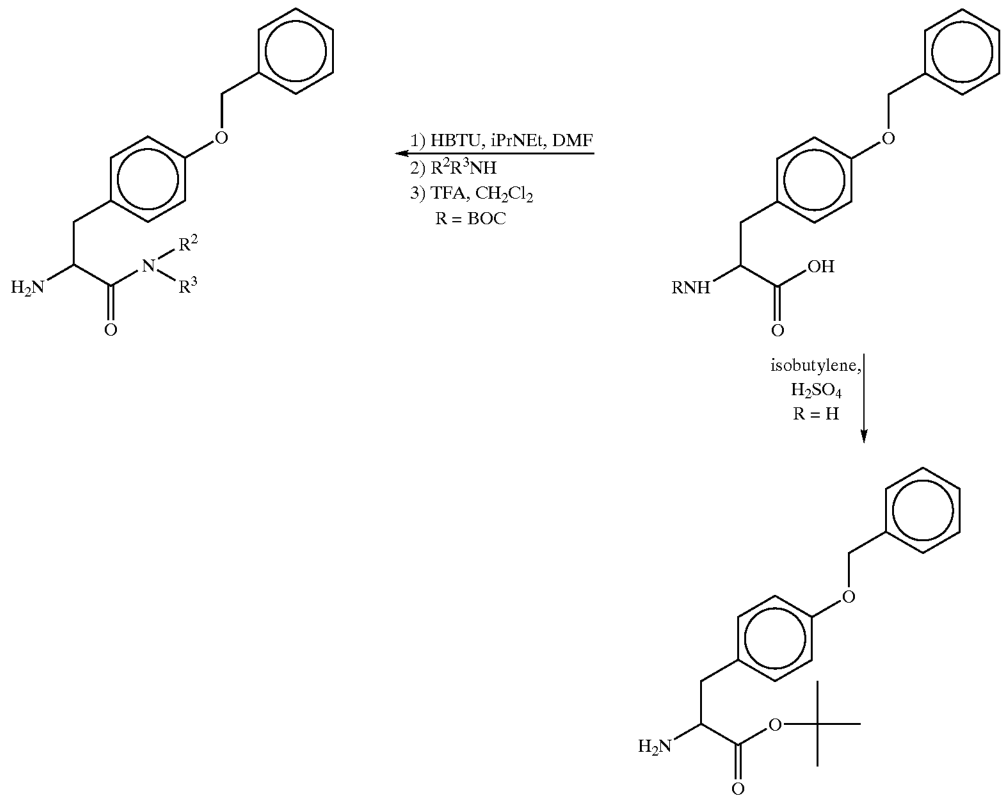

-continued
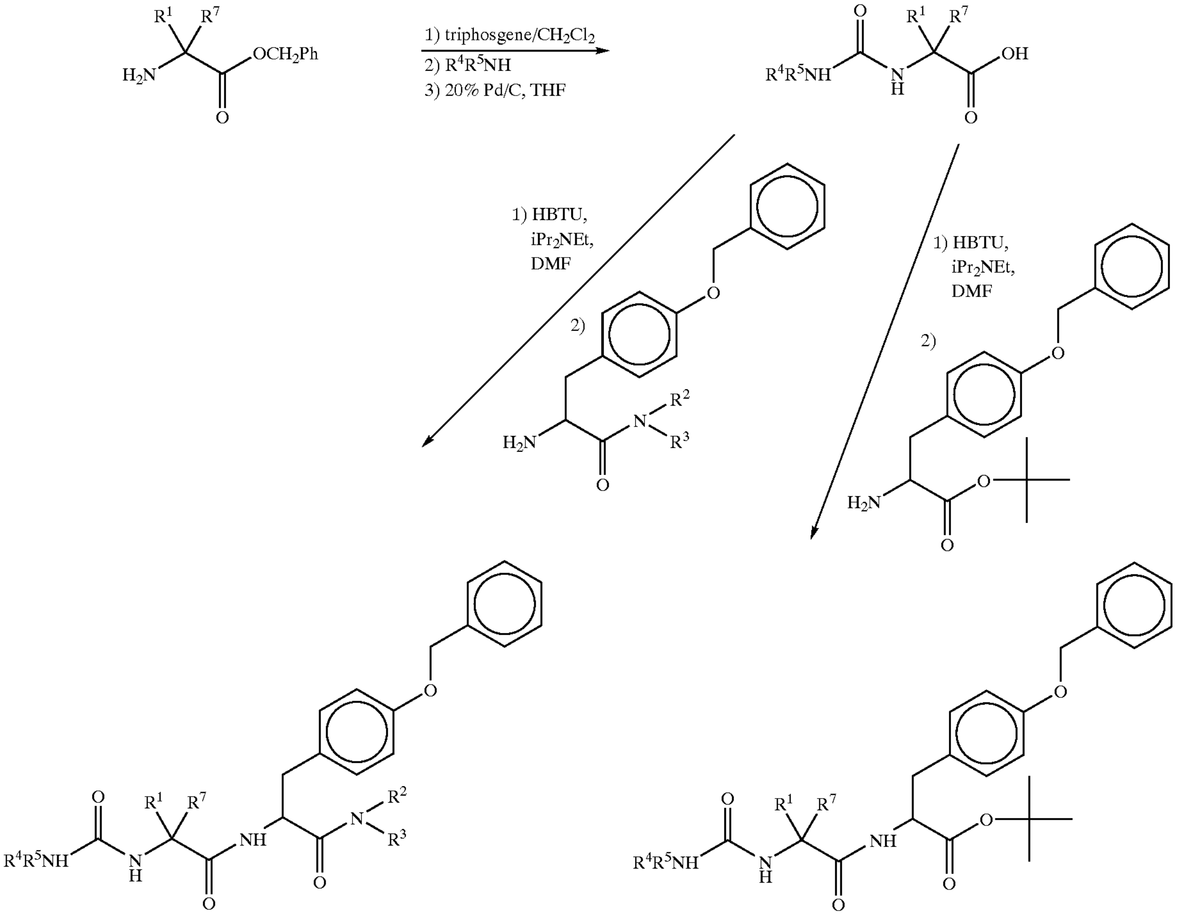
Scheme 2
Preparation of Isothiocyanate and Sulfamide Derivatives
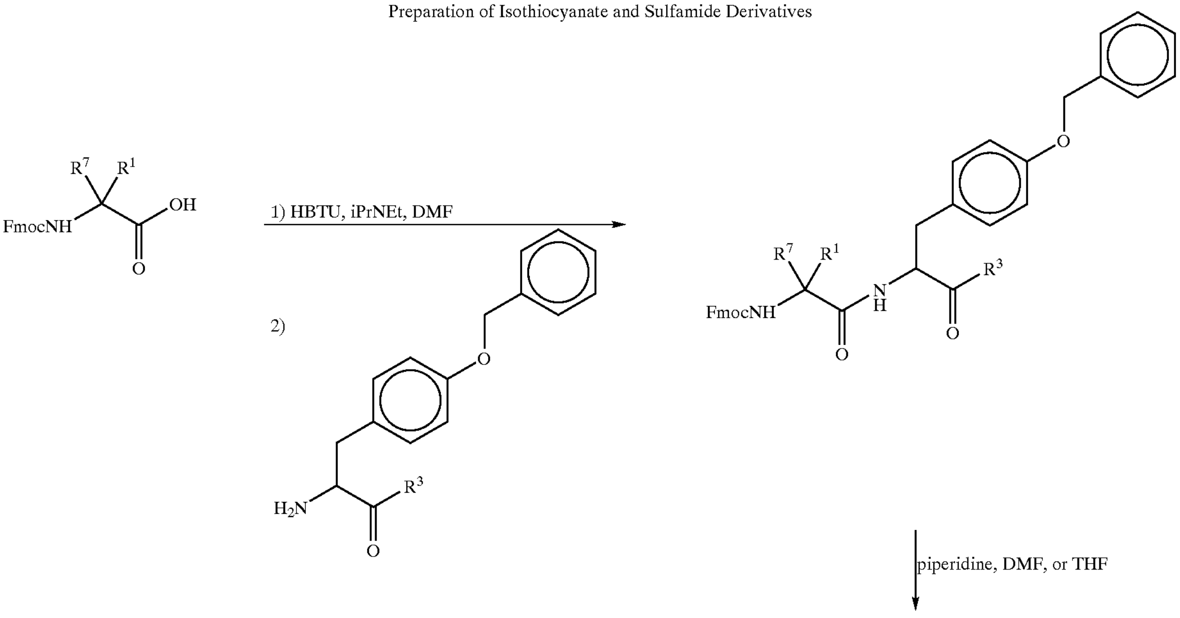

-continued
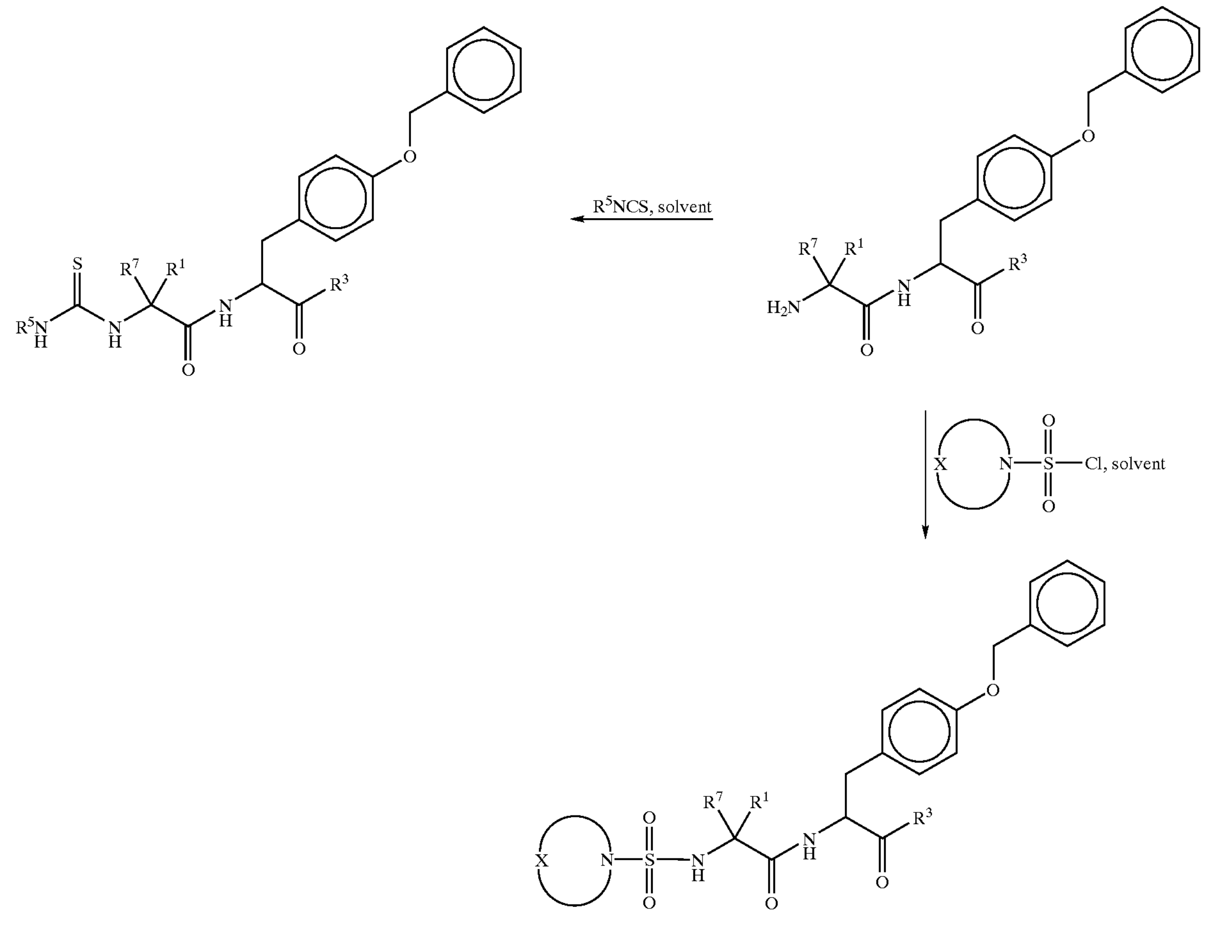
X = $(CH_2)_n$,O,S
Scheme 3
Multiple Parallel Synthesis of Urea, Amide, and Sulfonamide Derivatives
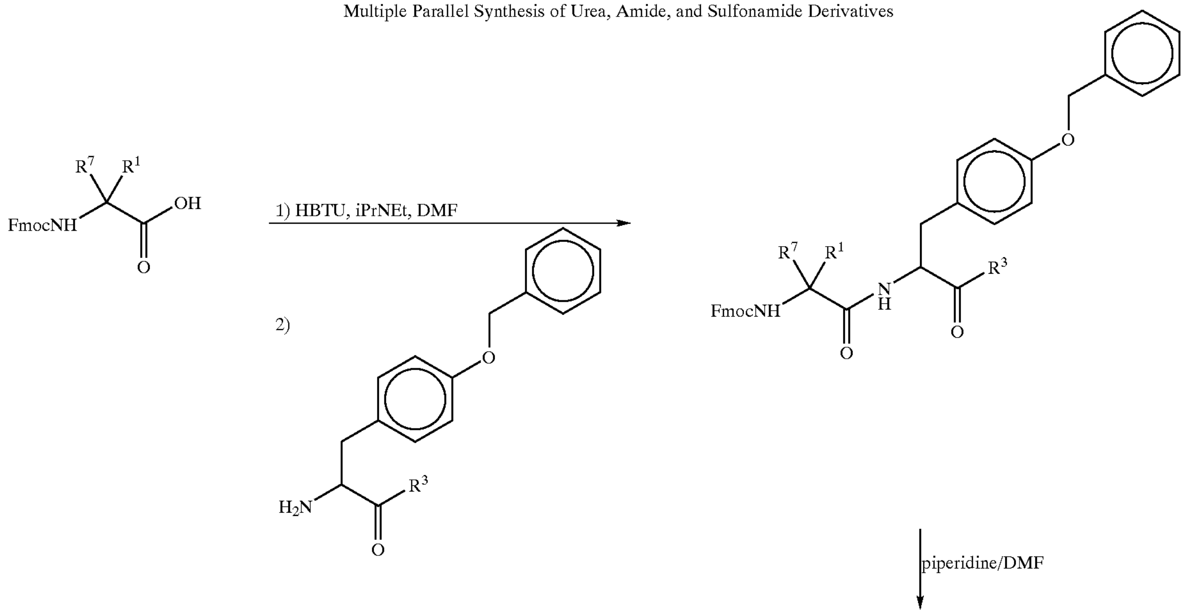

-continued
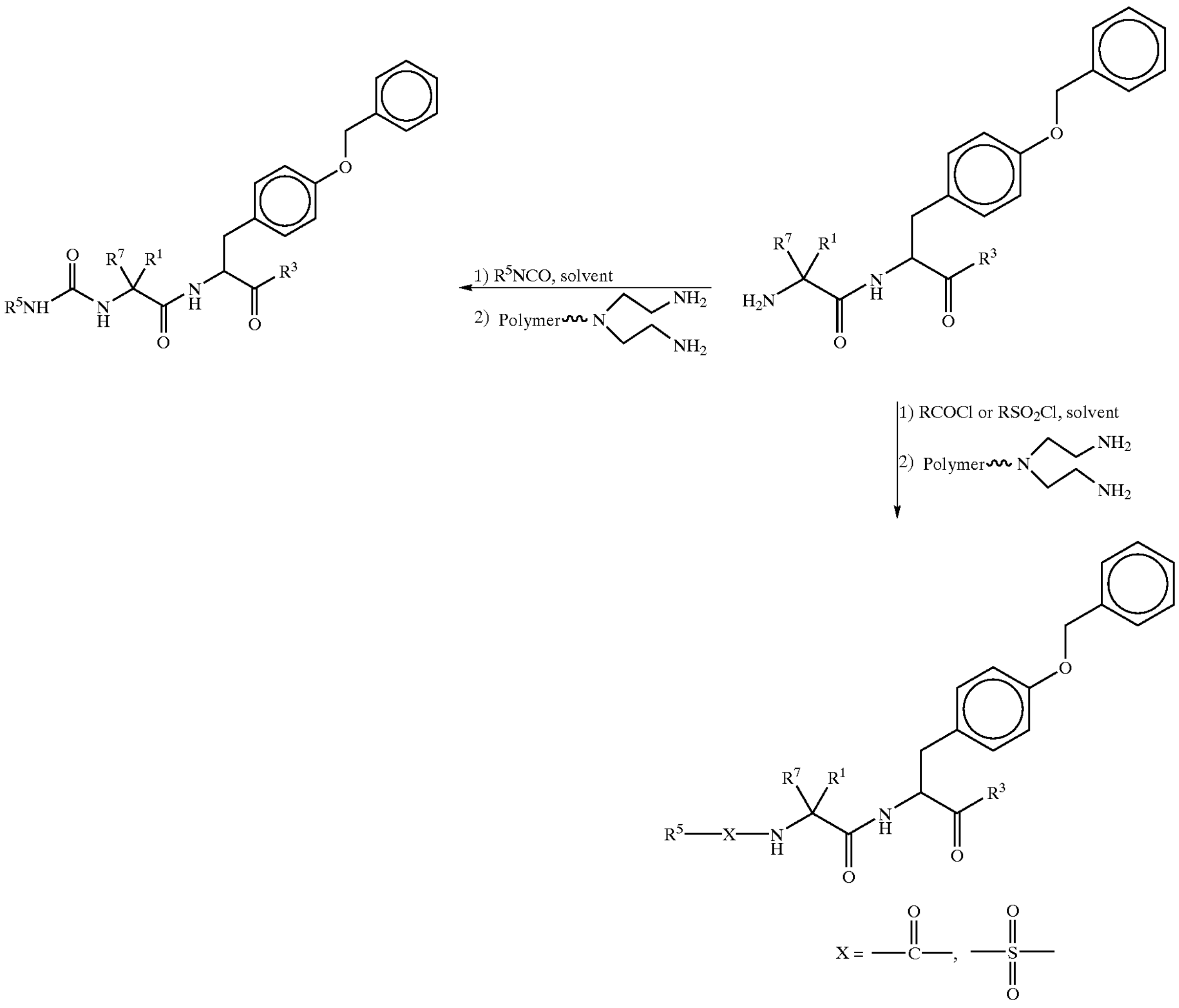
Scheme 4
Multiple Parallel Synthesis Using Kaiser Oxime Resin as Solid Support
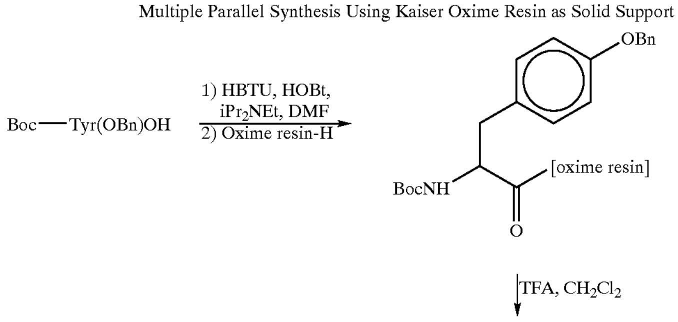

-continued
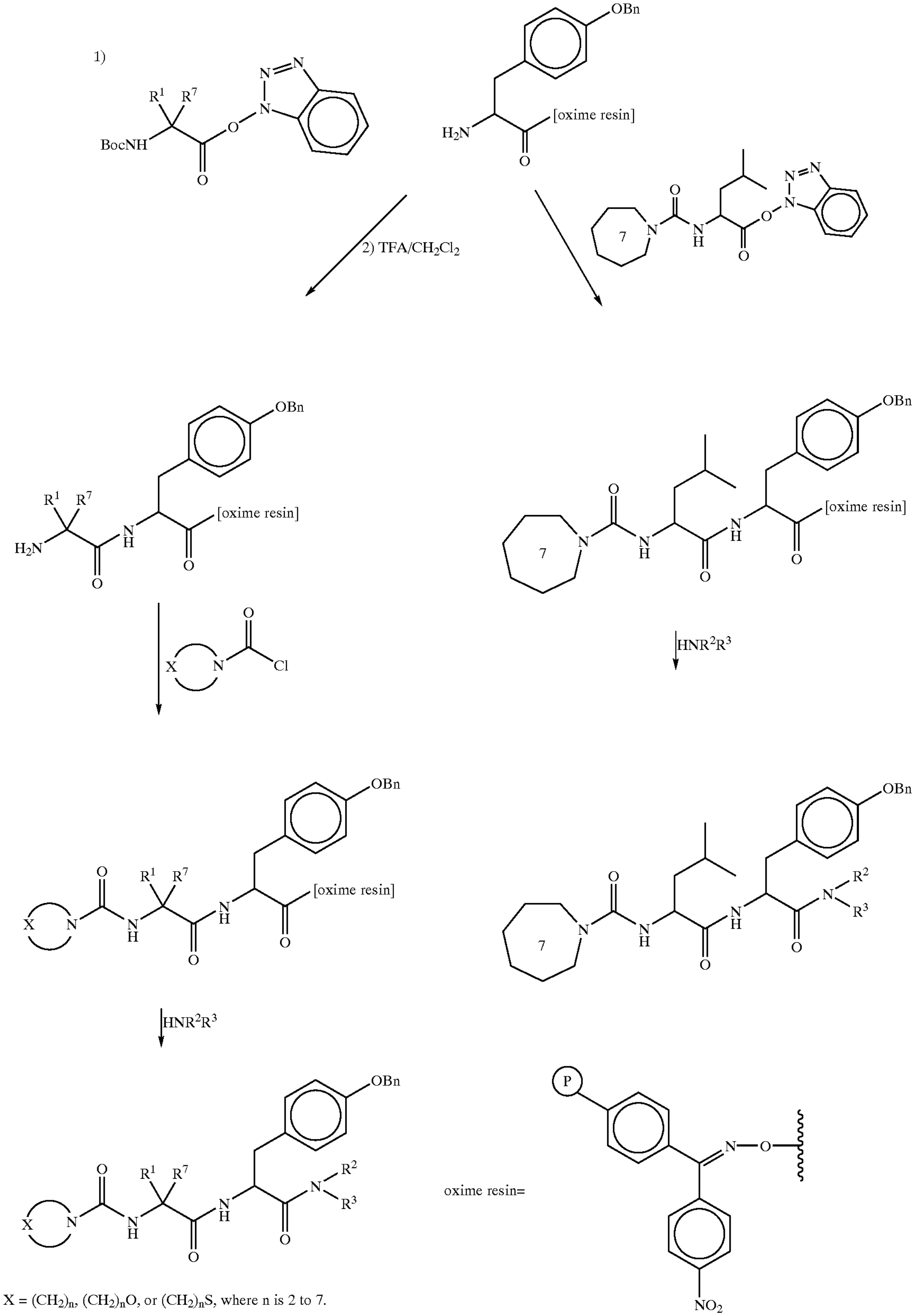
X = $(CH_2)_n$, $(CH_2)_nO$, or $(CH_2)_nS$, where n is 2 to 7.

Scheme 5
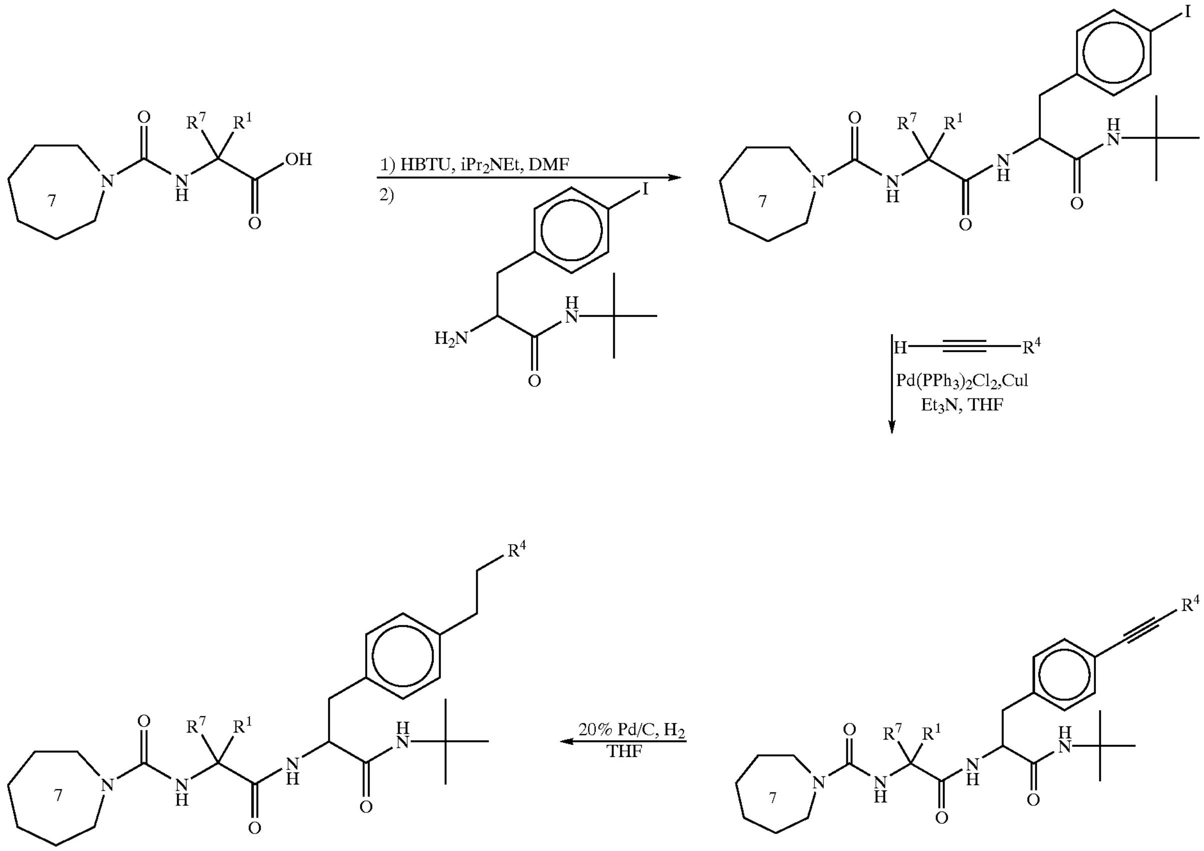
Scheme 6
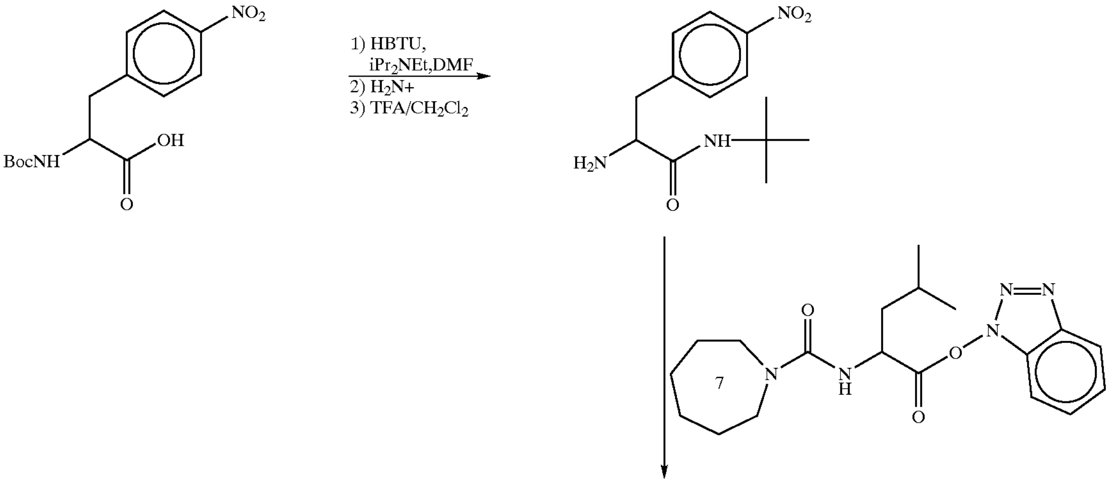

-continued

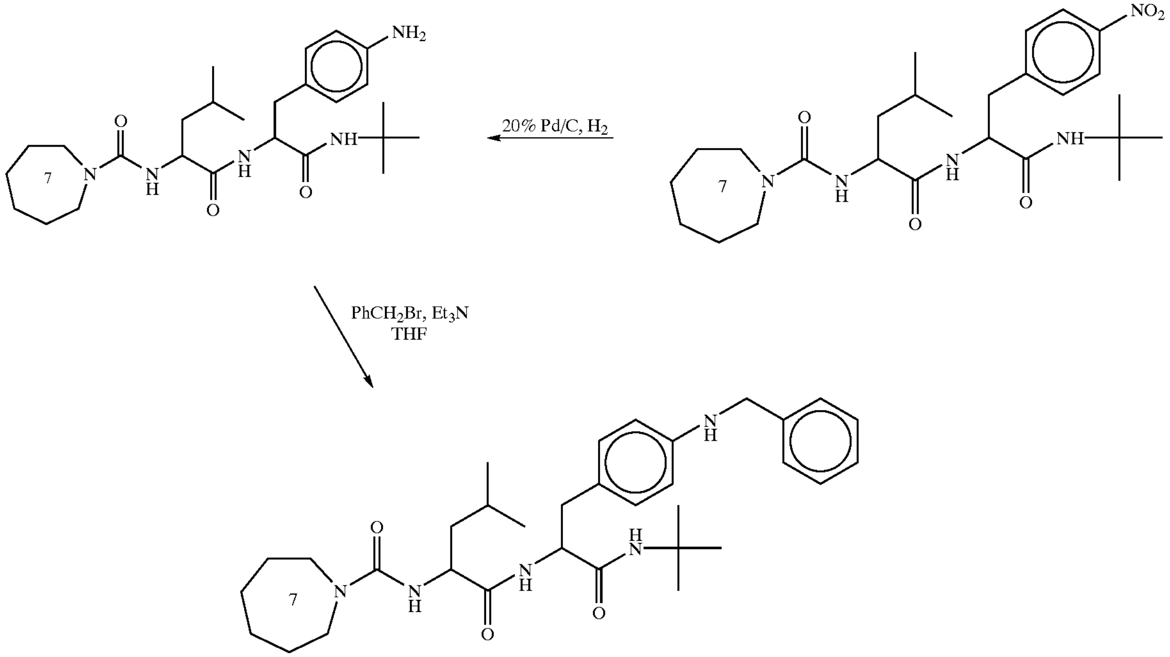

The following abbreviations are used throughout the application.

| | |
|---|---|
| APCI | Atmospheric pressure chemical ionization |
| BOC or Boc | tertiary butyloxy carbonyl |
| BOC-Asu(OtBu)-OH | BOC-Aminosuberic acid tert-butyl ester |
| BOC-OIC | BOC-Octahydroindole-2-carboxylic acid |
| BOP | Benzotriazole-1-yl-oxy-tris-(dimethylamino)-phosphonium hexafluorophosphate |
| BSA | Bovine Serum Albumin |
| Bz or Bn | Benzyl |
| CI | Chemical Ionization |
| DBU | Diazabicycloundecane |
| DCC | N,N'-Dicyclohexylcarbodimide |
| DCM | Dichloromethane |
| DIC | N,N'-Diisopropylcarbodimide |
| DIEA | Diisopropylethylamine |
| DMF | Dimethylformamide or dimethyl formamide |
| EDTA | Ethylenediaminetetraacetic acid |
| EGTA | (Ethylene glycol-bis[β-aminoethyl ether]-N,N,N'N'-tetracetic acid) |
| Et | Ethyl |
| $Et_2O$ | Diethyl ether |
| $Et_3N$ | Triethyl amine |
| EtOAc | Ethyl acetate |
| EtOH | Ethanol |
| FAB | Fast Atom Bombardment |
| FLIPR | Fluorescent Imaging Plate Reader |
| FMOC | 9-Fluorenylmethyloxycarbonyl |
| FMOC-OSu | N-FMOC-succinimide |
| HATU | O-(7-azabenzotriazol-1-yl)-1,1,3,3-tetramethyluronium fluorophosphate |
| HBTU | 2-(1H-benzotriazol-1-yl)-1,1,3,3-tetramethyl uranium hexafluorophosphate |
| HCl | Hydrochloric acid |
| HEPES | (N-[2-Hydroxyethyl]piperazine-N'-[2-ethansulfonic acid]) |
| HOBt | 1-Hydroxybenzotriazole |
| HPLC | High-pressure liquid chromatography |
| HRMS | High-resolution mass spectrum |
| $iPr_2NEt$ | Diisopropylethylamine |
| IR | Infrared |
| iso-pr | Iso-propyl |

-continued

| | |
|---|---|
| MRC | Merrifield Resin Chloromethylpolystyrene-divinylbenzene |
| MS | Mass spectrum |
| msec | millisecond |
| mV | millivolt |
| NMR | nuclear magnetic resonance |
| Pr | propyl |
| SCG | Superior cervical ganglion |
| $SiO_2$ | Silica gel |
| TFA | trifluoroacetic acid |
| THF | tetrahydrofuran |
| TLC | thin layer chromatograph or thin layer chromatography |
| Tyr(OBn)OH | O-Benzyl-tyrosine |

Example A

(S)-2-Amino-3-(4-benzyloxy-phenyl)-propionic acid tert-butyl ester

A solution of L-tyrosine-OBn (Bachem, 50.0 g, 0.184 mol) was dissolved in dioxane (500 mL). The reaction vessel was charged with isobutylene (500 mL) and concentrated sulfuric acid (50 mL). The reaction vessel was sealed and shaken for 64 hours. The reaction mixture was vented and poured into a rapidly stirring mixture of KOH (104 g) in ice water 1000 mL. The resulting mixture was extracted into ether (5×200 mL), and the combined organic extracts were dried ($MgSO_4$), filtered, and concentrated. The residue was purified by chromatography (silica gel, 2:1 $CHCl_3$/EtOAc). The residue obtained from the chromatography solidified on standing to give the product as a tan solid (35.27 g, 59%).

MS (CI) 328 $(MH)^+$

Example B

(R)-2-Amino-3-(4-benzyloxy-phenyl)-propionic acid tert-butyl ester

A solution of D-tyrosine-OBn (Bachem, 10.0 g, 36.9 mmol) was dissolved in dioxane (100 mL). The reaction vessel was charged with isobutylene (100 mL) and concentrated sulfuric acid (10 mL). The reaction vessel was sealed and shaken for 64 hours. The reaction mixture was vented and poured into a rapidly stirring mixture of KOH (26 g) in ice water (250 mL). The resulting mixture was extracted into ether (2×100 mL), and the combined organic extracts were dried ($MgSO_4$), filtered, and concentrated. The residue was purified by chromatography (silica gel, 2:1 $CHCl_3$/EtOAc). The residue obtained from the chromatography solidified on standing to give the product as a yellow oil (6.87 g, 57%).

MS (CI) 328 $(MH)^+$

Example C

2-Amino-2-methyl-3-(4-benzyloxy-phenyl)-propionic acid hydrobromide salt

A solution of α-methyltyrosine (Aldrich Chemical Co., 10.0 g, 51.2 mmol) in 50 mL of 2N NaOH solution was treated with 40 mL of a 0.5 M solution of aqueous $CuSO_4$. The resulting solution was stirred for 45 minutes. The resulting solution was treated with 150 mL of methanol and benzyl bromide (6.7 mL, 56.3 mmol) and stirred for an additional 45 minutes at 50° C. The light purple precipitate which formed was collected by suction filtration and dried under vacuum. The isolated solid was suspended in water and treated with 13 mL of concentrated hydrochloric acid. The suspended solid was collected by filtration, washed sequentially with 1N HCl solution and ether and then dried under vacuum at 45° C. (96 hr) to give the product as an off-white solid (8.7 g, 46%), mp=228–231° C. (dec).

MS (CI) 286 $(MH)^+$

Example D

2-Amino-2-methyl-3-(4-benzyloxy-phenyl)-propionic acid tert-butyl ester

In a manner similar to that described in Example A, the product from Example C (7.5 g) was converted to the title compound (3.4 g, 49%).

Anal. Calc'd for $C_{21}H_{27}NO_3$: C, 73.87; H, 7.97; N, 4.10. Found: C, 73.55; H, 8.04; N, 4.03.

Example E (S)-[2-[(1,1-dimethylethyl)amino]-2-oxo-1-(phenylmethyl)ethyl]-carbamic acid 1,1-dimethylethyl ester A solution of N-(tert-Butyloxycarbonyl)-O-benzyl-L-tyrosine (Bachem, 2.00 g, 5.38 mmol) in 20 mL of DMF was cooled to 0C and treated with $iPr_2NEt$ (1.5 mL) followed by HBTU (2.04 g, 5.38 mmol). The resulting suspension was stirred for 30 minutes at 0° C. and then treated with tert-butylamine (0.48 g, 6.56 mmol). The reaction mixture was stirred for 1 hour at 0° C. and warmed to room temperature. The reaction mixture was poured into $Et_2O$ and washed sequentially with saturated aqueous $NaHCO_3$ solution, and saturated aqueous NaCl solution. The organic phase was dried ($MgSO_4$), filtered, and concentrated. The crude residue was purified by chromatography (silica gel, 3:1 heptane/ethyl acetate) to give the product (2.65 g).

MS (CI) 427 $(MH)^+$

Example F (S)-2-Amino-3-(4-benzyloxy-phenyl)—N-tert-butyl-propionamide

A solution of the product from Example E ((S)-[2-(4-benzyloxy-phenyl)-1-tert-butylcarbamoyl-ethyl]-carbamic acid tert-butyl ester) (6.0 g, 14.1 mmol) in $CH_2Cl_2$ (28 mL) was treated with trifluoroacetic acid (28 mL). The resulting solution was stirred for 20 minutes and then concentrated. The residue was diluted with EtOAc (300 mL), washed with saturated bicarbonate solution (2×300 mL) and brine (300 mL), dried over $Na_2SO_4$, and concentrated to give 4.2 g (91%) of the title compound.

MS: 328 (M+1 for $C_{20}H_{26}N_2O_3$); TLC: Silica gel, $R_f$ 0.43 (10% MeOH/$CH_2Cl_2$).

Example G (S)-2-(9H-Fluoren-9-ylmethoxycarbonylamino)-3-(4-hydroxyphenyl)-propionic acid tert-butyl ester A solution of -tyrosine t-butyl ester (Bachem, 20.0 g, 84.3 mmol) and FMOC-OSu (Bachem, 24.68 g, 71.2 mmol) was dissolved in 400 mL of dioxane and 400 mL of water. The pH of the resulting solution was adjusted to pH=9 and the solution stirred overnight at room temperature. The reaction mixture was concentrated to ½ volume and treated with concentrated HCl until the pH=5. The resulting solution was extracted with ethyl acetate (5×150 mL), the combined organic extracts were dried with $MgSO_4$ and concentrated. The residue was crystallized from hot heptane/EtOAc. The solid that formed was collected by filtration and air dried to give the title compound (28.5 g, 87%) as a white solid.

APCI MS 460 $(MH)^+$

Example H (S)-2-(9H-Fluoren-9-ylmethoxycarbonylamino)-3-[4-(pyridin-2-ylmethoxy)-phenyl]-propionic acid tert-butyl ester The product from Example G ((S)-2-(9H-fluoren-9-ylmethoxycarbonylamino)-3-(4-hydroxyphenyl)-propionic acid tert-butyl ester) (4.00 g, 8.64 mmol), 2-pyridylcarbinol (0.92 mL, 9.50 mmol) and triphenylphosphine (2.24 g, 8.64 mmol) were dissolved in 50 mL of dry THF. The solution was cooled in an ice bath under an argon atmosphere and diethyl azidocarboxylate (1.36 mL, 8.64 mmol) was added dropwise over 20 minutes. The ice bath was removed and the solution allowed to stir overnight at room temperature. The solution was concentrated under reduced pressure and partitioned between ethyl acetate and water (100 mL each) and separated. The organic layer was washed with 10% aqueous HCl (2×50 mL), 10% sodium bicarbonate (2×50 mL), brine (2×50 mL), dried with magnesium sulfate, filtered, and concentrated under reduced pressure to a foam (4.80 g). The foam was purified by chromatography (silica gel, 1:1.5 ethyl acetate/hexane) to give the product as a white foam (3.90 g, 82%).

Example I (S)-2-(9H-Fluoren-9-ylmethoxycarbonylamino)-3-[4-(pyridin-3-ylmethoxy)-phenyl]-propionic acid tert-butyl ester In a manner similar to that described in Example H, the product from Example G ((S)-2-(9H-fluoren-9-ylmethoxycarbonylamino)-3-(4-hydroxyphenyl)-propionic acid tert-butyl ester) (4.39 g, 9.50 mmol) and 3-pyridylcarbinol (0.92 mL, 9.50 mmol) were converted to the title compound.

Example J (S)-2-(9H-Fluoren-9ylmethoxycarbonylamino)-3-[4-(pyridin-4-ylmethoxy)-phenyl]-propionic acid tert-butyl ester In a manner similar to that described in Example H, the product from Example G (0.5 g, 1.08 mmol) and 4-pyridylcarbinol (0.12 mL, 1.26 mmol) were converted to the title compound.

Example K (S)-2-(9H-Fluoren-9-ylmethoxycarbonylamino)3-[4-(4-cyano-benzyloxy)-phenyl]-propionic acid tert-butyl ester A solution of the product from Example G (1.0 g, 2.18 mmol) was dissolved in DMF and cooled to 0° C. The resulting solution treated with NaH (2.18 mmol) and was stirred for 1 hour at 0° C. and treated with α-bromo-p-tolunitrile (0.45 g, 2.30 mmol). The reaction mixture was warmed to room temperature and stirred overnight. The reaction mixture was poured into a separatory funnel containing ethyl acetate (50 mL) and water (50 mL) and shaken. The organic phase was separated and washed with brine, dried, and concentrated to give the title compound (0.76 g, 61%).

Example L (S)-2-(9H-Fluoren-9-ylmethoxycarbonylamino)-3-[4-(3-tert-butoxycarbonylamino-benzyloxy)-phenyl]-propionic acid tert-butyl ester In a manner similar to that described in Example H, the product from Example G (0.50 g, 1.08 mmol) and BOC-3-aminobenzylalcohol (0.24 g, 1.08 mmol) were converted to the title compound (0.40 g, 60%).

Example M (S)-2-Amino-3-[4-(pyridin-2-ylmethoxy)-phenyl]-propionic acid tert-butyl ester The product from Example H (3.90 g, 8.42 mmol) was suspended in 50 mL of 20% piperidine in dichloromethane at room temperature with stirring (2 h). The solution was concentrated under reduced pressure and partitioned between ethyl acetate and water (100 mL each) and separated. The organic layer was washed with 5% sodium bicarbonate (2×50 mL), brine (2×50 mL), dried with magnesium sulfate, filtered and concentrated under reduced pressure to an oil. The oil was purified by silica gel chromatography with ethyl acetate and methanol (3:1). Appropriate fractions were combined and concentrated under reduced pressure to a solid (1.34 g).

Example N cl (S)-2-Amino-3-[4-(pyridin-3-ylmethoxy)-phenyl]-propionic acid tert-butyl ester In a manner similar to that described in Example M, the product from Example I is converted to the title compound.

Example O (S)-2-Amino-3-[4-(pyridin-4-ylmethoxy)-phenyl]-propionic acid tert-butyl ester In a manner similar to that described in Example M, the product from Example J (0.20 g, 0.36 mmol) was converted to the title compound. The material was used directly in the preparation of Example 26.

Example P (S)-2-amino-3-[4-(4-cyano-benzyloxy)-phenyl]-propionic acid tert-butyl ester In a manner similar to that described in Example M, the product from Example K is converted to the title compound.

Example Q (S)-2-amino-3-[4-(3-tert-butoxycarbonylamino-benzyloxy)-phenyl]-propionic acid tert-butyl ester In a manner similar to that described in Example M, the product from Example L is converted to the title compound.

Example R (S)-2-[(Azepane-1-carbonyl)-amino]-4-methyl-pentanoic acid benzyl ester A solution of triphosgene (15.7 g, 52.9 mmol) in $CH_2Cl_2$ (600 mL) was cooled to −10° C. under a nitrogen atmosphere. The solution was treated dropwise with a solution of (S)-2-amino-4-methyl-pentanoic acid benzyl ester (Bachem, 28.1 g, 0.127 mol) and pyridine (26 mL, 0.32 mol) in 150 mL of $CH_2Cl_2$. The resulting solution was stirred at −10° C. for 90 minutes and then treated with a solution of hexamethylenimine (22 mL, 0.38 mmol) in 75 mL of $CH_2Cl_2$ The resulting solution was stirred for 48 hours at room temperature. The reaction mixture was concentrated, and the residue was dissolved in ether and washed with 1N HCl solution, water, and saturated aqueous $CuSO_4$ solution. The organic layer was dried ($MgSO_4$), treated with activated charcoal, and filtered. The filtrate was concentrated to approximately ½ volume and treated with hexane. The resulting suspension was stored overnight at −10° C. The solid was collected by filtration, washed with hexane, and dried under vacuum to give the title compound as a white solid (38.6 g, 88%), mp=87–88° C.

MS (CI) 347 $(MH)^+$

Example S (R)-2-[(Azepane-1-carbonyl)-amino]-4-methyl-pentanoic acid benzyl ester A solution of (R)-2-amino-4-methyl-pentanoic acid benzyl ester (Bachem, 14.1 g, 63.6 mmol) and pyridine (25 mL, 0.31 mmol) in 400 mL of $CH_2Cl_2$ was cooled to 0° C. and treated rapidly with phosgene (40 mL of a 1.9 M solution in toluene) in one portion. The resulting solution was stirred at 0° C. for 2 hours and then treated with hexamethylenimine (9.3 mL, 82.7 mmol) in $CHCl_3$ (25 mL). The resulting solution was warmed to room temperature and concentrated. The residue was dissolved in ether and washed with aqueous 1N HCl solution. The organic phase was dried ($MgSO_4$), filtered, and concentrated. The crude residue was purified by chromatography (silica gel, 2:1 heptane/ethyl acetate) to give the title compound as a yellow solid (4.96 g, 68%), mp=88–89° C.

CI MS 347 $(MH)^+$

Example T (S)-2-[(Azepane-1-carbonyl)-amino]-3-methyl-pentanoic acid benzyl ester In a manner similar to that described in Example S, (S)-2-amino-3-methyl-pentanoic acid benzyl ester (Bachem, 4.89 g, 22.1 mmol) was converted to the title compound (6.09 g, 79%).

Example U (S)-2-[(Azepane-1-carbonyl)-amino]-3-methyl-butanoic acid benzyl ester In a manner similar to that described in Example S, (S)-2-amino-3-methyl-butanoic acid benzyl ester (Bachem, 8.79 g, 42.1 mmol) was converted to the title compound (2.43 g, 17%).

MS (CI) 332 $(MH)^+$

Example V (S)-2-[(Azepane-1-carbonyl)-amino]-propanoic acid benzyl ester

In a manner similar to that described in Example S, L-alanine benzyl ester (Bachem, 15.0 g, 69.6 mmol) was converted to the title compound (9.00 g, 42%). MS (CI) 306 $(MH)^+$ Example W 2-[(Azepane-1-carbonyl)-amino]-acetic acid benzyl ester In a manner similar to that described in Example U, glycine benzyl ester (Bachem, 15.0 g, 74.4 mmol) was converted to the title compound (16.7 g, 77%).

MS (CI) 241 $(MH)^+$

Example X (S)-2-[(4-methyl-piperazine-1-carbonyl)-amino]-4-methyl-pentanoic acid benzyl ester In a manner similar to that described in Example S, (S)-2-amino4-methyl-pentanoic acid benzyl ester (Bachem, 3.01 g, 13.6 mmol) and N-methlypiperazine (1.63 g, 16.3 mmol) were converted to the title compound (3.17 g, 67%).

Example Y (S)-4-Methyl-2-[(4-phenyl-piperazine-1-carbonyl)-amino]-pentanoic acid benzyl ester In a manner similar to that described in Example S, (S)-2-amino-4-methyl-pentanoic acid benzyl ester (Bachem, 2.80 g, 12.7 mmol) and N-phenylpiperazine (4.12 g, 25.4 mmol) were converted to the title compound (3.8 g, 73%), mp=88° C.

Anal. Calc'd for $C_{24}H_{31}N_3O_3$: C, 70.39; H, 7.63; N, 10.26. Found: C, 70.50; H, 7.61; N, 10.24.

Example Z (S)-2-[(Azepane-1-carbonyl)-amino]-4-methyl-pentanoic acid

A solution of the product from Example R (2(S)-[(azepane-1-carbonyl)-amino]-4-methyl-pentanoic acid benzyl ester) (38.5 g, 111 mmol) in 600 mL of THF was hydrogenated at 50 psi over 20% Pd/C (2.00 g) for 17 minutes. The reaction mixture was filtered through celite and concentrated to dryness. The residue was heated in 50 mL of hexane. The resulting suspension was cooled and the solid collected by filtration and washed with hexane. The solid was dried at room temperature under vacuum to give the title compound as a white solid (26.6 g, 93%), mp=88–89° C.

Anal. Calc'd for $C_{13}H_{24}N_2O_3$: C, 60.91; H, 9.44; N, 10.93. Found: C, 60.99; H, 9.46; N, 10.85.

Example AA (R)-2-[(Azepane-1-carbonyl)-amino]-4-methyl-pentanoic acid

In a manner similar to that described in Example Z, the product from Example S ((R)-2-[(azepane-1-carbonyl)-amino]-4-methyl-pentanoic acid benzyl ester) (9.03 g, 26.1 mmol) was converted to the title compound (6.25 g, 93%), mp=87–88° C.

Anal. Calc'd for $C_{13}H_{24}N_2O_3$: C, 60.91; H, 9.44; N, 10.93. Found: C, 60.85; H, 9.33; N, 10.92.

Example AB (S)-2-[(Azepane-1-carbonyl)-amino]-3-methyl-pentanoic acid

In a manner similar to that described in Example Z, the product from Example T ((S)-2-[(azepane-1-carbonyl)-amino]-3-methyl-pentanoic acid benzyl ester) (6.03 g, 17.4 mmol) was converted to the title compound (3.57 g, 80%).

MS (CI) 247 $(MH)^+$

Example AC (S)-2-[(Azepane-1-carbonyl)-amino]-3-methyl-butanoic acid

In a manner similar to that described in Example Z, the product from Example U ((S)-2-[(azepane-1-carbonyl)-amino]-3-methyl-butanoic acid benzyl ester) (2.33 g, 7.01 mmol) was converted to the title compound (1.40 g, 82%).

Example AD (S)-2-[(Azepane-1-carbonyl)-amino]-propanoic acid

In a manner similar to that described in Example Z, the product from Example V ((S)-2-[(azepane-1-carbonyl)-amino]-propanoic acid benzyl ester) (9.00 g, 31.0 mmol) was converted to the title compound (4.90 g, 77%).

MS (CI) 215 $(MH)^+$

Example AE

2-[(Azepane-1-carbonyl)-amino]-acetic acid

In a manner similar to that described in Example Z, the product from Example W (2-[(azepane-1-carbonyl)-amino]-acetic acid benzyl ester) (2.07 g, 7.1 mmol) was converted to the title compound (0.50 g, 70%).

MS (CI) 201 $(MH)^+$

Example AF (S)-2-[(4-methyl-piperazine-1-carbonyl)-amino]-4-methyl-pentanoic acid In a manner similar to that described in Example Z, the product from Example X ((S)-2-[(4-methyl-piperazine-1-carbonyl)-amino]-4-methyl-pentanoic acid benzyl ester) (1.70 g, 4.89 mmol) was converted to the title compound (0.95 g, 77%).

Anal. Calc'd for $C_{12}H_{23}N_3O_3$: C, 56.03; H, 8.95; N, 16.34. Found: C, 55.85; H, 8.87;N, 16.21.

Example AG (S)-4-Methyl-2-[(4-phenyl-piperazine-1-carbonyl)-amino]-pentanoic acid In a manner similar to that described in Example Z, the product from Example Y ((S)-4-methyl-2-[(4-phenyl-piperazine-1-carbonyl)-amino]-pentanoic acid benzyl ester)

(2.8 g, 6.78 mmol) was converted to the title compound (0.93 g, 43%).

MS (CI) 321 $(MH)^+$

Example AH

[S-(R*,R*)]-3-(4-Benzyloxy-phenyl)-2-{2-[(9H-fluoren-9-ylmethyl)-amino]-4-methyl-pentanoylamino}-propionic acid tert-butyl ester A solution of FMOC-leucine (10.3 g, 29 mmol) in 300 mL of DMF was cooled to 0° C. and treated with diisopropylethyl amine (73 mL) and HBTU (11.1 g, 29.2 mmol). The resulting solution was stirred at 0° C. for 30 minutes and treated with the product from Example A ((S)-2-amino-3-(4-benzyloxy-phenyl)-propionic acid tert-butyl ester) (11.0 g, 36.9 mmol). The resulting solution was stirred for 30 minutes at 0° C. and warmed to room temperature. The reaction mixture was poured into 500 mL of ether and washed sequentially with 1N aqueous HCl, saturated aqueous $NaHCO_3$ (100 mL) and brine (5×100 mL). The organic phase was collected, dried $MgSO_4$ and concentrated to near dryness. The residue was triturated with hexane. The product was collected by suction filtration and air dried to give the title compound as a white solid (12.16 g, 70%), mp=158–160° C.

Anal. Calc'd for $C_{41}H_{46}N_2O_6$: C, 74.30; H, 7.00; N, 4.23. Found: C, 74.21; H, 7.25; N, 4.20.

Example AI

[S-(R*,R*)]-2-{2-Amino-4-methyl-pentanoylamino}-3-(4-benzyloxy-phenyl)-propionic acid tert-butyl ester A solution of the product from Example AH (3-(4-benzyloxy-phenyl)-2-{2-[(9H-fluoren-9-ylmethyl)-amino]-4-methyl-pentanoylamino}-propionic acid tert-butyl ester) (12.2 g, 20.0 mmol) in 500 mL of tetrahydrofuran was treated with piperidine (80 mL). The resulting solution was stirred at room temperature for 48 hours. The reaction mixture was concentrated and the residue purified by chromatography (silica gel, gradient elution EtOAc—15% EtOH/EtOAc). The resulting yellow solid was broken up in heptane to give the title compound as a white solid (6.77 g, 77%), mp=56–60° C.

Anal. Calc'd for $C_{26}H_{36}N_2O_4$: C, 70.88; H, 8.24; N, 6.36. Found: C, 70.91; H, 8.51; N, 6.28.

Example AJ (S)-[2-(4-nitrophenyl)-1-tert-butylcarbamoyl-ethyl]-carbamic acid tert-butyl ester A reaction mixture of BOC-L-4-nitrophenylalanine (4.65 g, 1.5 mmol), tert-butylamine (2.19 g, 30 mmol), DMF (10 mL), HBTU (5.69 g, 15 mmol), and diisopropylethylamine (2.48 g, 22 mmol) was stirred for 2 hours. After the reaction was finished, the reaction mixture was added EtOAc (75 mL), and the EtOAc solution was washed with $NaHCO_3$ (100 mL, 4 times), dried over $NaHCO_3$, and concentrated to dryness. The crude reaction mixture was further purified by column chromatography ($SiO_2$, EtOAc/hexane 1:1) to yield the title compound (5.3 g), mp=158–159° C.

Anal. Calc'd for $C_{18}H_{28}N_3O_5$: C, 59.00; H, 7.70; N, 11.47. Found: C, 59.15; H, 7.33; N, 11.36.

Example AK (S)-2-Amino-3-(4-nitrophenyl)-N-tert-butylpropionamide

A solution of the product from Example AJ ((S)-[2-(4-nitrophenyl)-1-tert-butylcarbamoyl-ethyl]-carbamic acid tert-butyl ester) (2, 2.0 g, 5.25 mmol) was stirred in a solution of $TFA/CH_2Cl_2$ (15 mL/15 mL) for 30 minutes and concentrated to dryness. This crude reaction product was redissolved in $CH_2Cl_2$ (50 mL) then washed with $NaHCO_3$ (aq) and brine. The EtOAc solution was further dried over $NaHCO_3$ and concentrated to dryness to yield the title compound (1.34 g).

APCI MS 266 $(MH)^+$

Example AL

[S-(R*,R*)]-Azepane-1-carboxylic acid {1-[1-tert-butylcarbamoyl-2-(4-nitro-phenyl)-ethylcarbamoyl]-3-methyl-butyl}-amide The crude product from Example AK ((S)-2-Amino-3-(4-nitrophenyl)-N-tert-butylpropionamide) (1.34 g, 5.25 mmol) and the product from Example Z (1.35 g, 5.25 mmol) were dissolved in DMF (40 mL), then HBTU (1.99 g, 5.25 mmol) and diisopropylethylamine (4.3 g, 33 mol) were added and stirred for 1 hour. The mixture was poured into $CH_2Cl_2$ (100 mL); the $CH_2Cl_2$ solution was washed with aqueous sodium bicarbonate (3×) and dried over sodium bicarbonate. The crude reaction mixture was further purified by column chromatography ($SiO_2$, EtOAc) to yield the title compound (2.5 g), mp 194–195° C.

Anal. Calc'd for $C_{26}H_{41}N_5O_5.0.75H_2O$: C, 60.38; H, 8.28; N, 13.54. Found: C, 59.99; H, 8.01; N, 13.31.

Example AM

[S-(R*,R*)]-Azepane-1-carboxylic acid {1-[1-tert-butylcarbamoyl-2-(4-amino-phenyl)-ethylcarbamoyl]-3-methyl-butyl}-amide A reaction mixture of the product from Example AL (0.5 g) and Pd/C (5%, 0.1 g) in MeOH (50 mL) was hydrogenated under $H_2$. Then the catalyst was removed by filtration, and the reaction mixture was concentrated down to yield the 25 title compound (0.45 g). For analysis, a small amount of material was converted to the hydrochloride salt, mp=177–178° C.

Anal. Calc'd for $C_{26}H_{43}N_5O_3.HCl.H_2O$: C, 57.18; H, 8.86; N, 12.83. Found: C, 57.50; H, 8.62; N, 12.40.

Example AN (S)-[2-(4-iodophenyl)-1-tert-butylcarbamoyl-ethyl]-carbamic acid tert-butyl ester A reaction mixture of BOC-L-4-iodophenylalanine (10 g, 25.6 mmol), tert-butylamine (2.19 g, 30 mmol), DMF (25 mL), HBTU (9.7 g, 25.6 mmol), and diisopropylethylamine (6.6 g, 51 mmol) was stirred for 2 hours. The mixture was diluted with 40 mL of diethylether, washed with 1N HCl (2×25 mL), saturated $NaHCO_3$ (2×25 mL), and saturated solution of brine (2×25 mL). The organic layer was separated, dried with $Na_2SO_4$, and evaporated to dryness. The crude was purified by column chromatography (silica gel, 25% EtOAc/hexanes) to yield the title compound (10.2 g).

APCI MS 447 $(MH^+)$

Example AO (S)-2-Amino-3-(4-iodophenyl)-N-tert-butylpropionamide

A solution of the product from Example AN (10.2 g, 22.8 mmol) was stirred in a solution of $TFA/CH_2Cl_2$=1:1 (30 mL)

for 30 minutes and concentrated to dryness. This crude reaction product was dissolved in $CH_2Cl_2$ (50 mL) then washed with $NaHCO_3$ (aq) and brine. The $CH_2Cl_2$ solution was further dried over $NaHCO_3$ and concentrated to dryness to yield the title compound (7.6 g).

Example AP

[S-(R*,R*)]-Azepane-1-carboxylic acid {1-[1-tert-butylcarbamoyl-2-(4-iodo-phenyl)-ethylcarbamoyl]-3-methyl-butyl}-amide To a solution of the product from Example AO (0.29 g, 1.13 mmol) in 10 mL of DMF was added HBTU (0.43 g, 1.13 mmol) and 5 mL of $iPr_2NEt$. The mixture was stirred for 30 minutes at 0° C. A solution of the product from Example Z (0.39 g, 1.13 mmol) was added to the reaction mixture. The reaction mixture was allowed to reach the room temperature and was stirred for another 30 minutes. The mixture was diluted with 20 mL of diethylether, washed with 1N HCl (2×10 mL), saturated $NaHCO_3$ (2×10 mL), and saturated solution of brine (2×10 mL). The organic layer was separated, dried with $Na_2SO_4$, and evaporated to dryness. The crude was crystallized from $CH_2Cl_2$ and petroleum ether to give the title compound (0.56 g, 85%) of white solid, mp=190–191° C.

Anal. Calc'd for $C_{26}H_{41}N_4O_3I$: C, 53.42; H, 7.07; N, 9.58. Found: C, 53.53; H, 7.20; N, 9.43.

Example AQ

BOC-Tyr(OBn)-OH coupled to Kaiser oxime resin

A reaction vessel equipped with a fritted glass filter was charged with Kaiser oxime resin (10.0 g, load 0.91 mmol/g) and washed sequentially with $CH_2Cl_2$ (3×) and dimethylformamide (3×). In a separate reaction vessel, a solution of N-(tert-Butyloxycarbonyl)-O-benzyl-L-tyrosine (8.44 g, 22.7 mmol) in 40 mL of DMF was treated with $iPr_2NEt$ (7.82 mL, 45.5 mmol), HBTU (8.62 g, 22.7 mmol) and HOBt (1.74 g, 11.37 mmol). The resulting solution was stirred for 10 minutes and added to the reaction vessel containing the washed Kaiser oxime resin. The resulting suspension was shaken overnight at room temperature and then washed with dimethyl formamide (5×). The entire procedure was repeated 3×. After the third coupling, the resulting suspension was then washed with dimethylformamide (3×) and $CH_2Cl_2$ (3×).

Example AR

H-Tyr(OBn)-OH coupled to Kaiser oxime resin

The resin prepared in Example AQ was washed with dimethylformamide (3×) and $CH_2Cl_2$ (3×) and then treated with a solution of 25% trifluoroacetic acid in $CH_2Cl_2$ (v/v) for 30 minutes. The resin was then washed with $CH_2Cl_2$ (3×), 5% diisopropylamine in $CH_2Cl_2$ (v/v), $CH_2Cl_2$ (3×), and dimethylformamide (3×).

Example AS

2-{2-[(Azepane-1-carbonyl-carbonyl)-amino]-4-methyl-pentanoylamino}-3-(4-benzyloxy-phenyl)-propionic acid Kaiser oxime resin ester A solution of the product from Example Z ((S)-2-[(azepane-1-carbonyl)-amino]-4-methyl-pentanoic acid) (1.16 g, 4.55 mmol) in 30 mL of DMF was treated with $iPr_2NEt$ (1.6 mL, 9.1 mmol), HBTU (1.72 g, 4.55 mmol), and HOBt (0.97 g, 4.55 mmol) and the resulting solution stirred for 10 minutes at room temperature. The reaction mixture was added to the resin obtained from Example AR, and the resulting suspension was shaken for 1 hour. The resin was washed with DMF (5×) and collected.

Example AT

Hexahydroazepinecarbonyl Chloride

To a cold solution of hexamethyleneimine (100 g, 1.008 mol) and disopropylethylamine (130 g, 1.008 mol) in 600 mL of dichloromethane at −0° C. $CO_2$ was bubbled for 45 minutes. This cold mixture was then added dropwise to a solution of thionyl chloride (120 g, 1.008 mol) in 1 L of dichloromethane kept at −10° C. The reaction mixture was stirred for 2 hours at −10° C. The mixture was then poured into 1.2 L of 0.1N HCl solution. Layers were separated, the organic layer was dried over anhydrous $Na_2SO_4$, and concentrated. The crude mixture was distilled via a short-path fractionating column to yield the title compound at 66–67° C. at 0.08 mm of Hg as a clear oil (56 g).

Example AU

N-BOC-p-benzyl-L-phenylalanine

A solution of N-BOC-P-benzoyl-L-phenylalanine (Bachem, 3.89 g, 10.5 mmol) in 100 mL of tetrahydrofuran was hydrogenated (50 psi) for 40 hours over 20% palladium on carbon. The reaction mixture was filtered and concentrated to give the title compound as a white solid (3.89 g), mp=103–107° C.

Example AV (S)-[2-(4-Benzyl-phenyl)-1-tert-butylcarbamoyl-ethyl]-carbamic acid tert-butyl ester A reaction mixture of the product from Example AU (0.498 g, 1.4 mmol), tert-butylamine (0.102 g, 1.4 mmol), DMF (10 mL), HBTU (0.379 g, 1.4 mmol), and diisopropylethylamine (0.36 g, 2.8 mmol) was stirred for 2 hours. The mixture was diluted with 10 mL of diethylether, washed with 1N HCl (2×5 mL), saturated $NaHCO_3$ (2×5 mL), and saturated solution of brine (2×5 mL). The organic layer was separated, dried with $Na_2SO_4$, and evaporated to dryness. The crude was purified by column chromatography ($SiO_2$, EtOAc/hexanes=3:7) to yield the title compound (0.52 g).

Example AW (S)-2-Amino-3-(4-benzyl-pheny)-N-tert-butyl propionamide

A solution of the product from Example AV (0.52 g, 1.27 mmol) was stirred in a solution of TFA/$CH_2Cl_2$=1:1 (10 mL) for 30 minutes and concentrated to dryness. This crude reaction product was redissolved in $CH_2Cl_2$ (50 mL) then washed with $NaHCO_3$ (aq) and brine. The $CH_2Cl_2$ solution was further dried over $NaHCO_3$ and concentrated to dryness to yield the title compound (0.392 g).

Example AX (S)-[2-(4-(2,6-dichloro-benzyloxy)-phenyl)-1-tert-butylcarbamoyl-ethyl]-carbamic acid tert-butyl ester A solution of BOC-O-(2,6-dichlorobenzyl)-L-tyrosine (Bachem, 2.00 g, 4.54 mmol) in 20 mL of DMF and $iPr_2NEt$ (1.6 mL) was cooled to 0° C. and treated with HBTU (1.72 g, 4.54 mmol). The resulting solution was stirred at 0° C. for 30 minutes and treated with tert-butyl amine (0.48 mL, 4.54 mmol). The resulting solution was stirred overnight. The reaction mixture was poured into ether (100 mL) and washed sequentially with saturated aqueous $NaHCO_3$ solution (20 mL) and brine (4×20 mL). The organic phase was collected and dried ($MgSO_4$) and concentrated. The crude reaction product was purified by chromatography (silica gel, 2:1 heptane/EtOAc). The solid obtained was crystallized from hot heptane, collected by suction filtration and dried to give the title compound as a white solid (1.56 g, 69%), mp=82–86° C.

Example AY (S)-2-Amino-3-[4-(2,6-dichloro-benzyloxy)-pheny]-N-tert-butyl propionamide A solution of the product from Example AX (0.52 g, 1.27 mmol) was stirred in a solution of TFA (5 mL) and $CH_2Cl_2$ (5 mL) for 30 minutes and concentrated to dryness. The crude reaction product was dissolved in $CH_2Cl_2$ (50 mL) and washed with saturated aqueous $NaHCO_3$ solution and brine. The organic phase was dried ($Na_2SO_4$) and concentrated to give the title compound (0.39 g).

Example AZ

Preparation of Merrifields Resin Coupled to Guanidine

To a stirred suspension of Merrifields resin (10 g, 1.7 mmol Cl/g) in DMF (200 mL) were added guanidine hydrochloride (16 g) and DBU (20.5 mL). The reaction mixture was heated at 90° C. for 36 hours and cooled to room temperature. The resin was washed sequentially with DMF/DBU (70:30) (1×200 mL), DMF (2×200 mL), MeOH (2×200 mL), water (2×200 mL), MeOH (2×200 mL), THF (3×200 mL), $Et_2O$ (3×200 mL). The resin was dried in a vacuum oven at 40° C. for 18 hours and used without further purification.

Example BA (S)-2-[(Azepane-1-carbonyl)-amino]-3-phenyl-propionic acid benzyl ester A solution of phenylalanine benzyl ester (8.80 g, 23.4 mmol) in toluene was treated with diphosgene (4.63 g, 23.4 mmol) and activated charcoal (100 mg). The resulting suspension was heated at reflux for 4.5 hours then cooled to room temperature and stirred overnight. The reaction mixture was filtered through celite and concentrated. The residue was dissolved in EtOAc, cooled to 0° C. and treated with hexamethyleneimine (2.32 g, 23.4 mmol) and stirred for 2 hours. Additional hexamethyleneimine (1.0 mL) was added and the reaction mixture warmed to room temperature and stirred overnight. The reaction mixture was washed with 1N HCl solution, brine, dried ($MgSO_4$) and concentrated. The residue was purified by chromatography (silica gel, gradient elution 4:1 hexane/EtOAc to 1:1 hexane/EtOAc) to give the title compound as a white solid (3.94 g, 44%).

Example BB (S)-2-[(Azepane-1-carbonyl)-amino]-3-(1-formyl-1H-indol-3-yl)-propionic acid benzyl ester A solution of BOC-L-Trp(formyl)-OBn in toluene was converted to the title compound by the procedure described in Example BA (1.60 g).

MS (CI) 448 $(MH)^+$

Example BC (S)-2-[(Azepane-1-carbonyl)-amino]-3-phenyl-propionic acid

A solution of the product from Example BA (3.80 g, 10.0 mmol) in methanol was hydrogenated at 50 psi over 20% Pd/C for 3 hours. The reaction mixture was filtered through celite filtered and concentrated to give the title compound as a glassy solid (2.88 g, 98%).

MS (CI) 291 $(MH)^+$

Example BD (S)-2-[(Azepane-1-carbonyl)-amino]-3-(1H-indol-3-yl)-propionic acid

A solution of the product from Example BB (1.01 g, 2.25 mmol) in methanol was hydrogenated at 50 psi over 20% Pd/C (0.10 g) for 30 minutes. The reaction mixture was filtered through celite and the filtrate concentrated to give the title compound as a foam (0.29 g, 39%).

Example BE (S)-2-Amino-3-[4-(4-methyl-benzyloxy)-phenyl]-propionic acid

A mixture of tyrosine (1.83 g, 10 mmol) and $CuSO_4$ (0.81 g, 5 mmol) in 10 mL of 2N NaOH and 5 mL $H_2O$ was heated to 60° C. and cooled to room temperature. The reaction mixture was treated with MeOH (35 mL) and 2N NaOH (1.5 mL) followed by α-bromo-p-xylene. The resulting mixture was stirred at 25° C. for 2 hours and filtered. The solid obtained was washed with a 17.5:5 $H_2O$/MeOH solution followed by MeOH. The solid was triturated with 1N HCl (3×10 mL), $H_2O$ (2×5 mL), 1.5N $NH_4OH$ solution (3×10 mL), and $H_2O$ (2×5 mL). The solid obtained was dried overnight under vacuum to give the title compound as a solid (1.99 g, 70%).

Anal. Calc'd for $C_{17}H_{19}NO_3$: C, 71.56; H, 6.71; N, 4.91. Found: C, 71.64; H, 6.60; N, 4.86.

Example BF (S)-2-Amino-3-[4-(4-methyl-benzyloxy)-phenyl]-propionic acid tert-butyl ester In a manner similar to that described in Example A, the product from Example BE (1.90 g, 6.7 mmol) was converted to the title compound (1.90 g, 84%).

MS (CI) 342 $(MH)^+$

Example 1

[S-(R*,R*)]-2-{2-[(Azepane-1-carbonyl-carbonyl)-amino]-4-methyl-pentanoylamino}-3-(4-benzyloxy-phenyl)-propionic acid tert-butyl ester A solution of the product from Example Z ((S)-2-[(azepane-1-carbonyl)-amino]-4-methyl-pentanoic acid)

(0.78 g, 3.05 mmol) and the product from Example A ((S)-2-amino-3-(4-benzyloxy-phenyl)-propionic acid tert-butyl ester) (1.00 g, 3.35 mmol) were coupled according to the procedure described in Example AH. The crude reaction product was purified by chromatography (silica gel, 1:1 heptane/ethyl acetate) to give the title compound as a white foam (1.02 g, 60%), mp=56–60° C.

Anal. Calc'd for $C_{33}H_{47}N_3O_5$: C, 70.06; H, 8.37; N, 7.43. Found: C, 70.10; H. 8.56; N, 7.34.

Example 2

2(R)-{2(S)-[(Azepane-1-carbonyl)-amino]-4-methyl-pentanoylamino}-3-(4-benzyloxy-phenyl)-propionic acid tert-butyl ester A solution of the product from Example Z ((S)-2-[(azepane-1-carbonyl)-amino]-4-methyl-pentanoic acid) (0.8 g, 3.1 mmol) and triethylamine (1.6 mL, 6.2 mmol) HBTU (1.3 g, 3.4 mmol) in acetonitrile (15 mL) was treated with HBTU (1.54 g, 4.06 mmol). The resulting solution was treated with the product from Example B ((R)-2-amino-3-(4-benzyloxy-phenyl)-propionic acid tert-butyl ester) (1.08 g, 3.30 mmol), and the resulting solution was stirred at room temperature for 30 minutes and allowed to stand overnight. The reaction mixture was concentrated and the residue dissolved in ethyl acetate (100 mL) and washed sequentially with 0.6 M aqueous $NaHCO_3$ solution, saturated aqueous NaCl solution, and water. The organic phase was dried over $MgSO_4$ and activate charcoal, filtered, and concentrated. The residue was purified by chromatography (silica gel, 25% ethyl acetate/hexane) to give the title compound as a white solid (1.4 g, 79%), mp=38–40° C.

Anal. Calc'd for $C_{33}H_{47}N_3O_5$: C, 70.06; H, 8.37; N, 7.43. Found: C, 69.87; H, 8.28; N, 7.26.

Example 3

2(S)-{2(R)-[(Azepane-1-carbonyl)-amino]-4-methyl-pentanoylamino}-3-(4-benzyloxy-phenyl)-propionic acid tert-butyl ester A solution of the product from Example AA ((R)-2-[(azepane-1-carbonyl)-amino]-4-methyl-pentanoic acid) (1.0 g, 3.9 mmol) and triethylamine (1.1 mL, 7.8 mmol) in acetonitrile (15 mL) was treated with HBTU (1.54 g, 4.06 mmol). The resulting solution was treated with the product from Example A ((S)-2-amino-3-(4-benzyloxy-phenyl)-propionic acid tert-butyl ester) (1.33 g, 4.06 mmol), and the resulting solution was stirred at room temperature for 30 minutes and allowed to stand overnight. The reaction mixture was concentrated and the residue dissolved in ethyl acetate (100 mL) and washed sequentially with 0.6 M aqueous $NaHCO_3$ solution, saturated aqueous NaCl solution, and water. The organic phase was dried over $MgSO_4$ and activated charcoal, filtered, and concentrated. The residue was purified by chromatography (silica gel, 25% ethyl acetate/hexane) to give the title compound as a white solid (1.9 g, 86%), mp=64–66° C.

Anal. Calc'd for $C_{33}H_{47}N_3O_5$: C, 70.06; H, 8.37; N, 7.43. Found: C, 69.69; H, 8.21; N, 7.28.

Example 4

[R-(R*,R*)]-2-{2-(Azepane-1-carbonyl)-amino]-4-methyl-pentanoylamino}-3-(4-benzyloxy-phenyl)-propionic acid tert-butyl ester A solution of the product from Example AA ((R)-2-[(azepane-1-carbonyl)-amino]-4-methyl-pentanoic acid) (1.0 g, 3.9 mmol) and the product from Example B ((R)-2-amino-3-(4-benzyloxy-phenyl)-propionic acid tert-butyl ester) (1.33 g, 4.06 mmol) were coupled according to the procedure described in Example 3. The title compound was isolated as a white solid (1.65 g, 75%), mp=42–44° C.

Anal. Calc'd for $C_{33}H_{47}N_3O_5$: C, 70.06; H, 8.37; N, 7.43. Found: C, 69.72; H, 8.23; N, 7.26.

Example 5

(S)-2-{(S)-2-[(Azepane-1-carbonyl)-amino]-3-methyl-pentanoylamino}-3-(4-benzyloxy-phenyl)-propionic acid tert-butyl ester A solution of the product from Example AB ((S)-2-[(azepane-1-carbonyl)-amino]-3-methyl-pentanoic acid) (0.50 g, 1.95 mmol) and the product from Example A ((S)-2-amino-3-(4-benzyloxy-phenyl)-propionic acid tert-butyl ester) (0.63 g, 1.95 mmol) were coupled according to the procedure described in Example AH. The crude reaction product was purified by chromatography (silica gel, 1:1 EtOAc/heptane) to give the title compound as a white foam, mp=53–57° C.

Anal. Calc'd for $C_{33}H_{47}N_3O_5$: C, 70.06; H, 8.37; N, 7.43. Found: C, 69.97; H, 8.41; N, 7.36. $[\alpha]^{D}_{25}$=−17.1° (c=1.06, MeOH).

Example 6

[S-(R*,R*)]-2-{2-[(Azepane-1-carbonyl)-amino]-3-methyl-butyrylamino}-3-(4-benzyloxy-phenyl)-propionic acid tert-butyl ester A solution of the product from Example AC ((S)-2-[(azepane-1-carbonyl)-amino]-3-methyl-butanoic acid) (0.50 g, 2.07 mmol) and the product from Example A ((S)-2-amino-3-(4-benzyloxy-phenyl)-propionic acid tert-butyl ester) (0.67 g, 2.07 mmol) were coupled according to the procedure described in Example AH. The crude reaction product was purified by chromatography (silica gel, EtOAc) to give the title compound as a white foam (0.55 g, 48%).

Anal. Calc'd for $C_{32}H_{45}N_3O_5$: C, 69.66; H, 8.22; N, 7.52. Found: C, 69.05; H, 8.21; N, 7.52. $[\alpha]^{D}_{25}$=−14.3° (c=0.98, MeOH).

Example 7

[S-(R*,R*)]-2-{2-[(Azepane-1-carbonyl)-amino]-propionylamino}-3-(4-benzyloxy-phenyl)-propionic acid tert-butyl ester A solution of the product from Example AD (2-[(azepane-1-carbonyl)-amino]-acetic acid) (0.50 g, 2.50 mmol) and the product from Example A ((S)-2-amino-3-(4-benzyloxy-phenyl)-propionic acid tert-butyl ester) (0.82 g, 2.50 mmol) were coupled according to the procedure described in Example AK. The crude reaction product was purified by chromatography (silica gel, 1:1 EtOAc/heptane) to give the title compound as a white foam (0.25 g, 20%).

Anal. Calc'd for $C_{30}H_{41}N_3O_5$: C, 68.81; H, 7.89; N, 8.02. Found: C, 68.06; H, 7.81; N, 7.72. $[\alpha]^{D}_{25}$=+4.7° (c=0.98, MeOH).

Example 8

[S-(R*,R*)]-2-{2-[(Azepane-1-carbonyl)-amino]-acetylamino}-3-(4-benzyloxy-phenyl)-propionic acid tert-butyl ester A solution of the product from Example AE ((S)-2-[(azepane-1-carbonyl)-amino]-propanoic acid) (0.50 g, 2.38 mmol) and the product from Example A ((S)-2-amino-3-(4-benzyloxy-phenyl)-propionic acid tert-butyl ester) (0.76 g, 2.33 mmol) were coupled according to the procedure described in Example AH. The reaction mixture was purified by chromatography (silica gel, 1:1 EtOAc/heptane) to give the title compound as a white foam (0.55 g, 43%).

Anal. Calc'd for $C_{29}H_{39}N_3O_5$: C, 68.36; H, 7.66; N, 8.25. Found: C, 68.11; H, 7.68; N, 8.09. $[\alpha]^D_{25}$=+10.0° (c=0.95, MeOH).

Example 9

[S-(R*,R*)]-3-(4-Benzyloxy-phenyl)-2-{4-methyl-2-[(4-methyl-piperazine-1-carbonyl)-amino]-pentanoylamino}-propionic acid tert-butyl ester A solution of the product from Example AF (2(S)-[(4-methyl-piperazine-1-carbonyl)-amino]-4-methyl-pentanoic acid) (0.25 g, 1.03 mmol) and the product from Example A ((S)-2-amino-3-(4-benzyloxy-phenyl)-propionic acid tert-butyl ester) (0.35 g, 1.03 mmol) were coupled according to the procedure described in Example AH. The reaction mixture was purified by chromatography (silica gel, gradient elution 1:1 EtOAc/heptane; 9:1 EtOAc/EtOH; 9:1:0.1 EtOAc/EtOH/$NH_4OH$) to give the title compound as a white foam (0.35 g, 60%).

Anal. Calc'd for $C_{32}H_{46}N_4O_5$: C, 67.81; H, 8.18; N, 9.89. Found: C, 67.57; H, 8.02; N, 9.84. $[\alpha]^D_{25}$=−1.4° (c=0.92, MeOH).

Example 10

[S-(R*,R*)]-3-(4-Benzyloxy-phenyl)-2-{4-methyl-2-[(4-phenyl-piperazine-1-carbonyl)-amino]-pentanoylamino}-propionic acid tert-butyl ester A solution of the product from Example AG ((2S)-4-methyl-2-[(4-phenyl-piperazine-1-carbonyl)-amino]-pentanoic acid) (0.93 g, 2.9 mmol) and the product from Example A ((S)-2-amino-3-(4-benzyloxy-phenyl)-propionic acid tert-butyl ester) (1.0 g, 2.9 mmol) were coupled according to the procedure described in Example AH. The reaction mixture was purified by chromatography (silica gel, 1:1 EtOAc/heptane) to give the title compound as a white crystals (0.84 g, 46%), mp=67–69° C.

Anal. Calc'd for $C_{37}H_{48}N_4O_5$: C, 70.67; H, 7.69; N, 8.91. Found: C, 70.42; H, 7.74; N, 8.75. $[\alpha]^D_{25}$=−11° (c=0.94, MeOH).

Example 11A

[S-(R*,R*)]-2-{2-[(Azepane-1-carbonyl)-amino]-4-methyl-pentanoylamino}-3-(4-benzyloxy-phenyl)-2-methyl-propionic acid tert-butyl ester, and Example 11B 2(R)-{2(S)-[(Azepane-1-carbonyl)-amino]-4-methyl-pentanoylamino}-3-(4-benzyloxy-phenyl)-2-methyl-propionic acid tert-butyl ester A solution of the product from Example Z ((2S)-2-[(azepane-1-carbonyl)-amino]-4-methyl-pentanoic acid) (0.5 g, 1.95 mmol) and the product from Example D (2-amino-2-methyl-3-(4-benzyloxy-phenyl)-propionic acid tert-butyl ester) (0.73 g, 2.15 mmol) were coupled according to the procedure described in Example 3. The two diastereomeric products were separated by chromatography (silica gel, 1:1 heptane/EtOAc) to give a high Rf product as a white solid (0.43 g, 38%), mp=46–49° C.

Anal. Calc'd for $C_{34}H_{49}N_3O_5$: C, 70.44; H, 8.52; N, 7.25. Found: C, 69.85; H, 8.77; N, 7.10.

The lower Rf diastereomer was also isolated as a white solid (0.62 g, 55%), mp=62–66° C.

Anal. Calc'd for $C_{34}H_{49}N_3O_5$: C, 70.44; H, 8.52; N, 7.25. Found: C, 70.49; H, 8.77; N, 7.10

Example 12

[S-(R*,R*)]-2-{2-[(Azepane-1-carbonyl)-amino]-4-methyl-pentanoylamino}-3-(4-tert-butoxy-phenyl)-propionic acid tert-butyl ester A solution of the product from Example Z (2(S)-[(azepane-1-carbonyl)-amino]-4-methyl-pentanoic acid) (0.20 g, 0.78 mmol) and 2(S)-amino-3-(4-tert-butoxy-phenyl)-propionic acid tert-butyl ester (Bachem, 0.284 g, 0.86 mmol) were coupled according to the procedure described in Example 3. The residue was purified by chromatography (silica gel, 1:1 ethyl acetate/hexane) to give the title compound as a white solid (0.096 g, 29%), mp=87–90° C.

Anal. Calc'd for $C_{30}H_{49}N_3O_5$: C, 67.66; H, 9.29; N, 7.90. Found: C, 65.57; H, 8.99; N, 7.58

Example 13

[S-(R*,R*)]-2-{2-[(Azepane-1-carbonyl)-amino]-4-methyl-pentanoylamino}-3-(4-methoxy-phenyl)-propionic acid tert-butyl ester (PD 167214)

A solution of the product from Example Z (2(S)-[(azepane-1-carbonyl)-amino]-4-methyl-pentanoic acid) (0.20 g, 0.78 mmol) and 2(S)-amino-3-(4-methoxy-phenyl)-propionic acid tert-butyl ester (Bachem, 0.216 g, 0.86 mmol) were coupled according to the procedure described in Example 3. The residue was purified by crystallization from hexane to give the title compound as a white solid (0.33 g, 87%), mp 105–106° C.

Anal. Calc'd for $C_{27}H_{43}N_3O_5$: C, 66.23; H, 8.85; N, 8.58. Found: C, 69.94; H, 8.84; N, 8.44.

Example 14

[S-(R*,R*)]-2-{2-[(Azepane-1-carbonyl)-amino]-4-methyl-pentanoylamino}-3-(4-benzyloxy-phenyl)-propionic acid benzyl ester A solution of the product from Example Z (2(S)-[(azepane-1-carbonyl)-amino]-4-methyl-pentanoic acid) (0.20 g, 0.78 mmol) and 2(S)-amino-3-(4-methoxy-phenyl)-propionic acid benzyl ester (Bachem, 0.459 g, 0.86 mmol) were coupled according to the procedure described in Example 3. The residue was passed through a plug of silica gel eluting with ethyl acetate. The material obtained was purified by crystallization from hot hexane/ethyl acetate to give the title compound as a white solid (0.2 g, 43%), mp=99–101° C.

Anal. Calc'd for $C_{36}H_{45}N_3O_5$: C, 72.09; H, 7.56; N, 7.01. Found: C, 71.18; H, 7.43; N, 6.90.

Example 15

[S-(R*,R*)]-2-{2-[(Azepane-1-carbonyl)-amino]-4-methyl-pentanoylamino}-3-(4-benzyloxy-phenyl)-propionic acid methyl ester A solution of the product from Example Z (2(S)-[(azepane-1-carbonyl)-amino]-4-methyl-pentanoic acid)

(0.20 g, 0.78 mmol) and 2(S)-amino-3-(4-methoxy-phenyl)-propionic acid methyl ester (Bachem, 0.277 g, 0.86 mmol) were coupled according to the procedure described in Example 3. The residue was passed through a plug of silica gel eluting with ethyl acetate. The material obtained was purified by crystallization from hot hexane/ethyl acetate to give the title compound as a white solid (0.34 g, 83%), mp=72–74° C.

Anal. Calc'd for $C_{30}H_{41}N_3O_5$: C, 68.81; H, 7.89; N, 8.02. Found: C, 68.74; H, 7.90; N, 8.00.

Example 16

[S-(R*,R*)]-2-{2-[(Azepane-1-carbonyl-carbonyl)-amino]-3-phenyl-propionylamino}-3-(4-benzyloxy-phenyl)-propionic acid tert-butyl ester A solution of the product from Example BC (1.59 g, 5.48 mmol) and the product form Example A (1.79 g, 5.47 mmol) in $CH_2Cl_2$ was cooled to 0° C. and treated with DCC (1.13 g, 5.49 mmol) and HOBT (0.74 g, 5.49 mmol). The resulting solution was stirred at room temperature overnight. The reaction mixture was concentrated, dissolved in EtOAc, washed with saturated aqueous $NaHCO_3$, brine. The organic phase was dried ($MgSO_4$), filtered, and concentrated. The residue was purified by chromatography (silica gel, 1:1 hexane/ethyl acetate) to give the title compound as a white solid (1.87 g, 57%).

MS (CI) 600 $(MH)^+$

Anal. Calc'd for $C_{36}H_{45}N_3O_5$: C, 72.09; H, 7.56; N, 7.01. Found: C, 72.76; H, 7.63; N, 7.01.

Example 17

2(R)-[2(S)-[(Azepane-1-carbonyl)-amino]-3-(1H-indol-3-yl)-propionylamino]-3-(4-benzyloxy-phenyl)-propionic acid tert-butyl ester Using a procedure similar to that described in Example 16, the product from Example B (0.38 g, 1.16 mmol) and the product from Example BD (0.38 g, 1.16 mmol) were coupled to give the title compound as a glassy solid (0.49 g, 66%).

MS (FAB) 639 $(MH)^+$

Example 18

2(R)-{2(S)-[(Azepane-1-carbonyl)-amino]-3-phenyl-propionylamino}-3-(4-benzyloxy-phenyl)-propionic acid tert-butyl ester Using a procedure similar to that described in Example 16, the product from Example B (0.56 g, 1.71 mmol) and the product from Example BC (0.50 g, 1.71 mmol) were coupled to give the title compound as a solid (0.97 g, 95%).

MS (CI) 601 $(MH)^+$

Example 19

[S-(R*,R*)]-2-{2-[(Azepane-1-carbonyl)-amino]-3-phenyl-propionylamino}-3-[4-(4-methyl-benzyloxy)-phenyl]-propionic acid tert-butyl ester Using a procedure similar to that described in Example 16, the product from Example BF (0.50 g, 1.70 mmol) and the product from Example BC (0.38 g, 1.80 mmol) were coupled to give the title compound as a glassy solid (0.83 g, 78%), mp=87–90° C.

MS (FAB) 614 $(MH)^+$

Example 20

[S-(R*,R*)]-2-[2-[(Azepane-1-carbonyl)-amino]-3-(1H-indol-3-yl)-propionylamino]-3-(4-benzyloxy-phenyl)-propionic acid tert-butyl ester Using a procedure similar to that described in Example 16, the product from Example A (0.25 g, 0.80 mmol) and the product from Example BD (0.25 g, 0.80 mmol) were coupled to give the title compound as a solid (0.25 g, 51%).

Example 21

[S-(R*,R*)]-Azepane-1-carboxylic acid {1-[2-(4-benzyloxy-phenyl)-1-carbamoyl-ethylcarbamoyl]-3-methyl-butyl}-amide Tricyclic amide linker resin (Bachem Biosciences, 9.99 g, 5.49 meq) was washed with NMP, 20% piperidine, and NMP. The resulting resin was coupled with FMOC-Tyr (OBn) activated as its HOBt ester in NMP, which was prepared by reaction a solution of FMOC-Tyr(OBn) (7.43 g, 15 mmol) and HOBt (2.31 g, 15.0 mmol) and DIC (2.34 mL, 15 mmol). The reaction mixture was washed with NMP (2×) and $CH_2Cl_2$ (2×) and dried under reduced pressure to give 12.13 g of coupled resin. A 2 g lot of the coupled resin was washed with $CH_2Cl_2$ (2×) and reacted with 20% piperidine for 2 minutes and then for an additional 20 minutes. The resin was then washed with NMP. The product from Example Z (0.61 g, 2.5 mmol) was converted to its HOBt activated ester by treatment with HOBt (2.5 mmol) and DIC (0.38 mL, 2.5 mmol) and added to the washed coupled resin. The resulting suspension was shaken for 6 hours. The resin was washed with NMP (2×) and $CH_2Cl_2$ (2×). The resin was then treated with 20% TFA for 120 minutes. The TFA solution was collected and concentrated. The residue was purified by HPLC (Vydac 218TP1022 column, 2.2×25 cm, mobile phase 10% to 70% $CH_3CN/H_2O$ containing 1% TFA over a 120-minute period). The title compound was isolated by lyophilization of the mobile phase.

APCI MS 509 $(MH)^+$

Example 22

[S-(R*,R*)]-2-{2-[(Azepane-1-carbonyl)-amino]-4-methyl-pentanoylamino}-3-(4-tert-butoxy-phenyl)-propionic acid methyl ester A solution of the product from Example Z (2(S)-[(azepane-1-carbonyl)-amino]-4-methyl-pentanoic acid) (0.20 g, 0.78 mmol) and 2(S)-amino-3-(4-tert-butoxy-phenyl)-propionic acid methyl ester (Bachem, 0.247 g, 0.86 mmol) were coupled according to the procedure described in Example 42. The residue was passed through a plug of silica gel eluting with 70% ethyl acetate/hexane. The material obtained was purified by crystallization from hot hexane/ethyl acetate to give the title compound as a white solid (0.31 g, 81%), mp=96–99° C.

Anal. Calc'd for $C_{27}H_{43}N_3O_5$: C, 66.23; H, 8.85; N, 8.5. Found: C, 65.84; H, 8.72; N, 8.49.

Example 23

[S-(R*,R*)]-Azepane-1-carboxylic acid {1-[2-(4-benzyloxy-phenyl)-1-tert-butylcarbamoyl-ethylcarbamoyl]-3-methyl-butyl}-amide A solution of the product from Example Z ((S)-2-[(azepane-1-carbonyl)-amino]-4-methyl-pentanoic acid)

(0.199 g, 0.78 mmol) was dissolved in 25 mL of THF and treated with BOP (0.343 g, 0.776 mmol), HOBt (0.104 g, 0.776 mmol) and diisopropylethyl amine (0.271 g, 1.55 mmol). The resulting solution was stirred for 5 minutes and treated with the product from Example F ((S)-2-amino-3-(4-benzyloxy-phenyl)-N-tert-butyl-propionamide) (0.230 g, 0.705 mmol). The reaction was stirred for 45 minutes and concentrated. The residue was partitioned between $Et_2O$ (100 mL) and water (100 mL). The organic phase was collected and washed sequentially with 10% aqueous $NaHCO_3$, water, and brine. The organic phase was concentrated, and the residue was dissolved in MeOH and purified by high pressure chromatography (Vydac 218TP1022 column, gradient elution 1:5 0.1% TFA/$H_2O$: 0.1% TFA/$CH_3CN$ to 5:10.1% TFA/H2O: 0.1% TFA/ $CH_3CN$ over a 120 minute period). Appropriate fractions were combined and lyophilized to give the title compound as a white solid (0.303 g, 76%).

APCI MS=565.7 (MH+)

Example 24

[S-(R*,R*)]-2-{2-[(Azepane-1-carbonyl)-amino]-4-methyl-pentanoylamino}-3-(4-hydroxy-phenyl)-propionic acid tert-butyl ester A solution of the product from Example 1 (0.20 g, 0.35 mmol) in 16 mL of tetrahydrofuran was hydrogenated at 52 psi over 20% Pd/C for 48 hours. The reaction mixture was filtered through Celite using methanol and concentrated. The resulting foam was purified by chromatography (silica gel, 1:1 heptane/ethyl acetate). The product was isolated as a foam and dried under vacuum to give the title compound (0.16 g, 95%).

Anal. Calc'd for $C_{26}H_{41}N_3O_5$: C, 65.66; H, 8.69; N, 8.83. Found: C, 65.59; H, 8.67; N, 8.38.

Example 25

[S-(R*,R*)]-2-{2-[(Azepane-1-carbonyl)-amino]-4-methyl-pentanoylamino}-3-[4-(pyridin-2-ylmethoxy)-phenyl]-propionic acid tert-butyl ester The product from Example Z (1.15 g, 4.50 mmol) was dissolved in 50 mL of THF at room temperature with stirring. To the solution were added O-(7-azabenzotriazol-1-y-)-1,1,3,3-tetramethyluronium hexafluorophosphate (HATU, 3.11 g, 8.18 mmol), 1-hydroxy-7-azabenzotriazole (HOAt, 1.11 g, 8.18 mmol), N,N-diisopropylethylamine (DIEA, 2.84 mL, 16.36 mmol) followed by the product from Example M (1.34 g, 4.09 mmol) in 50 mL of THF. After 3 hours, the solution was concentrated under reduced pressure, partitioned between ethyl ether and water (100 mL each), and separated. The organic layer was washed with 5% sodium bicarbonate (2×50 mL), brine (2×50 mL), dried with magnesium sulfate, filtered, and concentrated under reduced pressure to a solid. The solid was purified by silica gel chromatography with ethyl acetate. Appropriate fractions were combined and concentrated under reduced pressure to a solid (2.17 g).

APCI MS 567.5

Example 26

[S-(R*,R*)]-2-{2-[(Azepane-1-carbonyl)-amino]-4-methyl-pentanoylamino}-3-[4-(pyridin-4-ylmethoxy)-phenyl]-propionic acid tert-butyl ester In a manner similar to that described in Example 25, the product from Example O and the product from Example Z were coupled to give the title compound.

APCI MS 567.4

Example 27

[S-(R*,R*)]-2-{2-[(Azepane-1-carbonyl)-amino]-4-methyl-pentanoylamino}-3-[4-(4-cyano-benzyloxy)-phenyl]-propionic acid tert-butyl ester A solution of the product from Example 24 (1.00 g, 2.12 mmol) in DMF was cooled to 0° C. and treated with NaH (60% in dispersion oil, 0.083° g, 2.12° mmol). The resulting solution was stirred at 0° C. for 1 hour and treated with α-bromo-p-toluenitrile (0.45 g, 2.3 mmol), and the resulting solution was stirred overnight. The reaction mixture was poured into a separatory funnel containing EtOAc (50 mL) and $H_2O$ (50 mL). The organic layer was collected and washed with saturated aqueous $NaHCO_3$ and brine. The organic phase was dried ($Na_2SO_4$), filtered, and concentrated. The product was crystallized from EtOAc/Hexane to give the title compound (1.05 g, 93%).

APCI MS 591.6

Example 28

[S-(R*,R*)]-2-{2-[(Azepane-1-carbonyl)-amino]-4-methyl-pentanoylamino}-3-[4-(3-tert-butoxycarbonylamino-benzyloxy)-phenyl]-propionic acid tert-butyl ester In a manner similar to that described in Example 25, the product from Example Q and the product from Example Z were coupled to give the title compound.

APCI MS 681.6

Example 29

[S-(R*,R*)]-3-[4-(3-Amino-benzyloxy)-phenyl]-2-{2-[(azepane-1-carbonyl)-amino]-4-methyl-pentanoylamino}-propionic acid tert-butyl ester The product from Example 28 was dissolved in $CH_2Cl_2$ and treated with trifluoroacetic acid. The reaction mixture was stirred at room temperature for 30 minutes. The reaction mixture was concentrated and purified to give the title compound.

APCI MS 596.6

Example 30

[S-(R*,R*)]-2-{2-[(Azepane-1-carbonyl)-amino]-4-methyl-pentanoylamino}-3-(4-cyclohexylmethoxy-phenyl)-propionic acid tert-butyl ester A solution of the product from Example 24 (0.20 g, 0.42 mmol) and bromomethylcyclohexane (0.6 μL, 0.45 mmol) in DMF (2 mL) was added sodium hydride (60% in dispersion oil, 0.016 g, 0.42 mmol). The reaction mixture was stirred at 0° C. for 30 minutes and warmed to room temperature. The reaction mixture was poured into a separatory funnel containing ethyl acetate (50 mL) and water (50 mL). The organic phase was collected, washed with brine, and dried. The residue was purified by chromatography (silica gel, ethyl acetate/hexane) to give the title compound (0.13 g).

APCI MS 572.6 $(MH)^+$

Example 31

[S-(R*,R*)]-2-{2-[(Azepane-1-carbonyl)-amino]-4-methyl-pentanoylamino}-3-[4-(pyridin-3-ylmethoxy)-phenyl]-propionic acid tert-butyl ester A solution of the product from Example 24 (0.3 g, 0.63 mmol), 3-pyridylmethanol (0.061 mL, 0.63 mmol) and triphenylphosphine (0.165 g, 0.63 mmol) in 10 mL of tetrahydrofuran at 0° C. was treated with diethylazodicarboxylate (0.11 g, 0.63 mmol). The reaction mixture was warmed to room temperature and stirred for 4 hours. The reaction mixture was concentrated, and the residue was taken up in EtOAc and washed with sat. aqueous $NaHCO_3$ and brine. The organic phase was dried with $Na_2SO_4$, filtered, and concentrated. The residue was purified by HPLC to give the title compound (0.047 g).

APCI MS 567.4 $(MH)^+$

Example 32

[S-(R*,R*)]-2-{2-[(Azepane-1-carbonyl)-amino]-4-methyl-pentanoylamino}-3-[4-(4-methoxy-benzyloxy)-phenyl]-propionic acid tert-butyl ester In a manner similar to the procedure described in Example 27, the product from Example 24 (0.2 g, 0.42 mmol) and 4-methoxybenzyl chloride (75 mg, 0.42 mmol) were converted to the title compound (0.34 g).

APCI MS 596.6 $(MH)^+$

Example 33

[S-(R*,R*)]-3-(4-Benzyloxy-phenyl)-2-{4-methyl-2-[(piperidine-1-carbonyl)-amino]-pentanoylamino}-propionic acid tert-butyl ester A solution of the product from Example AI ([S-(R*,R*)]-2-{2-amino-4-methyl-pentanoylamino}-3-(4-benzyloxy-phenyl)-propionic acid tert-butyl ester) (0.75 g, 1.7 mmol) in $CH_2Cl_2$ was added dropwise to a 0.09 M solution of phosgene in $CH_2Cl_2$ at 0° C. The resulting solution was stirred at 0° C. for 2.5 hours, and then anhydrous nitrogen was bubbled through the solution to remove the excess phosgene. The resulting solution was treated with $CH_2Cl_2$ to a volume of 100 mL. Piperidine was added dropwise to 33 mL of the above solution at room temperature. The resulting solution was stirred at room temperature overnight. The reaction mixture was treated with ethyl acetate (125 mL) and then washed with saturated aqueous $NaHCO_3$ solution (2×25 mL) and brine (2×25 mL). The organic phase was dried ($Na_2SO_4$), filtered, and concentrated. The residue was purified by chromatography (silica gel, 1:1 heptane/ethyl acetate) to give the title compound as an oil (0.25 g).

APCI MS 552 (MH+)

Example 34

[S-(R*,R*)]-3-(4-Benzyloxy-phenyl)-2(S)-{4-methyl-2(S)-[(morpholine-4-carbonyl)-amino]-pentanoylamino}-propionic acid tert-butyl ester Using a procedure identical to that described in Example 33, the product from Example AI and morpholine were converted to give the title compound as an oil (0.15 g).

Anal. Calc'd for $C_{31}H_{43}N_3O_6$: C, 67.25; H, 7.83; N, 7.59. Found: C, 66.96; H, 7.99; N, 7.32.

Example 35

[S-(R*,R*)]-3-(4-Benzyloxy-phenyl)-2-(2-methanesulfonylamino-4-methyl-pentanoylamino)-propionic acid tert-butyl ester A solution of the product from Example AI ([S-(R*,R*)]-2-{2-amino-4-methyl-pentanoylamino}-3-(4-benzyloxy-phenyl)-propionic acid tert-butyl ester) (0.25 g, 1.7 mmol) and triethylamine (0.5 mL) in $CH_2Cl_2$ (10 mL) was treated with methansulfonyl chloride (0.25 mL). The resulting solution was stirred overnight at room temperature. The reaction mixture was treated with ethyl acetate (100 mL) and washed sequentially with aqueous 1N HCl solution (3×20 mL), saturated aqueous $NaHCO_3$ solution (3×20 mL), and brine (3×20 mL). The organic phase was dried ($MgSO_4$), filtered, and concentrated. The residue was purified by chromatography (silica gel, 1:1 ethyl acetate/heptane) to give the title compound as a pale peach powder (0.15 g, 51%), mp=83–84° C.

Anal. Calc'd for $C_{27}H_{38}N_2O_6S$: C, 62.52; H, 7.38; N, 5.40. Found: C, 62.07; H, 7.29; N, 5.38.

Example 36

[S-(R*,R*)]-3-(4-Benzyloxy-phenyl)-2(S)-[2(S)-(4-tert-butyl-benzenesulfonylamino)-4-methyl-pentanoylamino]-propionic acid tert-butyl ester A solution of the product from Example AI ([S-(R*,R*)]-2-{2-amino-4-methyl-pentanoylamino}-3-(4-benzyloxy-phenyl)-propionic acid tert-butyl ester) (0.20 g, 0.45 mmol) and triethylamine (0.13 mL, 0.90 mmol) in 5 mL of $CHCl_3$ was cooled to 0° C. and treated with 4-tert-butylphenylsulfonyl chloride (0.10 g, 0.45 mmol). The reaction mixture was warmed to room temperature and treated with saturated aqueous $NaHCO_3$. The organic phase was separated from the aqueous phase. The aqueous phase was extracted with additional $CHCl_3$, and the combined organic extracts were dried MgSO4, filtered, and concentrated. The residue was purified by chromatography (silica gel, 1:1 heptane/ethyl acetate). The chromatography product was crystallized from hot heptane/ethyl acetate to give the title compound as a white solid 0.20 g 70%), mp=142–143° C.

Anal. Calc'd for $C_{36}H_{48}N_2O_6S$: C, 67.90; H, 7.60; N, 4.40. Found: C, 67.81; H, 7.62; N, 4.38.

Example 37

[S-(R*,R*)]-3-(4-Benzyloxy-phenyl)-2(S)-[2(S)-(4-isopropyl-benzenesulfonylamino)-4-methyl-pentanoylamino]-propionic acid tert-butyl ester Using a procedure similar to that described in Example 36, the product from Example AI ([S-(R*,R*)]-2-{2-amino-4-methyl-pentanoylamino}-3-(4-benzyloxy-phenyl)-propionic acid tert-butyl ester) (0.20 g, 0.45 mmol) and 4-isopropylphenylsulfonyl chloride (0.10 g, 0.45 mmol) were coupled to give the title compound as a white solid (0.20 g, 71%), mp=147–148° C.

Anal. Calc'd for $C_{35}H_{46}N_2O_6S$: C, 67.49; H, 7.45; N, 4.50. Found: C, 67.71; H, 7.53; N, 4.44.

Example 38

[S-(R*,R*)]-2-{2-[(4-Bromobenzene-1-sulfonyl-carbonyl)-amino]-4-methyl-pentanoylamino-3-(4-benzyloxyphenyl)-propionic acid, tert-butyl ester Using a procedure similar to that described in Example 36, the product from Example AI ([S-(R*,R*)]-2-{2-amino-4-methyl-pentanoylamino}-3-(4-benzyloxy-phenyl)-propionic acid tert-butyl ester) and 4-bromophenylsulfonyl chloride (0.10 g, 0.45 mmol) were coupled to give the title compound, mp=148–149° C.

MS: 660 (M+ for $C_{33}H_{39}S_1O_6N_2Br$)

Example 39

[S-(R*,R*)]-3-(4-Benzyloxy-phenyl)-2-[4-methyl-2-(4-nitro-benzenesulfonylamino)-pentanoylamino]-propionic acid tert-butyl ester A solution of the product from Example AI ([S-(R*,R*)]-2-(2-amino-4-methyl-pentanoylamino)-3-(4-benzyloxyphenyl)-propionic acid tert-butyl ester) (308 mg, 0.70 mmol), 4-nitrobenzenesulfonyl chloride (190 mg, 0.77 mmol), N,N-diisopropylethyl-amine (181 mg, 1.4 mmol) and DMAP (20 mg), in benzene (5 mL) was heated under reflux for 3 hours, then concentrated in vacuo and the residue dissolved in ethyl acetate, and washed with saturated $NaHCO_3$ solution, water, and brine, dried over anhydrous sodium sulfate, and concentrated in vacuo. The tan solid thus obtained was triurated in warm tert-butylmethyl ether, and filtered to give 419 mg (95%) of the title compound as a white solid, mp=121–123° C.

APCI MS m/z (relative intensity) 570 (100); 571 (42)

Anal. Calc'd for $C_{32}H_{39}N_3O_8S.0.5H_2O$: C, 60.55; H, 6.35; N, 6.62. Found: C, 60.61; H, 6.07; N, 6.49.

Example 40

[S-(R*,R*)]-2-[2-(Azepane-1-sulfonylamino)-4-methyl-pentanoylamino]-3-(4-benzyloxy-phenyl)-propionic acid tert-butyl ester A solution of the product from Example AI ([S-(R*,R*)]-2-(2-amino-4-methyl-pentanoylamino)-3-(4-benzyloxy-phenyl)-propionic acid tert-butyl ester) (220 mg, 0.50 mmol), homopiperidinesulfonyl chloride (110 mg, 0.55 mmol, prepared by the method of Von Geldem, et al., *J. Med. Chem.,* 1996;39:968–981), N,N-diisopropylethylamine (129 mg, 1.00 mmol), and DMAP (20 mg) in DMF (1 mL) is stirred at room temperature for 72 hours, diluted with ethyl acetate, and washed with water, 1N HCl, saturated $NaHCO_3$ solution and brine, dried over anhydrous sodium sulfate, and concentrated. The oily residue thus obtained was purified via flash chromatography (30% EtOAc/hexane) followed by preparative TLC (2 elutions, 30% EtOAc/Hexane) to afford 39 mg of a clear colorless oil which is dissolved in 0.5 mL $CHCl_3$, diluted with 4 mL hexane, and maintained at 3° C. until crystallization occurred. The crystals are collected and weigh 10.1 mg (3%), mp=123–124° C.

APCI MS 602 (MH+)

Anal. Calc'd for $C_{32}H_{47}N_3O_6S$: C, 63.87; H, 7.87; N, 6.98. Found: C, 63.56; H. 7.65; N, 6.78.

Example 41

[S-(R*,R*)]-3-(4-Benzyloxy-phenyl)-2-[4-methyl-2-(piperidine-1-sulfonylamino)-pentanoylamino]-propionic acid tert-butyl ester A solution of the product from Example AI ([S-(R*,R*)]-2-(2-amino-4-methyl-pentanoylamino)-3-(4-benzyloxy-phenyl)-propionic acid tert-butyl ester) (220 mg, 0.50 mmol), piperidinesulfonyl chloride (102 mg, 0.55 mmol, prepared by the method of Von Geldern, et al., *J. Med. Chem.,* 1996;39:968–981), N,N-diisopropylethylamine (129 mg, 1.00 mmol), and DMAP (20 mg) in DMF (1 mL) is stirred at room temperature for 48 hours, diluted with ethyl acetate, and washed with water, 1N HCl, saturated $NaHCO_3$ solution and brine, dried over anhydrous sodium sulfate, and concentrated. The remaining oily residue was purified via preparative TLC (50% EtOAc/hexane) giving a clear oil which was dissolved in 0.5 mL $CHCl_3$, and diluted with 5 mL hexane. After 3 days at 3° C., the crystals that had formed were collected, and weighed 34 mg (12%), mp=125–126° C.

APCI MS 588 $(MH)^+$

Microanalysis for $C_{31}H_{45}N_3O_6S_1$: Calc'd: C, 63.35; H, 7.72; N, 7.15. Found: C, 63.25; H, 7.60; N, 7.03.

Example 42

[S-(R*,R*)]-3-(4-Benzyloxy-phenyl)-2-[4-methyl-2-(morpholine-4-sulfonylamino)-pentanoylamino]-propionic acid tert-butyl ester A solution of the product from Example AI ([S-(R*,R*)]-2-(2-amino-4-methyl-pentanoylamino)-3-(4-benzyloxy-phenyl)-propionic acid tert-butyl ester) (397 mg, 0.90 mmol), morpholine-4-sulphonyl chloride (334 mg, 1.8 mmol, prepared by the method of von Geldem, et al., *J. Med. Chem.,* 1996;39:968–981), N,N-diisopropylethyl-amine (246 mg, 1.9 mmol), and DMAP (25 mg) in benzene (5 mL) was heated under reflux for 3 hours, then concentrated in vacuo and the residue dissolved in ethyl acetate, and washed with saturated $NaHCO_3$ solution, water and brine, dried over anhydrous sodium sulfate, and concentrated in vacuo. The amber oil thus obtained was purified via flash chromatography (silica gel, 35% EtOAc/Hexane) to give 346 mg (65%) of the title compound as a yellow foam, mp=54–57° C.

APCI MS 590 $(MH)^+$

Anal. Calc'd for $C_{30}H_{43}N_3O_7S_1$: C, 61.10; H, 7.35; N, 7.12. Found: C, 61.05; H, 7.25; N, 6.88.

Example 43

[S-(R*,R*)]-3-(4-Benzyloxy-phenyl)-2-{2-[3-(4-isopropyl-phenyl)-thioureido]-4-methyl-pentanoylamino}-propionic acid, tert-butyl ester A solution of the product from Example AI (0.44 g, 1 mmol) and 4-isopropylphenyl isothiocyanate (0.177 g, 1 mmol) and chloroform (20 mL) was heated at 60° C. for 4 hours. The mixture was concentrated to dryness and purified by column chromatography (silica gel, 5:1 hexanes/EtOAc). The title compound was obtained as a white solid (0.58 g, 94%), mp=62–63° C.

APCI MS 618

Example 44

[S-(R*,R*)]-3-(4-Benzyloxy-phenyl)-2-{2-[3-(4-tert-butyl-phenyl)-thioureido]-4-methyl-pentanoylamino}-propionic acid, tert-butyl ester In a manner similar described in Example 43, the product from Example AI and tert-butylphenylisothiocyanate (Aldrich Chemical Co.) were converted to the title compound, mp=63–64° C.

APCI MS 632

Example 45

[S-(R*,R*)]-3-(4-Benzyloxy-phenyl)-2-{2-[3-(4-bromophenyl)-thioureido]-4-methyl-pentanoyl-amino}-propionic acid, tert-butyl ester In a manner similar described in Example 43, the product from Example AI and 4-bromophenylisothiosyanate (Aldrich Chemical Co.) were converted to the title compound, mp=77–78° C.

APCI MS 654

Example 46

[S-(R*,R*)]-3-(4-Benzyloxy-phenyl)-2-{2-[3-(1-adamantyl)-thioureido]-4-methyl pentanoylamino}-propionic acid, tert-butyl ester In a manner similar described in Example 43, the product from Example AI and 1-adamantylisothiocyanate (Aldrich Chemical Co.) were converted to the title compound, mp=104–105° C.

APCI MS 634

Example 47

[S-(R*,R*)]-3-(4-benzyloxy-phenyl)-2-[2-(3-cyclohexyl-thioureido)-4-methyl-pentanoylamino}-propionic acid, tert-butyl ester In a manner similar described in Example 43, the product from Example AI and cyclohexylisothiocyantate (Aldrich Chemical Co.) were converted to the title compound, mp 161–162° C.

APCI MS 582

Example 48

[S-(R*,R*)]-3-(4-Benzyloxy-phenyl)-2-{2-[3-(2-chloro-phenyl)-thioureido]-4-methyl-pentanoylamino}-propionic acid tert-butyl ester In a manner similar described in Example 43, the product from Example AI and 2-chlorophenylisothiocyantate (Aldrich Chemical Co.) were converted to the title compound, mp=66–67° C.

APCI MS 610

Example 49

[S-(R*,R*)]-3-(4-Benzyloxy-phenyl)-2-[2-(3-butyl-thioureido)-4-methyl-pentanoylamino]-propionic acid tert-butyl ester In a manner similar described in Example 43, the product from Example AI and n-butylisothiocyantate (Aldrich Chemical Co.) were converted to the title compound, mp=53–54° C.

APCI MS 654

Example 50

[S-(R*,R*)]-3-(4-Benzyloxy-phenyl)-2-[4-methyl-2-(3-p-tolyl-thioureido)-pentanoylamino]-propionic acid tert-butyl ester In a manner similar described in Example 43, the product from Example AI and p-tolylisothiocyantate (Aldrich Chemical Co.) were converted to the title compound, mp=68–69° C.

APCI MS 589

Example 51

[S-(R*,R*)]-3-(4-Benzyloxy-phenyl)-2-[4-methyl-2-(3-methyl-thioureido)-pentanoylamino]-propionic acid tert-butyl ester In a manner similar described in Example 43, the product from Example AI and methylisothiocyantate (Aldrich Chemical Co.) were converted to the title compound, mp=157–158° C.

APCI MS 513

Example 52

[S-(R*,R*)]-Azepane-1-carboxylic acid (1-{1-tert-butylcarbamoyl-2-[4-(2,6-dichloro-benzyloxy)-phenyl]-ethylcarbamoyl}-3-methyl-butyl)-amide A solution of the product from Example Z. (0.26 g, 1.02 mmol) in 10 mL of DMF and diisopropylethylamine (0.263 g, 2.04 mmol) was cooled to 0° C. The resulting solution was treated with HBTU (0.387 g, 1.02 mmol) and stirred for 30 minutes at 0° C. A solution of the product from Example AY (0.40 g, 1.02 mmol) was added to the reaction mixture. The reaction mixture was warmed to room temperature and was stirred for another 30 minutes. The mixture was diluted with 20 mL of ether, washed with 1N HCl (2×10 mL), saturated $NaHCO_3$ (2×10 mL), and saturated solution of brine (2×10 mL). The organic layer was separated, dried with $Na_2SO_4$, and evaporated to dryness. The crude residue was crystallized from $CH_2Cl_2$ and petroleum ether to yield the title compound (0.4 g) as a white solid, mp 141–142° C.

Anal. Calc'd for $C_{33}H_{46}N_4O_4Cl_2$: C, 62.55; H, 7.32; N, 8.84. Found: C, 62.65; H, 7.5 1; N, 8.82.

Example 53

[S-(R*,R*)]-Azepane-1-carboxylic acid {1-[2-(4-benzyl-phenyl)-1-tert-butylcarbamoyl-ethylcarbamoyl]-3-methyl-butyl}-amide To a solution of the product from Example Z (0.32 g, 1.26 mmol) in 10 mL of DMF was added HBTU (0.48 g, 1.26 mmol) and 5 mL of diisopropylethylamine (0.33 g, 2.52 mmol). The mixture was stirred for 30 minutes at 0° C. A solution of the product from Example AW (0.392 g, 1.26 mmol)was added to the reaction mixture. The reaction mixture was allowed to warm to room temperature and was stirred for another 30 minutes. The mixture was diluted with 20 mL of ether, washed with 1N HCl (2×10 mL), saturated $NaHCO_3$ (2×10 mL), and saturated solution of brine (2×10 mL). The organic layer was separated, dried with $Na_2SO_4$, and evaporated to dryness. The crude product was crystallized from ether to give the title compound as a white solid (0.3 g), mp=165–166° C.

Anal. Calc'd for $C_{33}H_{48}N_4O_3$: C, 66.26; H, 8.24; N, 13.32. Found: C, 65.58; H, 8.23; N, 12.93.

APCI MS 549.4 $(MH)^+$.

Example 54

[S-(R*,R*)]-3-(4-Benzyloxy-phenyl)-2-[4-methyl-2-(3-phenyl-ureido)-pentanoylamino]propionic acid tert-butyl ester A solution of the product from Example AI (40 mg, 0.09 mmol) in dichloromethane (1 mL) was treated with phenyl isocyanate (8 μL, 0.07 mmol). The reaction mixture was shaken on an orbital shaker for 5 hours and then polystyrene-divinylbenzene-supported tris(2-aminoethy)lamine (Bachem, 80 mg) was added. The reaction mixture was shaken for 2 hours and then left overnight. The resin was filtered and washed with dichloromethane (2×1.5 mL). The combined organic phases, where concentrated to dryness to give the title compound (46 mg, 79%).

APCI MS 560 (MH)+

Example 55

[S-(R*,R*)]-3-(4-Benzyloxy-phenyl)-2-{4-methyl-2-[3-(4-nitro-phenyl)-ureido]pentanoylamino}-propionic acid tert-butyl ester By a procedure identical to that described in Example 54, the product from Example AI and [4]-nitrophenyl isocyantate (Aldrich Chemical Co.) was reacted to give the title compound.

APCI MS 605 (MH)+

Example 56

[S-(R*,R*)]-3-(4-Benzyloxy-phenyl)-2-[2-(3-cyclohexyl-ureido)-4-methyl-pentanoylamino] propionic acid tert-butyl ester By a procedure identical to that described in Example 54, the product from Example AI and cyclohexyl isocyanate (Aldrich Chemical Co.) was reacted to give the title compound.

APCI MS 566 $(MH)^+$

Example 57

[S-(R*,R*)]-3-(4-Benzyloxy-phenyl)-2-{2-[3-(3-methoxy-phenyl)-ureido]-4-methyl-pentanoylamino}-propionic acid tert-butyl ester By a procedure identical to that described in Example 54, the product from Example AI and 3-methoxyphenyl isocyanate (Aldrich Chemical Co.) was reacted to give the title compound.

APCI MS 589 $(MH)^+$

Example 58

[S-(R*,R*)]-3-(4-Benzyloxy-phenyl)-2-[4-methyl-2-(3-p-tolyl-ureido)-pentanoylamino]propionic acid tert-butyl ester By a procedure identical to that described in Example 54, the product from Example AI and p-tolyl isocyantate (Aldrich Chemical Co.) was reacted to give the title compound.

APCI MS 574 (MH)+

Example 59

[S-(R*,R*)]-3-(4-Benzyloxy-phenyl)-2-[2-(3-butyl-ureido)-4-methyl-pentanoylamino]-propionic acid tert-butyl ester By a procedure identical to that described in Example 54, the product from Example AI and n-butyl isocyanate (Aldrich Chemical Co.) was reacted to give the title compound.

APCI MS 540 (MH)+

Example 60

[S-(R*,R*)]-3-(4-Benzyloxy-phenyl)-2-[2-(3-benzyl-ureido)-4-methyl-pentanoylamino]-propionic acid tert-butyl ester By a procedure identical to that described in Example 54, the product from Example AI and benzyl isocyanate (Aldrich Chemical Co.) was reacted to give the title compound.

APCI MS 574 (MH)+

Example 61

[S-(R*,R*)]-3-(4-Benzyloxy-phenyl)-2-[4-methyl-2-(3-o-tolyl-ureido)-pentanoylamino]-propionic acid tert-butyl ester By a procedure identical to that described in Example 54, the product from Example AI and o-tolyl isocyantate (Aldrich Chemical Co.) was reacted to give the title compound.

APCI MS 574 (MH)+

Example 62

[S-(R*,R*)]-3-(4-Benzyloxy-phenyl)-2-{2-[3-(2,6-dimethyl-phenyl)-ureido]-4-methyl-pentanoylamino}-propionic acid tert-butyl ester By a procedure identical to that described in Example 54, the product from Example AI and 2,6-dimethylphenyl isocynate (Aldrich Chemical Co.) was reacted to give the title compound.

APCI MS 588 (MH)+

Example 63

3-(4-Benzyloxy-phenyl)-(S)-2-{4-methyl-(S)-2-[3-[(R)-1-phenyl-ethyl]-ureido]-pentanoylamino}-propionic acid tert-butyl ester By a procedure identical to that described in Example 54, the product from Example AI and (R)-(+)-α-methylbenzyl isocyanate (Aldrich Chemical Co.) was reacted to give the title compound.

APCI MS 588 (MH)+

Example 64

[S-(R*,R*)]-3-(4-Benzyloxy-phenyl)-2-{4-methyl-2-[3-(4-methylsulfanyl-phenyl)-ureido]-pentanoylamino}-propionic acid tert-butyl ester By a procedure identical to that described in Example 54, the product from Example AI and 4-(methylthio)phenyl isocyanate (Aldrich Chemical Co.) was reacted to give the title compound.

APCI MS 605 (M)+

Example 65

[S-(R*,R*)]-3-(4-Benzyloxy-phenyl)-2-{4-methyl-2-[3-(4-phenoxy-phenyl)-ureido]pentanoylamino}-propionic acid tert-butyl ester By a procedure identical to that described in Example 54, the product from Example AI and 4-phenoxyphenyl isocyanate (Aldrich Chemical Co.) was reacted to give the title compound.

APCI MS 652 (MH)+

Example 66

[S-(R*,R*)]-3-(4-Benzyloxy-phenyl)-{2-[3-(1-methoxycarbonyl-2-phenyl-ethyl)-ureido]-4-methyl-pentanoylamino}-propionic acid tert-butyl ester By a procedure identical to that described in Example 54, the product from Example AI and 1-methoxyphenyl isocyanate (Aldrich Chemical Co.) was reacted to give the title compound.

APCI MS 646 (MH)+

Example 67

[S-(R*,R*)]-3-(4-Benzyloxy-phenyl)-2-{4-methyl-2-[3-(3,4,5-trimethoxy-phenyl)-ureido]-pentanoylamino}-propionic acid tert-butyl ester By a procedure identical to that described in Example 54, the product from Example AI and 3,4,5-trimethoxyphenyl isocyanate (Aldrich Chemical Co.) was reacted to give the title compound.

APCI MS 649 $(MH)^+$

Example 68

[S-(R*,R*)]-3-(4-Benzyloxy-phenyl)-2-{2-[3-(4-methoxy-phenyl)-ureido]-4-methyl-pentanoylamino}-propionic acid tert-butyl ester By a procedure identical to that described in Example 54, the product from Example AI and 4-methoxyphenyl isocyanate (Aldrich Chemical Co.) was reacted to give the title compound.

APCI MS 589 $(MH)^+$

Example 69

[S-(R*,R*)]-3-(4-Benzyloxy-phenyl)-2-{2-[3-(2,4-difluoro-phenyl)-ureido]-4-methyl-pentanoylamino}-propionic acid tert-butyl ester By a procedure identical to that described in Example 54, the product from Example AI and 2,4-difluorophenyl isocyanate (Aldrich Chemical Co.) was reacted to give the title compound.

APCI MS 596 (MH)+

Example 70

[S-(R*,R*)]-3-(4-Benzyloxy-phenyl)-2-{4-methyl-2-[3-(4-trifluoromethyl-phenyl)-ureido]-pentanoylamino}-propionic acid tert-butyl ester By a procedure identical to that described in Example 54, the product from Example AI and 4-trifluoromethylphenyl isocyanate (Aldrich Chemical Co.) was reacted to give the title compound.

APCI MS 628 (MH)+

Example 71

[S-(R*,R*)]-3-(4-Benzyloxy-phenyl)-2-{2-[3-(2-methoxy-phenyl)-ureido]-4-methyl-pentanoylamino}-propionic acid tert-butyl ester By a procedure identical to that described in Example 54, the product from Example AI and 2-methoxyphenyl isocyanate (Aldrich Chemical Co.) was reacted to give the title compound.

APCI MS 590 (MH)+

Example 72

[S-(R*,R*)]-3-(4-Benzyloxy-phenyl)-2-{2-[3-(3,5-dimethyl-phenyl)-ureido]-4-methyl-pentanoylamino}-propionic acid tert-butyl ester By a procedure identical to that described in Example 54, the product from Example AI and 3,5-dimethylphenyl isocyanate (Aldrich Chemical Co.) was reacted to give the title compound.

APCI MS 588 (MH)+

Example 73

[S-(R*,R*)]-3-(4-Benzyloxy-phenyl)-2-{2-[3-(2-chloro-phenyl)-ureido]-4-methyl pentanoylamino}-propionic acid tert-butyl ester By a procedure identical to that described in Example 54, the product from Example AI and 2-chlorophenyl isocyanate (Aldrich Chemical Co.) was reacted to give the title compound.

APCI MS 594 (MH)+

Example 74

[S-(R*,R*)]-3-(4-Benzyloxy-phenyl)-2-{2-[3-(3-chloro-phenyl)-ureido]-4-methyl-pentanoylamino}-propionic acid tert-butyl ester By a procedure identical to that described in Example 54, the product from Example AI and 3-chlorophenyl isocyanate (Aldrich Chemical Co.) was reacted to give the title compound.

APCI MS 594 (MH)+

Example 75

[S-(R*,R*)]-3-(4-Benzyloxy-phenyl)-2-{4-methyl-2-[3-(2-phenyl-cyclopropyl)-ureido]-pentanoylamino}-propionic acid tert-butyl ester By a procedure identical to that described in Example 54, the product from Example AI and trans-2-phenylcyclopropyl isocyanate (Aldrich Chemical Co.) was reacted to give the title compound.

APCI MS 600 (MH)+

Example 76

[S-(R*,R*)]-3-(4-Benzyloxy-phenyl)-2-{4-methyl-2-[3-(3-trifluoromethyl-phenyl)-ureido]-pentanoylamino}-propionic acid tert-butyl ester By a procedure identical to that described in Example 54, the product from Example AI and 3-trifluoromethylphenyl isocyanate (Aldrich Chemical Co.) was reacted to give the title compound.

APCI MS 628 (MH)+

Example 77

[S-(R*,R*)]-4-(3-{1-[2-(4-Benzyloxy-phenyl)-1tert-butoxycarbonyl-ethylcarbamoyl]-3-methyl butyl}-ureido)-benzoic acid ethyl ester By a procedure identical to that described in Example 54, the product from Example AI and ethyl 4-isocyantobenzoate (Aldrich Chemical Co.) was reacted to give the title compound.

APCI MS 632 (MH)+

Example 78

[S-(R*,R*)]-3-(4-Benzyloxy-phenyl)-2-{2-[3-(4-chloro-3-trifluoromethyl-phenyl)-ureido]-4-methyl-pentanoylamino}-propionic acid tert-butyl ester By a procedure identical to that described in Example 54, the product from Example AI and 4-chloro-3-trifluoromethylphenyl isocyanate (Aldrich Chemical Co.) was reacted to give the title compound.

APCI MS 662 (MH)+

Example 79

[S-(R*,R*)]-3-(4-Benzyloxy-phenyl)-2-[4-methyl-2-(3-naphthalen-1-yl-ureido)-pentanoylamino]-propionic acid tert-butyl ester By a procedure identical to that described in Example 54, the product from Example AI and 1-napthyl isocyanate (Aldrich Chemical Co.) was reacted to give the title compound.

APCI MS 610 (MH)+

Example 80

[S-(R*,R*)]-3-(4-Benzyloxy-phenyl)-2-{2-[3-(4-chloro-phenyl)-ureido]-4-methyl-pentanoylamino}-propionic acid tert-butyl ester By a procedure identical to that described in Example 54, the product from Example AI and 4-chlorophenyl isocyanate (Aldrich Chemical Co.) was reacted to give the title compound.

APCI MS 594 (MH)+

Example 81

[S-(R*,R*)]-3-(4-Benzyloxy-phenyl)-2-{2-[3-(2,3-dichloro-phenyl)-ureido]-4-methyl-pentanoylamino}-propionic acid tert-butyl ester By a procedure identical to that described in Example 54, the product from Example AI and 2,3-dichlorophenyl isocyanate (Aldrich Chemical Co.) was reacted to give the title compound.

APCI MS 628 (MH)+

Example 82

[S-(R*,R*)]-3-(4-Benzyloxy-phenyl)-2-{2-[3-(2,4-dichloro-phenyl)-ureido]-4-methyl-pentanoylamino}-propionic acid tert-butyl ester By a procedure identical to that described in Example 54, the product from Example AI and 2,4-dichlorophenyl isocyanate (Aldrich Chemical Co.) was reacted to give the title compound.

APCI MS 628 (MH)+

Example 83

[S-(R*,R*)]-3-(4-Benzyloxy-phenyl)-2-{2-[3-(3,5-bis-trifluoromethyl-phenyl)-ureido]-4-methyl-pentanoylamino}-propionic acid tert-butyl ester By a procedure identical to that described in Example 54, the product from Example AI and 3,5-bis-trifluoromethylphenyl isocyanate (Aldrich Chemical Co.) was reacted to give the title compound.

APCI MS 696 (MH)+

Example 84

[S-(R*,R*)]-3-(4-Benzyloxy-phenyl)-2-{2-[3-(4-bromo-phenyl)-ureido]-4-methyl-pentanoylamino}-propionic acid tert-butyl ester By a procedure identical to that described in Example 54, the product from Example AI and 4-bromophenyl isocyanate (Aldrich Chemical Co.) was reacted to give the title compound.

APCI MS 638 (MH)+

Example 85

[S-(R*,R*)]-3-(4-Benzyloxy-phenyl)-2-{2-[3-(3,4-dichloro-phenyl)-ureido]-4-methyl-pentanoylamino}-propionic acid tert-butyl ester By a procedure identical to that described in Example 54, the product from Example AI and 3,4-dichlorophenyl isocyanate (Aldrich Chemical Co.) was reacted to give the title compound.

APCI MS 628 (MH)+

Example 86

[S-(R*,R*)]-3-(4-Benzyloxy-phenyl)-2-{2-[3-(3,5-dichloro-phenyl)-ureido]-4-methyl-pentanoylamino}-propionic acid tert-butyl ester By a procedure identical to that described in Example 54, the product from Example AI and 3,5-dichlorophenyl isocyanate (Aldrich Chemical Co.) was reacted to give the title compound.

APCI MS 627 $(MH)^+$

Example 87

[S-(R*,R*)]-3-(4-Benzyloxy-phenyl)-2-[2-(3-isopropyl-ureido)-4-methyl-pentanoylamino]-propionic acid tert-butyl ester By a procedure identical to that described in Example 54, the product from Example AI and isopropyl isocyanate (Aldrich Chemical Co.) was reacted to give the title compound.

APCI MS 526 (MH)+

Example 88

[S-(R*,R*)]-3-(4-Benzyloxy-phenyl)-2-[4-methyl-2-(3-methyl-ureido)-pentanoylamino]-propionic acid tert-butyl ester By a procedure identical to that described in Example 54, the product from Example AI and m-tolyl isocyanate (Aldrich Chemical Co.) was reacted to give the title compound.

APCI MS 498 $(MH)^+$

Example 89

[S-(R*,R*)]-3-(4-Benzyloxy-phenyl)-2-[2-(3-ethyl-ureido)-4-methyl-pentanoylamino]-propionic acid tert-butyl ester By a procedure identical to that described in Example 54, the product from Example AI and ethyl isocyanate (Aldrich Chemical Co.) was reacted to give the title compound.

APCI MS 512 (MH)+

Example 90

[S-(R*,R*)]-2-(4-Benzyloxy-benzyl)-5-[(furan-2-carbonyl)-amino]-7-methyl-4-oxo-octanoic acid tert-butyl ester A suspension of polystyrene-divinylbenzene morpholine (31 mg), the product from Example AI (20 mg) and 2-furoyl chloride (6.7 gL) in $CH_2Cl_2$ (1 mL) was shaken for 16 hours. The product from Example AZ (100 mg) (or alternatively polystyrene-divinylbenzene-supported tris(2-aminoethyl) amine, 100 mg) and polystyrene-divinylbenzene-supported methyl isocyanate (Nova Biochem, 50 mg) were added, and the reaction mixture was shaken for 2 hours. The resin was filtered and washed with DCM (2×1.5 mL). The combined organic phases, when concentrated to dryness, gave the title compound (24 mg, 98%).

APCI MS 535 $(MH)^+$

Example 91

[S-(R*,R*)]-3-(4-Benzyloxy-phenyl)-2-[2-(4-ethoxy-benzoylamino)-4-methyl-pentanoylamino]-propionic acid tert-butyl ester To a solution of the product from Example AI (20 mg), triethylamine (0.1 mL) in $CH_2Cl_2$ (1 mL) was added a 1 M solution of 4-ethoxybenzoyl chloride (0.12 mL) 1N $CH_2Cl_2$, and the reaction mixture was shaken for 2 hours. Then, polystyrene-divinylbenzene-supported tris(2-aminoethyl) amine (100 mg) and $CH_2Cl_2$ (2.5 mL) were added. After 16 hours, the resin was filtered and washed with $CH_2Cl_2$ (2 mL). The combined organic phases was concentrated to dryness. Partition between ethyl acetate and dilute sodium hydroxide, followed by concentration of the organic layer, gave the title compound (30 mg, 57%).

APCI MS 589 $(MH)^+$

Example 92

[S(R*,R*)]-3-(4-Benzyloxy-phenyl)-2-[4-methyl-2-(3,4,5-trimethoxy-benzoylamino)-pentanoylamino]-propionic acid tert-butyl ester By a procedure identical to that described in Example 91, the product from Example AI and 3,4,5-trimethoxybenzoyl chloride (Aldrich Chemical Co.) was reacted to give the title compound.

APCI MS 635 (MH)+.

Example 93

[S-(R*,R*)]-3-(4-Benzyloxy-phenyl)-2-[2-(4-tert-butyl-benzoylamino)-4-methyl-pentanoylamino]-propionic acid tert-butyl ester By a procedure identical to that described in Example 91, the product from Example AI and 4-tert-butylbenzoyl chloride (Aldrich Chemical Co.) was reacted to give the title compound.

APCI MS 601 (MH)+

Example 94

[S-(R*,R*)]-3-(4-Benzyloxy-phenyl)-2-[2-(4-fluoro-benzoylamino)-4-methyl-pentanoylamino]-propionic acid tert-butyl ester By a procedure identical to that described in Example 91, the product from Example AI and 4-fluorobenzoyl chloride (Aldrich Chemical Co.) was reacted to give the title compound.

APCI MS 563 (MH)+

Example 95

[S-(R*,R*)]-3-(4-Benzyloxy-phenyl)-2-[2-(4-methoxy-benzoylamino)-4-methyl-pentanoylamino]-propionic acid tert-butyl ester By a procedure identical to that described in Example 91, the product from Example AI and 4-methoxybenzoyl chloride (Aldrich Chemical Co.) was reacted to give the title compound.

APCI MS 575 (MH)+

Example 96

[S-(R*,R*)]-3-(4-Benzyloxy-phenyl)-2-[2-(3-methoxy-benzoylamino)-4-methyl-pentanoylamino]-propionic acid tert-butyl ester By a procedure identical to that described in Example 91, the product from Example AI and 3-methoxybenzoyl chloride (Aldrich Chemical Co.) was reacted to give the title compound.

APCI MS 575 (MH)+

Example 97

[S-(R*,R*)]-2-{2-[(Benzo[1,3]dioxole-5-carbonyl)-amino]-4-methyl-pentanoylamino}-3-(4-benzyloxy-phenyl)-propionic acid tert-butyl ester By a procedure identical to that described in Example 91, the product from Example AI and piperonyl chloride (Aldrich Chemical Co.) was reacted to give the title compound.

APCI MS 589 (MH)+

Example 98

[S-(R*,R*)]-3-(4-Benzyloxy-phenyl)-2-[2-(2-methoxy-benzoylamino)-4-methyl-pentanoylamino]-propionic acid tert-butyl ester By a procedure identical to that described in Example 91, the product from Example AI and 2-methoxybenzoyl chloride (Aldrich Chemical Co.) was reacted to give the title compound.

APCI MS 575 (MH)+

Example 99

[S-(R*,R*)]-3-(4-Benzyloxy-phenyl)-2-{4-methyl-2-[(naphthalene-2-carbonyl)-amino]pentanoylamino}-propionic acid tert-butyl ester By a procedure identical to that described in Example 91, the product from Example AI and 2-naphthoyl chloride (Aldrich Chemical Co.) was reacted to give the title compound.

APCI MS 592 $(MH)^+$

Example 100

[S-(R*,R*)]-3-(4-Benzyloxy-phenyl)-2-[2-(3,4-dimethoxy-benzoylamino)-4-methyl-pentanoylamino]-propionic acid tert-butyl ester By a procedure identical to that described in Example 91, the product from Example AI and 3,4-dimethoxybenzoyl chloride (Aldrich Chemical Co.) was reacted to give the title compound.

APCI MS 605 (MH)+

Example 101

[S-(R*,R*)]-3-(4-Benzyloxy-phenyl)-2-{2-[(biphenyl-4-carbonyl)-amino]-4-methyl-pentanoylamino}-propionic acid tert-butyl ester By a procedure identical to that described in Example 91, the product from Example AI and 4-biphenylcarbonyl chloride (Aldrich Chemical Co.) was reacted to give the title compound.

APCI MS 621 (MH)+

Example 102

[S-(R*,R*)]-5-(Benzo[1,2,5]thiadiazole-4-sulfonylamino)-2-(4-benzyloxybenzyl)-7-methyl-4-oxo-octanoic acid tert-butyl ester A suspension of polystyrene-divinylbenzene morpholine (31 mg), the product from Example AI (20 mg) and benzo- 2,1,3-thiadazole-4-sulphonyl chloride (Maybridge International Chemical Co., 12 mg) in $CH_2Cl_2$ (1 mL) was shaken on an orbital stirrer for 16 hours. Polystyrene-divinylbenzene-supported tris(2-aminoethy)lamine (100 mg) and $CH_2Cl_2$ (2.5 mL) were added. After 2 hours, the resin was filtered and washed with $CH_2Cl_2$ (2×1.5 mL). The combined organic phases, when concentrated to dryness, gave the title compound (23 mg, 80%).

APCI MS 639 (MH)+

Example 103

[S-(R*,R*)]-3-(4-Benzyloxy-phenyl)-2-[2-(4-methoxy-benzenesulfonylamino)-4-methyl-pentanoylamino]-propionic acid tert-butyl ester To a solution of the product from Example AI (40 mg), triethylamine (0.1 mL) in $CH_2Cl_2$ (1 mL) was added a 1 M solution of 4-methoxybenzenesufonyl chloride (Aldrich Chemical Co., 0.14 mL) in $CH_2Cl_2$, and the reaction mixture was shaken for 4 hours. Then, polystyrene-divinylbenzene-supported tris(2-aminoethyl)amine (150 mg) was added. After 16 hours, the resin was filtered and washed with $CH_2Cl_2$ (2 mL). The combined organic phases was concentrated to dryness to gave the title compound (33 mg. 60%).

APCI MS 611 $(MH)^+$

Example 104

[S-(R*,R*)]-3-(4-Benzyloxy-phenyl)-2-[2-(4-fluoro-benzenesulfonylamino)-4-methyl-pentanoylamino]-propionic acid tert-butyl ester By a procedure identical to that described in Example 103, the product from Example AI and 4-fluorobenzensulfonyl chloride (Aldrich Chemical Co.) was reacted to give the title compound.

APCI MS 599 $(MH)^+$

Example 105

[S-(R*,R*)]-3-(4-Benzyloxy-phenyl)-2-[4-methyl-2-(toluene-2-sulfonylamino)-pentanoylamino]-propionic acid tert-butyl ester By a procedure identical to that described in Example 103, the product from Example AI and o-toluenesulfonyl chloride (TCI America) was reacted to give the title compound.

APCI MS 595 $(MH)^+$

Example 106

[S-(R*,R*)]-3-(4-Benzyloxy-phenyl)-2-[2-(3,5-dichloro-benzenesulfonylamino)-4-methyl pentanoylamino]-propionic acid tert-butyl ester By a procedure identical to that described in Example 103, the product from Example AI and 3,5-dichlorobenzenesulfonyl chloride (Aldrich Chemical Co.) was reacted to give the title compound.

Example 107

[S-(R*,R*)]-3-(4-Benzyloxy-phenyl)-2-[4-methyl-2-(thiophene-2-sulfonylamino)-pentanoylamino]-propionic acid tert-butyl ester By a procedure identical to that described in Example 90, the product from Example AI and 2-thiophenesulfonyl chloride (Aldrich Chemical Co.) was reacted to give the title compound.

APCI MS 586 $(MH)^+$

Example 108

[S-(R*,R*)]-3-(4-Benzyloxy-phenyl)-2-[2-(5-dimethylamino-naphthalene-1-sulfonylamino)-4-methyl-pentanoylamino]-propionic acid tert-butyl ester By a procedure identical to that described in Example 90, the product from Example AI and dansyl chloride (Aldrich Chemical Co.) was reacted to give the title compound.

APCI MS 673 $(MH)^+$

Example 109

[S-(R*,R*)]-3-(4-Benzyloxy-phenyl)-2-[4-methyl-2-(quinoline-7-sulfonylamino)-pentanoylamino]-propionic acid tert-butyl ester By a procedure identical to that described in Example 90, the product from Example AI and quinloine-7-sulfonyl chloride was reacted to give the title compound.

APCI MS 632 $(MH)^+$

Example 110

[S-(R*,R*)]-3-(4-Benzyloxy-phenyl)-2-[2-(5-chloro-1,3-dimethyl-1H-pyrazole-4-sulfonylamino)-4-methyl-pentanoylamino]-propionic acid tert-butyl ester By a procedure identical to that described in Example 90, the product from Example AI and 5-chloro-1,3-dimethylpyrazole-4-sulphonyl chloride (Maybridge Chemical Company Ltd.) was reacted to give the title compound.

APCI MS 633 $(MH)^+$

Example 111

[S-(R*,R*)]-3-(4-Benzyloxy-phenyl)-2-[2-(3,5-dimethyl-isoxazole-4-sulfonylamino)-4-methyl-pentanoylamino]-propionic acid tert-butyl ester By a procedure identical to that described in Example 90, the product from Example AI and 3,5-dimethylisoxazole-4-sulphonyl chloride (Maybridge Chemical Company Ltd.) was reacted to give the title compound.

APCI MS 600 $(MH)^+$

Example 112

[S-(R*,R*)]-3-(4-Benzyloxy-phenyl)-2-[2-(3-diethylamino-propionylamino)-4-methyl-pentanoylamino]-propionic acid tert-butyl ester A suspention of polystyrene-divinylbenzene-supported carbodiimide (ref: *Org. Syn. Collective*, Vol. VI, Page 951) (300 mg), the product from Example AI (10 mg) and 3-(diethylamino)propionic acid hydrochloride (5 mg) in $CH_2Cl_2$ were shaken for 16 hours. The resin was filtered and washed with $CH_2Cl_2$ (2×1.5 mL). The combined organic phases, when concentrated to dryness, gave the title compound (13 mg, 99%).

APCI MS 568 $(MH)^+$

Example 113

[S-(R*,R*)]-2-(4-Benzyloxy-benzyl)-5-(2-1H-indol-3-yl-acetylamino)-7-methyl-4-oxo-octanoic acid tert-butyl ester To a suspension of polystyrene divinylbenzene morpholine (80 mg) and indole-3-acetic acid (11 mg) in $CH_2Cl_2$ (0.5 mL) was added isobutyl chloroformate (7.5mL in $CH_2Cl_2$ 0.5 mL). The reaction mixture was shaken for 1½ hours. Then a solution of the product from Example AI (2(S)-(2 (S)-amino-4-methyl-pentanoylamino)-3-(4-benzyloxy-phenyl) propionic acid tert-butyl ester (21 mg)) in $CH_2Cl_2$ (0.5 mL) was added. The reaction mixture was shaken for 16 hours. Polystyrene-divinylbenzene-supported tris(2-aminoethyl)amine (100 mg) and $CH_2Cl_2$ (2.5 mL) were added. After 1 hour, the resin was filtered and washed with $CH_2Cl_2$ (2×1.5 mL). The combined organic phases, when concentrated to dryness, gave the title compound (23 mg, 84%).

APCI MS 597(MH)+

Example 114

[S-(R*,R*)]-3-(4-Benzyloxy-phenyl)-2-(2-heptanoylamino-4-methyl-pentanoylamino)-propionic acid tert-butyl ester A suspension of polystyrene-divinylbenzene morpholine (31 mg), the product from Example AI (20 mg) and heptanoic anhydride (6.7 μL) in $CH_2Cl_2$ 20 (1 mL) was shaken for 1 hour. The product from Example AZ (80 mg) was added together with $CH_2Cl_2$ (1 mL), and the reaction mixture was shaken for 1 hour. The resin was filtered and washed with $CH_2Cl_2$ (2×1.5 mL). The combined organic phases, when concentrated to dryness, gave the title compound (19 mg, 74%).

APCI MS 553 $(MH)^+$

Example 115

[S-(R*,R*)]-3-(4-Benzyloxy-phenyl)-2-(2-isobutyrylamino-4-methyl-pentanoylamino)-propionic acid tert-butyl ester By a procedure identical to that described in Example 114, the product from Example AI and isobutyric acid (Aldrich Chemical Co.) was reacted to give the title compound.

APCI MS 511(MH)+

Example 116

[S-(R*,R*)]-2-(2-Acetylamino-4-methyl-pentanoylamino)-3-(4-benzyloxy-phenyl)-propionic acid tert-butyl ester By a procedure identical to that described in Example 114, the product from Example AI and acetic acid (Aldrich Chemical Co.) was reacted to give the title compound.

APCI MS 483 (MH)+

Example 117

[S-(R*,R*)]-3-(4-Benzyloxy-phenyl)-2-(4-methyl-2-propionylamino-pentanoylamino)-propionic acid tert-butyl ester By a procedure identical to that described in Example 114, the product from Example AI and propionic acid (Aldrich Chemical Co.) was reacted to give the title compound.

APCI MS 497 (MH)+

Example 118

[S-(R*,R*)]-3-(4-Benzyloxy-phenyl)-2-(2-butyrylamino-4-methyl-pentanoylamino)-propionic acid tert-butyl ester By a procedure identical to that described in Example 127, the product from Example AI and butyric acid (Aldrich Chemical Co.) was reacted to give the title compound.

APCI MS 511 (MH)+

Example 119

[S-(R*,R*)]-3-(4-Benzyloxy-phenyl)-2-[4-methyl-2-(2-pyridin-3-yl-acetylamino)pentanoylamino]-propionic acid tert-butyl ester A suspension of polystyrene-divinylbenzene-supported carbodiimide (ref: *Org. Syn. Collective*, Vol. VI, Page 951) (300 mg), polystyrene-divinylbenzene morpholine (10 mg), the product from Example AI (10 mg) and 3-pyridylacetic acid hydrochloride (Acros Organics) (4.7 mg) in $CH_2Cl_2$ were shaken for 18 hours. The resin was filtered and washed with $CH_2Cl_2$ (2×1.5 mL). The combined organic phases, when concentrated to dryness, gave the title compound (13 mg, 99%).

APCI MS 560 $(MH)^+$

Example 120

[S-(R*,R*)]-3-(4-Benzyloxy-phenyl)-2-[2-(3-1H-indol-3-yl-propionylamino)-4-methyl-pentanoylamino]-propionic acid tert-butyl ester By a procedure identical to that described in Example 119, the product from Example AI and 3-indolepropionic acid (Aldrich Chemical Co.) was reacted to give the title compound.

Example 121

[S-(R*,R*)]-3-(4-Benzyloxy-phenyl)-2-{4-methyl-2-[(5-methyl-2-phenyl-2H-[1,2,3]triazole-4-carbonyl)-amino]-pentanoylamino}-propionic acid tert-butyl ester By a procedure identical to that described in Example 90, the product from Example AI and 4-methyl-2-phenyl-1,2,3-triazole-5-carboxylic acid (Lancaster Synthesis Ltd.) was reacted to give the title compound.

APCI MS 626 (MH)+

Example 122

[S-(R*,R*)]-3-(4-Benzyloxy-phenyl)-2-[4-methyl-2-(2-thiophen-2-yl-acetylamino)pentanoylamino]-propionic acid tert-butyl ester By a procedure identical to that described in Example 90, the product from Example AI and thiophene-2-acetic acid (Aldrich Chemical Co.) was reacted to give the title compound.

APCI MS 565 (MH)+

Example 123

[S-(R*,R*)]-3-(4-Benzyloxy-phenyl)-2-{2-1 (isoxazole-5-carbonyl)-amino]-4-methyl-pentanoylamino}-propionic acid tert-butyl ester By a procedure identical to that described in Example 90, the product from Example AI and isoxazole-5-carboxylic acid (Maybridge Chemical Company Ltd.) was reacted to give the title compound.

APCI MS 536 (MH)+

Example 124

[S-(R*,R*)]-3-(4-Benzyloxy-phenyl)-2-{4-methyl-2-[(pyridine-3-carbonyl)-amino]pentanoylamino}-propionic acid tert-butyl ester By a procedure identical to that described in Example 90, the product from Example AI and nicotinic acid (Aldrich Chemical Co.) was reacted to give the title compound.

APCI MS 546 (MH)+

Example 126

[S-(R*,R*)]-3-(4-Benzyloxy-phenyl)-2-{4-methyl-2-[(quinoxaline-2-carbonyl)-amino]pentanoylamino}-propionic acid tert-butyl ester By a procedure identical to that described in Example 90, the product from Example AI and 2-quinoxaline carboxylic acid (Aldrich Chemical Co.) was reacted to give the title compound.

APCI MS 597 (MH)+

Example 127

[S-(R*,R*)]-2-(4-Benzyloxy-benzyl)-7-methyl-4-oxo-5-(2,2,3,3,3-pentafluoro-propionylamino)-octanoic acid tert-butyl ester A suspension of polystyrene-divinylbenzene morpholine (31 mg), the product from Example AI (20 mg) and pentafluoropropinic anhydride (6.7 $\mu$L) in $CH_2Cl_2$ (1 mL) was shaken for 1 hour. Resin A (50 mg) and polystyrene-divinylbenzene-supported tris(2-aminoethyl)amine (50 mg) was added together with $CH_2Cl_2$ (1 mL), and the reaction mixture was shaken for 2 hours. The resin was filtered and washed with $CH_2Cl_2$ (2×1.5 mL). The combined organic phases, when concentrated to dryness, gave the title compound (19 mg, 74%).

APCI MS=553

Example 128

[S-(R*,R*)]-3-(4-Benzyloxy-phenyl)-2-[4-methyl-2-(2,2,2-trifluoro-acetylamino)pentanoylamino]-propionic acid tert-butyl ester By a procedure identical to that described in Example 127, the product from Example AI and trifluoroacetic acid (Aldrich Chemical Co.) was reacted to give the title compound.

APCI MS 536 (MH)+

Example 129

[S-(R*,R*)]-3-(4-Benzyloxy-phenyl)-2-[2-(2,2-dimethyl-propionylamino)-4-methyl-pentanoylamino]-propionic acid tert-butyl ester By a procedure identical to that described in Example 127, the product from Example AI and pivalic acid (Aldrich Chemical Co.) was reacted to give the title compound.

APCI MS 525 (MH)+

Example 130

[S-(R*,R*)]-2-(2-Benzoylamino-4-methyl-pentanoylamino)-3-(4-benzyloxy-phenyl)-propionic acid tert-butyl ester By a procedure identical to that described in Example 127, the product from Example AI and benzoic acid (Aldrich Chemical Co.) was reacted to give the title compound. APCI MS 545 (MH)+

Example 131

[(S-(R*,R*)]-3-(4-Benzyloxy-phenyl)-2-{4-methyl-2-[(5-methyl-3-phenyl-isoxazole-4-carbonyl)amino]-pentanoylamino}-propionic acid tert-butyl ester By a procedure identical to that described in Example 90, the product from Example AI and 5-methyl-3-phenylisoxazole-4-carboxylic acid (Lancaster Synthesis Ltd.) was reacted to give the title compound.

APCI MS 625 (MH)+

Example 132

[S-(R*,R*)]-Azepane-1-carboxylic acid {1-[2-(4-benzylamino-phenyl)-1-tert-butylcarbamoyl-ethylcarbamoyl]-3-methyl-butyl}-amide A mixture of the product from Example AM (1.89 g, 4 mmol), diisopropylethylamine (1.38 g, 8 mmol), benzylbromide (0.68 g, 4 mmol), toluene (30 ML), and THF (30 mL) was stirred at 25° C. for 24 hours. The precipitate was removed, and the reaction mixture was concentrated to dryness. The mixture was further dissolved in EtOAc, washed with $NaHCO_3$ (aq), and concentrated to dryness. The crude product was purified by column chromatography ($SiO_2$, 3:1 EtOAc/hexane) to give the title compound (20% yield), mp=89–90° C.

Anal. Calc'd for $C_{33}H_{49}N_5O_3.0.5H_2O$: C, 69.19, H, 8.80, N, 12.23. Found: C, 69.56, H, 8.74, N, 12.15.

Example 133

[S-(R*,R*)]-Azepane-1-carboxylic acid {1-[2-(4-dibenzylamino-phenyl)-1-tert-butylcarbamoyl-ethylcarbamoyl]-3-methyl-butyl}-amide The title compound is isolated from the reaction described in Example 132 (40% yield), mp=174–175° C.

APCI MS 654 $(MH)^+$

Example 134

[S(R*,R*)]-Azepane-1-carboxylic acid {1-[1-tert-butylcarbamoyl-2-(4-phenylethynyl-phenyl)-ethylcarbamoyl]-3-methyl-butyl}-amide In a 100 mL round bottomed flask, the product from Example AP (1.01 g, 1.7 mmol), phenyl acetylene (0.174 g, 1.17 mmol), and triethyl amine (1.2 mL, 8.5 mmol) were stirred together in 25 mL of THF for 15 minutes. Dichlorobis (triphenylphosphine) palladium (II) (0.08 g, 0.1 mmol) and copper iodide (0.011 g, 0.05 mmol) were added to the reaction mixture, and the resultant mixture was stirred for 1 hour at nitrogen atmosphere. After completion, the reaction mixture was evaporated to dryness under vacuum. The crude mixture was purified by flash chromatography (silica gel, 30% ethyl acetate/hexane). The material obtained was further purified by crystallizing from petroleum ether and toluene to give the title compound (0.8 g, 84%) as a white solid, mp 115–117° C.

APCI MS 559.3 $(MH)^+$

Example 135

[S-(R*,R*)]-Azepane-1-carboxylic acid (1-{1-tert-butylcarbamoyl-2-[4-(3,3-dimethyl-but-1-ynyl)-phenyl]-ethylcarbamoyl}-3-methyl-butyl)-amide In a manner similar to the procedure described in Example 134, the product of Example AP (1.1 g, 1.7 mmol) and 3,3-dimethylbutyne (300 $\mu$L, 2.4 mmol) was reacted. The crude product was purified by chromatography (silica gel, 50% ethyl acetate/hexane) to give the title compound (0.50 g, 84%) as a white solid, mp 180–181° C.

APCI MS 539 $(MH)^+$

Example 136

[S-(R*,R*)]-Azepane-1-carboxylic acid {1-[1-tert-butylcarbamoyl-2-(4-cyclohexylethynyl-phenyl)-ethylcarbamoyl]-3-methyl-butyl}-amide In a manner similar to the procedure described in Example 134, the product of Example AP (1.01 g, 1.7 mmol)

and cyclohexylethyne (0.185 g,1.7 mmol) was reacted to give the title compound (0.82 g, 85%) as a white solid, mp 171–172° C.

Anal. Calc'd. for $C_{34}H_{52}N_4O_3$: C, 72.30; H,9.28; N, 9.92. Found: C, 71.91; H, 9.32; N, 9.77.

Example 137

[S-(R*,R*)]-Azepane-1-carboxylic acid {1-[1-tert-butylcarbamoyl-2-(4-pyridin-2-ylethynyl-phenyl)-ethylcarbamoyl]-3-methyl-butyl}-amide In a manner similar to the procedure described in Example 134, the product of Example AP (2.0 g, 3.4 mmol) and 2-ethynylpyridine (0.356 g, 3.5 mmol) are reacted to give the title compound (1.52 g, 77%) as a brown solid, mp 118–120° C.

For $C_{33}H_{45}N_5O_3$: HRMS (ESI) calculated (M+H) 560.3600, Found 560.3599.

Example 138

[S-(R*,R*)]-Azepane-1-carboxylic acid (1-({-tert-butylcarbamoyl-2-[4-(1-hydroxy-cyclohexylethynyl)-phenyl]-ethylcarbamoyl}-3-methyl-butyl)-amide In a manner similar to the procedure described in Example 134, the product of Example AP (1.0 g, 1.7 mmol) and 1-ethynyl 1-cyclohexanol (0.220 g, 1.7 mmol) was reacted. The crude product was purified by chromatography (silica gel, 70% ethyl acetate/hexane) to give the title compound (0.61 g, 62%) as a white solid, mp 120–122° C.

Anal. Calc'd for $C_{34}H_{52}N_4O_4$: C, 70.31; H, 9.02; N, 9.65. Found: C, 70.24; H, 8.98; N, 8.31

Example 139

[S-(R*,R*)]-Azepane-1-carboxylic acid (1-{1-tert-butylcarbamoyl-2-[4-(3-dimethylamino-prop-1-ynyl)-phenyl]-ethylcarbamoyl}-3-methyl-butyl)-amide In a manner similar to the procedure described in Example 134, the product of Example AP (1.12 g, 1.91 mmol) and 1-dimethylamino 2-propyne (0.259 g, 3.12 mmol) was reacted. The crude reaction mixture was purified by chromatography (silica gel, 1% ammonia in ethyl acetate) to give the title compound (0.82 g, 89%) as a light brown solid, mp 95–97° C.

APCI MS 540.5 $(MH)^+$

Example 140

[S-(R*,R*)]-Azepane-1-carboxylic acid [1-(1-tert-butylcarbamoyl-2-{4-[3-(1,1-dioxo-11,6-thiomorpholin-4-yl)-prop-1-ynyl]-phenyl}-ethylcarbamoyl)-3-methyl-butyl]-amide In a manner similar to the procedure described in Example 134, the product of Example AP (0.892 g, 1.53 mmol) and 4-propargylthiomorpholine 1,1-dioxide (0.265 g, 1.53 mmol) was reacted. The crude mixture was purified by chromatography (silica gel, ethyl acetate to give the title compound (0.798 g, 83%) of yellow solid, mp 117–118° C.

APCI MS 630.4 $(MH)^+$

Example 141

[S-(R*,R*)]-Azepane-1-carboxylic acid {1-[1-tert-butylcarbamoyl-2-(4-styryl-phenyl)-ethylcarbamoyl]-3-methyl-butyl}-amide To a solution of the product from Example 134 (0.178 g, 0.32 mmol) in 15 mL of THF was added 5% Pd/C (0.02 g) and 1 mL of pyridine. The mixture was subjected to hydrogenation for 15.5 hours at 20 psi. The crude reaction mixture was evaporated to dryness and purified by chromatography (silica gel, 50% ethyl acetate/hexane). The product was further purified by crystallizing from petroleum ether and toluene to give the title compound (0.089 g, 50%) as a white solid, mp 95–96° C.

Anal. Calc'd for $C_{34}H_{48}N_4O_3$: C, 72.82; H, 8.62; N, 9.99. Found: C, 72.33; H, 8.14; N, 9.69.

Example 142

[S-(R*,R*),Z]-Azepane-1-carboxylic acid (1-{1-tert-butylcarbamoyl-2-[4-(2-cyclohexyl -vinyl)-phenyl]-ethyl carbamoyl}-3-methyl-butyl)-amide In a manner similar to the procedure described in Example 141, the product of Example 136 (0.173 g, 0.305 mmol) was converted to the title compound (0.080 g, 46%) as a white solid, mp 168–169° C.

APCI MS 567.5 $(MH)^+$

Example 143

[S-(R*,R*)]-Azepane-1-carboxylic acid [1-(1-tert-butylcarbamoyl-2-{4-[2-(1-hydroxy-cyclohexyl)-vinyl]-phenyl}-ethylcarbamoyl)-3-methyl-butyl]-amide In a manner similar to the procedure described in Example 141, the product of Example 138 (0.184 g, 0.32 mmol) was reacted. The crude reaction mixture was purified by chromatography (silica gel, 70% ethyl acetate/hexane) to give the title compound (0.11 g) as a white solid, mp 125° C. (dec.).

Anal. Calc'd for $C_{34}H_{54}N_4O_4$: C, 70.07; H, 9.34; N, 9.61. Found C, 70.00; H, 9.15; N, 9.21.

Example 144

[S-(R*,R*)]-Azepane-1-carboxylic acid {1-[1-tert-butylcarbamoyl-2-(4-phenethyl-phenyl)-ethylcarbamoyl]-3-methyl-butyl}-amide To a solution of the product from Example 134 (0.187 g, 0.33 mmol) in 16 mL of 1:1 THF/methanol mixture was added 20% Pd/C (0.1 g). The resulting solution was hydrogenated for 20.5 hours at 20 psi. The crude mixture was evaporated to dryness and was purified by chromatography (silica gel, 30% ethyl acetate/hexane). It was further purified by crystallizing from petroleum ether and toluene to give the title compound (0.12 g, 65%) as a white solid, mp 155–156° C. Anal. Calc'd for $C_{34}H_{50}N_4O_3$: C, 72.56; H, 8.95; N, 9.95. Found: C, 72.2; H, 9.03; N, 9.80

Example 145

[S-(R*,R*)]-Azepane-1-carboxylic acid (1-{1-tert-butylcarbamoyl-2-[4-(3,3-dimethyl-butyl)-phenyl]-ethylcarbamoyl}-3-methyl-butyl)-amide In a manner similar to the procedure described in Example 142, the product of Example 133 (0.175 g, 0.324 mmol) and 0.1 g 20% Pd/C was reacted. The crude product was purified by chromatography (silica gel, 50% ethyl acetate/hexane) to give the title compound (0.062 g, 35%) as a white solid, mp 180–181° C.

Anal. Calc'd for $C_{32}H_{54}N_4O_3$: C, 70.80; H, 10.03; N, 10.32. Found: C, 70.57; H, 9.91; N, 10.26.

Example 146

[S-(R*,R*)]-Azepane-1-carboxylic acid (1-{1-tert-butylcarbamoyl-2-[4-(2-cyclohexyl-ethyl)-phenyl]-ethylcarbamoyl}-3-methyl-butyl)-amide In a manner similar to the procedure described in Example 144, the product of Example 135 (0.174 g, 0.308 mmol) was reacted to give the title compound (0.092 g, 57%) as a white solid, mp 165° C.

Anal. Calc'd for $C_{34}H_{56}N_4O_3$: C, 71.79; H, 9.92; N, 9.85. Found: C, 71.68; H, 9.96; N, 9.73.

Example 147

[S-(R*,R*)]-Azepane-1-carboxylic acid (1-{1-tert-butylcarbamoyl-2-[4-(2-pyridin-2-yl-ethyl)-phenyl]-ethylcarbamoyl}-3-methyl-butyl)-amide In a manner similar to the procedure described in Example 144, the product of Example 136 (0.166 g, 0.296 mmol) was reacted to give the title compound (0.072 g, 43%) as a light brown solid, mp 154–156° C.

Anal. Calc'd for $C_{33}H_{49}N_5O_3$: C, 70.30; H, 8.76; N, 12.43. Found: C, 69.76; H, 8.70; N, 12.2.

Example 148

[S-(R*,R*)]-Azepane-1-carboxylic acid [1-(1-tert-butylcarbamoyl-2-{4-[2-(1-hydroxy-cyclohexyl)-ethyl]-phenyl}-ethylcarbamoyl)-3-methyl-butyl]-amide In a manner similar to the procedure described in Example 144, the product of Example 138 (0.177 g, 0.3 mmol) was reacted. The crude reaction mixture was purified by chromatography (silica gel, 70% ethyl acetate/hexane to give the title compound (0.091 g, 51%) as a white solid, mp 101–102° C.

Anal. Calc'd for $C_{34}H_{56}N_4O_4$: C, 69.83; H, 9.65; N, 9.58. Found: C, 69.59; H, 9.64; N. 9.28.

Example 149

[S-(R*,R*)]-Azepane-1-carboxylic acid (1-{1-tert-butylcarbamoyl-2-[4-(3-dimethylamino-propyl)-phenyl]-ethylcarbamoyl}-3-methyl-butyl)-amide In a manner similar to the procedure described in Example 144, the product of Example 139 (0.15 g, 0.28 mmol) was reacted. The crude product was purified by chromatography (silica gel, 1% ammonia in ethyl acetate) to give the title compound (0.1 g, 65%) as a white solid, mp 142–145° C.

APCI MS 544.5 $(MH)^+$

Example 150

[S-(R*,R*)]-Azepane-1-carboxylic acid [1-(1-tert-butylcarbamoyl-2-{4-[3-(1,1-dioxo-1l,6-thiomorpholin-4-yl)-propyl]-phenyl}-ethylcarbamoyl)-3-methyl-butyl]-amide In a manner similar to the procedure described in Example 144, the product of Example 140 (0.175 g, 0.31 mmol) was reacted. The crude product was purified by chromatography (silica gel, ethyl acetate) to give the title compound (0.11 g, 65%) as a light brown solid, mp 92–93° C.

APCI MS 634.5 $(MH)^+$

Examples 151–164

Multiple Parallel Synthesis using H-Tyr(OBn)-OH Coupled to Kaiser Oxime Resin

A solution of the appropriate BOC-amino acid (4.55 mmol) in 30 mL of DMF was treated with $iPr_2NEt$ (1.6 mL, 9.1 mmol), HBTU (1.72 g, 4.55 mmol), and HOBt (0.97 g, 4.55 mmol) and the resulting solution stirred for 10 minutes at room temperature. The reaction mixture was added to the resin obtained from Example AR and the resulting suspension was shaken for 1 hour. The resin was washed with DMF (5×). The resin was then split into 1 g portions and treated with a solution of 25% trifluroacetic acid in $CH_2Cl_2$ (v/v) for 30 minutes. The resin was then washed with $CH_2Cl_2$ (3×), 5% diisopropylamine in $CH_2Cl_2$ (v/v), $CH_2Cl_2$ (3×), and dimethylformamide (3×). The resin was then treated with 10 equivalents of the appropriate carbamoyl chloride and 5 equivalents of diisopropylethylamine and shaken overnight. The resulting resins were then further divided into 0.5 g units (0.5 g, load Å0.3–0.5 mmol/g resin) and suspended in 4 mL of DMF and treated with the appropriate amine (2.5 mmol). The resulting suspension was shaken overnight, and the resin was removed by filtration. The resin was washed with additional DMF, and the combined solvent was removed under vacuum. The residue was dissolved in $CH_2Cl_2$ or ethyl acetate and washed with aqueous 0.5N HCl solution. The organic phase was dried and concentrated. The residue was purified give the title compound by preparative HPLC using the following conditions:

Column: 4.14×25 cm with a 5 cm precolumn C18, 8 uM, 300A

Solvent A; 0.1% TFA/water

Solvent B; 0.1% TFA/acetonitrile

Linear gradient 5–75% in 70 minutes

Flow rate: 80 mL/minute

The following compounds were prepared by employing the following BOC-amino acids,carbamoyl chlorides, and amines in various combinations:

| Boc-Amino Acids | Amines | Carbamoyl Chlorides |
|---|---|---|
| Boc-Leucine (Bachem) | tert-butyl amine (Aldrich Chemical Co.) | morpholine-4-carbonyl chloride (Aldrich Chemical Co.) |
| Boc-L-proline (Bachem) | piperidine (Aldrich Chemical Co.) | hexahdroazepinylcarbonyl chloride |
| Boc-D-proline (Bachem) | 1-(2-amino-ethyl)piperidine (Aldrich Chemical Co.) | |
| Boc-L-Met-OH (Bachem) | | |
| Boc-L-Tyr-OH (Bachem) | | |
| Boc-L-Tyr(OBn)-OH (Bachem) | | |
| Boc-L-p-bromo-Phe-OH (Bachem) | | |
| Boc-β-t-Bu-Ala-OH (Bachem) | | |
| N-Boc-L-octahydroindole-2-carboxylic acid (Bachem) | | |
| N-Boc-cyclohexyl-L-alanine (Bachem) | | |
| Boc-L-Tyr(OtBu)-OH (Bachem) | | |
| Boc-L-α-aminosuberic | | |

-continued

| Boc-Amino Acids | Amines | Carbamoyl Chlorides |
|---|---|---|
| acid (O-tBu)-OH (Bachem) | | |

Example 151

[S(R*,R*)]-Morpholine-4-carboxylic acid {1-[1-(4-benzyloxy-benzyl)-2oxo-2-piperidin-1-ylethylcarbamoyl]-3-methyl-butyl}amide

APCI MS 56 $(MH)^+$

Example 152

[S-(R*,R*)]-1-(Azepane-1-carbonyl)-pyrrolidine-2-carboxylic acid [2-(4-benzyloxy-phenyl)-1-(2-piperidin-1-yl-ethylcarbamoyl)-ethyl]-amide

FAB MS 604 $(MH)^+$

Example 153

[S-(R*,R*)]-1-(Azepane-1-carbonyl)-pyrrolidine-2-carboxylic acid [2-(4-benzyloxy-phenyl)-1tert-butylcarbamoyl-ethyl]-amide

FAB MS 549 $(MH)^+$

Example 154

[S-(R*,R*)]-Azepane-1-carboxylic acid {1-[2-(4-benzyloxy-phenyl)-1-(2-piperidin-1-ylethylcarbamoyl)-ethylcarbamoyl]-3-methylsulfanyl-propyl}-amide

FAB MS 638 $(MH)^+$

Example 155

[S-(R*,R*)]-Azepane1-carboxylic acid {1-[2-(4-benzyloxy-phenyl)-1-tert-butylcarbamoyl-ethylcarbamoyl]-3-methylsulfanyl-propyl}-amide

FAB MS 583 $(MH)^+$

Example 156

[S-(R*,R*)]-Azepane-1-carboxylic acid [1-[2-(4-benzyloxy-phenyl)-1-(2-piperidin-1-ylethylcarbamoyl)-ethylcarbamoyl]-2-(4-hydroxy-phenyl)-ethyl]-amide

FAB MS 670 $(MH)^+$

Example 157

[S-(R*,R*)]-Azepane-1-carboxylic acid [1-[2-(4-benzyloxy-phenyl)-1-(2-piperidin-1-ylethylcarbamoyl)-ethylcarbamoyl]-2-(4-bromo-phenyl)-ethyl]-amide

FAB MS 734, 736 $(MH)^+$

Example 158

[S-(R*,R*)]-Azepane-1-carboxylic acid [1-[1-(4-benzyloxy-benzyl)-4,4-dimethyl2oxo-pentylcarbamoyl]-2-(4-benzyloxy-phenyl)-ethyl]-amide

FAB MS 566 $(MH)^+$

Example 159

[S-(R*,R*)]-Azepane-1-carboxylic acid {1-[2-(4-benzyloxy-phenyl)-1-(2-piperidin-1-ylethylcarbamoyl)-ethylcarbamoyl]-3,3-dimethyl-butyl}-amide

FAB MS 635 $(MH)^+$

Example 160

[S-(R*,R*)]-Azepane-1-carboxylic acid [1-[2-(4-benzyloxy-phenyl)-1-tert-butylcarbamoyl-ethylcarbamoyl ]-2-(4-hydroxy-phenyl)-ethyl]-amide

FAB MS 615 $(MH)^+$

Example 161

[S-(R*,R*)]-1-(Azepane-1-carbonyl)-octahydro-indole-2-carboxylic acid [2-(4-benzyloxy-phenyl)-1-tert-butylcarbamoyl-ethyl]-amide

FAB MS 603 $(MH)^+$

Example 162

[S-(R*,R*)]-Azepane-1-carboxylic acid {1-[2-(4-benzyloxy-phenyl)-1-(2-piperidin-1-ylethylcarbamoyl)-ethylcarbamoyl]-2-cyclohexyl-ethyl}-amide

FAB MS 660 $(MH)^+$

Example 163

[S-(R*,R*)]-Azepane-1-carboxylic acid [1-[2-(4-benzyloxy-phenyl)-1-tert-butylcarbamoyl-ethylcarbamoyl ]-2-(4-tert-butoxy-phenyl)-ethyl]-amide

FAB MS 671 $(MH)^+$

Example 164

[S-(R*,R*)]-6-[(Azepane-1-carbonyl)-amino]-6-[2-(4-benzyloxy-phenyl)-1-tert-butylcarbamoyl-ethylcarbamoyl]-hexanoic acid tert-butyl ester Example 165

[S-(R*,R*)]-Azepane-1-carboxylic acid {1-[2-(4-benzyloxy-phenyl)-1-(2-hydroxy-ethylcarbamoyl)-ethylcarbamoyl]-3-methyl-butyl}-amide A suspension of the resin prepared in Example AS (2-{2 [(Azepane-1-carbonyl-carbonyl)-amino]-4-methyl-pentanoylamino }-3-(4-benzyloxy-phenyl) propionic acid kaiser oxime resin ester) (0.5 g, load Å 0.3–0.5 mmol/g resin) in 4 mL of DMF was treated with 2-hydroxyethylamine (2.5 mmol). The resulting suspension was shaken overnight, and the resin was removed by filtration. The resin was washed with additional DMF, and the combined solvent was removed under vacuum. The residue was dissolved in $CH_2Cl_2$ or ethyl acetate and washed with aqueous 0.5N HCl solution. The organic phase was dried and concentrated. The residue was purified give the title compound by preparative HPLC using the following conditions:

Column: 4.14×25 cm with a 5 cm precolumn C18, 8 μM, 300A

Solvent A; 0.1% TFA/water

Solvent B; 0.1% TFA/acetonitrile

Linear gradient 5–75% in 70 minutes

Flow rate: 80 mL/minute

APCI MS 553 $(MH)^+$

Example 166

[S-(R*,R*)]-Azepane-1-carboxylic acid {1-[1-(4-benzyloxy-benzyl)-2-morpholin-4-yl-2-oxo-ethylcarbamoyl]-3-methyl-butyl}-amide By a procedure identical to that described in Example 165, the resin obtained in Example AS and morpholine (Aldrich Chemical Co.) was reacted to give the title compound. APCI MS 579 $(MH)^+$ Example 167

[S-(R*,R*)]-Azepane-1-carboxylic acid {1-[1-(4-benzyloxy-benzyl)-2-oxo-2-piperidin-1-ylethylcarbamoyl]-3-methyl-butyl}-amide By a procedure identical to that described in Example 165, the resin obtained in Example AS and piperidine (Aldrich Chemical Co.) was reacted to give the title compound.

APCI MS 577 $(MH)^+$

Example 168

[S-(R*,R*)]-Azepane-1-carboxylic acid {1-[2-(4-benzyloxy-phenyl)-1-hexylcarbamoyl-ethylcarbamoyl]-3-methyl-butyl}-amide By a procedure identical to that described in Example 165, the resin obtained in Example AS and n-hexylamine (Aldrich Chemical Co.) was reacted to give the title compound.

Example 169

[S-(R*,R*)]-Azepane-1-carboxylic acid {1-[2-(4-benzyloxy-phenyl)-1-propylcarbamoyl-ethylcarbamoyl]-3-methyl-butyl}-amide By a procedure identical to that described in Example 165, the resin obtained in Example AS and n-propylamine (Aldrich Chemical Co.) was reacted to give the title compound.

Example 170

[S-(R*,R*)]-Azepane-1-carboxylic acid (1-{2-(4-benzyloxy-phenyl)-1-[2-(2-oxo-pyrrolidin-1yl)-ethylcarbamoyl]-ethylcarbamoyl}-3-methyl-butyl)-amide By a procedure identical to that described in Example 165, the resin obtained in Example AS and 1-(2-aminoethyl)-2-pyrrolidinone was reacted to give the title compound.

Example 171

[S-(R*,R*)]-Azepane-1-carboxylic acid {1-[2-(4-benzyloxy-phenyl)-1-(2-piperidin-1-yl-ethylcarbamoyl)-ethylcarbamoyl]-3-methyl-butyl}-amide By a procedure identical to that described in Example 165, the resin obtained in Example AS and 1-(2-aminoethyl) piperidine (Aldrich Chemical Co.) was reacted to give the title compound.

FAB MS 621 $(MH)^+$

Example 172

[S-(R*,R*)]-Azepane-1-carboxylic acid (1-{2-(4-benzyloxy-phenyl)-1-[2-(1H-imidazol-4-yl) ethylcarbamoyl]-ethylcarbamoyl}-3-methyl-butyl)-amide By a procedure identical to that described in Example 165, the resin obtained in Example AS and histamine (Aldrich Chemical Co.) was reacted to give the title compound.

APCI MS 603 $(MH)^+$

Example 173

[S-(R*,R*)]-Azepane-1-carboxylic acid {1-[2-(4-benzyloxy-phenyl)-1-(4-bromophenylcarbamoyl)-ethylcarbamoyl]-3-methyl-butyl}-amide By a procedure identical to that described in Example 165, the resin obtained in Example AS and 4-bromo-aniline (Aldrich Chemical Co.) was reacted to give the title compound.

APCI MS 664 $(MH)^+$

Example 174

[S-(R*,R*)]-Azepane-1-carboxylic acid {1-[2-(4-benzyloxy-phenyl)-1-(2-furan-2-ylethylcarbamoyl)-ethylcarbamoyl]-3-methyl-butyl}-amide By a procedure identical to that described in Example 165, the resin obtained in Example AS and 1-(2-aminoethyl)-2-furan (Aldrich Chemical Co.) was reacted to give the title compound.

Example 175

[S-(R*,R*)]-Azepane-1-carboxylic acid {1-[2-(4-benzyloxy-phenyl)-1-(2-dimethylamino-ethylcarbamoyl)-ethylcarbamoyl]-3-methyl-butyl}-amide By a procedure identical to that described in Example 165, the resin obtained in Example AS and N,N-dimethylethylenediamine (Aldrich Chemical Co.) was reacted to give the title compound.

FAB MS 580 $(MH)^+$

Example 176

[S-(R*,R*)]-Azepane-1-carboxylic acid {1-[1-(4-benzyloxy-benzyl)-2-(4-methyl-piperazin-1-yl)-2-oxo-ethylcarbamoyl]-3-methyl-butyl}-amide By a procedure identical to that described in Example 165, the resin obtained in Example AS and N-methylpiperazine (Aldrich Chemical Co.) was reacted to give the title compound.

APCI MS 592 $(MH)^+$

Example 177

[S-(R*,R*)]-Morpholine-4-carboxylic acid {1-[2-(4-benzyloxy-phenyl)-1-(2-piperidin-1-ylethylcarbamoyl)-ethylcarbamoyl]-3-methyl-butyl}-amide By a procedure identical to that described in Example 165, the resin obtained in Example AS and 1-(2-aminoethyl)

piperidine (Aldrich Chemical Co.) was reacted to give the title compound.

Example 178

[S-(R*,R*)]-Azepane-1-carboxylic acid (1-{2-(4-benzyloxy-phenyl)-1-[(pyridin-4-ylmethyl) carbamoyl]-ethylcarbamoyl}-3-methyl-butyl)-amide By a procedure identical to that described in Example 165, the resin obtained in Example AS and 4-aminomethylpyridine (Aldrich Chemical Co.) was reacted to give the title compound.

FAB MS 600 $(MH)^+$

Example 179

Azepane-1-carboxylic acid {(S)-1-[(S)-1-(4-benzyloxy-benzyl)-2-oxo-2-[(S)-2-pyrrolidin-1-ylmethyl-pyrrolidin-1-yl]-ethylcarbamoyl]-3-methyl-butyl}-amide By a procedure identical to that described in Example 165, the resin obtained in Example AS and (S)-(+)-1-(2-pyrrolidinylmethyl)pyrrolidine (Aldrich Chemical Co.) was reacted to give the title compound.

Example 180

[S-(R*,R*)]-Azepane-1-carboxylic acid {1-[1-(4-benzyloxy-benzyl)-2-(4-benzyl-piperazin-1-yl)-2-oxo-ethylcarbamoyl]-3-methyl-butyl}-amide By a procedure identical to that described in Example 165 the resin obtained in Example AS and 1-benzylpiperazine (Aldrich Chemical Co.) was reacted to give the title compound.

FAB MS 683 $(MH)^+$

Example 181

[S-(R*,R*)]-Azepane-1-carboxylic acid {1-[2-(4-benzyloxy-phenyl)-1-(2-pyrrolidin-1-ylethylcarbamoyl)-ethylcarbamoyl]3-methyl-butyl}-amide By a procedure identical to that described in Example 165, the resin obtained in Example AS and 1-(2-aminoethyl) pyrrollidine (Aldrich Chemical Co.) was reacted to give the title compound.

FAB MS 606 $(MH)^+$

Example 182

Azepane-1-carboxylic acid {(S)-1-[-1-[(S)-1-aza-bicyclo [2.2.2]-3-ylcarbamoyl]-2-(4-benzyloxy-phenyl)-ethylcarbamoyl]-3-methyl-butyl}-amide By a procedure identical to that described in Example 165, the resin obtained in Example AS and (R)-(+)-3-amineoquinuclidine (Aldrich Chemical Co.) was reacted to give the title compound.

FAB MS 618 $(MH)^+$

Example 183

Azepane-1-carboxylic acid {(S)-1-[(S)-2-(4-benzyloxy-phenyl)-1-[1-benzyl-(S)-pyrrolidin-3-ylcarbamoyl]-ethylcarbamoyl]-3-methyl-butyl}-amide By a procedure identical to that described in Example 165, the resin obtained in Example AS and (3R)-(−)-1-benzyl-3-aminopyrrolidine (Lancaster Synthesis Ltd.) was reacted to give the title compound.

FAB MS 668 $(MH)^+$

Example 184

[S-(R*,R*)]-Azepane-1-carboxylic acid {1-[2-(4-benzyloxy-phenyl)-1-(3-cyclohexylamino-propylcarbamoyl)-ethylcarbamoyl]-3-methyl-butyl}-amide By a procedure identical to that described in Example 165, the resin obtained in Example AS and N-(3-aminopropyl)cyclohexylamine (Aldrich Chemical Co.) was reacted to give the title compound.

FAB MS 648 $(MH)^+$

Example 185

[S-(R*,R*)]-Azepane-1-carboxylic acid {1-[1-(4-benzyloxy-benzyl)-2-[1,4']bipiperidinyl-1'-yl-2-oxo-ethylcarbamoyl]-3-methyl-butyl}-amide By a procedure identical to that described in Example 165, the resin obtained in Example AS and 4-piperidinylpiperidine (Aldrich Chemical Co.) was reacted to give the title compound.

FAB MS 660 $(MH)^+$

Example 186

[S-(R*,R*)]-Azepane-1-carboxylic acid {1-[2-(4-benzyloxy-phenyl)-1-(2-morpholin-4-ylethylcarbamoyl)-ethylcarbamoyl]-3-methyl-butyl}-amide By a procedure identical to that described in Example 165, the resin obtained in Example AS and N-(2-aminoethyl)morpholine (Aldrich Chemical Co.) was reacted to give the title compound.

FAB MS 622 $(MH)^+$

Example 187

[S-(R*,R*)]-Azepane-1-carboxylic acid (1-{2-(4-benzyloxy-phenyl)-1-[3-(4-methyl-piperazin-1-yl)-propylcarbamoyl]-ethylcarbamoyl}-3-methyl-butyl)-amide By a procedure identical to that described in Example 165, the resin obtained in Example AS and 1-(3-aminopropyl)-4-methylpiperazine (Lancaster Synthesis Ltd.) was reacted to give the title compound.

FAB MS 650 $(MH)^+$

Example 188

Azepane-1-carboxylic acid {1-[1-(4-benzyloxy-benzyl)-2-(3-diethylcarbamoyl-piperidin-1-yl)-2-oxo-ethylcarbamoyl]-3-methyl-butyl}-amide By a procedure identical to that described in Example 165, the resin obtained in Example AS and N,N-diethylnipectoamide (Aldrich Chemical Co.) was reacted to give the title compound.

APCI MS 676 $(MH)^+$

Example 189

Azepane-1-carboxylic acid {1-[1-(4-benzyloxy-benzyl)-2-(3-diethylcarbamoyl-piperidin-1-yl)-2-oxo-ethylcarbamoyl]-3-methyl-butyl}-amide By a procedure identical to that described in Example 165, the resin obtained in Example AS and N,N- diethylnipectoamide (Aldrich Chemical Co.) was reacted to give the title compound.

APCI MS 676 $(MH)^+$

Example 190

Azepane-1-carboxylic acid {1-[2-(4-benzyloxy-phenyl)-1-(2-hydroxy-2phenyl-ethylcarbamoyl)-ethylcarbamoyl]-3-methyl-butyl}-amide By a procedure identical to that described in Example 165, the resin obtained in Example AS and 2-amino-1-phenylethanol (Aldrich Chemical Co.) was reacted to give the title compound.

APCI MS 629 $(MH)^+$

Example 191

Azepane-1-carboxylic acid {1-[2-(4-benzyloxy-phenyl)-1-(1,2-dimethyl-propylcarbamoyl)-ethylcarbamoyl]-3-methyl-butyl}-amide By a procedure identical to that described in Example 165, the resin obtained in Example AS and 1,2-dimethylpropylamine (Aldrich Chemical Co.) was reacted to give the title compound.

APCI MS 579 $(MH)^+$

Example 192

Azepane-1-carboxylic acid {1-[2-(4-benzyloxy-phenyl)-1-(1,2-dimethyl propylcarbamoyl)-ethylcarbamoyl]-3-methyl-butyl}-amide By a procedure identical to that described in Example 165, the resin obtained in Example AS and 1,2-dimethylpropylamine (Aldrich Chemical Co.) was reacted to give the title compound.

Example 193

Azepane-1-carboxylic acid (1-{2-(4-benzyloxy-phenyl)-1-[2-(1-methyl-pyrrolidin-2-yl)-ethylcarbamoyl]-ethylcarbamoyl}-3-methyl-butyl)-amide By a procedure identical to that described in Example 165, the resin obtained in Example AS and 2-(2-aminoethyl)-1-methylpyrrolidine (Aldrich Chemical Co.) was reacted to give the title compound.

FAB MS 620 $(MH)^+$

Example 194

Azepane-1-carboxylic acid {(S)-1-[(S)-2-(4-benzyloxy-phenyl)-1-[1-benzyl-(S)-pyrrolidin-3-ylcarbamoyl]-ethylcarbamoyl]-3-methyl-butyl}-amide By a procedure identical to that described in Example 165, the resin obtained in Example AS and (3S)-(+)-1-benzyl-3-aminopyrrolidine (Lancaster Synthesis Ltd.) was reacted to give the title compound.

FAB MS 668 $(MH)^+$

Example 195

Azepane-1-carboxylic acid {1-[2-(4-benzyloxy-phenyl)-1-(1-propyl-piperidin-3-ylcarbamoyl)-ethylcarbamoyl]-3-methyl-butyl}-amide By a procedure identical to that described in Example 165, the resin obtained in Example AS and 1-propyl-3-piperidinamine was reacted to give the title compound.

FAB MS 635 $(MH)^+$

Example 196

Azepane-1-carboxylic acid (1-{2-(4-benzyloxy-phenyl)-1-[3-(2-methyl-piperidin-1-yl)-propylcarbamoyl]-ethylcarbamoyl}-3-methyl-butyl)-amide By a procedure identical to that described in Example 165, the resin obtained in Example AS and 1-(3-aminopropyl)-2-pipecoline (Aldrich Chemical Co.) was reacted to give the title compound.

FAB MS 648 $(MH)^+$

Example 197

Azepane-1-carboxylic acid {1-[2-(4-benzyloxy-phenyl)-1-(1-methyl-2-phenyl-piperidin-3-ylcarbamoyl)-ethylcarbamoyl]-3-methyl-butyl}-amide By a procedure identical to that described in Example 165, the resin obtained in Example AS and 3-amino-2-phenyl-1-methylpiperidine was reacted to give the title compound.

FAB MS 682 $(MH)^+$

Example 198

Azepane-1-carboxylic acid {1-[2-(4-benzyloxy-phenyl)-1-(1-isobutyl-piperidin-3-ylcarbamoyl)-ethylcarbamoyl]-3-methyl-butyl}-amide By a procedure identical to that described in Example 165, the resin obtained in Example AS and 3-amino-1-(2-methyl-propyl)piperidine was reacted to give the title compound.

FAB MS 649 $(MH)^+$

Example 199

[S-(R*,R*)]-Azepane-1-carboxylic acid {1-[1-(4-benzyloxy-benzyl)-2-(2,6-dimethyl-morpholin-4-yl)-2-oxo-ethylcarbamoyl]-3-methyl-butyl}-amide The resin that was prepared in Example AS was suspended in $CH_2Cl_2$, and 1.5 equivalents of 2,6-dimethylmorpholine (Aldrich Chemical Co.) was added. The suspension was shaken for 48 hours. After the reaction was completed, additional $CH_2Cl_2$ was added, with one equivalent of isocyanate derivatized polystyrene resin. The resulting suspension was shaken for 24 hours, then the resin was filtered off, and the solvent was evaporated to give the title compound.

APCI MS 607 $(MH)^+$

Example 200

Azepane-1-carboxylic acid {1-[1-(4-benzyloxy-benzyl)-2-(3-methyl-piperidin-1-yl)-2-oxo-ethylcarbamoyl]-3-methyl-butyl}-amide By a procedure identical to that described in Example 199, the resin obtained in Example AS and 3-methylpiperidine (Aldrich Chemical Co.) was reacted to give the title compound.

APCI MS 591 $(MH)^+$

Example 201

[S-(R*,R*)]-Azepane-1-carboxylic acid {1-[1-(4-benzyloxy-benzyl)-2-(3,4-dihydro-1H-isoquinolin-2-yl)-2-oxo-ethylcarbamoyl]-3-methyl-butyl}-amide By a procedure identical to that described in Example 199, the resin obtained in Example AS and 1,2,3,4- tetrahydroisoquinoline (Aldrich Chemical Co.) was reacted to give the title compound.

APCI MS 625 $(MH)^+$

Example 202

[S-(R*,R*)]-Azepane-1-carboxylic acid (1-{1-(4-benzyloxy-benzyl)-2-[4-(2-hydroxy-ethyl)-piperazin-1-yl]-2-oxo-ethylcarbamoyl}-3-methyl-butyl)-amide By a procedure identical to that described in Example 199, the resin obtained in Example AS and N-(2-hydroxyethyl)piperazine (Aldrich Chemical Co) was reacted to give the title compound.

APCI MS 622 $(MH)^+$

Example 203

[S-(R*,R*)]-Azepane-1-carboxylic acid {1-[2-(4-benzyloxy-phenyl)-1-(2,2,6,6-tetramethyl-piperidin-4-ylcarbamoyl)-ethylcarbamoyl]-3-methyl-butyl}-amide By a procedure identical to that described in Example 199, the resin obtained in Example AS and 4-amino-2,2,6,6-tetramethylpiperidine (Aldrich Chemical Co.) was reacted to give the title compound.

APCI MS 648 $(MH)^+$

Example 204

[S-(R*,R*)]-Azepane-1-carboxylic acid {1-[2-(4-acetyl-piperazin-1-yl)-1-(4-benzyloxy-benzyl)-2-oxo-ethylcarbamoyl]-3-methyl-butyl}-amide By a procedure identical to that described in Example 199, the resin obtained in Example AS and 1-acetylpiperazine (Aldrich Chemical Co.) was reacted to give the title compound.

APCI MS 620 $(MH)^+$

Example 205

[S-(R*,R*)]-Azepane-1-carboxylic acid {1-[2-(4-benzyloxy-phenyl)-1-(cyclohexylmethyl-carbamoyl)-ethylcarbamoyl]-3-methyl-butyl}-amide By a procedure identical to that described in Example 199, the resin obtained in Example AS and aminomethyl-cyclohexane (Aldrich Chemical Co.) was reacted to give the title compound.

APCI MS 605 $(MH)^+$

Example 206

[S-(R*,R*)]-Azepane-1-carboxylic acid {1-[2-(4-benzyloxy-phenyl)-1-(cyclopropylmethyl-carbamoyl)-ethylcarbamoyl]-3-methyl-butyl}-amide By a procedure identical to that described in Example 199, the resin obtained in Example AS and aminomethyl-cyclopropane (Aldrich Chemical Co.) was reacted to give the title compound.

APCI MS 563 $(MH)^+$

Example 207

[S-(R*,R*)]-Azepane-1-carboxylic acid {1-[2-(4-benzyloxy-phenyl)-1-(thiazol-2-ylcarbamoyl)-ethylcarbamoyl]-3-methyl-butyl}-amide By a procedure identical to that described in Example 199, the resin obtained in Example AS and 2-aminothiazole (Aldrich Chemical Co.) was reacted to give the title compound.

APCI MS 592.0 $(MH)^+$

Example 208

[S-(R*,R*)]-Azepane-1-carboxylic acid {1-[2-(4-benzyloxy-phenyl)-1-cycloheptylcarbamoyl-ethylcarbamoyl]-3-methyl-butyl}-amide By a procedure identical to that described in Example 199, the resin obtained in Example AS and cycloheptylamine (Aldrich Chemical Co.) was reacted to give the title compound.

APCI MS 605.1 $(MH)^+$

Example 209

[S-(R*,R*)]-Azepane-1-carboxylic acid {1-[2-(4-benzyloxy-phenyl)-1-cyclopropylcarbamoyl-ethylcarbamoyl]-3-methyl-butyl}-amide By a procedure identical to that described in Example 199, the resin obtained in Example AS and cyclopropylamine (Aldrich Chemical Co.) was reacted to give the title compound.

APCI MS 549.0 $(MH)^+$

Example 210

[S-(R*,R*)]-Azepane-1-carboxylic acid {1-[2-(4-benzyloxy-phenyl)-1-(4-methoxy-phenylcarbamoyl)-ethylcarbamoyl]-3-methyl-butyl}-amide By a procedure identical to that described in Example 199, the resin obtained in Example AS and p-anisidine (Aldrich Chemical Co.) was reacted to give the title compound.

APCI MS 615.3 $(MH)^+$

Example 211

[S-(R*,R*)]-Azepane-1-carboxylic acid (1-{2-(4-benzyloxy-phenyl)-1-[4-(2-hydroxy-ethyl)-phenylcarbamoyl]-ethylcarbamoyl}-3-methyl-butyl)-amide By a procedure identical to that described in Example 199, the resin obtained in Example AS and 4-aminophenethyl alcohol (Aldrich Chemical Co.) was reacted to give the title compound.

APCI MS 629.3 $(MH)^+$

Example 212

[S-(R*,R*)]-Azepane-1-carboxylic acid {1-[1-(4-acetyl-phenylcarbamoyl)-2-(4-benzyloxy-phenyl)-ethylcarbamoyl]-3-methyl-butyl}-amide By a procedure identical to that described in Example 199, the resin obtained in Example AS and 4-aminoacetophenone (Aldrich Chemical Co.) was reacted to give the title compound.

APCI MS 627.3 $(MH)^+$

Example 213

[S-(R*,R*)]-Azepane-1-carboxylic acid {1-[2-(4-benzyloxy-phenyl)-1-(4-phenoxy-phenylcarbamoyl)-ethylcarbamoyl]-3-methyl-butyl}-amide By a procedure identical to that described in Example 199, the resin obtained in Example AS and 4-phenoxyaniline (Aldrich Chemical Co.) was reacted to give the title compound.

APCI MS 677.4 $(MH)^+$

Example 214

[S-(R*,R*)]-Azepane-1-carboxylic acid {1-[2-(4-benzyloxy-phenyl)-1-(3-trifluoromethyl-phenylcarbamoyl)-ethylcarbamoyl]-3-methyl-butyl}-amide By a procedure identical to that described in Example 199, the resin obtained in Example AS and 3-trifluoromethylaniline (Aldrich Chemical Co.) was reacted to give the title compound.

APCI MS 653.3 $(MH)^+$

Example 215

[S-(R*,R*)]-Azepane-1-carboxylic acid {1-[2-(4-benzyloxy-phenyl)-1-(4-dimethylamino-phenylcarbamoyl)-ethylcarbamoyl]-3-methyl-butyl}-amide By a procedure identical to that described in Example 199, the resin obtained in Example AS and N,N-dimethyl-p-phenylenediamine (Aldrich Chemical Co.) was reacted to give the title compound.

APCI MS 628.4 $(MH)^+$

Example 216

[S-(R*,R*)]-Azepane-1-carboxylic acid {1-[1-(4-acetylamino-phenylcarbamoyl)-2-(4-benzyloxy-phenyl)-ethylcarbamoyl]-3-methyl-butyl}-amide By a procedure identical to that described in Example 199, the resin obtained in Example AS and 4'-aminoacetaniline (Aldrich Chemical Co.) was reacted to give the title compound.

APCI MS 642.4 $(MH)^+$

Example 217

[S-(R*,R*)]-Azepane-1-carboxylic acid {1-[1-(4-aminomethyl-benzylcarbamoyl)-2-(4-benzyloxy-phenyl)-ethylcarbamoyl]-3-methyl-butyl}-amide By a procedure identical to that described in Example 199, the resin obtained in Example AS and p-xylylenediamine (Aldrich Chemical Co.) was reacted to give the title compound.

FAB MS 628 $(MH)^+$

Example 218

Azepane-1-carboxylic acid {1-[1-(4-benzyloxy-benzyl)-2-oxo-2-(2-phenylaminomethyl-pyrrolidin-1-yl)-ethylcarbamoyl]-3-methyl-butyl}-amide By a procedure identical to that described in Example 199, the resin obtained in Example AS and (S)-(+)-2-(anilinomethyl)pyrrolidine (Aldrich Chemical Co.) was reacted to give the title compound.

APCI MS 669 $(MH)^+$

Example 219

Azepane-1-carboxylic acid {1-[1-(3-amino-2-hydroxy-propylcarbamoyl)-2-(4-benzyloxy-phenyl)-ethylcarbamoyl]-3-methyl-butyl}-amide By a procedure identical to that described in Example 199, the resin obtained in Example AS and 1,3-diamino-2-propanol (Aldrich Chemical Co.) was reacted to give the title compound.

APCI MS 582 $(MH)^+$

Example 220

[S-(R*,R*)]-Azepane-1-carboxylic acid (1-{2-(4-benzyloxy-phenyl)-1-[(furan-2-ylmethyl)-carbamoyl]-ethylcarbamoyl}-3-methyl-butyl)-amide By a procedure identical to that described in Example 199, the resin obtained in Example AS and furfuralamine (Aldrich Chemical Co.) was reacted to give the title compound.

APCI MS 593.3 $(MH)^+$

Example 221

[S-(R*,R*)]-Azepane-1-carboxylic acid {1-[1-(4-benzyloxy-benzyl)-2-thiomorpholin-4-yl-2-oxo-ethylcarbamoyl]-3-methyl-butyl}-amide By a procedure identical to that described in Example 199, the resin obtained in Example AS and thiomorpholine (Aldrich Chemical Co.) was reacted to give the title compound.

APCI MS 595.3 $(MH)^+$

Example 222

[S-(R*,R*)]-Azepane-1-carboxylic acid {1-[1-[(benzo[1,3]dioxol-5-ylmethyl)-carbamoyl]-2-(4-benzyloxy-phenyl)-ethylcarbamoyl]-3-methyl-butyl}-amide By a procedure identical to that described in Example 199, the resin obtained in Example AS and piperonylamine (Aldrich Chemical Co.) was reacted to give the title compound.

APCI MS 643.3 $(MH)^+$

Example 223

[S-(R*,R*)]-Azepane-1-carboxylic acid {-1-[2-(4-benzyloxy-phenyl)-1-(3,4,5-trimethoxy-phenylcarbamoyl)-ethylcarbamoyl]-3-methyl-butyl}-amide By a procedure identical to that described in Example 199, the resin obtained in Example AS and 3,4,5-trimethoxyaniline (Aldrich Chemical Co.) was reacted to give the title compound.

APCI MS 675.3 $(MH)^+$

Example 224

[S-(R*,R*)]-Azepane-1-carboxylic acid (1-{2-(4-benzyloxy-phenyl)-1-[2-(1H-indol-3-yl)-ethylcarbamoyl]-ethylcarbamoyl}-3-methyl-butyl)-amide By a procedure identical to that described in Example 199, the resin obtained in Example AS and tryptamine (Aldrich Chemical Co.) was reacted to give the title compound.

APCI MS 652.4 $(MH)^+$

Example 225

[S-(R*,R*)]-Azepane-1-carboxylic acid (1-{2-(4-benzyloxy-phenyl)-1-[2-(4-hydroxy-phenyl)-ethylcarbamoyl]-ethylcarbamoyl}-3-methyl-butyl)-amide By a procedure identical to that described in Example 199, the resin obtained in Example AS and tyramine (Aldrich Chemical Co.) was reacted to give the title compound.

APCI MS 629.4 $(MH)^+$

Example 226

[S-(R*,R*)]-Azepane-1-carboxylic acid {1-[2-(4-benzyloxy-phenyl)-1-(1-hydroxymethyl-propylcarbamoyl)-ethylcarbamoyl]-3-methyl-butyl}-amide By a procedure identical to that described in Example 199, the resin obtained in Example AS and (±)-2-amino-1-butanol (Aldrich Chemical Co.) was reacted to give the title compound.

APCI MS 581.3 $(MH)^+$

Example 227

[S-(R*,R*)]-Azepane-1-carboxylic acid {1-[2-(4-benzyloxy-phenyl)-1-(2-hydroxy-1-hydroxymethyl-2-phenyl-ethylcarbamoyl)-ethylcarbamoyl]-3-methyl-butyl}-amide By a procedure identical to that described in Example 199, the resin obtained in Example AS and (1S,2S)-(+)-2-amino-1-phenyl-1,3-propanediol (Aldrich Chemical Co.) was reacted to give the title compound.

APCI MS 659.4 $(MH)^+$

Example 228

[S-(R*,R*)]-Azepane-1-carboxylic acid -[1-(1-(4-benzyloxy-benzyl)-2-{4-[2-(2-hydroxy-ethoxy)-ethyl]-piperazin-1-yl}-2-oxo-ethylcarbamoyl)-3-methyl-butyl]-amide By a procedure identical to that described in Example 199, the resin obtained in Example AS and 1-hydroxyethylethoxypiperazine (Aldrich Chemical Co.) was reacted to give the title compound.

APCI MS 666.4 (MH)

Example 229

[S-(R*,R*)]-Azepane-1-carboxylic acid {1-[2-(4-benzyloxy-phenyl)-1-(1,1-bis-hydroxymethyl-propylcarbamoyl)-ethylcarbamoyl]-3-methyl-butyl}-amide By a procedure identical to that described in Example 199, the resin obtained in Example AS and 2-amino-2-ethyl-1,3-propandiol (Aldrich Chemical Co.) was reacted to give the title compound.

APCI MS 611.4 $(MH)^+$

Example 230

Azepane-1-carboxylic acid {1-[2-(4-benzyloxy-phenyl)-1-(2-dimethylamino-1-methyl-ethylcarbamoyl)-ethylcarbamoyl]-3-methyl-butyl}-amide By a procedure identical to that described in Example 199, the resin obtained in Example AS and 1-dimethylamino-2-propylamine (Aldrich Chemical Co.) was reacted to give the title compound.

APCI MS 594.3 $(MH)^+$

Example 231

[S-(R*,R*)]-Azepane-1-carboxylic acid {1-[2-(4-benzyloxy-phenyl)-1-(2-pyridin-1-yl-ethylcarbamoyl)-ethylcarbamoyl]-3-methyl-butyl}-amide By a procedure identical to that described in Example 199, the resin obtained in Example AS and 2-(2-aminoethyl)pyridine (Aldrich Chemical Co.) was reacted to give the title compound.

APCI MS 614.3 $(MH)^+$

Example 232

Azepane-1-carboxylic acid {1-[2-(4-benzyloxy-phenyl)-1-(1,2,3,4-tetrahydro-naphthalen-1-ylcarbamoyl)-ethylcarbamoyl]-3-methyl-butyl}-amide By a procedure identical to that described in Example 199, the resin obtained in Example AS and 1,2,3,4-tetrahydro-1-napthylamine (Aldrich Chemical Co.) was reacted to give the title compound.

Example 233

[S-(R*,R*)]-Azepane-1-carboxylic acid (1-{2-(4-benzyloxy-phenyl)-1-[2-(2-hydroxy-ethylamino)-ethylcarbamoyl]-ethylcarbamoyl}-3-methyl-butyl)-amide By a procedure identical to that described in Example 199, the resin obtained in Example AS and 2-(2-aminoethylamino)ethanol (Aldrich Chemical Co.) was reacted to give the title compound.

Example 234

Azepane-1-carboxylic acid {1-[1-(4-benzyloxy-benzyl)-2-(3-hydroxy-piperidin-1-yl)-2-oxo-ethylcarbamoyl]-3-methyl-butyl}-amide By a procedure identical to that described in Example 199, the resin obtained in Example AS and 3-hydroxypiperidine (Aldrich Chemical Co.) was reacted to give the title compound.

APCI MS 593.3 $(MH)^+$

Example 235

[S-(R*,R*)]-Azepane-1-carboxylic acid {1-[1-(4-benzyloxy-benzyl)-2-(4-hydroxy-piperidin-1-yl)-2-oxo-ethylcarbamoyl]-3-methyl-butyl}-amide By a procedure identical to that described in Example 199, the resin obtained in Example AS and 4-hydroxypiperidine (Aldrich Chemical Co.) was reacted to give the title compound.

APCI MS 593.3 $(MH)^+$

Example 236

[S-(R*,R*)]-Azepane-1-carboxylic acid {1-[2-(4-benzyloxy-phenyl)-1-(2-cyano-ethylcarbamoyl)-ethylcarbamoyl]-3-methyl-butyl}-amide By a procedure identical to that described in Example 199, the resin obtained in Example AS and 3-aminopropionitrile (Aldrich Chemical Co.) was reacted to give the title compound.

APCI MS 562.3 $(MH)^+$

Example 237

[S-(R*,R*)]-Azepane-1-carboxylic acid {(1-[2-(4-benzyloxy phenyl)-1-(3-imidazol-1-yl-propylcarbamoyl)-ethylcarbamoyl]-3-methyl-butyl}-amide By a procedure identical to that described in Example 199, the resin obtained in Example AS and 1-(3- aminopropyl)imidazole (Aldrich Chemical Co.) was reacted to give the title compound.

APCI MS 617.3 $(MH)^+$

Example 238

Azepane-1-carboxylic acid {(R)-1-[(S)-2-(4-benzyloxy-phenyl)-(S)-1-(1-hydroxymethyl-3-methylsulfanyl-propylcarbamoyl)-ethylcarbamoyl]-3-methyl-butyl}-amide By a procedure identical to that described in Example 199, the resin obtained in Example AS and D-methioninol (Advanced ChemTech) was reacted to give the title compound.

APCI MS 627.3 $(MH)^+$

Example 239

Azepane-1-carboxylic acid {1-[1-[2-(2-amino-propylamino)-1-methyl-ethylcarbamoyl]-2-(4-benzyloxy-phenyl)-ethylcarbamoyl]-3-methyl-butyl}-amide By a procedure identical to that described in Example 199, the resin obtained in Example AS and bis(2-aminopropyl)-amine (ICN Pharmaceuticals, Inc.) was reacted to give the title compound.

APCI MS 623 $(MH)^+$

Example 240

[S-(R*,R*)]-Azepane-1-carboxylic acid (1-{1-(4-benzyloxy-benzyl)-2-[4-(4-fluoro-phenyl)-piperazin-1-yl]-2-oxo-ethylcarbamoyl}-3-methyl-butyl)-amide By a procedure identical to that described in Example 199, the resin obtained in Example AS and 1-(4-fluorophenyl)piperazine (Aldrich Chemical Co.) was reacted to give the title compound.

APCI MS 671 $(MH)^+$

Example 241

[S-(R*,R*)]-Azepane-1-carboxylic acid {1-[2-(4-benzyloxy-phenyl)-1-(3-iodo-benzylcarbamoyl)-ethylcarbamoyl]-3-methyl-butyl}-amide By a procedure identical to that described in Example 199, the resin obtained in Example AS and 3-iodobenzylamine (Aldrich Chemical Co.) was reacted to give the title compound.

APCI MS 725.3 $(MH)^+$

Example 242

Azepane-1-carboxylic acid {(S)-1-[2-(4-benzyloxy-phenyl-1-(2-isopropylamino-propylcarbamoyl)-(S)-ethylcarbamoyl-3-methyl-butyl}-amide By a procedure identical to that described in Example 199, the resin obtained in Example AS and 3-isopropylamino-N-propylamine (ICN Pharmaceuticals, Inc.) was reacted to give the title compound.

Example 243

Azepane-1-carboxylic acid {1-[2-(4-benzyloxy-phenyl)-1-sec-butylcarbamoyl-ethylcarbamoyl]-3-methyl-butyl}-amide By a procedure identical to that described in Example 199, the resin obtained in Example AS and sec-butylamine (Aldrich Chemical Co.) was reacted to give the title compound.

APCI MS 565 $(MH)^+$

Example 244

Azepane-1-carboxylic acid {(S)-1-[2-[(S)-3-acetylamino-pyrrolidin-1-yl]-(S)-1-(4-benzyloxy-benzyl)-2-oxo-ethylcarbamoyl-3-methyl-butyl}-amide By a procedure identical to that described in Example 199, the resin obtained in Example AS and (3S)-(−)-3-acetamidopyrrolidine (Lancaster) was reacted to give the title compound.

APCI MS 620.4 $(MH)^+$

Example 245

Azepane-1-carboxylic acid {1-[2-(4-benzyloxy-phenyl)-1-(1-methoxymethyl-propylcarbamoyl)-ethylcarbamoyl]-3-methyl-butyl}-amide By a procedure identical to that described in Example 165, the resin obtained in Example AS and 2-amino-1-methoxybutane (ICN Pharmaceuticals, Inc.) was reacted to give the title compound.

APCI MS 595.4 $(MH)^+$

Example 246

[S-(R*,R*)]-Azepane-1-carboxylic acid (1-{2-(4-benzyloxy-phenyl)-1-[3-(2-hydroxy-ethylamino)-1,1-dimethyl-propylcarbamoyl]-ethylcarbamoyl)-3-methyl-butyl}-amide By a procedure identical to that described in Example 199, the resin obtained in Example AS and 3-(2-hydroxy-ethylamino)-1,1-dimethyl-propylamine was reacted to give the title compound.

APCI MS 638 $(MH)^+$

Example 247

[S-(R*,R*)]-Azepane-1-carboxylic acid {1[-1-(4-benzyloxy-benzyl)-2-(3,6-dihydro-2H-pyridin-1-yl)-2-oxo-ethylcarbamoyl]-3-methyl-butyl}-amide By a procedure identical to that described in Example 199, the resin obtained in Example AS and 1,2,3,6-tetrahydropyridine (Aldrich Chemical Co.) was reacted to give the title compound.

APCI MS 575 $(MH)^+$

Example 248

[S-(R*,R*)]-Azepane-1-carboxylic acid {1-[1-(4-benzyloxy-benzyl)-2-(4-ethyl-piperazin-1-yl)-2-oxo-ethylcarbamoyl]-3-methyl-butyl}-amide By a procedure identical to that described in Example 199, the resin obtained in Example AS and N-ethylpiperazine (Aldrich Chemical Co.) was reacted to give the title compound.

APCI MS 606 $(MH)^+$

Example 249

[S-(R*,R*)]-Azepane-1-carboxylic acid {1-[1-(4-benzyloxy-benzyl)-2-(2,5-dimethyl-2,5-dihydro-pyrrol-1-yl)-2-oxo-ethylcarbamoyl]-3-methyl-butyl}-amide By a procedure identical to that described in Example 199, the resin obtained in Example AS and 2,5-dimethyl-3- pyrroline (Aldrich Chemical Co.) was reacted to give the title compound.

Example 250

Azepane-1-carboxylic acid (1-{2-(4-benzyloxy-phenyl)-1-[(1-benzyl-pyrrolidin-3-ylmethyl)-carbamoyl]-ethylcarbamoyl}-3-methyl-butyl)-amide By a procedure identical to that described in Example 199, the resin obtained in Example AS and 3-(aminomethyl)-1-benzyl-pyrrolidine, (source) was reacted to give the title compound.

FAB MS 682 $(MH)^+$

Example 251

S-(R*,R*)]-Azepane-1-carboxylic acid {1-[1-[benzyl-(2-hydroxy-ethyl)-carbamoyl]-2-(4-benzyloxy-phenyl)-ethylcarbamoyl]-3-methyl-butyl}-amide By a procedure identical to that described in Example 199, the resin obtained in Example AS and N-benzylethanolamine (Aldrich Chemical Co.) was reacted to give the title compound.

FAB MS 643 $(MH)^+$

Example 252

[S-(R*,R*)]-Azepane-1-carboxylic acid {1-[1-(2-benzylamino-ethylcarbamoyl)-2-(4-benzyloxy-phenyl)-ethylcarbamoyl]-3-methyl-butyl}-amide By a procedure identical to that described in Example 199, the resin obtained in Example AS and N-benzylethylenediamine (Lancaster) was reacted to give the title compound.

FAB MS 642 $(MH)^+$

Example 253

Azepane-1-carboxylic acid {1-[2-(4-benzyloxy-phenyl)-1-(1-hydroxymethyl-2-methyl-propylcarbamoyl)-ethylcarbamoyl]-3-methyl-butyl}-amide By a procedure identical to that described in Example 199, the resin obtained in Example AS and DL-valinol (Aldrich Chemical Co.) was reacted to give the title compound.

Example 254

[S-(R*,R*)]-Azepane-1-carboxylic acid {1-[2-(4-benzyloxy-phenyl)-1-(pyridin-3-ylcarbamoyl)-ethylcarbamoyl]-3-methyl-butyl}-amide By a procedure identical to that described in Example 199, the resin obtained in Example AS and 3-aminopyridine (Aldrich) was reacted to give the title compound.

FAB MS 586 $(MH)^+$

Example 255

[S-(R*,R*)]-Azepane-1-carboxylic acid {1-[2-(4-benzyloxy-phenyl)-1-(3-hydroxy-propylcarbamoyl)-ethylcarbamoyl]-3-methyl-butyl}-amide By a procedure identical to that described in Example 199, the resin obtained in Example AS and 3-amino-1-propanol (Aldrich) was reacted to give the title compound.

Example 256

Azepane-1-carboxylic acid {1-[1-(4-benzyloxy-benzyl)-2-(3-hydroxymethyl-piperidin-1-yl)-2-oxo-ethylcarbamoyl]-3-methyl-butyl}-amide By a procedure identical to that described in Example 199, the resin obtained in Example AS and 3-piperidinemethanol (Aldrich) was reacted to give the title compound.

FAB MS 607 $(MH)^+$

Example 257

[S-(R*,R*)]-Azepane-1-carboxylic acid {1-[2-(4-benzyloxy-phenyl)-1-(2-hydroxy-1-hydroxymethyl-ethylcarbamoyl)-ethylcarbamoyl]-3-methyl-butyl}-amide By a procedure identical to that described in Example 199, the resin obtained in Example AS and serinol (Aldrich) was reacted to give the title compound.

FAB MS 597 $(MH)^+$

Example 258

[S-(R*,R*)]-Azepane-1-carboxylic acid {1-[2-(4-benzyloxy-phenyl)-1-(pyrrolidin-3-ylcarbamoyl)-ethylcarbamoyl]-3-methyl-butyl}-amide By a procedure identical to that described in Example 199, the resin obtained in Example AS and 3-aminopyrrolidine (TCI Tokyo Kasei Kogyo Co., Ltd.) was reacted to give the title compound.

APCI MS 578 $(MH)^+$

Example 259

[S-(R*,R*)]-Azepane-1-carboxylic acid {1-[2-(4-benzyloxy-phenyl)-1-(1,4]diazepane-1-carbonyl)-ethylcarbamoyl]-3-methyl-butyl}-amide By a procedure identical to that described in Example 199, the resin obtained in Example AS and homopiperazine (Aldrich) was reacted to give the title compound.

Example 260

[S-(R*,R*)]-Azepane-1-carboxylic acid {1-[2-(4-benzyloxy-phenyl)-1-(4-piperidin-1-yl-phenylcarbamoyl)-ethylcarbamoyl]-3-methyl-butyl}-amide By a procedure identical to that described in Example 199, the resin obtained in Example AS and 4-piperidinoaniline (Maybridge) was reacted to give the title compound.

APCI MS 668 $(MH)^+$

Example 261

[S-(R*,R*)]-Azepane-1-carboxylic acid {1-[2-(4-benzyloxy-phenyl)-1-(pyrazole-3-carbonyl)-ethylcarbamoyl]-3-methyl-butyl}-amide By a procedure identical to that described in Example 199, the resin obtained in Example AS and pyrazole (Aldrich) was reacted to give the title compound.

Example 262

[S-(R*,R*)]-Azepane-1-carboxylic acid (1-{-2-(4-benzyloxy-phenyl)-1-[(piperidin-4-ylmethyl)-carbamoyl]-ethylcarbamoyl]-3-methyl-butyl}-amide By a procedure identical to that described in Example 199, the resin obtained in Example AS and 4-aminomethylpiperidine (Aldrich) was reacted to give the title compound.

APCI MS 606 $(MH)^+$

Example 263

[S-(R*,R*)]-Azepane-1-carboxylic acid {1-[1-benzylcarbamoyl-2-(4-benzyloxy-phenyl)-ethylcarbamoyl]-3-methyl-butyl}-amide By a procedure identical to that described in Example 199, the resin obtained in Example AS and benzylamine (Aldrich) was reacted to give the title compound.

Example 264

[S-(R*,R*)]-Azepane-1-carboxylic acid (1-{1-(4-benzyloxy-benzyl)-2-[4-(4-methoxy-phenyl)-piperazin-1-yl]-2-oxo-ethylcarbamoyl}-3-methyl-butyl)-amide By a procedure identical to that described in Example 199, the resin obtained in Example AS and 4-methoxyphenylpiperidine (Aldrich) was reacted to give the title compound.

APCI MS 684 $(MH)^+$

Example 265

[S-(R*,R*)]-Azepane-1-carboxylic acid {1-[1-(4-benzyloxy-benzyl)-2-(4-benzyl-piperidin-1-yl)-2-oxo-ethylcarbamoyl]-3-methyl-butyl}-amide By a procedure identical to that described in Example 199, the resin obtained in Example AS and 4-benzylpiperidine (Aldrich) was reacted to give the title compound.

APCI MS 667 $(MH)^+$

Example 266

Azepane-1-carboxylic acid {(S)-1-[(S)-2-(4-benzyloxy-phenyl)-1-(2-hydroxy-1,1-dimethyl-ethylcarbamoyl)-ethylcarbamoyl]-3-methyl-butyl}-amide By a procedure identical to that described in Example 199, the resin obtained in Example AS and 2-amino-2-methyl-1-propanol (Aldrich) was reacted to give the title compound.

Example 267

[S-(R*,R*)]-Azepane-1-carboxylic acid {1-[2-(4-benzyloxy-phenyl)-1-(4-hydroxy-2,5-dimethyl-phenylcarbamoyl)-ethylcarbamoyl]-3-methyl-butyl}-amide By a procedure identical to that described in Example 199, the resin obtained in Example AS and 4-hydroxy-2,5-dimethylaniline (Aldrich) was reacted to give the title compound.

FAB MS 629 $(MH)^+$

Example 268

[S-(R*,R*)]-Azepane-1-carboxylic acid {1-[2-(4-benzyloxy-phenyl)-1-(3-pyrrolidin-1-yl-propylcarbamoyl)-ethylcarbamoyl]-3-methyl-butyl}-amide By a procedure identical to that described in Example 199, the resin obtained in Example AS and 3-pyrrolidinopropylamine (Lancaster) was reacted to give the title compound.

FAB MS 620 $(MH)^+$

Example 269

[S-(R*,R*)]-Azepane-1-carboxylic acid {1-[2-(4-benzyloxy-phenyl)-1-(3-hydroxy-phenylcarbamoyl)-ethylcarbamoyl]-3-methyl-butyl}-amide By a procedure identical to that described in Example 199, the resin obtained in Example AS and 3-hydroxyaniline (Aldrich) was reacted to give the title compound.

FAB MS 602 $(MH)^+$

Example 270

[S-(R*,R*)]-Azepane-1-carboxylic acid {1-[2-(4-benzhydryl-piperazin-1-yl)-1-(4-benzyloxy-benzyl)-2-oxo-ethylcarbamoyl]-3-methyl-butyl}-amide By a procedure identical to that described in Example 199, the resin obtained in Example AS and 1-(dimethylphenyl)piperazine (Lancaster) was reacted to give the title compound.

APCI MS 744 $(MH)^+$

Example 271

[S-(R*,R*)]-Azepane-1-carboxylic acid {1-[2-(4-benzyloxy-phenyl)-1-(1-benzyl-piperidin-4-ylcarbamoyl)-ethylcarbamoyl]-3-methyl-butyl}-amide By a procedure identical to that described in Example 199, the resin obtained in Example AS and 4-amino-1-benzylpiperidine (Aldrich Chemical Co.) was reacted to give the title compound.

FAB MS 683 $(MH)^+$

BIOLOGICAL ACTIVITY

The compounds of the present invention exhibit valuable biological properties because of their ability to block calcium flux through N-type voltage-gated calcium channels. To measure interaction at the N-type $Ca^{2+}$ channel and calcium flux inhibition, the effects of the compounds of the present invention were measured in the assays described below. In addition to their ability to block N-type $Ca^{2+}$ channels, the compounds of the present invention were also evaluated for their ability to inhibit calcium flux through L-type $Ca^{2+}$ channels and $Na^+$ and $K^+$ channels in superior cervical ganglia (SCG) neurons.

Measurement of N-type $Ca^{2+}$ Channel Blocking Potencies of Compounds in IMR-32 Cells Using the Fluorescent $Ca^{2+}$ Indicator Indo-1

IMR-32 cells are a human tumoral cell line of neural origin. The IMR-32 cell line has been shown to contain both N- and L-type voltage sensitive calcium channels. Calcium flux into these cells may be induced by stimulation with elevated potassium concentrations. The L-channel component of calcium flux may be blocked by adding 5 $\mu$M nitrendipine. The remaining component of calcium entry into the IMR-32 cells is due to calcium flux through N-type calcium channels. Intracellular calcium concentrations are measured using the fluorescent calcium indicator Indo 1. The effect of drug concentration on calcium uptake is studied.

Methods

The IMR-32 cell line was obtained from the American Type Culture Collection (Rockville, Md.). Cells were grown in Eagle's Minimum Essential Medium with Eagle's salts supplemented with 10% fetal bovine serum, 2 mM L-Gln and antibiotic/antimycotic mixture (Gibco). At approximately 80% confluency, differentiation was induced by the addition of 1 mM dibutyryl cAMP and 2.5 μM bromodeoxyuridine to the medium. After 7 to 13 days of differentiation, cells were detached using 0.5 mM EDTA and loaded with 5 μM Indo-1 acetoxymethyl ester (Molecular Probes, Eugene, OR) at 300° C. for 45 minutes. Loaded cells were washed twice, resuspended (~$10^7$ cells/mL) in assay buffer (10 mM HEPES/Tris pH 7.4 in Hank's Balanced Salt Solution without bicarbonate or phenol red containing 0.5% bovine serum albumin) and kept on ice until use. Fluorescence measurements were carried out in a Photon Technology International (PTI, South Brunswick, N.J.) Model RF-F3004 spectrofluorometer with dual emission monochromators using excitation at 350 nm and emission at 400 and 490 nm. The instrument was equipped with a thermostated cuvette holder with stirring capabilities as well as with a computer-controlled pump which allowed for reagent addition during measurement. Instrument control and data collection was done by PTI's OSCAR software running on an IBM compatible computer. Different concentrations of the test compounds (60 μL in dimethyl sulfoxide) were added to 5.94 mL of assay buffer containing approximately 3x106 loaded cells, and 5 μM Nitrendipine (in 30 μL EtOH) to block L-type $Ca^{2+}$ channels. Samples were incubated for 10 minutes at 30° C. and then aliquoted into three 10x10 mm disposable acrylic cuvettes. Emission signals at 400 and 490 nm were acquired from each cuvette at 30° C. for 50 seconds. At 20 seconds after the start of reading, cells were depolarized by the addition of 160 μL of stimulation solution (1M KCl, 68 mM $CaCl_2$) to the cuvette via the computer-controlled pump. Ratio of dual emission signals (400 nm/490 nm), which is proportional to intracellular $Ca^{2+}$ concentration, was plotted against time, and the difference between maximal response after stimulation and basal value (before stimulation) was determined. Values obtained in this way were plotted as a function of drug concentration. $IC_{50}$ values of test compounds were calculated by fitting a four-parameter logistic function to the data using the least squares method.

Measurement of L-type $Ca^{2+}$ Channel Blocking Potencies of Compounds in GH3 Cells Using the Fluorescent $Ca^{2+}$ Indicator Indo-1

The GH3 rat pituitary cell line was obtained from the American Type Culture Collection (Rockville, Md.). Cells were grown in Ham's F-10 medium with 15% horse serum, 2.5% fetal bovine serum (FBS), and antibiotic/antibiotic mixture (Gibco, Gaithersburg, Md.). Confluent cells were detached using 0.5 mM EDTA and loaded with 5 μM Indo-acetoxymethyl ester (Molecular Probes, Eugene, Oreg.) in 1% bovine serum albumin (BSA) containing assay buffer (10 mM HEPES/Tris pH 7.4 in Hank's Balanced Salt Solution without bicarbonate or phenol red) for 60 minutes at 30° C. Loaded cells were washed twice, resuspended (approx. $10^7$ cells/mL) in assay buffer containing 0.5% BSA, and kept on ice until use (<3 hrs). Different concentrations of the test compounds (60 μL in dimethyl sulfoxide) or controls were added to 5.94 mL of assay buffer containing approximately 3x106 loaded cells, and the samples were incubated for 10 minutes at 30° C. After incubation, samples were aliquoted into 3 cuvettes, and their fluorescence was measured with a Photon Technology International (PTI, South Brunswick, N.J.) Model RF-F3004 spectrofluorometer thermostatted at 30° C. Excitation was set at 350 nm and dual emissions were recorded at 400 and 490 nm. Basal emission signals were acquired for 20 seconds, followed by the depolarization of cells by the addition of 200 μL of a stimulation solution (1 M KCl, 68 mM $CaCl_2$) to the stirred cuvette. Emission signals were acquired for an additional 50 seconds after depolarization. Ratio of emission signals ($F_{400\ nm}/F_{490\ nm}$), which is proportional to intracellular $Ca^{2+}$ concentration, was plotted against time, and the difference between the emission ratio 50 seconds after stimulation and its basal value (before stimulation) was determined. Values obtained in this way were considered as measures of depolarization-induced Ca-flux through L-type channels and plotted as a function of drug concentration. $IC_{50}$ values of test compounds were calculated by fitting a four-parameter logistic function to the data using the least squares method.

Measurement of L-type $Ca^{2+}$ Channel Blocking Potencies of Compounds in A10 cells Calcium flux through voltage-sensitive calcium channels was assessed by time-resolved monitoring of the fluorescence of pre-loaded calcium-sensitive dyes using FLIPR, a fluorescent image plate reader (Molecular Devices Co.). The A10 smooth muscle cell line derived from embryonic thoracic aorta of the DBIX rat (ATCC, CRL-1476) which endogenously expresses L-type calcium channels. The growth media for A10 cells was Ham's F12/DME high glucose (Irvine Scientific, 9052), supplemented with 20% fetal bovine serum (HyClone Labs, A-1115-L), and 1% each of L-glutamine and antibiotic-antimycotic (same source as above).

Cells were grown to confluency and replated on black-sided 96-well plates (Costar, 3603) for use in FLIPR. Two days after replating, growth media was removed and cells were loaded at 37° C. with 100 μL media containing 1 μM Oregon Green 488 Bapta-1 dye (Molecular Probes, O-6807) for 1 to 3 hours. The dye-containing media was then washed away with buffer (composition in mM: 1.25 $CaCl_2$, 1.2 $MgSO_4$, 11 glucose, 10 HEPES, 3.0 KCl, 137.0 NaCl, pH 7.4 with Tris base) in a Denley Cellwash (Labsystems, CW018B). The residual buffer volume was adjusted to 50 μL. A 5 minute drug-pre-incubation period at 35° C. was initiated when 50 μL of drug-containing buffer was pipetted into the cell plate with the 96-well pipettor integrated in the FLIPR apparatus. Fluorescent counts were monitored at 20 second intervals for 360 seconds, beginning 60 seconds prior to the delivery of drug-containing buffer. Following drug addition, 100 μL aliquots of a high $K^+$, depolarizing stimulus (composition in mM: 1.25 $CaCl_2$, 1.2 $MgSO_4$, 11 glucose, 10 HEPES, 140.0 KCl, pH 7.4 with Tris base) were added to each well and fluorescence was monitored at 1 second intervals for 120 seconds, beginning 10 seconds prior to the stimulus addition. CCD camera exposure time was 0.4 seconds, laser excitation was at 488 nm with a power of 0.2–0.5W, and a 510 to 560 nm bandpass interference filter preceded the camera.

Data was analyzed as a summation of fluorescent counts above basal during the stimulation period (an approximation of area under the curve), after normalizing the data with a spatial uniformity correction (for variations in laser illumination and cell density) and a negative control correction (zero calcium increase defined as the fluorescence reading in the presence of saturating pharmacologic block of the respective calcium channel). Drug effects were expressed as percent inhibition of fluorescence from an average of 8 $K^+$-stimulated wells which were pre-treated in the drug incubation period with buffer only.

In the A10 cells, the pharmacologic agent used to define zero calcium influx was nitrendipine (RBI, N-144), at a final concentration of $1.0\times10^{-6}$ M.

Measurement of Calcium, Sodium, and Potassium Current in Superior Cervical Ganglion Cells Electrophysiological techniques were used to measure the effects of experimental compounds on voltage-gated $Ca^{2+}$, $Na^+$ and $K^+$ channels. $Ca^{2+}$ channel currents were measured from N-type $Ca^{2+}$ channels in cultured superior cervical ganglion (SCG) neurons. Sodium and potassium channel currents were measured from acutely dissociated SCG neurons.

Superior cervical ganglia (SCG) were isolated from 1–4 day Sprague Dawley neonatal rats following sacrifice by carbon dioxide asphyxiation. Dissociation of the neurons from the ganglia was accomplished using a 30 to 45 minute treatment in 0.25% trypsin, similar to methods outlined in Higgins, et al. [see Higgins D., et al. "Tissue culture of mammalian autonomic neurons." In Banker G. and Goslin K. (Eds), *Culturing Nerve Cells*, Cambridge, Mass., MIT Press (1991)].

$Ca^{2+}$, $Na^+$ and $K^+$ channel currents in SCG neurons were measured using conventional single electrode whole-cell voltage-clamp techniques, outlined in Hamill, et al., (see Hamill O.P., et al. "Improved patch-clamp techniques for high resolution current recordings from cells and cell-free membrane patches". *Pflugers Arch.* 1981;391:85–100) For $Ca^{2+}$ channel experiments, the external bathing solution contained tetraethylammonium chloride (100 mM), choline chloride (52 mM), NaCl (15 mM), HEPES (10 mM), glucose (5.6 mM), $CaCl_2$ (2 mM), and $MgCl_2$ (0.8 mM) pH 7.35 with KOH; with the internal pipette solution containing cesium methane sulfonate (140 mM), EGTA (10 mM), and HEPES (10 mM), supplemented with 5 mM $Mg^{2+}$ -ATP on the day of the experiment, pH 7.4 with CsOH. For $Na^+$ and $K^+$ channel experiments, the external bathing solution contained NaCl (150 mM), KCl (5 mM), $MgCl_2$ (1.1 mM), $CaCl_2$ (2.6 mM), Na-HEPES (10 mM), and glucose (10 mM), pH 7.4; with the internal pipette solution containing KCl (80 mM), K-gluconate (50 mM), HEPES (10 mM), and EGTA (10 mM), pH 7.4 with KOH. Experimental compounds were diluted into the external solution and applied to the soma of cells by local perfusion from large diameter (20–50 $\mu$m) glass micropipettes or from a U-tube applicator.

After obtaining a whole-cell recording, $Ca^{2+}$ channels were elicited by stepping to test potentials between −40 and +20 mV for 120 msec from the holding potential of −90 mV to determine if the amplitude of the current and clamp control were adequate for evaluation of drug effects. $Ca^{2+}$ channel currents were evoked by stepping from a holding potentials between −65 mV and −−55 mV to a test potential of +20 mV for 150 msec every 40 seconds. The amplitude of the $Ca^{2+}$ channel currents were compared before and during drug application and drug effects expressed as percent inhibition of the amplitude of control currents.

For $Na^+$ and $K^+$ channel currents, following the determination of the I/V relationship for each cell in control solution, currents were evoked from a holding potential between −65 and −55 mV by stepping every 10 sec to a test potential of either 0 mV for $Na^+$ or +50 mV for $K^+$ current for a duration of 35 msec. Peak inward current was measured for $Na^+$ and sustained current for $K^+$ channel currents. After stable current amplitudes were observed in control solution, the external solution was rapidly exchanged with an external solution containing test compound. Test compounds were applied until steady-state block was achieved. Data were expressed as percent inhibition of control amplitudes for $Na^+$ and $K^+$ channel currents.

TABLE I

Inhibition of N- and L-type Calcium Flux

| Example Number | Inhibition of Calcium Flux in IMR-32 Cells $IC_{50}$ ($\mu$M) | Inhibition of Calcium Flux in IMR-32 Cells % Inhibition at 1 $\mu$M | Inhibition of Calcium Flux in IMR-32 Cells % Inhibition at 10 $\mu$M | Inhibition of Calcium Flux in A10 Cells $IC_{50}$ ($\mu$M) | Inhibition of Calcium Flux in GH3 Cells $IC_{50}$ ($\mu$M) |
|---|---|---|---|---|---|
| 1 | 0.35 | 71 | 95 | 1.72 | 4.48 |
| 2 | 1.70 | 38 | 90 | | |
| 3 | 0.99 | 53 | 90 | | |
| 4 | 0.90 | 51 | 90 | | |
| 5 | 0.82 | 60 | 94 | | |
| 6 | 0.72 | 63 | 98 | | |
| 7 | 1.50 | 44 | 96 | | |
| 8 | 2.40 | 29 | 86 | 0.18 | |
| 9 | | 28 | | | |
| 10 | 2.10 | 46 | 73 | | |
| 12 | 0.48 | 57 | 95 | | |
| 13 | 1.70 | 40 | 86 | | |
| 14 | | 45 | | | |
| 15 | 1.10 | 45 | 99 | | |
| 16 | 1.10 | 44 | 92 | 0.28 | 4.30 |
| 17 | 1.85 | 41 | 85 | | 5.80 |
| 18 | 0.93 | 50 | 97 | | 3.50 |
| 19 | 0.50 | 68 | 91 | | 4.30 |
| 20 | 0.91 | 52 | 90 | | 4.60 |
| 21 | 2.70 | 26 | 83 | 1.60 | |
| 22 | | 29 | | | |
| 23 | 0.58 | 55 | 95 | | 18.0 |
| 25 | 2.09 | 32 | 82 | 1.70 | |
| 26 | 1.60 | 44 | 84 | 3.00 | |
| 27 | 0.81 | 51 | 92 | | |
| 28 | 1.80 | 42 | 65 | | |
| 29 | | 43 | 87 | | |
| 30 | 0.63 | 56 | 83 | | |
| 31 | 1.85 | 28 | 85 | | |
| 32 | 0.82 | 52 | 86 | | |
| 33 | 2.20 | 48 | 79 | | |
| 34 | | 29 | 78 | | |
| 36 | 0.17 | 71 | 86 | 3.00 | |
| 37 | 0.28 | 65 | 91 | | |
| 38 | 0.94 | 48 | 83 | | |
| 39 | 0.52 | 61 | 91 | | |
| 40 | 1.00 | 48 | 86 | | |
| 41 | 0.80 | 51 | 86 | | |
| 42 | 0.95 | 50 | 95 | | |
| 43 | | 17 | 38 | | |
| 44 | | 28 | 71 | | |
| 45 | | 29 | 68 | | |
| 46 | | 29 | 49 | | |
| 47 | 1.30 | 42 | 63 | | |
| 48 | 1.20 | 52 | 81 | | |
| 49 | 0.27 | 77 | 99 | | |
| 50 | | 53 | 85 | | |
| 51 | | 32 | 85 | | |
| 52 | | 56 | 76 | | |
| 53 | | 61 | 89 | 0.14 | |
| 54 | | 44 | 63 | | |
| 55 | | 14 | 46 | | |
| 56 | | 24 | 56 | | |
| 57 | | 34 | 74 | | |
| 58 | | 52 | 35 | | |
| 59 | | 41 | 61 | | |
| 60 | | 24 | | | |
| 61 | | 34 | | | |
| 62 | | 29 | | | |
| 63 | | 33 | | | |
| 64 | | 31 | | | |
| 65 | | 28 | | | |
| 66 | | 42 | | | |
| 67 | | 10 | 19 | 3.00 | |
| 68 | | 31 | | | |
| 69 | | 31 | | | |
| 70 | | 25 | | | |
| 71 | | 55 | | | |

TABLE I-continued

Inhibition of N- and L-type Calcium Flux

| Example Number | Inhibition of Calcium Flux in IMR-32 Cells $IC_{50}$ ($\mu M$) | Inhibition of Calcium Flux in IMR-32 Cells % Inhibition at 1 $\mu M$ | Inhibition of Calcium Flux in IMR-32 Cells % Inhibition at 10 $\mu M$ | Inhibition of Calcium Flux in A10 Cells $IC_{50}$ ($\mu M$) | Inhibition of Calcium Flux in GH3 Cells $IC_{50}$ ($\mu M$) |
|---|---|---|---|---|---|
| 72 | | 31 | | | |
| 73 | | 60 | | | |
| 74 | | 45 | | | |
| 75 | | 28 | | | |
| 76 | | 27 | | | |
| 77 | | 22 | | | |
| 78 | | 24 | | | |
| 79 | | 23 | | | |
| 80 | | 40 | | | |
| 81 | | 32 | | | |
| 82 | | 55 | | | |
| 83 | | 19 | | | |
| 84 | | 49 | | | |
| 85 | | 30 | | | |
| 86 | | 40 | | | |
| 87 | | 37 | | | |
| 88 | | 30 | | | |
| 89 | | 30 | | | |
| 90 | | 37 | | | |
| 90 | | | 83 | | |
| 91 | | 34 | 48 | | |
| 92 | | 1 | 65 | | |
| 93 | | 17 | | | |
| 94 | | 29 | | | |
| 95 | | 27 | | | |
| 96 | | 33 | | | |
| 97 | | 30 | | | |
| 98 | | 34 | | | |
| 99 | | 19 | | | |
| 100 | | 18 | | | |
| 102 | | | 75 | | |
| 103 | | 28 | | | |
| 104 | | 35 | | | |
| 105 | | 29 | | | |
| 106 | | 32 | | | |
| 107 | | | 57 | | |
| 109 | | | 56 | | |
| 110 | | | 76 | | |
| 111 | 1.10 | 50 | 96 | | |
| 113 | | | 83 | | |
| 114 | | | 66 | | |
| 115 | | | 71 | | |
| 116 | | | 53 | | |
| 117 | | | 66 | | |
| 118 | | | 80 | | |
| 119 | | | 65 | | |
| 120 | | | 65 | | |
| 121 | | | 25 | | |
| 122 | | | 84 | | |
| 123 | | | 67 | | |
| 124 | | | 60 | | |
| 126 | | | 28 | | |
| 127 | | | 61 | | |
| 128 | | | 78 | | |
| 129 | | | 74 | | |
| 130 | | | 78 | | |
| 131 | | | 44 | | |
| 132 | 0.90 | 37 | 83 | 0.91 | |
| 133 | | 54 | 72 | | |
| 134 | | 29 | 56 | | |
| 135 | | 43 | 71 | 0.67 | |
| 136 | | 45 | 64 | 1.55 | |
| 137 | | | | 2.60 | |
| 138 | | 23 | 67 | 1.60 | |
| 140 | | | | 3.00 | |
| 141 | | 37 | 66 | 0.41 | |
| 142 | | | | 0.68 | |
| 143 | | 7 | 58 | 1.30 | |

TABLE I-continued

Inhibition of N- and L-type Calcium Flux

| Example Number | Inhibition of Calcium Flux in IMR-32 Cells $IC_{50}$ ($\mu M$) | Inhibition of Calcium Flux in IMR-32 Cells % Inhibition at 1 $\mu M$ | Inhibition of Calcium Flux in IMR-32 Cells % Inhibition at 10 $\mu M$ | Inhibition of Calcium Flux in A10 Cells $IC_{50}$ ($\mu M$) | Inhibition of Calcium Flux in GH3 Cells $IC_{50}$ ($\mu M$) |
|---|---|---|---|---|---|
| 144 | | 61 | 86 | 0.55 | |
| 145 | | 48 | | 0.25 | |
| 146 | | 51 | | 0.22 | |
| 147 | | 25 | 71 | 5.10 | |
| 148 | | 30 | 68 | 0.97 | |
| 150 | | | | 3.00 | |
| 151 | 4.30 | | | | |
| 152 | 1.90 | | | | |
| 153 | 3.70 | | | | |
| 154 | 9.60 | | | | |
| 155 | 2.50 | | | | |
| 156 | 5.30 | | | | |
| 157 | 2.30 | | | | |
| 159 | 0.83 | | | | |
| 160 | 2.50 | | | | |
| 161 | 2.50 | | | | |
| 162 | 0.96 | | | | |
| 163 | 0.49 | | | | |
| 164 | 0.90 | | | | |
| 165 | 3.60 | | | | |
| 166 | 1.30 | | | | |
| 167 | 0.53 | 58 | | | |
| 168 | 0.68 | | | | |
| 169 | 1.60 | | | | |
| 170 | 1.30 | | | | |
| 171 | 0.46 | 62 | | 0.27 | |
| 172 | 2.30 | | | | |
| 173 | 0.28 | | | | |
| 174 | 1.40 | | | | |
| 175 | 2.70 | | | | |
| 176 | 1.40 | 38 | 86 | | |
| 177 | 2.90 | | | | |
| 178 | 3.10 | | | | |
| 179 | 1.40 | | | | |
| 180 | 0.82 | 55 | | | |
| 181 | 2.80 | | | | |
| 182 | 7.70 | | | | |
| 183 | 0.30 | | | 0.22 | |
| 184 | 2.60 | | | | |
| 185 | 2.30 | | | | |
| 186 | 1.80 | | | 3.00 | |
| 187 | 4.00 | 20 | 77 | | |
| 188 | 0.78 | | | | |
| 189 | 0.94 | | | | |
| 190 | 0.79 | | | | |
| 191 | 0.72 | | | | |
| 192 | 0.92 | | | | |
| 193 | 3.20 | | | | |
| 194 | 0.45 | | | | |
| 195 | 0.58 | | | | |
| 196 | 0.70 | | | | |
| 197 | 0.22 | | | | |
| 198 | 0.36 | | | | |
| 199 | 1.80 | 36 | 86 | | |
| 200 | 0.90 | 53 | 88 | | |
| 201 | 2.40 | 29 | 81 | | |
| 202 | 2.80 | 25 | 79 | | |
| 203 | 4.70 | 15 | 70 | | |
| 204 | 5.50 | 13 | 66 | | |
| 205 | 2.40 | 36 | 72 | | |
| 206 | 1.70 | 37 | 87 | | |
| 207 | 6.20 | 21 | 59 | | |
| 208 | 1.80 | 38 | 81 | | |
| 209 | 2.50 | 27 | 82 | | |
| 210 | 1.50 | 39 | | | |
| 211 | 1.10 | 49 | 81 | | |
| 212 | 1.90 | 34 | 66 | | |
| 213 | 2.40 | 30 | 33 | | |

TABLE I-continued

Inhibition of N- and L-type Calcium Flux

| Example Number | Inhibition of Calcium Flux in IMR-32 Cells $IC_{50}$ ($\mu$M) | Inhibition of Calcium Flux in IMR-32 Cells % Inhibition at 1 $\mu$M | Inhibition of Calcium Flux in IMR-32 Cells % Inhibition at 10 $\mu$M | Inhibition of Calcium Flux in A10 Cells $IC_{50}$ ($\mu$M) | Inhibition of Calcium Flux in GH3 Cells $IC_{50}$ ($\mu$M) |
|---|---|---|---|---|---|
| 214 | 1.40 | 42 | 51 | | |
| 215 | | 35 | 44 | | |
| 216 | | 16 | 37 | | |
| 217 | 5.00 | 35 | 75 | | |
| 218 | | 62 | 93 | | |
| 219 | | 6 | 23 | | |
| 220 | | 40 | 88 | | |
| 221 | | 65 | 93 | 0.60 | |
| 222 | | 36 | 84 | | |
| 223 | | 36 | 74 | | |
| 224 | | 50 | 87 | | |
| 225 | | 55 | 94 | | |
| 226 | | 37 | 84 | | |
| 227 | | 19 | 86 | | |
| 228 | | 24 | 82 | | |
| 229 | | 30 | 80 | | |
| 230 | | 34 | 81 | | |
| 231 | 1.11 | 55 | 95 | 0.67 | |
| 234 | | 32 | 67 | | |
| 235 | | 20 | 64 | | |
| 236 | | 50 | 93 | | |
| 237 | 0.96 | 52 | 93 | 2.20 | |
| 238 | 0.74 | 62 | 95 | | |
| 239 | | 22 | 23 | | |
| 240 | 0.75 | 63 | 86 | | |
| 241 | | 53 | 83 | | |
| 242 | | 23 | | | |
| 243 | | 48 | 89 | | |
| 244 | | 24 | 73 | | |
| 245 | | 57 | 89 | | |
| 250 | 0.27 | | | | |
| 251 | 0.74 | | | | |
| 252 | 0.28 | | | | |
| 253 | 1.10 | 60 | 93 | | |
| 254 | 1.60 | 39 | 83 | | |

TABLE I-continued

Inhibition of N- and L-type Calcium Flux

| Example Number | Inhibition of Calcium Flux in IMR-32 Cells $IC_{50}$ ($\mu$M) | Inhibition of Calcium Flux in IMR-32 Cells % Inhibition at 1 $\mu$M | Inhibition of Calcium Flux in IMR-32 Cells % Inhibition at 10 $\mu$M | Inhibition of Calcium Flux in A10 Cells $IC_{50}$ ($\mu$M) | Inhibition of Calcium Flux in GH3 Cells $IC_{50}$ ($\mu$M) |
|---|---|---|---|---|---|
| 255 | 4.30 | | | | |
| 256 | 1.50 | | | | |
| 257 | 1.40 | 42 | 90 | | |
| 258 | 3.60 | | | | |
| 259 | 2.40 | | | | |
| 260 | | | 33 | | |
| 261 | 2.00 | | | | |
| 262 | 51.0 | | 17 | | |
| 263 | 1.20 | | | | |
| 264 | 0.74 | | | | |
| 265 | 1.00 | | | | |
| 266 | 1.80 | | | | |
| 267 | 4.40 | | | | |
| 268 | 2.90 | | | | |
| 269 | 2.80 | | | | |
| 270 | 1.20 | | | | |
| 271 | 0.84 | 70 | | | |
| 11A | 0.53 | 61 | 88 | | |
| 11B | 2.30 | 35 | 80 | | |

TABLE 2

Potency of Selected Analogs for Blocking Mono and Divalent Ion Channels in SCG Neurons

| Example Number | Inhibition of N-type $Ca^{2+}$ Current $IC_{50}$ ($\mu$M) | Inhibition of N-type $Ca^{2+}$ Current, % Inhibition at 10 $\mu$M | Inhibition of $K^+$ Current $IC_{50}$ ($\mu$M) | Inhibition of $K^+$ Current, % Inhibition at 10 $\mu$M | Inhibition of $Na^+$ Current $IC_{50}$ ($\mu$M) | Inhibition of $Na^+$ Current, % Inhibition at 10 $\mu$M |
|---|---|---|---|---|---|---|
| 1 | 1.27 | 68 | 24.0 | 31 | 14.0 | 28 |
| 2 | | 32 | | 41 | | 35 |
| 3 | | 69 | | 39 | | 12 |
| 4 | | 51 | | 38 | | 13 |
| 5 | 0.62 | 70 | | 13 | | 10 |
| 7 | 2.30 | 81 | | 70 | | 52 |
| 8 | 1.92 | 86 | | 72 | | 43 |
| 9 | | 81 | | 61 | | 44 |
| 12 | 6.78 | 65 | | 38 | | 14 |
| 16 | | 19 | | 20 | | 38 |
| 21 | | 45 | | 56 | | 16 |
| 23 | 3.24 | 78 | | 61 | | 30 |
| 25 | 5.33 | 66 | | 51 | | 16 |
| 26 | | 58 | | 41 | | 13 |
| 28 | | 40 | | 11 | | 5 |
| 30 | | 38 | | 8 | | 19 |
| 31 | 3.34 | 68 | 12.4 | 41 | 185 | 21 |
| 36 | | | | 92 | | 91 |

TABLE 2-continued

Potency of Selected Analogs for Blocking Mono and Divalent Ion Channels in SCG Neurons

| Example Number | Inhibition of N-type $Ca^{2+}$ Current $IC_{50}$ ($\mu$M) | Inhibition of N-type $Ca^{2+}$ Current, % Inhibition at 10 $\mu$M | Inhibition of $K^+$ Current $IC_{50}$ ($\mu$M) | Inhibition of $K^+$ Current, % Inhibition at 10 $\mu$M | Inhibition of $Na^+$ Current $IC_{50}$ ($\mu$M) | Inhibition of $Na^+$ Current, % Inhibition at 10 $\mu$M |
|---|---|---|---|---|---|---|
| 37 | | | | 9 | | 5 |
| 39 | | | | 22 | | 28 |
| 42 | | 64 | | | | |
| 49 | | 45 | | −3 | | 6 |
| 130 | | −7 | | | | |
| 132 | | | | | | |
| 137 | | | | | | |
| 138 | | 17 | | 43 | | 31 |
| 141 | | 39 | | 42 | | 18 |
| 159 | | 28 | | 46 | | 30 |
| 166 | | | | | | |
| 161 | | 61 | 5.45 | 68 | 14.0 | 42 |
| 162 | | 47 | | 40 | | 32 |
| 165 | 2.33 | 84 | 1.60E-05 | 86 | 6.90 | 46 |
| 167 | | 4 | | 8 | | −2 |
| 174 | | | | 32 | | 14 |
| 177 | 2.03 | 87 | | 68 | | 31 |
| 180 | | 81 | | 60 | | 20 |
| 184 | 1.19 | 54 | 0.49 | 89 | 4.85 | 82 |
| 191 | 4.37 | 61 | 5.70 | 64 | 42.3 | 38 |
| 192 | 2.84 | 58 | | 58 | | 26 |
| 194 | | 84 | | | | |
| 237 | | 79 | | | | |
| 253 | | | | 62 | | 5 |
| 257 | | | | 43 | | 5 |
| 11A | | 47 | | 47 | | 11 |
| 11B | | 17 | | 46 | | 48 |

Audiogenic Seizure Model in DBA/2 Mice

In Vivo Biological Protocol

A compound of the present invention was dissolved in water using 10% (weight/volume) Emulphor (GAF Cop., Wayne N.J. surfactant. Substances were administered by intravenous injection the retro-orbital venous sinus. All testing was preformed 15 minutes or 45 minutes after drug injection. All the male mice, 3–4 weeks old were obtained from Jackson Laboratories Bar Harbour, Me. Immediately before anticonvulsant testing, mice were placed upon a wire mesh, 4 inches square suspended from a steel rod. The square was slowly inverted through 180 degree and mice observed for 30 seconds. Any mouse falling from the wire mesh was scored as ataxia.

Mice were placed into an enclosed acrylic plastic chamber (21 cm in height, approximately 30 cm diameter) with a high-frequency speaker (4 cm diameter) in the center of the top lid. An audio signal generator (Protek model B-810) was used to produce a continuous sinusoidal tone that was swept linearly in frequency between 8 kHz and 16 kHz once each 10 msec. The average sound pressure level (SPL) during stimulation was approximately 100 dB at the floor of the chamber. Mice were placed within the chamber and allowed to acclimatize for 1 minute. DBA/2 mice in the vehicle-treated group responded to the sound stimulus (applied until tonic extension occurred, or for a maximum of 60 sec) with a characteristic seizure sequence consisting of wild running followed by clonic seizures, and later by tonic extension, and finally by respiratory arrest and death in 80% or more of the mice. In vehicle-treated mice, the entire sequence of seizures to respiratory arrest lasts approximately 15–20 seconds.

The incidence of all the seizure phases in the drug-treated and vehicle-treated mice was recorded, and the occurrence of tonic seizures were used for calculating anticonvulsant $ED_{50}$ values by probit analysis. Mice were used only once for testing at each time and dose point. Results of this assay are shown below in Table 3.

TABLE 3

Audiogenic Seizure Model in DBA/2 Mice

| Example Number | Dose (mg/Kg, iv) | Time Post Treatment (min.) | Number of Mice Protected from Tonic Convulsions |
|---|---|---|---|
| 1 | 100 | 15 | 5/5 |
| 1 | 100 | 30 | 5/5 |
| 1 | 100 | 60 | 0/5 |
| 1 | 30 | 15 | 5/5 |
| 1 | 10 | 15 | 0/5 |
| 1 | 10 | 45 | 0/5 |
| 8 | 30 | 15 | 4/5 |
| 21 | 30 | 45 | 0/5 |
| 25 | 30 | 15 | 5/5 |
| 26 | 10 | 15 | 5/5 |
| 44 | 30 | 15 | 0/5 |
| 171 | 30 | 45 | 0/5 |
| 183 | 30 | 15 | 5/5 dead |
| 257 | 30 | 15 | 3/4 (1 dead) |
| 257 | 30 | 45 | 3/3 2 (dead) |
| 253 | 30 | 15 | 0/5 |
| 221 | 30 | 15 | 1/5 |
| 221 | 30 | 45 | 0/5 |
| 231 | 30 | 15 | 0/5 |
| 237 | 30 | 15 | 0/5 |

Acetic Acid Writhing Test

The mouse acetic acid writhing test measures the acute nociceptive response elicited injection of dilute acetic acid into the peritoneal cavity (Collier ,et al., Br. J. Pharmac. Chemother., 1968;32:295–310). Nociceptive behavior is quantified by counting the incidence of abdominal constrictions in a fix observation interval.

Male Swiss-Webster mice weighing between 26 and 30 grams are used. Animals are given a single, intraperitoneal injection of 0.6% acetic acid (250 fL). Evoke abdominal constrictions, defined as discrete episodes of torso and hind limb stretching with or without neck arching, are counted and recorded for 5 minutes, beginning 7 minutes after acetic acid injection. The mice are individually housed in Nalgene cages and allowed to move freely during the experimental period (12 minutes). Animals are killed by $CO_2$ asphyxiation immediately after the 5-minute observation period. Test compounds are administered by intravenous, subcutaneous, or intraperitoneal routes approximately 10 minutes prior to administering the acetic acid.

The dose-response relationship for antinociceptive effects during the acetic acid writhing test are assessed by plotting the incidence of abdominal constrictions against test article dose. $ED_{50}$ values are calculated using a four parameter logistic function. The results of this test are shown in FIG. 1.

Formalin Pain Test

The rat paw formalin test measures acute and persistent nociceptive responses elicited by subcutaneous injection of dilute formalin into the dorsal hindpaw (Dubuisson and Dennis, Pain, 1977;4:161–174). Nociceptive behavior is quantified by measuring paw flinches at regular intervals across a 90-minute observation period.

Adult male, Sprague-Dawley rats are briefly anesthetized with 2% halothane, and 5% formalin (50 fL) is injected subcutaneously into the dorsal surface of the right hindpaw using a tuberculin syringe with a 25 gauge needle. After injecting the formalin solution, the rat is immediately placed in a 23 cm×35 cm×19 cm polycarbonate box, and pain behavior is quantified by counting the number of paw flexions in 1-minute observation periods. Paw flinching during acute (0–9 minutes posttreatment) and tonic (10–90 minutes posttreatment) nociceptive phases are recorded. Measurements are taken at 5-minute intervals beginning immediately after formalin injection. The dose-response relationship for antinociceptive effects during the acute and tonic phases of the formalin test are assessed by expressing summed flinch counts in each phase as a percentage of control values. $ED_{50}$ values are determined using a four parameter logistic function.

Figure 2:
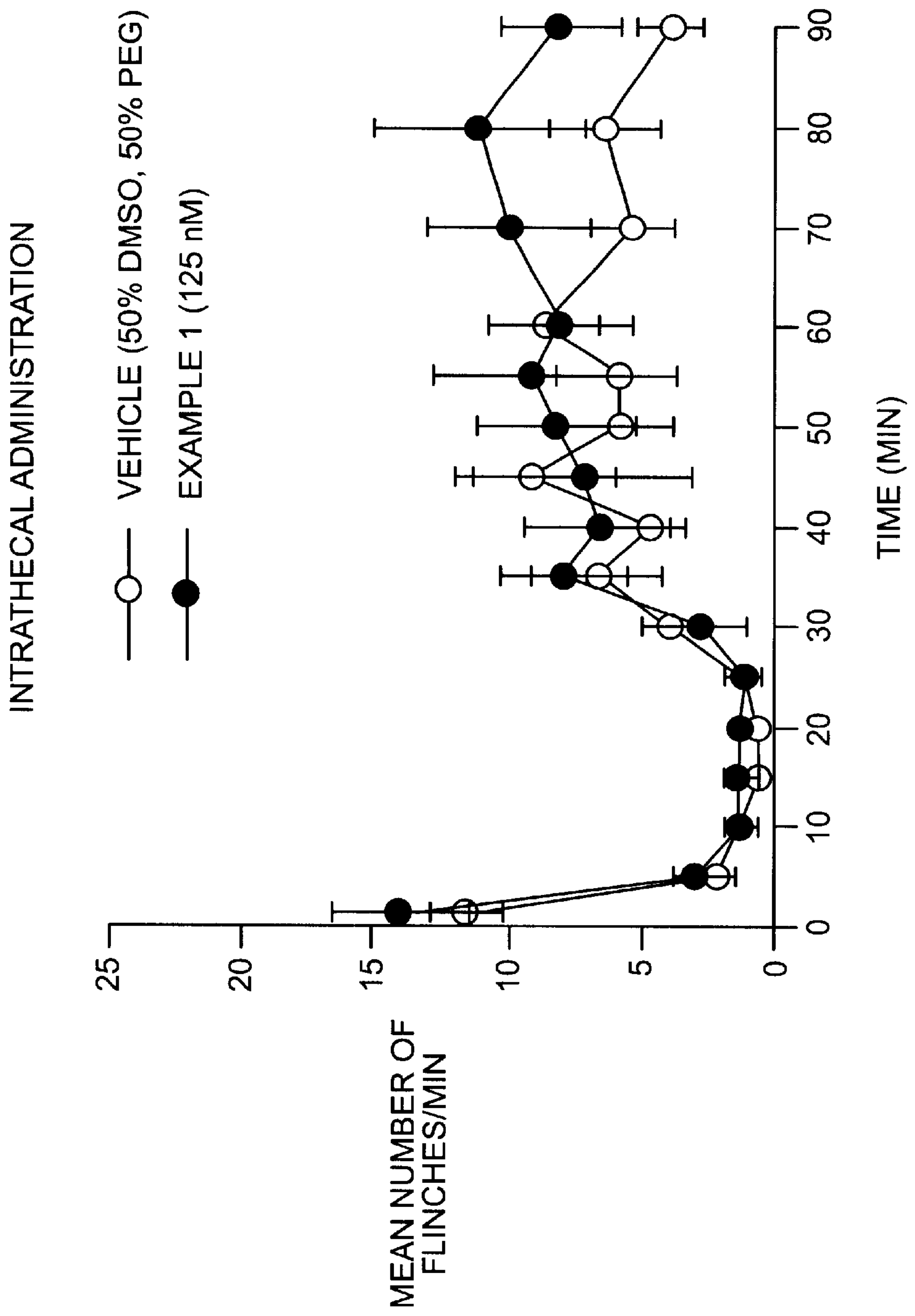
FIG. 2 shows the results of intrathecal administration of Example 1.
Figure 3:
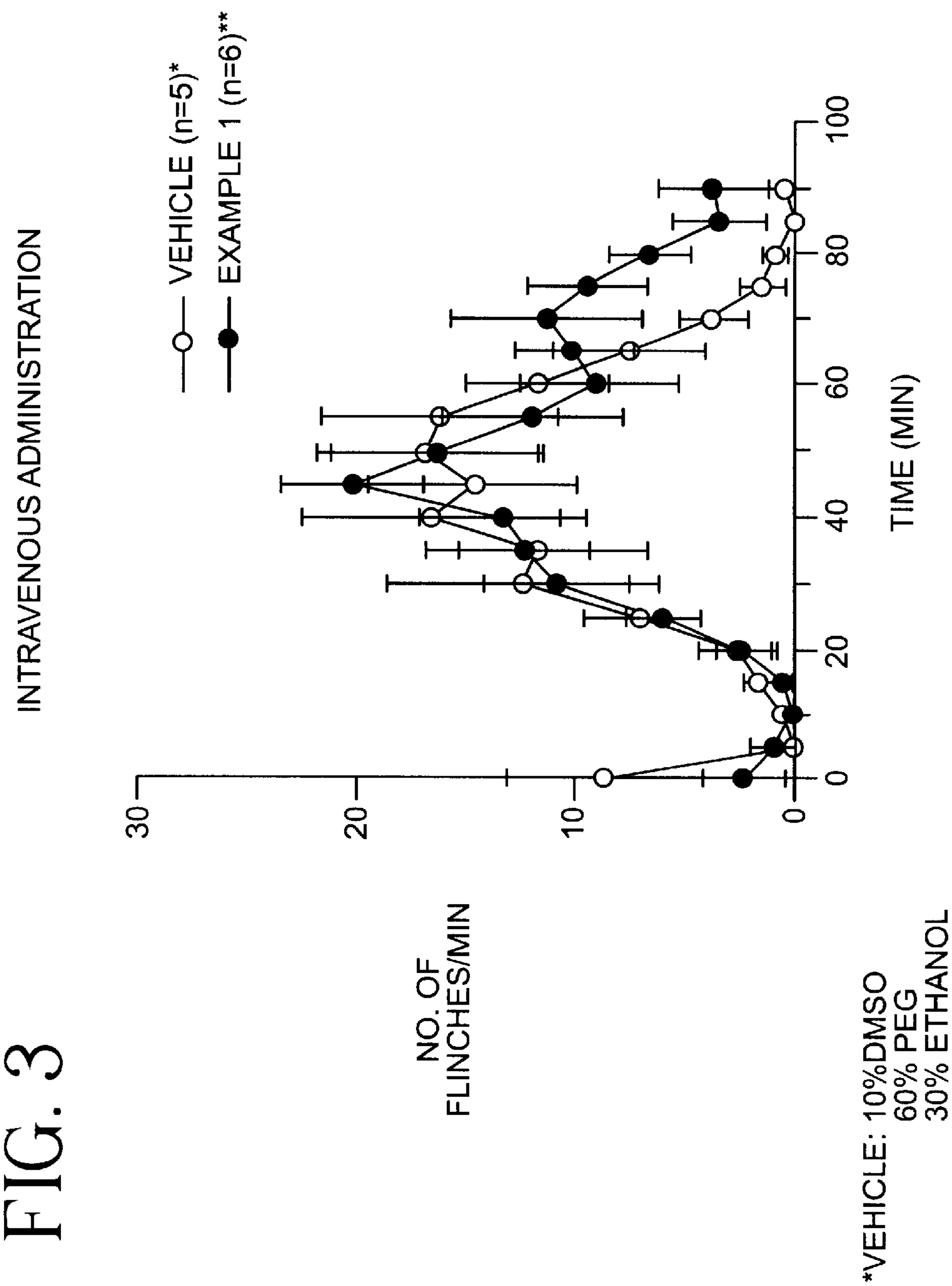
FIG. 3 shows the results of intravenous administration of Example 1.

Test compounds are administered approximately 10 minutes prior to formalin injection by either spinal (intrathecal), intravenous, or intraperitoneal routes. For spinal delivery, an indwelling intrathecal catheter is permanently implanted approximately 48 hours prior to testing. After inducing anesthesia (Halothane) carried in 30% oxygen and 70% nitrous oxide, the animal is placed into a stereotaxic frame to stabilize the head at a 45 angle, a midline incision is made over the top of the head and neck, the nuchal musculature is separated, and the atlanto-occipital membrane is exposed. A small incision is made in the membrane and the catheter is advanced 9 cm caudally into the intrathecal space. The catheter is prepared from polyethylene (PE-10, PE-60) and shrink tubing. The main body of the catheter consists of a 9 cm length of PE-10 tubing loosely knotted at the end both to limit the depth of insertion and provide an anchor so that the catheter can be sutured in place. A 3 cm length of PE-60 tubing is attached to one end of the catheter (rostral to the knot) and shrink tubing is used to reinforce the connecting junction. Cyanomethacrylate glue is applied to this junction to prevent leakage. The exteriorized end of the catheter is anchored with a suture to the overlying musculature. All animals are observed to verify the absence of neurological deficits due to the spinal catheterization procedure before formalin testing. The results of this test are shown in FIGS. 2 and 3.

What is claimed is:

1. Compounds having Formula I

I

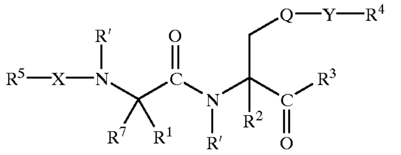

wherein each R' is hydrogen;

$R^1$ is $C_1$–$C_6$ alkyl, —$CH_2$-phenyl, hydrogen, —$CH_2$-indolyl, —$(CH_2)_n$—S—$C_1$–$C_6$ alkyl, —$(CH_2)_n$-substituted phenyl, —$(CH_2)_n$ cycloalkyl, —$(CH_2)_n$-heteroaryl, or

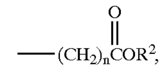

$R^2$ is hydrogen or $C_1$–$C_6$ alkyl;

$R^3$ is —O($C_1$–$C_6$alkyl), —O$(CH_2)_n$phenyl,

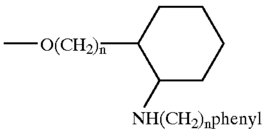

, —$NH_2$,

—NH($C_1$–$C_6$alkyl), —N($C_1$–$C_6$alkyl)$_2$, —NH$(CH_2)_n$ cycloalkyl, —NH$(CH_2)_n$ NH cycloalkyl,

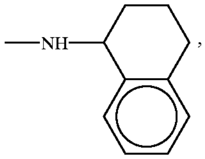

, —NH—substituted phenyl,

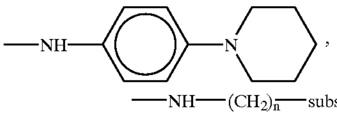

, —NH—$(CH_2)_n$—phenyl,

—NH—$(CH_2)_n$—substituted phenyl, phenyl, —NH—$(CH_2)_n$-phenyl-$CH_2NH_2$, —NH—$(CH_2)_n$ pyridyl, —NH—$(CH_2)_n$ imidazolyl, —NH—$(CH_2)_n$ furyl,

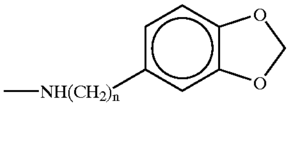

, —NH—$(CH_2)_n$—indolyl, $—NH—(CH_2)_nOH$, $—NH—(CH_2)_n—CN$,
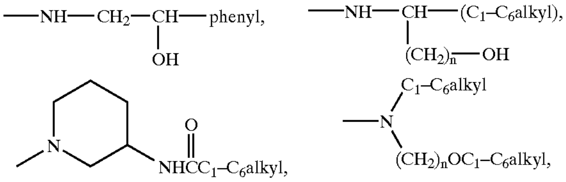
$—NH(CR'R')_nNH(CR'R')_nOH$,
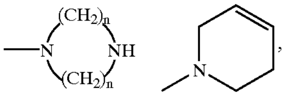
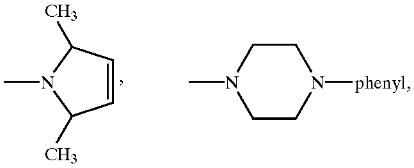
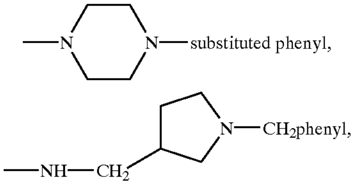
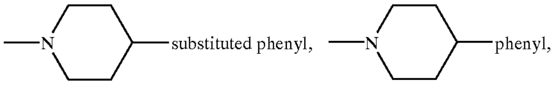
$—NH(CH_2)_n—NHCH_2phenyl$,
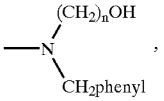
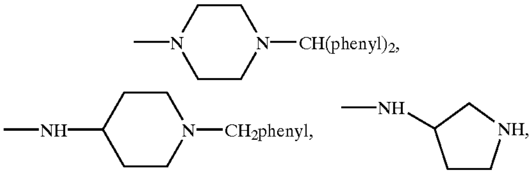
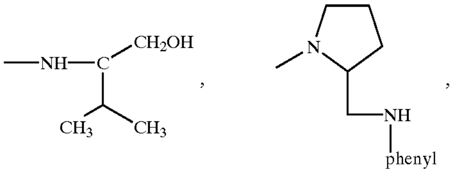
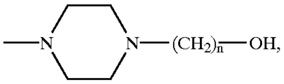
$—NH(CR'R')_nN(CR'R')_nNH_2$,
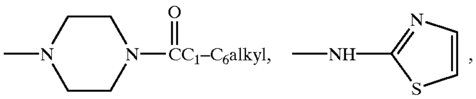
$—NH(CR'R')_nNH(C_1–C_6alkyl)$, $—NH(CH_2)_n$-piperidinyl,
$—NH(CH_2)_n$-substituted piperidinyl,
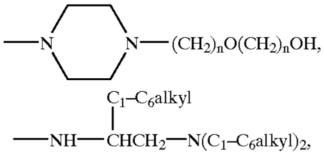
-continued
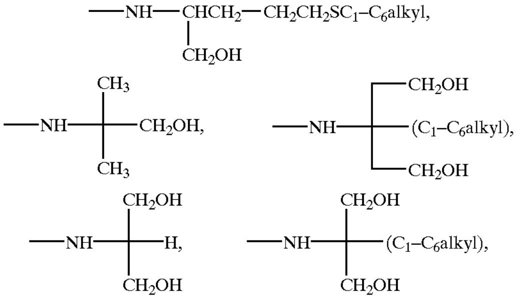
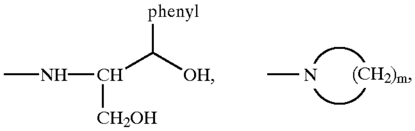
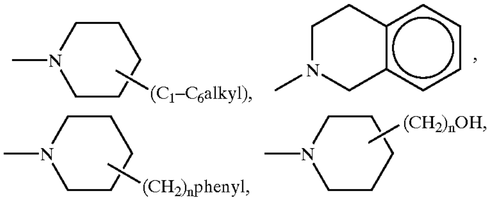
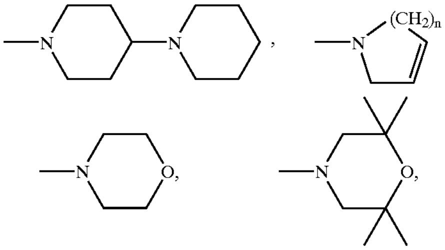
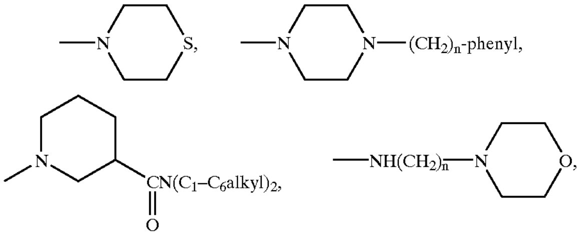
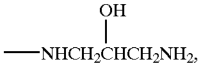
$—NH(CH_2)_nNH(CH_2)_mOH$,
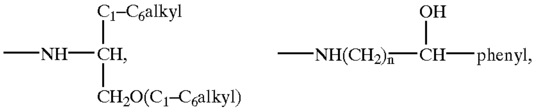
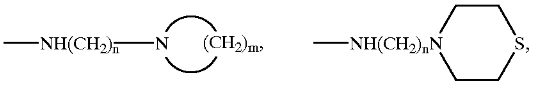
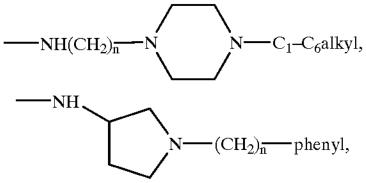
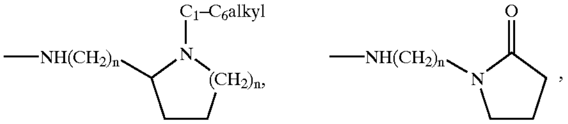

-continued

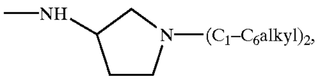, 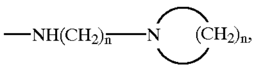,

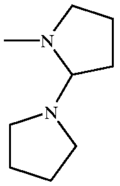, 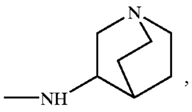,

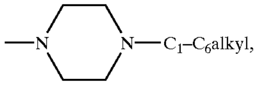, 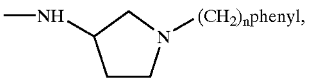,

—NH(CH$_2$)$_n$NH(C$_1$–C$_6$alkyl), or

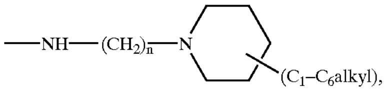, each $R^4$ is independently —(CH$_2$)$_n$-phenyl, —(CH$_2$)$_n$-substituted phenyl, —(CH$_2$)$_n$—NH$_2$, —(CH$_2$)$_n$N(C$_1$–C$_6$alkyl)$_2$, —(CH$_2$)$_n$NH(C$_1$–C$_6$alkyl), —(CH$_2$)$_n$-pyridyl, C$_1$–C$_6$ alkyl

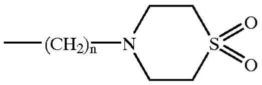

—(CH$_2$)$_n$-C$_3$–C$_8$ cycloalkyl, or —(CH$_2$)$_n$ substituted C$_3$–C$_8$ cycloalkyl;

$R^5$ is

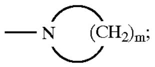;

$R^6$ is C$_1$–C$_6$alkyl, phenyl, substituted phenyl, —(CH$_2$)$_n$-phenyl, or —(CH$_2$)$_n$-substituted phenyl;

$R^7$ is hydrogen or C$_1$–C$_6$ alkyl;

X is 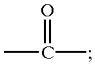; Y is —O—, 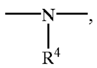, 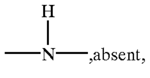, absent, —CH═CH—, or —C≡C—;

Q is 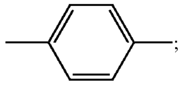;

each n is independently 0 to 5; and each m is independently 2 to 7;

each p is 0, 1, or 2, and the pharmaceutically acceptable salts, esters, amides, and prodrugs thereof.

2. A compound according to claim 1 wherein $R^3$ is —OC$_1$–C$_6$ alkyl, each R' is hydrogen, and X is 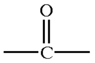

.

3. A compound according to claim 1 wherein $R^3$ is —NH(C$_1$–C$_6$alkyl), each R' is hydrogen, and X is 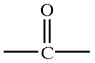

.

4. A compound according to claim 1 wherein

Q is 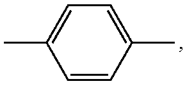,

Y is —O—, and $R^4$ is —CH$_2$-phenyl or —CH$_2$-substituted phenyl.

5. A compound according to claim 1 wherein $R^5$ is 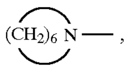,

X is

X is 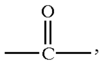, $R^4$ is —CH$_2$-phenyl, and $R^1$ is isobutyl.

6. A compound according to claim 1 wherein

Q is 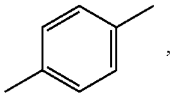,

Y is —C≡— and $R^4$ is —(CH$_2$)$_n$ phenyl or —(CH$_2$)$_n$ substituted phenyl.

7. A compound according to claim 1 wherein

Q is 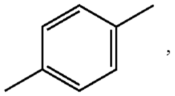,

Y is absent, and $R^4$ is —(CH$_2$)$_n$ phenyl or —(CH$_2$)$_n$ substituted phenyl.

8. A compound according to claim 1 wherein $R^3$ is —O-tert-butyl.

9. A compound according to claim 1 wherein $R^1$ is —CH$_2$-phenyl.

10. A compound according to claim 1 wherein

Q is 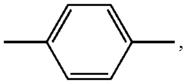,

Y is O, and $R^4$ is —(CH$_2$)$_n$ pyridyl.

11. A compound according to claim 1 wherein

Q is 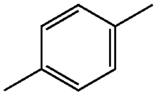 ,

Y is —C≡C— and $R^4$ is $—(CH_2)_n$ pyridyl.

12. A compound according to claim 1 wherein

Q is 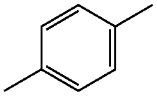 ,

Y is absent, and $R^4$ is $—(CH_2)_n$ pyridyl.

13. A compound according to claim 1 wherein

Q is 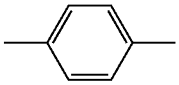 ;

Y is O; $R^4$ is $—CH_2$-phenyl; each R' is hydrogen; $R^1$ is isopropyl; and $R^3$ is —O-tert-butyl.

14. Compounds having the Formula II

II

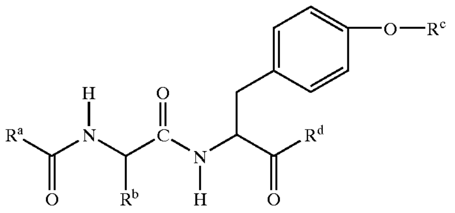

wherein $R^a$ is 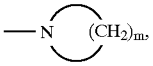

—NH-phenyl, or —NH-substituted phenyl;

$R^b$ is $C_1$–$C_6$ alkyl, $—(CH_2)_n$-aryl, or $—(CH_2)_n$-heteroaryl;

$R^c$ is $—CH_2$-phenyl, $C_1$–$C_6$ alkyl, $—CH_2$-substituted phenyl, or $—CH_2$-heteroaryl;

$R^d$ is $—OC_1$–$C_6$ alkyl, $—N(C_1$–$C_6alkyl)_2$, —NH—$C_1$–$C_6$ alkyl,

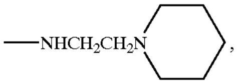 , 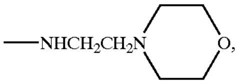

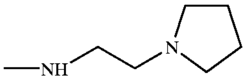 , $—NHCH_2CH_2NHCH_2$phenyl, $—NHCH_2CH_2NHCH_2$pyridyl, 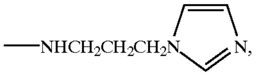

-continued

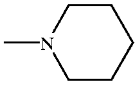 , 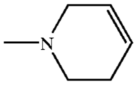 , 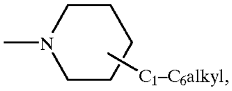

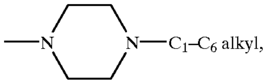

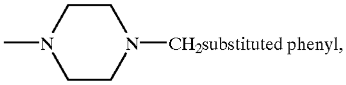

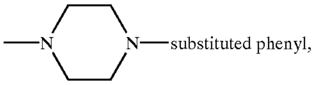

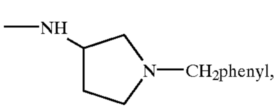 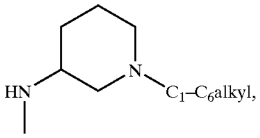

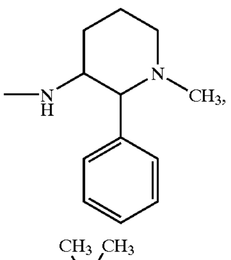 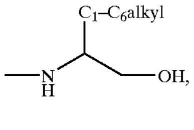

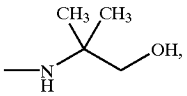 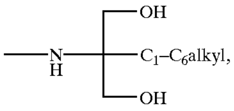

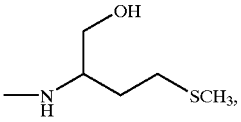 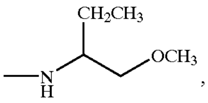 ,

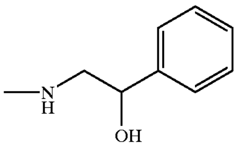 , 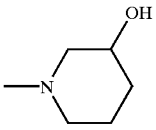 ,

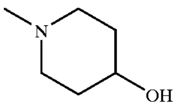 , or 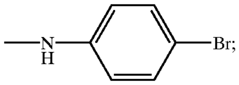

each n is independently 0 to 5; and each m is independently 2 to 7, and the pharmaceutically acceptable salts, esters, amides, and prodrugs thereof.

15. A compound in accordance with claim 14 wherein $R^a$ is 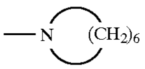

$R^b$ is $—CH_2CH(CH_3)_2$;

$R^c$ is $—CH_2$-phenyl or $—CH_2$ pyridyl; and $R^d$ is —O-tert-butyl, or —NH-tert-butyl.

16. Compounds having the Formula III

III

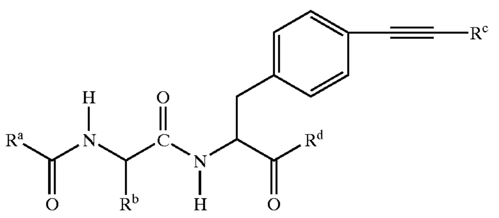

wherein $R^a$ is 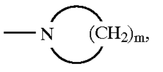

—NH-phenyl, or —NH-substituted phenyl;

$R^b$ is $C_1$–$C_6$ alkyl, —$(CH_2)_n$-aryl, or —$(CH_2)_n$-heteroaryl;

$R^c$ is phenyl, $C_1$–$C_6$ alkyl, substituted phenyl, or heteroaryl;

$R^d$ is —$OC_1$–$C_6$ alkyl, —$N(C_1$–$C_6alkyl)_2$, —NH—$C_1$–$C_6$ alkyl,

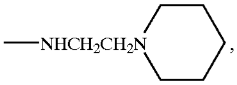, 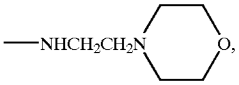

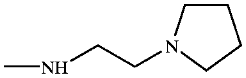, —$NHCH_2CH_2NHCH_2$phenyl,

—$NHCH_2CH_2NHCH_2$pyridyl, 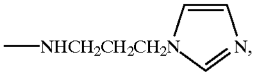

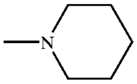, 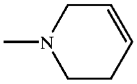, 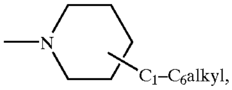

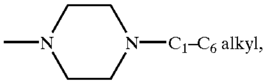

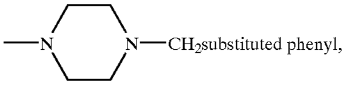

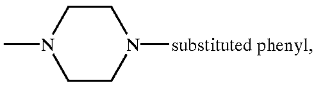

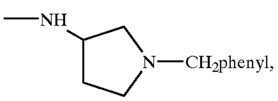 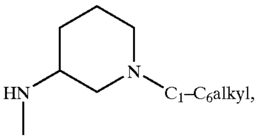

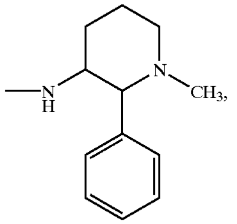 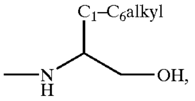

-continued

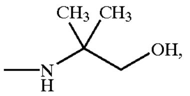 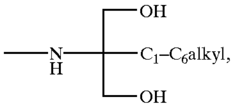

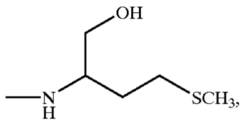 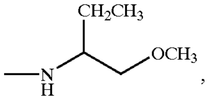,

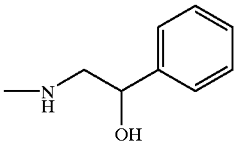, 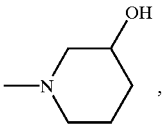,

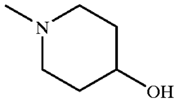, or 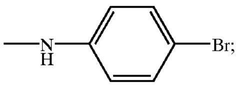

each n is independently 0 to 5; and each m is independently 2 to 7, and the pharmaceutically acceptable salts, esters, amides, and prodrugs thereof.

17. Compounds having the Formula IV

IV

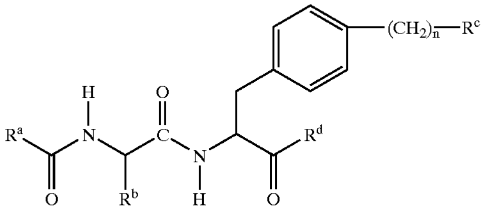

wherein $R^a$ is 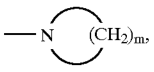

—NH-phenyl, or —NH-substituted phenyl;

$R^b$ is $C_1$–$C_6$ alkyl, —$(CH_2)_n$-aryl, or —$(CH_2)_n$-heteroaryl;

$R^c$ is —$CH_2$-phenyl, $C_1$–$C_6$ alkyl, —$CH_2$-substituted phenyl, or —$CH_2$-heteroaryl;

$R^d$ is —$OC_1$–$C_6$ alkyl, —$N(C_1$–$C_6alkyl)_2$, —NH—$C_1$–$C_6$ alkyl,

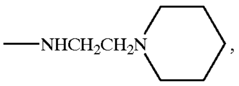, 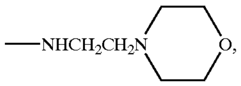

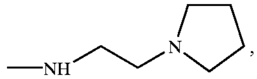, —$NHCH_2CH_2NHCH_2$phenyl,

—$NHCH_2CH_2NHCH_2$pyridyl, 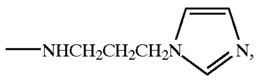

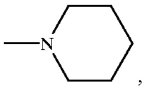, 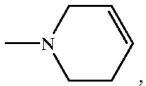, 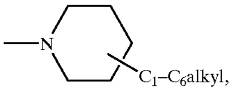

-continued

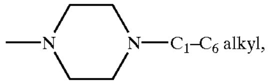

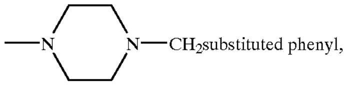

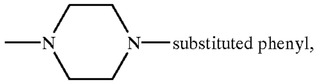

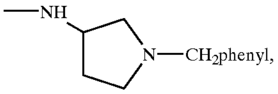 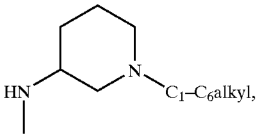

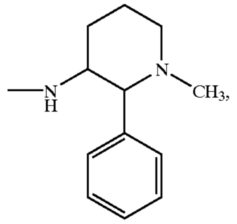 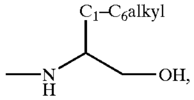

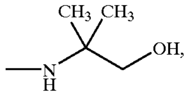 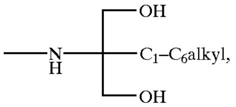

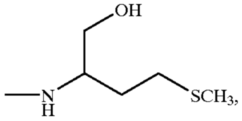 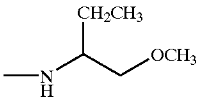 ,

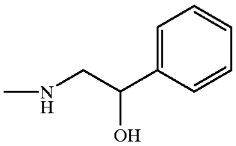 , 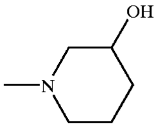 ,

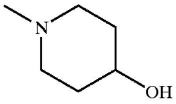 , or 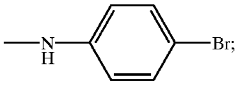

each n is independently 0 to 5; and each m is independently 2 to 7, and the pharmaceutically acceptable salts, esters, amides, and prodrugs thereof.

18. Compounds having the Formula V

V

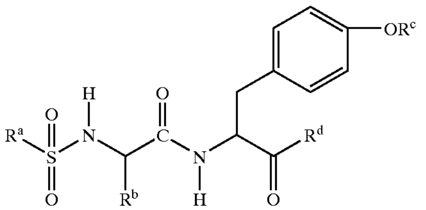

wherein $R^a$ is 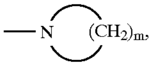

—NH-phenyl, or —NH-substituted phenyl, $C_1$–$C_6$ alkyl, aryl, heteroaryl, or substituted alkyl;

$R^b$ is $C_1$–$C_6$ alkyl, —$(CH_2)_n$-aryl, or —$(CH_2)_n$-heteroaryl;

$R^c$ is —$CH_2$-phenyl, $C_1$–$C_6$ alkyl, —$CH_2$-substituted phenyl, or —$CH_2$-heteroaryl;

$R^d$ is —$OC_1$–$C_6$ alkyl, —$N(C_1$–$C_6alkyl)_2$, —NH—$C_1$–$C_6$ alkyl,

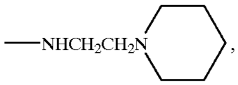 , 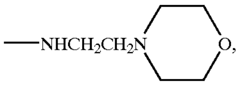

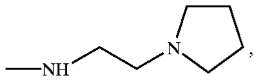 , —$NHCH_2CH_2NHCH_2$phenyl,

—$NHCH_2CH_2NHCH_2$pyridyl, 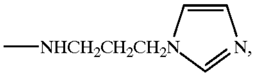

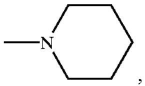 , 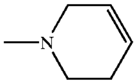 , 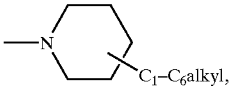

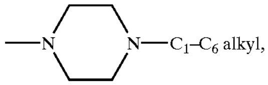

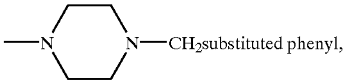

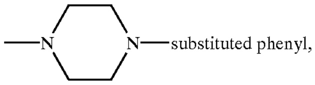

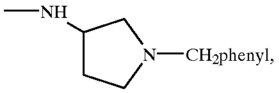 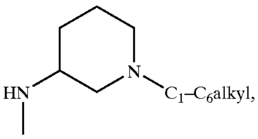

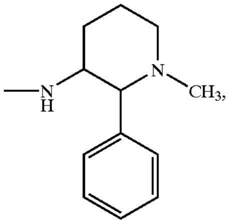 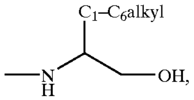

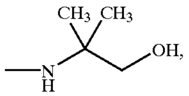 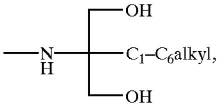

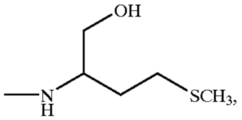 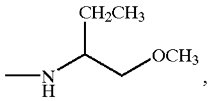 ,

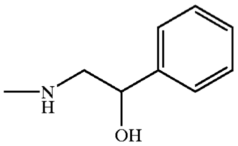 , 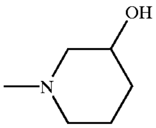 ,

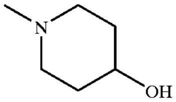 , or 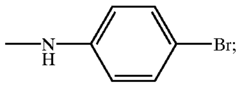

each n is independently 0 to 5; and each m is independently 2 to 7, and the pharmaceutically acceptable salts, esters, amides, and prodrugs thereof.

19. Compounds having the Formula VI

VI

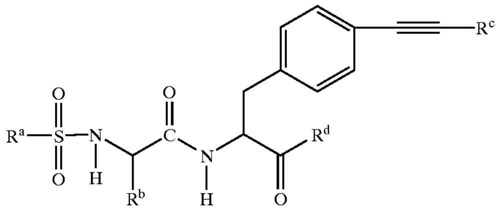

wherein $R^a$ is 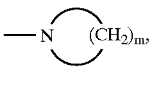

—NH-phenyl, or —NH-substituted phenyl, $C_1$–$C_6$ alkyl, aryl, heteroaryl, or substituted alkyl;

$R^b$ is $C_1$–$C_6$ alkyl, —$(CH_2)_n$-aryl, or —$(CH_2)_n$-heteroaryl;

$R^c$ is phenyl, $C_1$–$C_6$ alkyl, substituted phenyl, or heteroaryl;

$R^d$ is —$OC_1$–$C_6$ alkyl, —$N(C_1$–$C_6alkyl)_2$, —NH—$C_1$–$C_6$ alkyl,

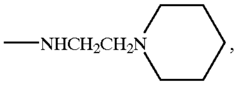

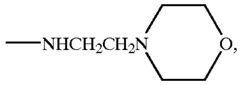

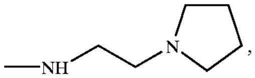

—$NHCH_2CH_2NHCH_2$phenyl,

—$NHCH_2CH_2NHCH_2$pyridyl,

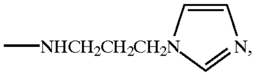

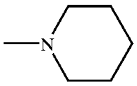

,

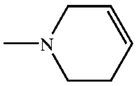

,

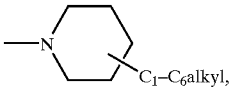

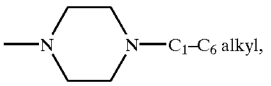

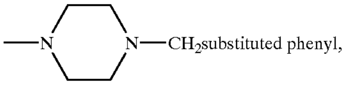

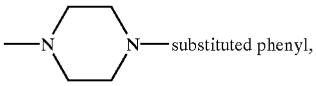

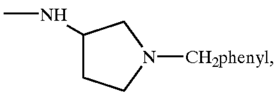

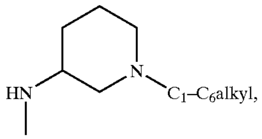

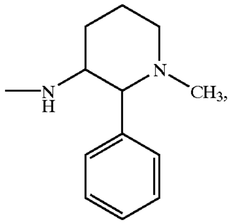

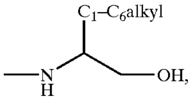

-continued

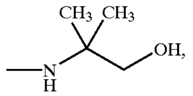

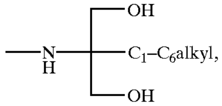

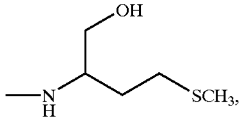

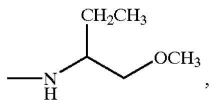

,

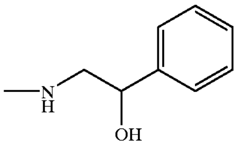

,

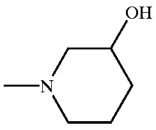

,

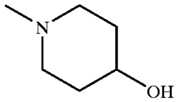

, or

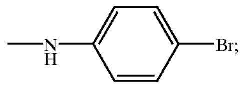

each n is independently 0 to 5; and each m in independently 2 to 7, and the pharmaceutically acceptable salts, esters, amides, and prodrugs thereof.

20. Compounds having the Formula VII

VII

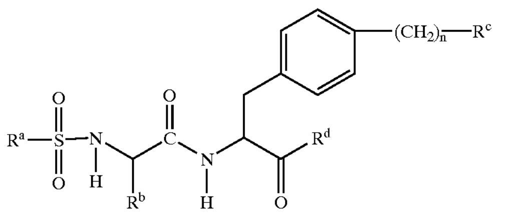

wherein $R^a$ is 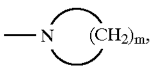

—NH-phenyl, —NH-substituted phenyl, $C_1$–$C_6$ alkyl, aryl, heteroaryl, or substituted aryl;

$R^b$ is $C_1$–$C_6$ alkyl, —$(CH_2)_n$-aryl, or —$(CH_2)_n$-heteroaryl;

$R^c$ is —$CH_2$-phenyl, $C_1$–$C_6$ alkyl, —$CH_2$-substituted phenyl, or —$CH_2$-heteroaryl;

$R^d$ is —$OC_1$–$C_6$ alkyl, —$N(C_1$–$C_6alkyl)_2$, —NH—$C_1$–$C_6$ alkyl,

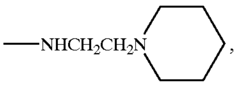

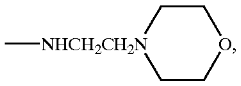

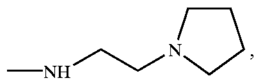

—$NHCH_2CH_2NHCH_2$phenyl,

—$NHCH_2CH_2NHCH_2$pyridyl,

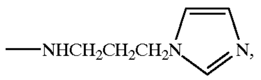

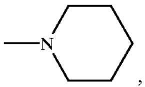

,

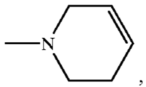

,

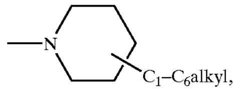

-continued

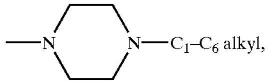

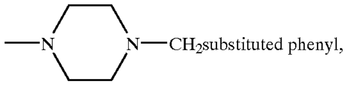

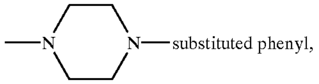

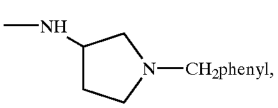

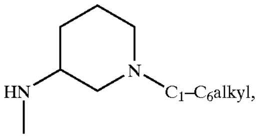

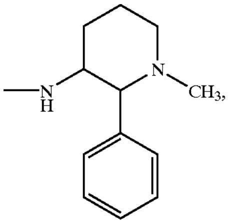

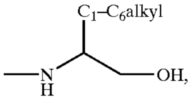

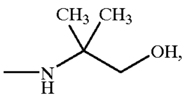

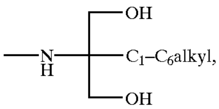

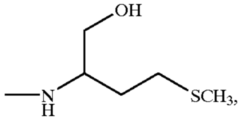

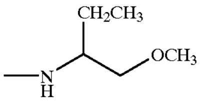
,

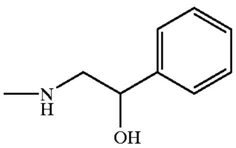
,

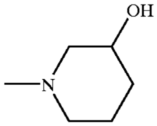
,

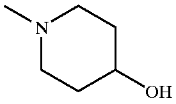
, or

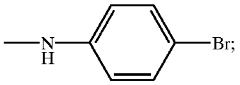

each n is independently 0 to 5; and each m is independently 2 to 7, and the pharmaceutically acceptable salts, esters, amides, and prodrugs thereof.

21. Compounds having the Formula VIII

VIII

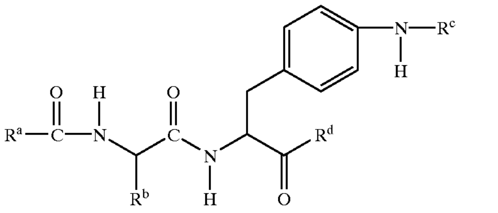

wherein $R^a$ is 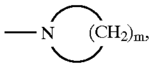

—NH-phenyl, or —NH-substituted phenyl;

$R^b$ $C_1$–$C_6$ alkyl, —$(CH_2)_n$-aryl, or —$(CH_2)_n$-heteroaryl;

$R^c$ —$CH_2$-phenyl, $C_1$–$C_6$ alkyl, —$CH_2$-substituted phenyl, or —$CH_2$-heteroaryl;

$R^d$ —$OC_1$–$C_6$ alkyl, —$N(C_1$–$C_6alkyl)_2$, —NH—$C_1$–$C_6$ alkyl,

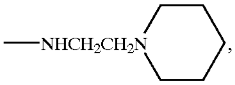
,

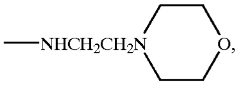

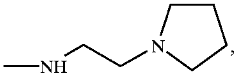
,

—$NHCH_2CH_2NHCH_2$ phenyl,

—$NHCH_2CH_2NHCH_2$ pyridyl,

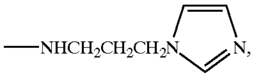

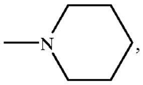
,

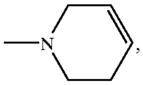
,

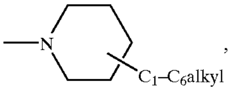
,

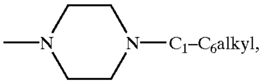

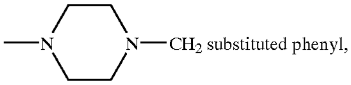

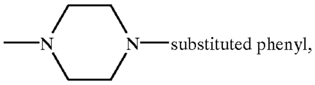

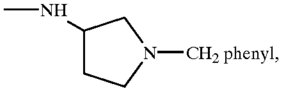

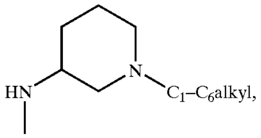

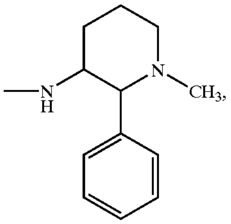

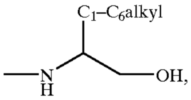

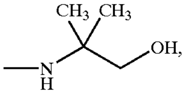

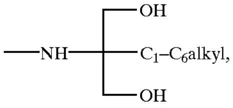

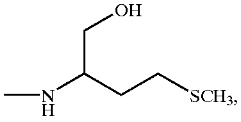

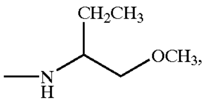

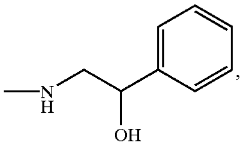

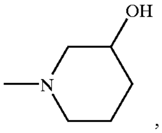
,

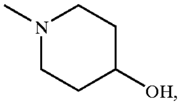
or

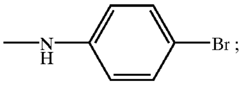

each n is independently 0 to 5; and each m is independently 2 to 7, and the pharmaceutically acceptable salts, esters, amides, and prodrugs thereof.

22. Compounds having the Formula IX

IX

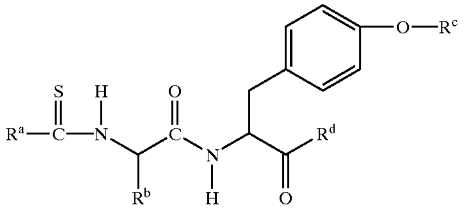

wherein $R^a$ is 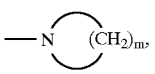

—NH-phenyl, or —NH-substituted phenyl;

$R^b$ is $C_1$–$C_6$ alkyl, —$(CH_2)_n$-aryl, or —$(CH_2)_n$-heteroaryl;

$R^c$ is —$CH_2$-phenyl, $C_1$–$C_6$ alkyl, —$CH_2$-substituted phenyl, or —$CH_2$-heteroaryl;

$R^d$ is —$OC_1$–$C_6$ alkyl, —$N(C_1$–$C_6alkyl)_2$, —NH—$C_1$–$C_6$ alkyl,

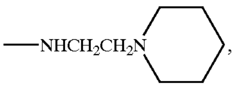 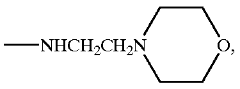

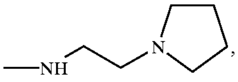 —$NHCH_2CH_2NHCH_2$ phenyl,

—$NHCH_2CH_2NHCH_2$ pyridyl, 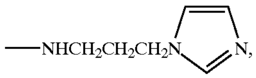

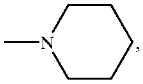 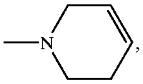 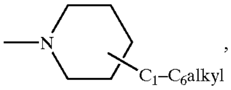

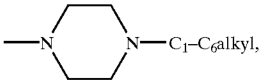

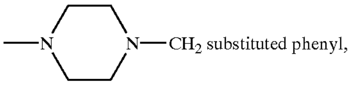

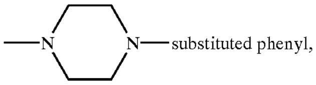

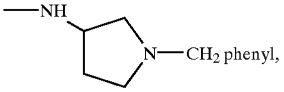

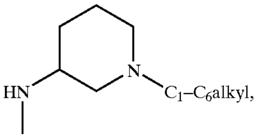 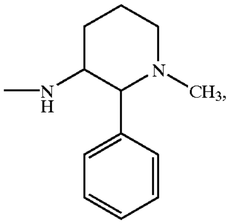

-continued

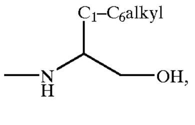 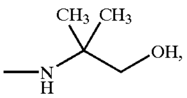

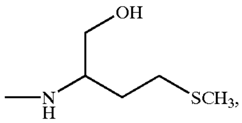 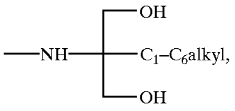

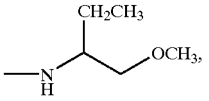 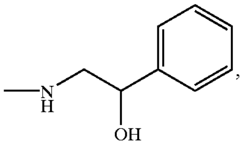

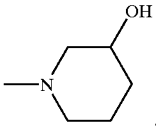 , 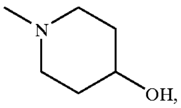 or

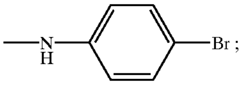

each n is independently 0 to 5; and each m is independently 2 to 7, and the pharmaceutically acceptable salts, esters, amides, and prodrugs thereof.

23. Compounds having the Formula X

X

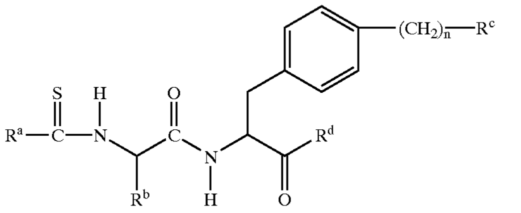

wherein $R^a$ is 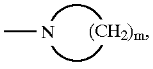

—NH-phenyl, or —NH-substituted phenyl;

$R^b$ is $C_1$–$C_6$ alkyl, —$(CH_2)_n$-aryl, or —$(CH_2)_n$-heteroaryl;

$R^c$ is —$CH_2$-phenyl, $C_1$–$C_6$ alkyl, —$CH_2$-substituted phenyl, or —$CH_2$-heteroaryl;

$R^d$ is —$OC_1$–$C_6$ alkyl, —$N(C_1$–$C_6alkyl)_2$, —NH—$C_1$–$C_6$ alkyl,

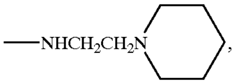 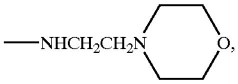

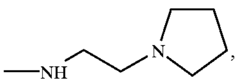 —$NHCH_2CH_2NHCH_2$ phenyl,

-continued

—NHCH₂CH₂NHCH₂ pyridyl,

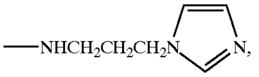

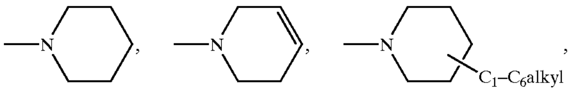

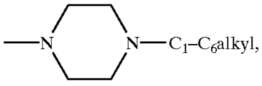

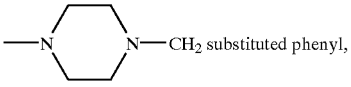

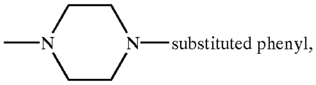

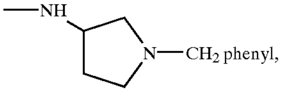

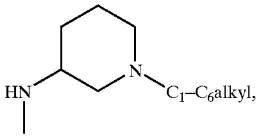

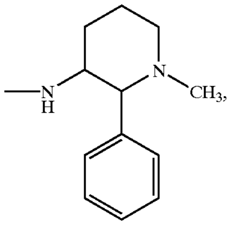

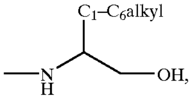

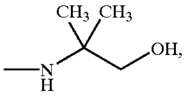

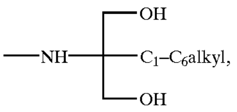

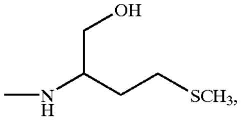

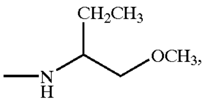

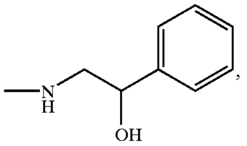

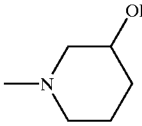

,

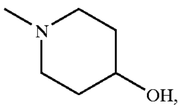

or

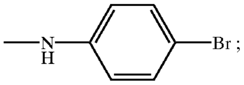

each n is independently 0 to 5; and each m is independently 2 to 7, and the pharmaceutically acceptable salts, esters, amides, and prodrugs thereof.

24. A pharmaceutical composition comprising a compound of claim 1.

25. A pharmaceutical composition comprising a compound of claim 14.

26. A pharmaceutical composition comprising a compound of claim 16.

27. A pharmaceutical composition comprising a compound of claim 17.

28. A pharmaceutical composition comprising a compound of claim 18.

29. A pharmaceutical composition comprising a compound of claim 19.

30. A pharmaceutical composition comprising a compound of claim 20.

31. A pharmaceutical composition comprising a compound of claim 21.

32. A pharmaceutical composition comprising a compound of claim 22.

33. A pharmaceutical composition comprising a compound of claim 23.

34. A method of blocking calcium channels, the method comprising administering to a patient in need of calcium channel blocking a therapeutically effective amount of a compound of claim 1 to block calcium channels.

35. The method of claim 34 wherein the calcium channels are N-type calcium channels.

36. A method of blocking N-type calcium channels, the method comprising administering to a patient in need of N-type calcium channel blocking a therapeutically effective amount of a compound of claim 1 to block N-type calcium channels.

37. A method of treating stroke, the method comprising administering to a patient having a stroke a therapeutically effective amount of a compound of claim 1.

38. A method of preventing a stroke, the method comprising administering to a patient at risk of having a stroke a therapeutically effective amount of a compound of claim 1.

39. A method of treating cerebral ischemia, the method comprising administering to a patient having cerebral ischemia a therapeutically effective amount of a compound of claim 1.

40. A method of treating head trauma, the method comprising administering to a patient having head trauma a therapeutically effective amount of a compound of claim 1.

41. A method of treating epilepsy, the method comprising administering to a patient having epilepsy a therapeutically effective amount of a compound of claim 1.

42. A method of treating pain, the method comprising administering to a patient having pain a therapeutically effective amount of a compound of claim 1.

43. A method of blocking calcium channels, the method comprising administering to a patient in need of calcium channel blocking a therapeutically effective amount of a compound of claim 14 to block calcium channels.

44. The method of claim 43 wherein the calcium channels are N-type calcium channels.

45. A method of blocking N-type calcium channels, the method comprising administering to a patient in need of N-type calcium channel blocking a therapeutically effective amount of a compound of claim 14 to block N-type calcium channels.

46. A method of treating stroke, the method comprising administering to a patient having a stroke a therapeutically effective amount of a compound of claim 14.

47. A method of preventing a stroke, the method comprising administering to a patient at risk of having a stroke a therapeutically effective amount of a compound of claim 14.

48. A method of treating cerebral ischemia, the method comprising administering to a patient having cerebral ischemia a therapeutically effective amount of a compound of claim 14.

49. A method of treating head trauma, the method comprising administering to a patient having head trauma a therapeutically effective amount of a compound of claim 14.

50. A method of treating epilepsy, the method comprising administering to a patient having epilepsy a therapeutically effective amount of a compound of claim 14.

51. A method of treating pain, the method comprising administering to a patient having pain a therapeutically effective amount of a compound of claim 14.

52. A method of blocking calcium channels, the method comprising administering to a patient in need of calcium channel blocking a therapeutically effective amount of a compound of claim 16 to block calcium channels.

53. The method of claim 52 wherein the calcium channels are N-type calcium channels.

54. A method of blocking N-type calcium channels, the method comprising administering to a patient in need of N-type calcium channel blocking a therapeutically effective amount of a compound of claim 16 to block N-type calcium channels.

55. A method of treating stroke, the method comprising administering to a patient having a stroke a therapeutically effective amount of a compound of claim 16.

56. A method of preventing a stroke, the method comprising administering to a patient at risk of having a stroke a therapeutically effective amount of a compound of claim 16.

57. A method of treating cerebral ischemia, the method comprising administering to a patient having cerebral ischemia a therapeutically effective amount of a compound of claim 16.

58. A method of treating head trauma, the method comprising administering to a patient having head trauma a therapeutically effective amount of a compound of claim 16.

59. A method of treating epilepsy, the method comprising administering to a patient having epilepsy a therapeutically effective amount of a compound of claim 16.

60. A method of treating pain, the method comprising administering to a patient having pain a therapeutically effective amount of a compound of claim 16.

61. A method of blocking calcium channels, the method comprising administering to a patient in need of calcium channel blocking a therapeutically effective amount of a compound of claim 17 to block calcium channels.

62. The method of claim 61 wherein the calcium channels are N-type calcium channels.

63. A method of blocking N-type calcium channels, the method comprising administering to a patient in need of N-type calcium channel blocking a therapeutically effective amount of a compound of claim 17 to block N-type calcium channels.

64. A method of treating stroke, the method comprising administering to a patient having a stroke a therapeutically effective amount of a compound of claim 17.

65. A method of preventing a stroke, the method comprising administering to a patient at risk of having a stroke a therapeutically effective amount of a compound of claim 17.

66. A method of treating cerebral ischemia, the method comprising administering to a patient having cerebral ischemia a therapeutically effective amount of a compound of claim 17.

67. A method of treating head trauma, the method comprising administering to a patient having head trauma a therapeutically effective amount of a compound of claim 17.

68. A method of treating epilepsy, the method comprising administering to a patient having epilepsy a therapeutically effective amount of a compound of claim 17.

69. A method of treating pain, the method comprising administering to a patient having pain a therapeutically effective amount of a compound of claim 17.

70. A method of blocking calcium channels, the method comprising administering to a patient in need of calcium channel blocking a therapeutically effective amount of a compound of claim 18 to block calcium channels.

71. The method of claim 70 wherein the calcium channels are N-type calcium channels.

72. A method of blocking N-type calcium channels, the method comprising administering to a patient in need of N-type calcium channel blocking a therapeutically effective amount of a compound of claim 18 to block N-type calcium channels.

73. A method of treating stroke, the method comprising administering to a patient having a stroke a therapeutically effective amount of a compound of claim 18.

74. A method of preventing a stroke, the method comprising administering to a patient at risk of having a stroke a therapeutically effective amount of a compound of claim 18.

75. A method of treating cerebral ischemia, the method comprising administering to a patient having cerebral ischemia a therapeutically effective amount of a compound of claim 18.

76. A method of treating head trauma, the method comprising administering to a patient having head trauma a therapeutically effective amount of a compound of claim 18.

77. A method of treating epilepsy, the method comprising administering to a patient having epilepsy a therapeutically effective amount of a compound of claim 18.

78. A method of treating pain, the method comprising administering to a patient having pain a therapeutically effective amount of a compound of claim 18.

79. A method of blocking calcium channels, the method comprising administering to a patient in need of calcium channel blocking a therapeutically effective amount of a compound of claim 19 to block calcium channels.

80. The method of claim 79 wherein the calcium channels are N-type calcium channels.

81. A method of blocking N-type calcium channels, the method comprising administering to a patient in need of N-type calcium channel blocking a therapeutically effective amount of a compound of claim 19 to block N-type calcium channels.

82. A method of treating stroke, the method comprising administering to a patient having a stroke a therapeutically effective amount of a compound of claim 19.

83. A method of preventing a stroke, the method comprising administering to a patient at risk of having a stroke a therapeutically effective amount of a compound of claim 19.

84. A method of treating cerebral ischemia, the method comprising administering to a patient having cerebral ischemia a therapeutically effective amount of a compound of claim 19.

85. A method of treating head trauma, the method comprising administering to a patient having head trauma a therapeutically effective amount of a compound of claim 19.

86. A method of treating epilepsy, the method comprising administering to a patient having epilepsy a therapeutically effective amount of a compound of claim 19.

87. A method of treating pain, the method comprising administering to a patient having pain a therapeutically effective amount of a compound of claim 19.

88. A method of blocking calcium channels, the method comprising administering to a patient in need of calcium channel blocking a therapeutically effective amount of a compound of claim 20 to block calcium channels.

89. The method of claim 88 wherein the calcium channels are N-type calcium channels.

90. A method of blocking N-type calcium channels, the method comprising administering to a patient in need of N-type calcium channel blocking a therapeutically effective amount of a compound of claim 20 to block N-type calcium channels.

91. A method of treating stroke, the method comprising administering to a patient having a stroke a therapeutically effective amount of a compound of claim 20.

92. A method of preventing a stroke, the method comprising administering to a patient at risk of having a stroke a therapeutically effective amount of a compound of claim 20.

93. A method of treating cerebral ischemia, the method comprising administering to a patient having cerebral ischemia a therapeutically effective amount of a compound of claim 20.

94. A method of treating head trauma, the method comprising administering to a patient having head trauma a therapeutically effective amount of a compound of claim 20.

95. A method of treating epilepsy, the method comprising administering to a patient having epilepsy a therapeutically effective amount of a compound of claim 20.

96. A method of treating pain, the method comprising administering to a patient having pain a therapeutically effective amount of a compound of claim 20.

97. A method of blocking calcium channels, the method comprising administering to a patient in need of calcium channel blocking a therapeutically effective amount of a compound of claim 21 to block calcium channels.

98. The method of claim 97 wherein the calcium channels are N-type calcium channels.

99. A method of blocking N-type calcium channels, the method comprising administering to a patient in need of N-type calcium channel blocking a therapeutically effective amount of a compound of claim 21 to block N-type calcium channels.

100. A method of treating stroke, the method comprising administering to a patient having a stroke a therapeutically effective amount of a compound of claim 21.

101. A method of preventing a stroke, the method comprising administering to a patient at risk of having a stroke a therapeutically effective amount of a compound of claim 21.

102. A method of treating cerebral ischemia, the method comprising administering to a patient having cerebral ischemia a therapeutically effective amount of a compound of claim 21.

103. A method of treating head trauma, the method comprising administering to a patient having head trauma a therapeutically effective amount of a compound of claim 21.

104. A method of treating epilepsy, the method comprising administering to a patient having epilepsy a therapeutically effective amount of a compound of claim 21.

105. A method of treating pain, the method comprising administering to a patient having pain a therapeutically effective amount of a compound of claim 21.

106. A method of blocking calcium channels, the method comprising administering to a patient in need of calcium channel blocking a therapeutically effective amount of a compound of claim 22 to block calcium channels.

107. The method of claim 106 wherein the calcium channels are N-type calcium channels.

108. A method of blocking N-type calcium channels, the method comprising administering to a patient in need of N-type calcium channel blocking a therapeutically effective amount of a compound of claim 22 to block N-type calcium channels.

109. A method of treating stroke, the method comprising administering to a patient having a stroke a therapeutically effective amount of a compound of claim 22.

110. A method of preventing a stroke, the method comprising administering to a patient at risk of having a stroke a therapeutically effective amount of a compound of claim 22.

111. A method of treating cerebral ischemia, the method comprising administering to a patient having cerebral ischemia a therapeutically effective amount of a compound of claim 22.

112. A method of treating head trauma, the method comprising administering to a patient having head trauma a therapeutically effective amount of a compound of claim 22.

113. A method of treating epilepsy, the method comprising administering to a patient having epilepsy a therapeutically effective amount of a compound of claim 22.

114. A method of treating pain, the method comprising administering to a patient having pain a therapeutically effective amount of a compound of claim 22.

115. A method of blocking calcium channels, the method comprising administering to a patient in need of calcium channel blocking a therapeutically effective amount of a compound of claim 23 to block calcium channels.

116. The method of claim 115 wherein the calcium channels are N-type calcium channels.

117. A method of blocking N-type calcium channels, the method comprising administering to a patient in need of N-type calcium channel blocking a therapeutically effective amount of a compound of claim 23 to block N-type calcium channels.

118. A method of treating stroke, the method comprising administering to a patient having a stroke a therapeutically effective amount of a compound of claim 23.

119. A method of preventing a stroke, the method comprising administering to a patient at risk of having a stroke a therapeutically effective amount of a compound of claim 23.

120. A method of treating cerebral ischemia, the method comprising administering to a patient having cerebral ischemia a therapeutically effective amount of a compound of claim 23.

121. A method of treating head trauma, the method comprising administering to a patient having head trauma a therapeutically effective amount of a compound of claim 23.

122. A method of treating epilepsy, the method comprising administering to a patient having epilepsy a therapeutically effective amount of a compound of claim 23.

123. A method of treating pain, the method comprising administering to a patient having pain a therapeutically effective amount of a compound of claim 23.

124. The compounds:

[S-(R*,R*)]-2-{2-[(Azepane-1-carbonyl-carbonyl)-amino]-4-methyl-pentanoylamino}-3-(4-benzyloxy-phenyl)-propionic acid tert-butyl ester;

2(R)-{2(S)-[(Azepane-1-carbonyl)-amino]-4-methyl-pentanoylamino}-3-(4-benzyloxy-phenyl)-propionic acid tert-butyl ester (L,D);

2(S)-{2(R)-[(Azepane-1-carbonyl)-amino]-4-methyl-pentanoylamino}-3-(4-benzyloxy-phenyl)-propionic acid tert-butyl ester (D,L);

[S-(R*,R*)]-2-{2-(Azepane-1-carbonyl)-amino]-4-methyl-pentanoylamino}-3-(4-benzyloxy-phenyl)-propionic acid tert-butyl ester;

[S-(R*,R*)]-2-{2-[(Azepane-1-carbonyl)-amino]-3-methyl-pentanoylamino}-3-(4-benzyloxy-phenyl)-propionic acid tert-butyl ester;

[S-(R*,R*)]-2-{2-[(Azepane-1-carbonyl)-amino]-3-methyl-butyrylamino}-3-(4-benzyloxy-phenyl)-propionic acid tert-butyl ester;

[S-(R*,R*)]-2-(S)-{2-[(Azepane-1-carbonyl)-amino]-propionylamino}-3-(4-benzyloxy-phenyl)-propionic acid tert-butyl ester;

[S-(R*,R*)]-2-{2-[(Azepane-1-carbonyl)-amino]-acetylamino}-3-(4-benzyloxy-phenyl)-propionic acid tert-butyl ester; and

[S-(R*,R*)]-3-(4-Benzyloxy-phenyl)-2-{4-methyl-2-[(4-methyl-piperazine-1-carbonyl)-amino]-pentanoylamino}-propionic acid tert-butyl ester.

125. The compounds:

[S-(R*,R*)]-3-(4-Benzyloxy-phenyl)-2-{4-methyl-2-[(4-phenyl-piperazine-1-carbonyl)-amino]-pentanoylamino}-propionic acid tert-butyl ester;

[S-(R*,R*)]-2-{2-[(Azepane-1-carbonyl)-amino]-4-methyl-pentanoylamino}-3-(4-benzyloxy-phenyl)-2-methyl-propionic acid tert-butyl ester;

2(R)-{2(S)-[(Azepane-1-carbonyl)-amino]-4-methyl-pentanoylamino}-3-(4-benzyloxy-phenyl)-2-methyl-propionic acid tert-butyl ester;

[S-(R*,R*)]-2-{2-[(Azepane-1-carbonyl)-amino]-4-methyl-pentanoylamino}-3-(4-tert-butoxy-phenyl)-propionic acid tert-butyl ester;

[S-(R*,R*)]-2-{2-[(Azepane-1-carbonyl)-amino]-4-methyl-pentanoylamino}-3-(4-methoxy-phenyl)-propionic acid tert-butyl ester;

[S-(R*,R* )]-2-{2-[(Azepane-1-carbonyl)-amino]-4-methyl-pentanoylamino}-3-(4-benzyloxy-phenyl)-propionic acid benzyl ester;

[S-(R*,R*)]-2(S)-{2(S)-[(Azepane-1-carbonyl)-amino]-4-methyl-pentanoylamino}-3-(4-benzyloxy-phenyl)-propionic acid methyl ester;

[S-(R*,R*)]-2-{2-[(Azepane-1-carbonyl-carbonyl)-amino]-3-phenyl-propionylamino}-3-(4-benzyloxy-phenyl)-propionic acid tert-butyl ester;

[S-(R*,R*)]-2-[2-[(Azepane-1-carbonyl)-amino]-3-(1H-indol-3-yl)-propionylamino]-3-(4-benzyloxy-phenyl)-propionic acid tert-butyl ester;

[S-(R*,R*)]-2-{2-[(Azepane-1-carbonyl)-amino]-3-phenyl-propionylamino}-3-(4-benzyloxy-phenyl)-propionic acid tert-butyl ester;

[S-(R*,R*)]-2-{2-[(Azepane-1-carbonyl)-amino]-3-phenyl-propionylamino}-3-[4-(4-methyl-benzyloxy)-phenyl]-propionic acid tert-butyl ester; and

[S-(R*,R*)]-2-[2-[(Azepane-1-carbonyl)-amino]-3-(1H-indol-3-yl)-propionylamino]-3-(4-benzyloxy-phenyl)-propionic acid tert-butyl ester.

126. The compounds:

[S-(R*,R*)]-Azepane-1-carboxylic acid {1-[2-(4-benzyloxy-phenyl)-1-carbamoyl-ethylcarbamoyl]-3-methyl-butyl}-amide;

[S-(R*,R*)]-2-{2-[(Azepane-1-carbonyl)-amino]-4-methyl-pentanoylamino}-3-(4-tert-butoxy-phenyl)-propionic acid methyl ester;

[S-(R*,R*)]-Azepane-1-carboxylic acid {1-[2-(4-benzyloxy-phenyl)-1-tert-butylcarbamoyl-ethylcarbamoyl]-3-methyl-butyl}-amide;

[S-(R*,R*)]-2-{2-[(Azepane-1-carbonyl)-amino]-4-methyl-pentanoylamino}-3-[4-(pyridin-2-ylmethoxy)-phenyl]-propionic acid tert-butyl ester;

[S-(R*,R*)]-2-{2-[(Azepane-1-carbonyl)-amino]-4-methyl-pentanoylamino}-3-[4-(pyridin-4-ylmethoxy)-phenyl]-propionic acid tert-butyl ester;

[S-(R*,R*)]-2-{2-[(Azepane-1-carbonyl)-amino]-4-methyl-pentanoylamino}-3-[4-(4-cyano-benzyloxy)-phenyl]-propionic acid tert-butyl ester;

[S-(R*,R*)]-2-{2-[(Azepane-1-carbonyl)-amino]-4-methyl-pentanoylamino}-3-[4-(3-tert-butoxycarbonylamino-benzyloxy)-phenyl]-propionic acid tert-butyl ester;

[S-(R*,R*)]-3-[4-(3-Amino-benzyloxy)-phenyl]-2-{2-[(azepane-1-carbonyl)-amino]-4-methyl-pentanoylamino}-propionic acid tert-butyl ester;

[S-(R*,R*)]-2-{2-2[(Azepane-1-carbonyl)-amino]-4-methyl-pentanoylamino}-3-(4-cyclohexylmethoxy-phenyl)-propionic acid tert-butyl ester;

[S-(R*,R*)]-2-{2-[(Azepane-1-carbonyl)-amino]-4-methyl-pentanoylamino}-3-[4-(pyridin-3-ylmethoxy)-phenyl]-propionic acid tert-butyl ester; and

[S-(R*,R*)]-2-{2-[(Azepane-1-carbonyl)-amino]4-methyl-pentanoylamino}-3-[4-(4-methoxy-benzyloxy)-phenyl]-propionic acid tert-butyl ester.

127. The compounds:

[S-(R*,R*)]-3-(4-Benzyloxy-phenyl)-2-{4-methyl-2-[(piperidine-1-carbonyl)-amino]-pentanoylamino}-propionic acid tert-butyl ester;

[S-(R*,R*)]-3-(4-Benzyloxy-phenyl)-2(S)-{4-methyl-2(S)-[(morpholine-4-carbonyl)-amino]-pentanoylamino}-propionic acid tert-butyl ester;

[S-(R*,R*)]-3-(4-Benzyloxy-phenyl)-2-(2-methanesulfonylamino-4-methyl-pentanoylamino)-propionic acid tert-butyl ester;

[S-(R*,R*)]-3-(4-Benzyloxy-phenyl)-2(S)-[2(S)-(4-tert-butyl-benzenesulfonylamino)-4-methyl-pentanoylamino]-propionic acid tert-butyl ester;

[S-(R*,R*)]-3-(4-Benzyloxy-phenyl)-2(S)-[2(S)-(4-isopropyl-benzenesulfonylamino)-4-methyl-pentanoylamino]-propionic acid tert-butyl ester;

[S-(R*,R*)]-2-{2-[(4-Bromobenzene-1-sulfonyl-carbonyl)-amino]-4-methyl-pentanoylamino-3-(4-benzyloxyphenyl)-propionic acid}tert-butyl ester;

[S-(R*,R*)]-3-(4-Benzyloxy-phenyl)-2-[4-methyl-2-(4-nitro-benzenesulfonylamino)-pentanoylamino]-propionic acid tert-butyl ester;

[S-(R*,R*)]-2-[2-(Azepane-1-sulfonylamino)-4-methyl-pentanoylamino]-3-(4-benzyloxy-phenyl)-propionic acid tert-butyl ester;

[S-(R*,R*)]-3-(4-Benzyloxy-phenyl)-2-[4-methyl-2-(piperidine-1-sulfonylamino)-pentanoylamino]-propionic acid tert-butyl ester;

[S-(R*,R*)]-3-(4-Benzyloxy-phenyl)-2-[4-methyl-2-(morpholine-4-sulfonylamino)-pentanoylamino]-propionic acid tert-butyl ester;

[S-(R*,R*)]-3-(4-Benzyloxy-phenyl)-2-{2-[3-(4-isopropyl-phenyl)-thioureido]-4-methyl-pentanoylamino}-propionic acid, tert-butyl ester;

[S-(R*,R*)]-3-(4-Benzyloxy-phenyl)-2-{2-[3-(4-tert-butyl-phenyl)-thioureido]-4-methyl-pentanoylamino}-propionic acid, tert-butyl ester;

[S-(R*,R*)]-3-(4-Benzyloxy-phenyl)-2-{2-[3-(4-bromophenyl)-thioureido]-4-methyl-pentanoylamino}-propionic acid, tert-butyl ester; and

[S-(R*,R*)]-3-(4-Benzyloxy-phenyl)-2-{2-[3-(1-adamantyl)-thioureido]-4-methyl pentanoylamino}-propionic acid, tert-butyl ester.

128. The compounds:

[S-(R*,R*)]-3-(4-benzyloxy-phenyl)-2-[2-(3-cyclohexyl-thioureido)-4-methyl-pentanoylamino]-propionic acid, tert-butyl ester;

[S-(R*,R*)]-3-(4-Benzyloxy-phenyl)-2-{2-[3-(2-chloro-phenyl)-thioureido]-4-methyl-pentanoylamino}-propionic acid tert-butyl ester;

[S-(R*,R*)]-3-(4-Benzyloxy-phenyl)-2-[2-(3-butyl-thioureido)-4-methyl-pentanoylamino]-propionic acid tert-butyl ester;

[S-(R*,R*)]-3-(4-Benzyloxy-phenyl)-2-[4-methyl-2-(3-p-tolyl-thioureido)-pentanoylamino]-propionic acid tert-butyl ester;

[S-(R*,R*)]-3-(4-Benzyloxy-phenyl)-2-[4-methyl-2-(3-methyl-thioureido)-pentanoylamino]-propionic acid tert-butyl ester;

[S-(R*,R*)]-Azepane-1-carboxylic acid (1-{1-tert-butylcarbamoyl-2-[4-(2,6-dichloro-benzyloxy)-phenyl]-ethylcarbamoyl}-3-methyl-butyl)-amide;

[S-(R*,R*)]-Azepane-1-carboxylic acid {1-[2-(4-benzyl-phenyl)-1-tert-butylcarbamoyl-ethylcarbamoyl]-3-methyl-butyl}-amide;

[S-(R*,R*)]-3-(4-Benzyloxy-phenyl)-2-[4-methyl-2-(3-phenyl-ureido)-pentanoylamino]propionic acid tert-butyl ester;

[S-(R*,R*)]-3-(4-Benzyloxy-phenyl)-2-{4-methyl-2-[3-(4-nitro-phenyl)-ureido]pentanoylamino}-propionic acid tert-butyl ester;

[S-(R*,R*)]-3-(4-Benzyloxy-phenyl)-2-[2-(3-cyclohexyl-ureido)-4-methyl-pentanoylamino]propionic acid tert-butyl ester;

[S-(R*,R*)]-3-(4-Benzyloxy-phenyl)-2-{2-[3-(3-methoxy-phenyl)-ureido]-4-methyl-pentanoylamino}-propionic acid tert-butyl ester;

[S-(R*,R*)]-3-(4-Benzyloxy-phenyl)-2-[4-methyl-2-(3-p-tolyl-ureido)-pentanoylamino]propionic acid tert-butyl ester;

[S-(R*,R*)]-3-(4-Benzyloxy-phenyl)-2-[2-(3-butyl-ureido)-4-methyl-pentanoylamino]-propionic acid tert-butyl ester;

[S-(R*,R*)]-3-(4-Benzyloxy-phenyl)-2-[2-(3-benzyl-ureido)-4-methyl-pentanoylamino]-propionic acid tert-butyl ester; and

[S-(R*,R*)]-3(4-Benzyloxy-phenyl)-2-[4-methyl-2-(3-o-tolyl-ureido)-pentanoylamino]-propionic acid tert-butyl ester.

129. The compounds:

[S-(R*,R*)]-3-(4-Benzyloxy-phenyl)-2-{2-[3-(2,6-dimethyl-phenyl)-ureido]-4-methyl-pentanoylamino}-propionic acid tert-butyl ester;

[S-(R*,R*)]-3-(4-Benzyloxy-phenyl)-2-{4-methyl-2-[3-(1-phenyl-ethyl)-ureido]-pentanoylamino}-propionic acid tert-butyl ester;

[S-(R*,R*)]-3-(4-Benzyloxy-phenyl)-2-{4-methyl-2-[3-(4-methylsulfanyl-phenyl)-ureido]-pentanoylamino}-propionic acid tert-butyl ester;

[S-(R*,R*)]-3-(4-Benzyloxy-phenyl)-2-{4-methyl-2-[3-(4-phenoxy-phenyl)-ureido]pentanoylamino}-propionic acid tert-butyl ester;

[S-(R*,R*)]-3-(4-Benzyloxy-phenyl)-2-{2-[3-(1-methoxycarbonyl-2-phenyl-ethyl)-ureido]-4-methyl-pentanoylamino}-propionic acid tert-butyl ester;

[S-(R*,R*)]-3-(4-Benzyloxy-phenyl)-2-{4-methyl-2-[3-(3,4,5-trimethoxy-phenyl)-ureido]-pentanoylamino}-propionic acid tert-butyl ester;

[S-(R*,R*)]-3-(4-Benzyloxy-phenyl)-2-{2-[3-(4-methoxy-phenyl)-ureido]-4-methyl-pentanoylamino}-propionic acid tert-butyl ester;

[S-(R*,R*)]-3-(4-Benzyloxy-phenyl)-2-{2-[3-(2,4-difluoro-phenyl)-ureido]-4-methyl-pentanoylamino}-propionic acid tert-butyl ester;

[S-(R*,R*)]-3-(4-Benzyloxy-phenyl)-2-{4-methyl-2-[3-(4-trifluoromethyl-phenyl)-ureido]-pentanoylamino}-propionic acid tert-butyl ester;

[S-(R*,R*)]-3-(4-Benzyloxy-phenyl)-2-{2-[3-(2-methoxy-phenyl)-ureido]-4-methyl-pentanoylamino}-propionic acid tert-butyl ester;

[S-(R*,R*)]-3-(4-Benzyloxy-phenyl)-2-{2-[3-(3,5-dimethyl-phenyl)-ureido]-4-methyl-pentanoylamino}-propionic acid tert-butyl ester;

[S-(R*,R*)]-3-(4-Benzyloxy-phenyl)-2-{2-[3-(2-chloro-phenyl)-ureido]-4-methyl pentanoylamino}-propionic acid tert-butyl ester; and

[S-(R*,R*)]-3-(4-Benzyloxy-phenyl)-2-{2-[3-(3-chloro-phenyl)-ureido]-4-methyl-pentanoylamino}-propionic acid tert-butyl ester.

130. The compounds:

[S-(R*,R*)]-3-(4-Benzyloxy-phenyl)-2-{4-methyl-2-[3-(2-phenyl-cyclopropyl)-ureido]-pentanoylamino}-propionic acid tert-butyl ester;

[S-(R*,R*)]-3-(4-Benzyloxy-phenyl)-2-{4-methyl-2-[3-(3-trifluoromethyl-phenyl)-ureido]-pentanoylamino}-propionic acid tert-butyl ester;

[S-(R*,R*)]-4-(3-{1-[2-(4-Benzyloxy-phenyl)-1-tert-butoxycarbonyl-ethylcarbamoyl]-3-methyl butyl}-ureido)-benzoic acid ethyl ester;

[S-(R*,R*)]-3-(4-Benzyloxy-phenyl)-2-{2-[3-(4-chloro-3-trifluoromethyl-phenyl)-ureido]-4-methyl-pentanoylamino}-propionic acid tert-butyl ester;

[S-(R*,R*)]-3-(4-Benzyloxy-phenyl)-2-[4-methyl-2-(3-naphthalen-1-yl-ureido)-pentanoylamino]-propionic acid tert-butyl ester;

[S-(R*,R*)]-3-(4-Benzyloxy-phenyl)-2-{2-[3-(4-chloro-phenyl)-ureido]-4-methyl-pentanoylamino}-propionic acid tert-butyl ester;

[S-(R*,R*)]-3-(4-Benzyloxy-phenyl)-2-{2-[3-(2,3-dichloro-phenyl)-ureido]-4-methyl-pentanoylamino}-propionic acid tert-butyl ester;

[S-(R*,R*)]-3-(4-Benzyloxy-phenyl)-2-{2-[3-(2,4-dichloro-phenyl)-ureido]-4-methyl-pentanoylamino}-propionic acid tert-butyl ester;

[S-(R*,R*)]-3-(4-Benzyloxy-phenyl)-2-{2-[3-(3,5-bis-trifluoromethyl-phenyl)-ureido]-4-methyl-pentanoylamino}-propionic acid tert-butyl ester;

[S-(R*,R*)]-3-(4-Benzyloxy-phenyl)-2-{2-[3-(4-bromo-phenyl)-ureido]-4-methyl-pentanoylamino}-propionic acid tert-butyl ester;

[S-(R*,R*)]-3-(4-Benzyloxy-phenyl)-2-{2-[3-(3,4-dichloro-phenyl)-ureido]-4-methyl-pentanoylamino}-propionic acid tert-butyl ester;

[S-(R*,R*)]-3-(4-Benzyloxy-phenyl)-2-{2-[3-(3,5-dichloro-phenyl)-ureido]-4-methyl-pentanoylamino}-propionic acid tert-butyl ester;

[S-(R*,R*)]-3-(4-Benzyloxy-phenyl)-2-[2-(3-isopropyl-ureido)-4-methyl-pentanoylamino]-propionic acid tert-butyl ester; and

[S-(R*,R*)]-3-(4-Benzyloxy-phenyl)-2-[4-methyl-2-(3-methyl-ureido)-pentanoylamino]-propionic acid tert-butyl ester.

131. The compounds:

[S-(R*,R*)]-3-(4-Benzyloxy-phenyl)-2-[2-(3-ethyl-ureido)-4-methyl-pentanoylamino]-propionic acid tert-butyl ester;

[S-(R*,R*)]-2-(4-Benzyloxy-benzyl)-5-[(furan-2-carbonyl)-amino]-7-methyl-4-oxo-octanoic acid tert-butyl ester;

[S-(R*,R*)]-3-(4-Benzyloxy-phenyl)-2-[2-(4ethoxy-benzoylamino)-4-methyl-pentanoylamino]-propionic acid tert-butyl ester;

[S-(R*,R*)]-3-(4-Benzyloxy-phenyl)-2-[4-methyl-2-(3,4,5-trimethoxy-benzoylamino)-pentanoylamino]-propionic acid tert-butyl ester;

[S-(R*,R*)]-3-(4-Benzyloxy-phenyl)-2-[2-(4-tert-butyl-benzoylamino)-4-methyl-pentanoylamino]-propionic acid tert-butyl ester;

[S-(R*,R*)]-3-(4-Benzyloxy-phenyl)-2-[2-(4-fluoro-benzoylamino)-4-methyl-pentanoylamino]-propionic acid tert-butyl ester;

[S-(R*,R*)]-3-(4-Benzyloxy-phenyl)-2-[2-(4-methoxy-benzoylamino)-4-methyl-pentanoylamino]-propionic acid tert-butyl ester;

[S-(R*,R*)]-3-(4-Benzyloxy-phenyl)-2-[2-(3-methoxy-benzoylamino)-4-methyl-pentanoylamino]-propionic acid tert-butyl ester;

[S-(R*,R*)]-2-{2-[(Benzo[1,3]dioxole-5-carbonyl)-amino]-4-methyl-pentanoylamino}-3-(4-benzyloxy-phenyl)-propionic acid tert-butyl ester;

[S-(R*,R*)]-3-(4-Benzyloxy-phenyl)-2-[2-(2-methoxy-benzoylamino)-4-methyl-pentanoylamino]-propionic acid tert-butyl ester;

[S-(R*,R*)]-3-(4-Benzyloxy-phenyl)-2-{4-methyl-2-[(naphthalene-2-carbonyl)-amino]pentanoyl amino}-propionic acid tert-butyl ester;

[S-(R*,R*)]-3-(4-Benzyloxy-phenyl)-2-[2-(3,4-dimethoxy-benzoylamino)-4-methyl-pentanoylamino]-propionic acid tert-butyl ester;

[S-(R*,R*)]-3-(4-Benzyloxy-phenyl)-2-{2-[(biphenyl-4-carbonyl)-amino]-4-methyl-pentanoylamino}-propionic acid tert-butyl ester; and

[S-(R*,R*)]-5-(Benzo[1,2,5]thiadiazole-4-sulfonylamino)-2-(4-benzyloxybenzyl)-7-methyl-4-oxo-octanoic acid tert-butyl ester.

132. The compounds:

[S-(R*,R*)]-3-(4-Benzyloxy-phenyl)-2-[2-(4-methoxy-benzenesulfonylamino)-4-methyl-pentanoylamino]-propionic acid tert-butyl ester;

[S-(R*,R*)]-3-(4-Benzyloxy-phenyl)-2-[2-(4-fluoro-benzenesulfonylamino)-4-methyl-pentanoylamino]-propionic acid tert-butyl ester;

[S-(R*,R*)]-3-(4-Benzyloxy-phenyl)-2-[4-methyl-2-(toluene-2-sulfonylamino)-pentanoylamino]-propionic acid tert-butyl ester;

[S-(R*,R*)]-3-(4-Benzyloxy-phenyl)-2-[2-(3,5-dichloro-benzenesulfonylamino)-4-methyl-pentanoylamino]-propionic acid tert-butyl ester;

[S-(R*,R*)]-3-(4-Benzyloxy-phenyl)-2-[4-methyl-2-(thiophene-2-sulfonylamino)-pentanoylamino]-propionic acid tert-butyl ester;

[S-(R*,R*)]-3-(4-Benzyloxy-phenyl)-2-[2-(5-dimethylamino-naphthalene-1-sulfonylamino)-4-methyl-pentanoylamino]-propionic acid tert-butyl ester;

[S-(R*,R*)]-3-(4-Benzyloxy-phenyl)-2-[4-methyl-2-(quinoline-7-sulfonylamino)-pentanoylamino]-propionic acid tert-butyl ester;

[S-(R*,R*)]-3-(4-Benzyloxy-phenyl)-2-[2-(5-chloro-1,3-dimethyl-1H-pyrazole-4-sulfonylamino)-4-methyl-pentanoylamino]-propionic acid tert-butyl ester;

[S-(R*,R*)]-3-(4-Benzyloxy-phenyl)-2-[2-(3,5-dimethyl-isoxazole-4-sulfonylamino)-4-methyl-pentanoylamino]-propionic acid tert-butyl ester;

[S-(R*,R*)]-3-(4-Benzyloxy-phenyl)-2-[2-(3-diethylamino-propionylamino)-4-methyl-pentanoylamino]-propionic acid tert-butyl ester;

[S-(R*,R*)]-2-(4-Benzyloxy-benzyl)-5-(2-1H-indol-3-yl-acetylamino)-7-methyl-4-oxo-octanoic acid tert-butyl ester;

[S-(R*,R*)]-3-(4-Benzyloxy-phenyl)-2-(2-heptanoylamino-4-methyl-pentanoylamino)-propionic acid tert-butyl ester; and

[S-(R*,R*)]-3-(4-Benzyloxy-phenyl)-2-(2-isobutyrylamino-4-methyl-pentanoylamino)-propionic acid tert-butyl ester.

133. The compounds:

[S-(R*,R*)]-2-(2-Acetylamino-4-methyl-pentanoylamino)-3-(4-benzyloxy-phenyl)-propionic acid tert-butyl ester;

[S-(R*,R*)]-3-(4-Benzyloxy-phenyl)-2-(4-methyl-2-propionylamino-pentanoylamino)-propionic acid tert-butyl ester;

[S-(R*,R*)]-3-(4-Benzyloxy-phenyl)-2-(2-butyrylamino-4-methyl-pentanoylamino)-propionic acid tert-butyl ester;

[S-(R*,R*)]-3-(4-Benzyloxy-phenyl)-2-[4-methyl-2-(2-pyridin-3-yl-acetylamino)pentanoylamino]-propionic acid tert-butyl ester;

[S-(R*,R*)]-3-(4-Benzyloxy-phenyl)-2-[2-(3-1H-indol-3-yl-propionylamino)-4-methyl-pentanoylamino]-propionic acid tert-butyl ester;

[S-(R*,R*)]-3-(4-Benzyloxy-phenyl)-2-{4-methyl-2-[(5-methyl-2-phenyl-2H-[1,2,3]triazole-4-carbonyl)-amino]-pentanoylamino}-propionic acid tert-butyl ester;

[S-(R*,R*)]-3-(4-Benzyloxy-phenyl)-2-[4-methyl-2-(2-thiophen-2-yl-acetylamino)pentanoylamino]-propionic acid tert-butyl ester;

[S-(R*,R*)]-3-(4-Benzyloxy-phenyl)-2-{2-[(isoxazole-5-carbonyl)-amino]-4-methyl-pentanoylamino}-propionic acid tert-butyl ester;

[S-(R*,R*)]-3-(4-Benzyloxy-phenyl)-2-{4-methyl-2-[(pyridine-3-carbonyl)-amino]pentanoylamino}-propionic acid tert-butyl ester;

[S-(R*,R*)]-3-(4-Benzyloxy-phenyl)-2-{4-methyl-2-[(quinoxaline-2-carbonyl)-amino]pentanoylamino}-propionic acid tert-butyl ester;

[S-(R*,R*)]-2-(4-Benzyloxy-benzyl)-7-methyl-4-oxo-5-(2,2,3,3,3-pentafluoro-propionylamino)-octanoic acid tert-butyl ester;

[S-(R*,R*)]-3-(4-Benzyloxy-phenyl)-2-[4-methyl-2-(2,2,2-trifluoro-acetylamino)pentanoylamino]-propionic acid tert-butyl ester;

[S-(R*,R*)]-3-(4-Benzyloxy-phenyl)-2-[2-(2,2-dimethyl-propionylamino)-4-methyl-pentanoylamino]-propionic acid tert-butyl ester;

[S-(R*,R*)]-2-(2-Benzoylamino-4-methyl-pentanoylamino)-3-(4-benzyloxy-phenyl)-propionic acid tert-butyl ester; and

[S-(R*,R*)]-3-(4-Benzyloxy-phenyl)-2-{4-methyl-2-[(5-methyl-3-phenyl-isoxazole-4-carbonyl) amino]-pentanoylamino}-propionic acid tert-butyl ester.

134. The compounds:

[S-(R*,R*)]-Azepane-1-carboxylic acid {1-[2-(4-benzylamino-phenyl)-1-tert-butylcarbamoyl-ethylcarbamoyl]-3-methyl-butyl}-amide;

[S-(R*,R*)]-Azepane-1-carboxylic acid {1-[2-(4-dibenzylamino-phenyl)-1-tert-butylcarbamoyl-ethylcarbamoyl]-3-methyl-butyl}-amide;

[S-(R*,R*)]-Azepane-1-carboxylic acid {1-[1-tert-butylcarbamoyl-2-(4-phenylethynyl-phenyl)-ethylcarbamoyl]-3-methyl-butyl}-amide;

[S-(R*,R*)]-Azepane-1-carboxylic acid (1-{1-tert-butylcarbamoyl-2-[4-(3,3-dimethyl-but-1-ynyl)-phenyl]-ethylcarbamoyl}-3-methyl-butyl)-amide;

[S-(R*,R*)]-Azepane-1-carboxylic acid {1-[1-tert-butylcarbamoyl-2-(4-cyclohexylethynyl-phenyl)-ethylcarbamoyl]-3-methyl-butyl}-amide;

[S-(R*,R*)]-Azepane-1-carboxylic acid {1-[1-tert-butylcarbamoyl-2-(4-pyridin-2-ylethynyl-phenyl)-ethylcarbamoyl]-3-methyl-butyl}-amide;

[S-(R*,R*)]-Azepane-1-carboxylic acid (1-{1-tert-butylcarbamoyl-2-[4-(1-hydroxy-cyclohexylethynyl)-phenyl]-ethylcarbamoyl}-3-methyl-butyl)-amide;

Azepane-1-carboxylic acid (1-{1-tert-butylcarbamoyl-2-[4-(3-dimethylamino-prop-1-ynyl)-phenyl]-ethylcarbamoyl}-3-methyl-butyl)-amide;

Azepane-1-carboxylic acid [1-(1-tert-butylcarbamoyl-2-{4-[3-(1,1-dioxo-11,6-thiomorpholin-4-yl)-prop-1-ynyl]-phenyl}-ethylcarbamoyl)-3-methyl-butyl]-amide;

[S-(R*,R*)]-Azepane-1-carboxylic acid {1-[1-tert-butylcarbamoyl-2-(4-styryl-phenyl)-ethylcarbamoyl]-3-methyl-butyl}-amide;

[S-(R*,R*),Z]-Azepane-1-carboxylic acid (1-{1-tert-butylcarbamoyl-2-[4-(2-cyclohexyl-vinyl)-phenyl]-ethylcarbamoyl}-3-methyl-butyl)-amide;

Azepane-1-carboxylic acid [1-(1-tert-butylcarbamoyl-2-{4-[2-(1-hydroxy-cyclohexyl)-vinyl]-phenyl}-ethylcarbamoyl)-3-methyl-butyl]-amide; and

[S-(R*,R*)]-Azepane-1-carboxylic acid {1-[1-tert-butylcarbamoyl-2-(4-phenethyl-phenyl)-ethylcarbamoyl]-3-methyl-butyl}-amide.

135. The compounds:

[S-(R*,R*)]-Azepane-1-carboxylic acid (1-{1-tert-butylcarbamoyl-2-[4-(3,3-dimethyl-butyl)-phenyl]-ethylcarbamoyl}-3-methyl-butyl)-amide;

[S-(R*,R*)]-Azepane-1-carboxylic acid (1-{1-tert-butylcarbamoyl-2-[4-(2-cyclohexyl-ethyl)-phenyl]-ethylcarbamoyl}-3-methyl-butyl)-amide;

[S-(R*,R*)]-Azepane-1-carboxylic acid (1-{1-tert-butylcarbamoyl-2-[4-(2-pyridin-2-yl-ethyl)-phenyl]-ethylcarbamoyl}-3-methyl-butyl)-amide;

[S-(R*,R*)]-Azepane-1-carboxylic acid [1-(1-tert-butylcarbamoyl-2-{4-[2-(1-hydroxy-cyclohexyl)-ethyl]-phenyl}-ethylcarbamoyl)-3-methyl-butyl]-amide;

[S-(R*,R*)]-Azepane-1-carboxylic acid (1-{1-tert-butylcarbamoyl-2-[4-(3-dimethylamino-propyl)-phenyl]-ethylcarbamoyl}-3-methyl-butyl)-amide;

[S-(R*,R*)]-Azepane-1-carboxylic acid [1-(1-tert-butylcarbamoyl-2-{4-[3-(1,1-dioxo-11,6-thiomorpholin-4-yl)-propyl]-phenyl}-ethylcarbamoyl)-3-methyl-butyl]-amide;

[S-(R*,R*)]-Morpholine-4-carboxylic acid {1-[1-(4-benzyloxy-benzyl)-2-oxo-2-piperidin-1-ylethylcarbamoyl]-3-methyl-butyl}-amide;

[S-(R*,R*)]-1-(Azepane-1-carbonyl)-pyrrolidine-2-carboxylic acid [2-(4-benzyloxy-phenyl)-1-(2-piperidin-1-yl-ethylcarbamoyl)-ethyl]-amide;

[S-(R*,R*)]-1-(Azepane-1-carbonyl)-pyrrolidine-2-carboxylic acid [2-(4-benzyloxy-phenyl)-1-tert-butylcarbamoyl-ethyl]-amide;

[S-(R*,R*)]-Azepane-1-carboxylic acid {1-[2-(4-benzyloxy-phenyl)-1-(2-piperidin-1-ylethylcarbamoyl)-ethylcarbamoyl]-3-methylsulfanyl-propyl}-amide;

[S-(R*,R*)]-Azepane-1-carboxylic acid {1-[2-(4-benzyloxy-phenyl)-1-tert-butylcarbamoyl-ethylcarbamoyl]-3-methylsulfanyl-propyl}-amide; and

[S-(R*,R*)]-Azepane-1-carboxylic acid [1-[2-(4-benzyloxy-phenyl)-1-(2-piperidin-1-ylethylcarbamoyl)-ethylcarbamoyl]-2-(4-hydroxy-phenyl)-ethyl]-amide.

136. The compounds:

[S-(R*,R*)]-Azepane-1-carboxylic acid [1-[2-(4-benzyloxy-phenyl)-1-(2-piperidin-1-ylethylcarbamoyl)-ethylcarbamoyl]-2-(4-bromo-phenyl)-ethyl]-amide;

[S-(R*,R*)]-Azepane-1-carboxylic acid [1-[1-(4-benzyloxy-benzyl)-4,4-dimethyl-2-oxo-pentylcarbamoyl]-2-(4-benzyloxy-phenyl)-ethyl]-amide;

[S-(R*,R*)]-Azepane-1-carboxylic acid {1-[2-(4-benzyloxy-phenyl)-1-(2-piperidin-1-ylethylcarbamoyl)-ethylcarbamoyl]-3,3-dimethyl-butyl}-amide;

[S-(R*,R*)]-Azepane-1-carboxylic acid [1-[2-(4-benzyloxy-phenyl)-1-tert-butylcarbamoylethylcarbamoyl]-2-(4-hydroxy-phenyl)-ethyl]-amide;

[S-(R*,R*)]-1-(Azepane-1-carbonyl)-octahydro-indole-2-carboxylic acid [2-(4-benzyloxy-phenyl)-1-tert-butylcarbamoyl-ethyl]-amide;

[S-(R*,R*)]-Azepane-1-carboxylic acid {1-[2-(4-benzyloxy-phenyl)-1-(2-piperidin-1-ylethylcarbamoyl)-ethylcarbamoyl]-2-cyclohexyl-ethyl}-amide;

[S-(R*,R*)]-Azepane-1-carboxylic acid [1-[2-(4-benzyloxy-phenyl)-1-tert-butylcarbamoylethylcarbamoyl]-2-(4-tert-butoxy-phenyl)-ethyl]-amide;

[S-(R*,R*)]-6-[(Azepane-1-carbonyl)-amino]-6-[2-(4-benzyloxy-phenyl)-1-tert-butylcarbamoylethylcarbamoyl]-hexanoic acid tert-butyl ester;

[S-(R*,R*)]-Azepane-1-carboxylic acid {1-[2-(4-benzyloxy-phenyl)-1-(2-hydroxy-ethylcarbamoyl)-ethylcarbamoyl]-3-methyl-butyl}-amide;

[S-(R*,R*)]-Azepane-1-carboxylic acid {1-[1-(4-benzyloxy-benzyl)-2-morpholin-4-yl-2-oxo-ethylcarbamoyl]-3-methyl-butyl}-amide; and

[S-(R*,R*)]-Azepane-1-carboxylic acid {1-[1-(4-benzyloxy-benzyl)-2-oxo-2-piperidin-1-ylethylcarbamoyl]-3-methyl-butyl}-amide.

137. The compounds:

[S-(R*,R*)]-Azepane-1-carboxylic acid {1-[2-(4-benzyloxy-phenyl)-1-hexylcarbamoyl-ethylcarbamoyl]-3-methyl-butyl}-amide;

[S-(R*,R*)]-Azepane-1-carboxylic acid {1-[2-(4-benzyloxy-phenyl)-1-propylcarbamoyl-ethylcarbamoyl]-3-methyl-butyl}-amide;

[S-(R*,R*)]-Azepane-1-carboxylic acid (1-{2-(4-benzyloxy-phenyl)-1-[2-(2-oxo-pyrrolidin-1yl)-ethylcarbamoyl]-ethylcarbamoyl}-3-methyl-butyl)-amide;

[S-(R*,R*)]-Azepane-1-carboxylic acid {1-[2-(4-benzyloxy-phenyl)-1-(2-piperidin-1-yl-ethylcarbamoyl)-ethylcarbamoyl]-3-methyl-butyl}-amide;

[S-(R*,R*)]-Azepane-1-carboxylic acid (1-{2-(4-benzyloxy-phenyl)-1-[2-(1H-imidazol-4-yl) ethylcarbamoyl]-ethylcarbamoyl}-3-methyl-butyl)-amide;

[S-(R*,R*)]-Azepane-1-carboxylic acid {1-[2-(4-benzyloxy-phenyl)-1-(4-bromophenylcarbamoyl)-ethylcarbamoyl]-3-methyl-butyl}-amide;

[S-(R*,R*)]-Azepane-1-carboxylic acid {1-[2-(4-benzyloxy-phenyl)-1-(2-furan-2-ylethylcarbamoyl)-ethylcarbamoyl]-3-methyl-butyl}-amide;

[S-(R*,R*)]-Azepane-1-carboxylic acid {1-[2-(4-benzyloxy-phenyl)-1-(2-dimethylamino-ethylcarbamoyl)-ethylcarbamoyl]-3-methyl-butyl}-amide;

[S-(R*,R*)]-Azepane-1-carboxylic acid {1-[1-(4-benzyloxy-benzyl)-2-(4-methyl-piperazin-1-yl)-2-oxo-ethylcarbamoyl]-3-methyl-butyl}-amide;

[S-(R*,R*)]-Morpholine-4-carboxylic acid {1-[2-(4-benzyloxy-phenyl)-1-(2-piperidin-1-ylethylcarbamoyl)-ethylcarbamoyl]-3-methyl-butyl}-amide; and

[S-(R*,R*)]-Azepane-1-carboxylic acid (1-{2-(4-benzyloxy-phenyl)-1-[(pyridin-4-ylmethyl)carbamoyl]-ethylcarbamoyl}-3-methyl-butyl)-amide.

138. The compounds:

[S-(R*,R*)]-Azepane-1-carboxylic acid {1-[1-(4-benzyloxy-benzyl)-2-oxo-2-(2-pyrrolidin-1-ylmethyl-pyrrolidin-1-yl)-ethylcarbamoyl]-3-methyl-butyl}-amide;

[S-(R*,R*)]-Azepane-1-carboxylic acid {1-[1-(4-benzyloxy-benzyl)-2-(4-benzyl-piperazin-1-yl)-2-oxo-ethylcarbamoyl]-3-methyl-butyl}-amide;

[S-(R*,R*)]-Azepane-1-carboxylic acid {1-[2-(4-benzyloxy-phenyl)-1-(2-pyrrolidin-1-ylethylcarbamoyl)-ethylcarbamoyl]-3-methyl-butyl}-amide;

[S-(R*,R*)]-Azepane-1-carboxylic acid {1-[1-(1-aza-bicyclo[2.2.2]oct-3-ylcarbamoyl)-2-(4-benzyloxy-phenyl)-ethylcarbamoyl]-3-methyl-butyl}-amide;

[S-(R*,R*)]-Azepane-1-carboxylic acid {1-[2-(4-benzyloxy-phenyl)-1-(1-benzyl-pyrrolidin-3-ylcarbamoyl)-ethylcarbamoyl]-3-methyl-butyl}-amide;

[S-(R*,R*)]-Azepane-1-carboxylic acid {1-[2-(4benzyloxy-phenyl)-1-(3-cyclohexylamino-propylcarbamoyl)-ethylcarbamoyl]-3-methyl-butyl}-amide;

[S-(R*,R*)]-Azepane-1-carboxylic acid {1-[1-(4benzyloxy-benzyl)-2-[1,4']bipiperidinyl-1'-yl-2-oxo-ethylcarbamoyl]-3-methyl-butyl}-amide;

[S-(R*,R*)]-Azepane-1-carboxylic acid {1-[2-(4benzyloxy-phenyl)-1-(2-morpholin-4-ylethylcarbamoyl)-ethylcarbamoyl]-3-methyl-butyl}-amide;

[S-(R*,R*)]-Azepane-1-carboxylic acid (1-{2-(4-benzyloxy-phenyl)-1-[3-(4-methyl-piperazin-1-yl)-propylcarbamoyl]-ethylcarbamoyl}-3-methyl-butyl)-amide; and

[S-(R*,R*)]-Azepane-1-carboxylic acid {1-[1-(4-benzyloxy-benzyl)-2-(3-diethylcarbamoyl-piperidin-1-yl)-2-oxo-ethylcarbamoyl]-3-methyl-butyl}-amide.

139. The compounds:

[S-(R*,R*)]-Azepane-1-carboxylic acid {1-[1-(4-benzyloxy-benzyl)-2-(3-diethylcarbamoyl-piperidin-1-yl)-2-oxo-ethylcarbamoyl]-3-methyl-butyl}-amide;

[S-(R*,R*)]-Azepane-1-carboxylic acid {1-[2-(4-benzyloxy-phenyl)-1-(2-hydroxy-2-phenyl-ethylcarbamoyl)-ethylcarbamoyl]-3-methyl-butyl}-amide;

Azepane-1-carboxylic acid {1-[2-(4benzyloxy-phenyl)-1-(1,2-dimethyl propylcarbamoyl)-ethylcarbamoyl]-3-methyl-butyl}-amide;

Azepane-1-carboxylic acid {1-[2-(4-benzyloxy-phenyl)-1-(1,2-dimethyl propylcarbamoyl)-ethylcarbamoyl]-3-methyl-butyl}-amide;

[S-(R*,R*)]-Azepane-1-carboxylic acid (1-{2-(4-benzyloxy-phenyl)-1-[2-(1-methyl-pyrrolidin-2-yl)-ethylcarbamoyl]-ethylcarbamoyl}-3-methyl-butyl)-amide;

[S-(R*,R*)]-Azepane-1-carboxylic acid {1-[2-(4-benzyloxy-phenyl)-1-(1-benzyl-pyrrolidin-3-ylcarbamoyl)-ethylcarbamoyl]-3-methyl-butyl}-amide;

[S-(R*,R*)]-Azepane-1-carboxylic acid {1-[2-(4-benzyloxy-phenyl)-1-(1-propyl-piperidin-3-ylcarbamoyl)-ethylcarbamoyl]-3-methyl-butyl}-amide;

[S-(R*,R*)]-Azepane-1-carboxylic acid (1-{2-(4-benzyloxy-phenyl)-1-[3-(2-methyl-piperidin-1-yl)-propylcarbamoyl]-ethyl carbamoyl}-3-methyl -butyl)-amide;

[S-(R*,R*)]-Azepane-1-carboxylic acid {1-[2-(4-benzyloxy-phenyl)-1-(1-methyl-2-phenyl-piperidin-3-ylcarbamoyl)-ethylcarbamoyl]-3-methyl-butyl}-amide; and

[S-(R*,R*)]-Azepane-1-carboxylic acid {1-[2-(4-benzyloxy-phenyl)-1-(1-isobutyl-piperidin-3-ylcarbamoyl)-ethylcarbamoyl]-3-methyl-butyl}-amide.

140. The compounds:

[S-(R*,R*)]-Azepane-1-carboxylic acid {1-[1-(4-benzyloxy-benzyl)-2-(2,6-dimethyl-morpholin-4-yl)-2-oxo-ethylcarbamoyl]-3-methyl-butyl}-amide;

[S-(R*,R*)]-Azepane-1-carboxylic acid {1-[1-(4-benzyloxy-benzyl)-2-(3-methyl-piperidin-1-yl)-2-oxo-ethylcarbamoyl]-3-methyl-butyl}-amide;

[S-(R*,R*)]-Azepane-1-carboxylic acid {1-[1-(4-benzyloxy-benzyl)-2-(3,4-dihydro-1H-isoquinolin-2-yl)-2-oxo-ethylcarbamoyl]-3-methyl-butyl}-amide;

[S-(R*,R*)]-Azepane-1-carboxylic acid (1-{1-(4-benzyloxy-benzyl)-2-[4-(2-hydroxy-ethyl)-piperazin-1-yl]-2-oxo-ethylcarbamoyl}-3-methyl-butyl)-amide;

[S-(R*,R*)]-Azepane-1-carboxylic acid {1-[2-(4-benzyloxy-phenyl)-1-(2,2,6,6-tetramethyl-piperidin-4-ylcarbamoyl)-ethylcarbamoyl]-3-methyl-butyl}-amide;

[S-(R*,R*)]-Azepane-1-carboxylic acid {1-[2-(4-acetyl-piperazin-1-yl)-1-(4-benzyloxy-benzyl)-2-oxo-ethylcarbamoyl]-3-methyl-butyl}-amide;

[S-(R*,R*)]-Azepane-1-carboxylic acid {1-[2-(4-benzyloxy-phenyl)-1-(cyclohexylmethyl-carbamoyl)-ethylcarbamoyl]-3-methyl-butyl}-amide;

[S-(R*,R*)]-Azepane-1-carboxylic acid {1-[2-(4-benzyloxy-phenyl)-1-(cyclopropylmethyl-carbamoyl)-ethylcarbamoyl]-3-methyl-butyl}-amide;

[S-(R*,R*)]-Azepane-1-carboxylic acid {1-[2-(4-benzyloxy-phenyl)-1-(thiazol-2-ylcarbamoyl)-ethylcarbamoyl]-3-methyl-butyl}-amide;

[S-(R*,R*)]-Azepane-1-carboxylic acid {1-[2-(4-benzyloxy-phenyl)-1-cycloheptylcarbamoyl-ethylcarbamoyl]-3-methyl-butyl}-amide; and

[S-(R*,R*)]-Azepane-1-carboxylic acid {1-[2-(4-benzyloxy-phenyl)-1-cyclopropylcarbamoyl-ethylcarbamoyl]-3-methyl-butyl}-amide.

141. The compounds:

[S-(R*,R*)]-Azepane-1-carboxylic acid {1-[2-(4-benzyloxy-phenyl)-1-(4-methoxy-phenylcarbamoyl)-ethylcarbamoyl]-3-methyl-butyl}-amide;

[S-(R*,R*)]-Azepane-1-carboxylic acid (1-{2-(4-benzyloxy-phenyl)-1-[4-(2-hydroxy-ethyl)-phenylcarbamoyl]-ethylcarbamoyl}-3-methyl-butyl)-amide;

[S-(R*,R*)]-Azepane-1-carboxylic acid {-[1-(4-acetyl-phenylcarbamoyl)-2-(4-benzyloxy-phenyl)-ethylcarbamoyl]-3-methyl-butyl}-amide;

[S-(R*,R*)]-Azepane-1-carboxylic acid {1-[2-(4-benzyloxy-phenyl)-1-(4-phenoxy-phenylcarbamoyl)-ethylcarbamoyl]-3-methyl-butyl}-amide;

[S-(R*,R*)]-Azepane-1-carboxylic acid {1-[2-(4-benzyloxy-phenyl)-1-(3-trifluoromethyl-phenylcarbamoyl)-ethylcarbamoyl]-3-methyl-butyl}-amide;

[S-(R*,R*)]-Azepane-1-carboxylic acid {1-[2-(4-benzyloxy-phenyl)-1-(4-dimethylamino-phenylcarbamoyl)-ethylcarbamoyl]-3-methyl-butyl}-amide;

[S-(R*,R*)]-Azepane-1-carboxylic acid {1-[1-(4-acetylamino-phenylcarbamoyl)-2-(4-benzyloxy-phenyl)-ethylcarbamoyl]-3-methyl-butyl}-amide;

[S-(R*,R*)]-Azepane-1-carboxylic acid {1-[1-(4-aminomethyl-benzylcarbamoyl)-2-(4-benzyloxy-phenyl)-ethylcarbamoyl]-3-methyl-butyl}-amide;

[S-(R*,R*)]-Azepane-1-carboxylic acid {1-[1-(4-benzyloxy-benzyl)-2-oxo-2-(2-phenylaminomethyl-pyrrolidin-1-yl)-ethylcarbamoyl]-3-methyl-butyl}-amide; and

[S-(R*,R*)]-Azepane-1-carboxylic acid {1-[1-(3-amino-2-hydroxy-propylcarbamoyl)-2-(4-benzyloxy-phenyl)-ethylcarbamoyl]-3-methyl-butyl}-amide.

142. The compounds:

[S-(R*,R*)]-Azepane-1-carboxylic acid (1-{2-(4-benzyloxy-phenyl)-1-[(furan-2-ylmethyl)-carbamoyl]-ethylcarbamoyl}-3-methyl-butyl)-amide;

[S-(R*,R*)]-Azepane-1-carboxylic acid {1-[1-(4-benzyloxy-benzyl)-2-thiomorpholin-4-yl-2-oxo-ethylcarbamoyl]-3-methyl-butyl}-amide;

[S-(R*,R*)]-Azepane-1-carboxylic acid {1-[1-[(benzo[1,3]dioxol-5-ylmethyl)-carbamoyl]-2-(4-benzyloxy-phenyl)-ethylcarbamoyl]-3-methyl-butyl}-amide;

[S-(R*,R*)]-Azepane-1-carboxylic acid {1-[2-(4-benzyloxy-phenyl)-1-(3,4,5-trimethoxy-phenylcarbamoyl)-ethylcarbamoyl]-3-methyl-butyl}-amide;

[S-(R*,R*)]-Azepane-1-carboxylic acid (1-{2-(4-benzyloxy-phenyl)-1-[2-(1H-indol-3-yl)-ethylcarbamoyl]-ethylcarbamoyl}-3-methyl-butyl)-amide;

[S-(R*,R*)]-Azepane-1-carboxylic acid (1-{2-(4-benzyloxy-phenyl)-1-[2-(4-hydroxy-phenyl)-ethylcarbamoyl]-ethylcarbamoyl}-3-methyl-butyl)-amide;

[S-(R*,R*)]-Azepane-1-carboxylic acid {1-[2-(4-benzyloxy-phenyl)-1-(1-hydroxymethyl-propylcarbamoyl)-ethylcarbamoyl]-3-methyl-butyl}-amide;

[S-(R*,R*)]-Azepane-1-carboxylic acid {1-[2-(4-benzyloxy-phenyl)-1-(2-hydroxy-1-hydroxymethyl-2-phenyl-ethylcarbamoyl)-ethylcarbamoyl]-3-methyl-butyl}-amide;

[S-(R*,R*)]-Azepane-1-carboxylic acid [1-(1-(4-benzyloxy-benzyl)-2-{4-[2-(2-hydroxy-ethoxy)-ethyl]-piperazin-1-yl}-2-oxo-ethylcarbamoyl)-3-methyl-butyl]-amide; and

[S-(R*,R*)]-Azepane-1-carboxylic acid (1-[2-(4-benzyloxy-phenyl)-1-(1,1-bis-hydroxymethyl-propylcarbamoyl)-ethylcarbamoyl]-3-methyl-butyl}-amide.

143. The compounds:

[S-(R*,R*)]-Azepane-1-carboxylic acid {1-[2-(4-benzyloxy-phenyl)-1-(2-dimethylamino-1-methyl-ethylcarbamoyl)-ethylcarbamoyl]-3-methyl-butyl}-amide;

[S-(R*,R*)]-Azepane-1-carboxylic acid {1-[2-(4-benzyloxy-phenyl)-1-(2-pyridin-1-yl-ethylcarbamoyl)-ethylcarbamoyl]-3-methyl-butyl}-amide;

[S-(R*,R*)]-Azepane-1-carboxylic acid {1-[2-(4-benzyloxy-phenyl)-1-(1,2,3,4-tetrahydro-naphthalen-1-ylcarbamoyl)-ethylcarbamoyl]-3-methyl-butyl}-amide;

[S-(R*,R*)]-Azepane-1-carboxylic acid (1-{2-(4-benzyloxy-phenyl)-1-[2-(2-hydroxy-ethylamino)-ethylcarbamoyl]-ethylcarbamoyl}-3-methyl-butyl)-amide;

[S-(R*,R*)]-Azepane-1-carboxylic acid {1-[1-(4-benzyloxy-benzyl)-2-(3-hydroxy-piperidin-1-yl)-2-oxo-ethylcarbamoyl]-3-methyl-butyl}-amide;

[S-(R*,R*)]-Azepane-1-carboxylic acid {1-[1-(4-benzyloxy-benzyl)-2-(4-hydroxy-piperidin-1-yl)-2-oxo-ethylcarbamoyl]-3-methyl-butyl}-amide;

[S-(R*,R*)]-Azepane-1-carboxylic acid {1-[2-(4-benzyloxy-phenyl)-1-(2-cyano-ethylcarbamoyl)-ethylcarbamoyl]-3-methyl-butyl}-amide;

[S-(R*,R*)]-Azepane-1-carboxylic acid {1-[2-(4-benzyloxy phenyl)-1-(3-imidazol-1-yl-propylcarbamoyl)-ethylcarbamoyl]-3-methyl-butyl}-amide;

[S-(R*,R*)]-Azepane-1-carboxylic acid {1-[2-(4-benzyloxy-phenyl)-1-(1-hydroxymethyl-3-methylsulfanyl-propylcarbamoyl)-ethylcarbamoyl]-3-methyl-butyl}-amide; and

[S-(R*,R*)]-Azepane-1-carboxylic acid {1-[1-[2-(2-amino-propylamino)-1-methyl-ethylcarbamoyl]-2-(4-benzyloxy-phenyl)-ethylcarbamoyl]-3-methyl-butyl}-amide.

144. The compounds:

[S-(R*,R*)]-Azepane-1-carboxylic acid (1-{1-(4-benzyloxy-benzyl)-2-[4-(4-fluoro-phenyl)-piperazin-1-yl]-2-oxo-ethylcarbamoyl}-3-methyl-butyl)-amide;

[S-(R*,R*)]-Azepane-1-carboxylic acid {1-[2-(4-benzyloxy-phenyl)-1-(3-iodo-benzylcarbamoyl)-ethylcarbamoyl]-3-methyl-butyl}-amide;

[S-(R*,R*)]-Azepane-1-carboxylic acid {1-[2-(4-benzyloxy-phenyl)-1-(2-isopropylamino-propylcarbamoyl)-ethylcarbamoyl]-3-methyl-butyl}-amide;

[S-(R*,R*)]-Azepane-1-carboxylic acid {1-[2-(4-benzyloxy-phenyl)-1-sec-butylcarbamoyl-ethylcarbamoyl]-3-methyl-butyl}-amide;

[S-(R*,R*)]-Azepane-1-carboxylic acid {1-[2-(3-acetylamino-pyrrolidin-1-yl)-1-(4-benzyloxy-benzyl)-2-oxo-ethylcarbamoyl]-3-methyl-butyl}-amide;

[S-(R*,R*)]-Azepane-1-carboxylic acid {1-[2-(4-benzyloxy-phenyl)-1-(1-methoxymethyl-propylcarbamoyl)-ethylcarbamoyl]-3-methyl-butyl}-amide;

[S-(R*,R*)]-Azepane-1-carboxylic acid (1-{2-(4-benzyloxy-phenyl)-1-[3-(2-hydroxy-ethylamino)-1,1-dimethyl-propylcarbamoyl]-ethylcarbamoyl}-3-methyl-butyl)-amide;

[S-(R*,R*)]-Azepane-1-carboxylic acid {1-[1-(4-benzyloxy-benzyl)-2-(3,6-dihydro-2H-pyridin-1-yl)-2-oxo-ethylcarbamoyl]-3-methyl-butyl}-amide;

[S-(R*,R*)]-Azepane-1-carboxylic acid {1-[1-(4-benzyloxy-benzyl)-2-(4-ethyl-piperazin-1-yl)-2-oxo-ethylcarbamoyl]-3-methyl-butyl}-amide;

[S-(R*,R*)]-Azepane-1-carboxylic acid {1-[1-(4-benzyloxy-benzyl)-2-(2,5-dimethyl-2,5-dihydro-pyrrol-1-yl)-2-oxo-ethylcarbamoyl]-3-methyl-butyl}-amide; and

[S-(R*,R*)]-Azepane-1-carboxylic acid (1-{2-(4-benzyloxy-phenyl)-1-[(1-benzyl-pyrrolidin-3-ylmethyl)-carbamoyl]-ethylcarbamoyl}-3-methyl-butyl)-amide.

145. The compounds:

[S-(R*,R*)]-Azepane-1-carboxylic acid {1-[1-[benzyl-(2-hydroxy-ethyl)-carbamoyl]-2-(4-benzyloxy-phenyl)-ethylcarbamoyl]-3-methyl-butyl}-amide;

[S-(R*,R*)]-Azepane-1-carboxylic acid {1-[1-(2-benzylamino-ethylcarbamoyl)-2-(4-benzyloxy-phenyl)-ethylcarbamoyl]-3-methyl-butyl}-amide;

[S-(R*,R*)]-Azepane-1-carboxylic acid {1-[2-(4-benzyloxy-phenyl)-1-(1-hydroxymethyl-2-methyl-propylcarbamoyl)-ethylcarbamoyl]-3-methyl-butyl}-amide;

[S-(R*,R*)]-Azepane-1-carboxylic acid {1-[2-(4-benzyloxy-phenyl)-1-(pyridin-3-ylcarbamoyl)-ethylcarbamoyl]-3-methyl-butyl}-amide;

[S-(R*,R*)]-Azepane-1-carboxylic acid {1-[2-(4-benzyloxy-phenyl)-1-(3-hydroxy-propylcarbamoyl)-ethylcarbamoyl]-3-methyl-butyl}-amide;

[S-(R*,R*)]-Azepane-1-carboxylic acid {1-[1-(4-benzyloxy-benzyl)-2-(3-hydroxymethyl-piperidin-1-yl)-2-oxo-ethylcarbamoyl]-3-methyl-butyl}-amide;

[S-(R*,R*)]-Azepane-1-carboxylic acid {1-[2-(4-benzyloxy-phenyl)-1-(2-hydroxy-1-hydroxymethyl-ethylcarbamoyl)-ethylcarbamoyl]-3-methyl-butyl}-amide;

[S-(R*,R*)]-Azepane-1-carboxylic acid {1-[2-(4-benzyloxy-phenyl)-1-(pyrrolidin-3-ylcarbamoyl)-ethylcarbamoyl]-3-methyl-butyl}-amide;

[S-(R*,R*)]-Azepane-1-carboxylic acid {1-[2-(4-benzyloxy-phenyl)-1-([1,4]diazepane-1-carbonyl)-ethylcarbamoyl]-3-methyl-butyl}-amide;

[S-(R*,R*)]-Azepane-1-carboxylic acid {1-[2-(4-benzyloxy-phenyl)-1-(4-piperidin-1-yl-phenylcarbamoyl)-ethylcarbamoyl]-3-methyl-butyl}-amide; and

[S-(R*,R*)]-Azepane-1-carboxylic acid {1-[2-(4-benzyloxy-phenyl)-1-(pyrazole-3-carbonyl)-ethylcarbamoyl]-3-methyl-butyl}-amide.

146. The compounds:

[S-(R*,R*)]-Azepane-1-carboxylic acid (1-{2-(4-benzyloxy-phenyl)-1-[(piperidin-4-ylmethyl)-carbamoyl]-ethylcarbamoyl}-3-methyl-butyl)-amide;

[S-(R*,R*)]-Azepane-1-carboxylic acid {1-[1-benzylcarbamoyl-2-(4-benzyloxy-phenyl)-ethylcarbamoyl]-3-methyl-butyl}-amide;

[S-(R*,R*)]-Azepane-1-carboxylic acid (1-{1-(4-benzyloxy-benzyl)-2-[4-(4-methoxy-phenyl)-piperazin-1-yl]-2-oxo-ethylcarbamoyl}-3-methyl-butyl)-amide;

[S-(R*,R*)]-Azepane-1-carboxylic acid {1-[1-(4-benzyloxy-benzyl)-2-(4-benzyl-piperidin-1-yl)-2-oxo-ethylcarbamoyl]-3-methyl-butyl}-amide;

[S-(R*,R*)]-Azepane-1-carboxylic acid {1-[2-(4-benzyloxy-phenyl)-1-(2-hydroxy-1,1-dimethyl-ethylcarbamoyl)-ethylcarbamoyl]-3-methyl-butyl}-amide;

[S-(R*,R*)]-Azepane-1-carboxylic acid {1-[2-(4-benzyloxy-phenyl)-1-(4-hydroxy-2,5-dimethyl-phenylcarbamoyl)-ethylcarbamoyl]-3-methyl-butyl}-amide;

[S-(R*,R*)]-Azepane-1-carboxylic acid {1-[2-(4-benzyloxy-phenyl)-1-(3-pyrrolidin-1-yl-propylcarbamoyl)-ethylcarbamoyl]-3-methyl-butyl}-amide;

[S-(R*,R*)]-Azepane-1-carboxylic acid {1-[2-(4-benzyloxy-phenyl)-1-(3-hydroxy-phenylcarbamoyl)-ethylcarbamoyl]-3-methyl-butyl}-amide;

[S-(R*,R*)]-Azepane-1-carboxylic acid {1-[2-(4-benzhydryl-piperazin-1-yl)-1-(4-benzyloxy-benzyl)-2-oxo-ethylcarbamoyl]-3-methyl-butyl}-amide; and

[S-(R*,R*)]-Azepane-1-carboxylic acid {1-[2-(4-benzyloxy-phenyl)-1-(1-benzyl-piperidin-4-ylcarbamoyl)-ethylcarbamoyl]-3-methyl-butyl}-amide.

* * * * *